United States Patent
Vendely et al.

(10) Patent No.: US 9,839,423 B2
(45) Date of Patent: Dec. 12, 2017

(54) IMPLANTABLE LAYERS AND METHODS FOR MODIFYING THE SHAPE OF THE IMPLANTABLE LAYERS FOR USE WITH A SURGICAL FASTENING INSTRUMENT

(71) Applicant: Ethicon Endo-Surgery, Inc., Cincinnati, OH (US)

(72) Inventors: Michael J. Vendely, Lebanon, OH (US); Mark D. Timmer, Jersey City, NJ (US); Jackie J. Donners, Pennington, NJ (US); Donald L. Reynolds, II, West Chester, OH (US); Taylor W. Aronhalt, Loveland, OH (US); Trevor J. Barton, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 694 days.

(21) Appl. No.: 14/187,390

(22) Filed: Feb. 24, 2014

(65) Prior Publication Data
US 2015/0238188 A1    Aug. 27, 2015

(51) Int. Cl.
| A61B 17/04 | (2006.01) |
| A61B 17/10 | (2006.01) |
| A61B 17/068 | (2006.01) |
| B29C 43/52 | (2006.01) |
| B29C 55/00 | (2006.01) |

(Continued)

(52) U.S. Cl.
CPC ...... *A61B 17/068* (2013.01); *A61B 17/07207* (2013.01); *A61B 17/07292* (2013.01); *B29C 43/52* (2013.01); *B29C 55/00* (2013.01); *A61B 17/0644* (2013.01); *A61B 2017/00004* (2013.01); *A61B 2017/00526* (2013.01);

(Continued)

(58) Field of Classification Search
CPC . A61L 31/146; A61L 31/04; A61B 17/07292; A61B 17/07207; A61B 2017/00004; A61B 17/068; A61B 17/105
USPC .......................................... 227/175.1–182.1
See application file for complete search history.

(56) References Cited

U.S. PATENT DOCUMENTS

| 66,052 A | 6/1867 | Smith |
| 662,587 A | 11/1900 | Blake |

(Continued)

FOREIGN PATENT DOCUMENTS

| AU | 2008207624 A1 | 3/2009 |
| AU | 2010214687 A1 | 9/2010 |

(Continued)

OTHER PUBLICATIONS

U.S. Appl. No. 13/851,703, filed Mar. 27, 2013.

(Continued)

*Primary Examiner* — Robert Long

(57) ABSTRACT

A method is disclosed for altering an implantable layer for use with a surgical instrument which includes the steps of obtaining an implantable layer comprised at least partially from a material including a glass transition temperature and a melting temperature, wherein the implantable layer includes a first shape, heating the material to a temperature higher than the glass transition temperature and lower than the melting temperature, manipulating the implantable layer to a second shape different than the first shape, allowing the material to cool below the glass transition temperature, and releasing the implantable layer.

13 Claims, 39 Drawing Sheets

(51) Int. Cl.
*A61B 17/072* (2006.01)
*A61B 17/00* (2006.01)
*A61B 17/064* (2006.01)

(52) U.S. Cl.
CPC .............. *A61B 2017/07242* (2013.01); *A61B 2017/07278* (2013.01); *A61B 2017/07285* (2013.01)

(56) References Cited

U.S. PATENT DOCUMENTS

| | | |
|---|---|---|
| 670,748 A | 3/1901 | Weddeler |
| 951,393 A | 3/1910 | Hahn |
| 1,306,107 A | 6/1919 | Elliott |
| 1,314,601 A | 9/1919 | McCaskey |
| 1,677,337 A | 7/1928 | Grove |
| 1,794,907 A | 3/1931 | Kelly |
| 2,037,727 A | 4/1936 | La Chapelle |
| 2,132,295 A | 10/1938 | Hawkins |
| 2,161,632 A | 6/1939 | Nattenheimer |
| 2,211,117 A | 8/1940 | Hess |
| 2,214,870 A | 9/1940 | West |
| 2,318,379 A | 5/1943 | Davis et al. |
| 2,329,440 A | 9/1943 | La Place |
| 2,441,096 A | 5/1948 | Happe |
| 2,448,741 A | 9/1948 | Scott et al. |
| 2,450,527 A | 10/1948 | Smith et al. |
| 2,526,902 A | 10/1950 | Rublee |
| 2,527,256 A | 10/1950 | Jackson |
| 2,578,686 A | 12/1951 | Fish |
| 2,674,149 A | 4/1954 | Benson |
| 2,711,461 A | 6/1955 | Happe |
| 2,804,848 A | 9/1957 | O'Farrell et al. |
| 2,808,482 A | 10/1957 | Zanichkowsky et al. |
| 2,853,074 A | 9/1958 | Olson |
| 2,887,004 A | 5/1959 | Stewart |
| 2,959,974 A | 11/1960 | Emrick |
| 3,032,769 A | 5/1962 | Palmer |
| 3,075,062 A | 1/1963 | Iaccarino |
| 3,078,465 A | 2/1963 | Bobrov |
| 3,079,606 A | 3/1963 | Bobrov et al. |
| 3,166,072 A | 1/1965 | Sullivan, Jr. |
| 3,196,869 A | 7/1965 | Scholl |
| 3,204,731 A | 9/1965 | Bent et al. |
| 3,266,494 A | 8/1966 | Brownrigg et al. |
| 3,269,630 A | 8/1966 | Fleischer |
| 3,275,211 A | 9/1966 | Hirsch et al. |
| 3,317,103 A | 5/1967 | Cullen et al. |
| 3,317,105 A | 5/1967 | Astafjev et al. |
| 3,357,296 A | 12/1967 | Lefever |
| 3,490,675 A | 1/1970 | Green et al. |
| 3,494,533 A | 2/1970 | Green et al. |
| 3,499,591 A | 3/1970 | Green |
| 3,503,396 A | 3/1970 | Pierie et al. |
| 3,551,987 A | 1/1971 | Wilkinson |
| 3,568,675 A | 3/1971 | Harvey |
| 3,572,159 A | 3/1971 | Tschanz |
| 3,583,393 A | 6/1971 | Takahashi |
| 3,598,943 A | 8/1971 | Barrett |
| 3,608,549 A | 9/1971 | Merrill |
| 3,640,317 A | 2/1972 | Panfili |
| 3,643,851 A | 2/1972 | Green et al. |
| 3,661,666 A | 5/1972 | Foster et al. |
| 3,662,939 A | 5/1972 | Bryan |
| 3,695,646 A | 10/1972 | Mommsen |
| 3,709,221 A | 1/1973 | Riely |
| 3,717,294 A | 2/1973 | Green |
| 3,734,207 A | 5/1973 | Fishbein |
| 3,740,994 A | 6/1973 | DeCarlo, Jr. |
| 3,744,495 A | 7/1973 | Johnson |
| 3,746,002 A | 7/1973 | Haller |
| 3,751,902 A | 8/1973 | Kingsbury et al. |
| 3,799,151 A | 3/1974 | Fukaumi et al. |
| 3,819,100 A | 6/1974 | Noiles et al. |
| 3,821,919 A | 7/1974 | Knohl |
| 3,841,474 A | 10/1974 | Maier |
| 3,851,196 A | 11/1974 | Hinds |
| 3,885,491 A | 5/1975 | Curtis |
| 3,892,228 A | 7/1975 | Mitsui |
| 3,894,174 A | 7/1975 | Cartun |
| 3,940,844 A | 3/1976 | Colby et al. |
| 3,950,686 A | 4/1976 | Randall |
| 3,955,581 A | 5/1976 | Spasiano et al. |
| RE28,932 E | 8/1976 | Noiles et al. |
| 3,981,051 A | 9/1976 | Brumlik |
| 4,054,108 A | 10/1977 | Gill |
| 4,060,089 A | 11/1977 | Noiles |
| 4,106,446 A | 8/1978 | Yamada et al. |
| 4,111,206 A | 9/1978 | Vishnevsky et al. |
| 4,129,059 A | 12/1978 | Van Eck |
| 4,169,990 A | 10/1979 | Lerdman |
| 4,180,285 A | 12/1979 | Reneau |
| 4,198,734 A | 4/1980 | Brumlik |
| 4,198,982 A | 4/1980 | Fortner et al. |
| 4,207,898 A | 6/1980 | Becht |
| 4,213,562 A | 7/1980 | Garrett et al. |
| 4,226,242 A | 10/1980 | Jarvik |
| 4,244,372 A | 1/1981 | Kapitanov et al. |
| 4,250,436 A | 2/1981 | Weissman |
| 4,261,244 A | 4/1981 | Becht et al. |
| 4,272,002 A | 6/1981 | Moshofsky |
| 4,272,662 A | 6/1981 | Simpson |
| 4,274,304 A | 6/1981 | Curtiss |
| 4,275,813 A | 6/1981 | Noiles |
| 4,289,133 A | 9/1981 | Rothfuss |
| 4,296,654 A | 10/1981 | Mercer |
| 4,304,236 A | 12/1981 | Conta et al. |
| 4,305,539 A | 12/1981 | Korolkov et al. |
| 4,312,685 A | 1/1982 | Riedl |
| 4,317,451 A | 3/1982 | Cerwin et al. |
| 4,321,002 A | 3/1982 | Froehlich |
| 4,328,839 A | 5/1982 | Lyons et al. |
| 4,331,277 A | 5/1982 | Green |
| 4,340,331 A | 7/1982 | Savino |
| 4,347,450 A | 8/1982 | Colligan |
| 4,349,028 A | 9/1982 | Green |
| 4,353,371 A | 10/1982 | Cosman |
| 4,373,147 A | 2/1983 | Carlson, Jr. |
| 4,379,457 A | 4/1983 | Gravener et al. |
| 4,380,312 A | 4/1983 | Landrus |
| 4,382,326 A | 5/1983 | Rabuse |
| 4,383,634 A | 5/1983 | Green |
| 4,393,728 A | 7/1983 | Larson et al. |
| 4,396,139 A | 8/1983 | Hall et al. |
| 4,397,311 A | 8/1983 | Kanshin et al. |
| 4,402,445 A | 9/1983 | Green |
| 4,408,692 A | 10/1983 | Sigel et al. |
| 4,409,057 A | 10/1983 | Molenda et al. |
| 4,415,112 A | 11/1983 | Green |
| 4,416,276 A | 11/1983 | Newton et al. |
| 4,428,376 A | 1/1984 | Mericle |
| 4,429,695 A | 2/1984 | Green |
| 4,434,796 A | 3/1984 | Karapetian et al. |
| 4,438,659 A | 3/1984 | Desplats |
| 4,442,964 A | 4/1984 | Becht |
| 4,448,194 A | 5/1984 | DiGiovanni et al. |
| 4,451,743 A | 5/1984 | Suzuki et al. |
| 4,454,887 A | 6/1984 | Krüger |
| 4,467,805 A | 8/1984 | Fukuda |
| 4,470,414 A | 9/1984 | Imagawa et al. |
| 4,473,077 A | 9/1984 | Noiles et al. |
| 4,475,679 A | 10/1984 | Fleury, Jr. |
| 4,485,816 A | 12/1984 | Krumme |
| 4,485,817 A | 12/1984 | Swiggett |
| 4,486,928 A | 12/1984 | Tucker et al. |
| 4,488,523 A | 12/1984 | Shichman |
| 4,489,875 A | 12/1984 | Crawford et al. |
| 4,499,895 A | 2/1985 | Takayama |
| 4,500,024 A | 2/1985 | DiGiovanni et al. |
| 4,505,272 A | 3/1985 | Utyamyshev et al. |
| 4,505,273 A | 3/1985 | Braun et al. |
| 4,505,414 A | 3/1985 | Filipi |
| 4,506,671 A | 3/1985 | Green |
| 4,512,038 A | 4/1985 | Alexander et al. |

(56) References Cited

U.S. PATENT DOCUMENTS

| | | |
|---|---|---|
| 4,520,817 A | 6/1985 | Green |
| 4,522,327 A | 6/1985 | Korthoff et al. |
| 4,526,174 A | 7/1985 | Froehlich |
| 4,527,724 A | 7/1985 | Chow et al. |
| 4,530,453 A | 7/1985 | Green |
| 4,531,522 A | 7/1985 | Bedi et al. |
| 4,532,927 A | 8/1985 | Miksza, Jr. |
| 4,548,202 A | 10/1985 | Duncan |
| 4,565,109 A | 1/1986 | Tsay |
| 4,565,189 A | 1/1986 | Mabuchi |
| 4,566,620 A | 1/1986 | Green et al. |
| 4,569,469 A | 2/1986 | Mongeon et al. |
| 4,571,213 A | 2/1986 | Ishimoto |
| 4,573,468 A | 3/1986 | Conta et al. |
| 4,573,469 A | 3/1986 | Golden et al. |
| 4,573,622 A | 3/1986 | Green et al. |
| 4,576,167 A | 3/1986 | Noiles et al. |
| 4,580,712 A | 4/1986 | Green |
| 4,585,153 A | 4/1986 | Failla et al. |
| 4,589,416 A | 5/1986 | Green |
| 4,591,085 A | 5/1986 | Di Giovanni |
| 4,597,753 A | 7/1986 | Turley |
| 4,600,037 A | 7/1986 | Hatten |
| 4,604,786 A | 8/1986 | Howie, Jr. |
| 4,605,001 A | 8/1986 | Rothfuss et al. |
| 4,605,004 A | 8/1986 | Di Giovanni et al. |
| 4,606,343 A | 8/1986 | Conta et al. |
| 4,607,638 A | 8/1986 | Crainich |
| 4,608,981 A | 9/1986 | Rothfuss et al. |
| 4,610,250 A | 9/1986 | Green |
| 4,610,383 A | 9/1986 | Rothfuss et al. |
| 4,619,262 A | 10/1986 | Taylor |
| 4,619,391 A | 10/1986 | Sharkany et al. |
| 4,628,459 A | 12/1986 | Shinohara et al. |
| 4,629,107 A | 12/1986 | Fedotov et al. |
| 4,632,290 A | 12/1986 | Green et al. |
| 4,633,874 A | 1/1987 | Chow et al. |
| 4,634,419 A | 1/1987 | Kreizman et al. |
| 4,641,076 A | 2/1987 | Linden |
| 4,643,731 A | 2/1987 | Eckenhoff |
| 4,646,722 A | 3/1987 | Silverstein et al. |
| 4,655,222 A | 4/1987 | Florez et al. |
| 4,662,555 A | 5/1987 | Thornton |
| 4,663,874 A | 5/1987 | Sano et al. |
| 4,664,305 A | 5/1987 | Blake, III et al. |
| 4,665,916 A | 5/1987 | Green |
| 4,667,674 A | 5/1987 | Korthoff et al. |
| 4,669,647 A | 6/1987 | Storace |
| 4,671,445 A | 6/1987 | Barker et al. |
| 4,676,245 A | 6/1987 | Fukuda |
| 4,684,051 A | 8/1987 | Akopov et al. |
| 4,691,703 A | 9/1987 | Auth et al. |
| 4,693,248 A | 9/1987 | Failla |
| 4,700,703 A | 10/1987 | Resnick et al. |
| 4,708,141 A | 11/1987 | Inoue et al. |
| 4,709,120 A | 11/1987 | Pearson |
| 4,715,520 A | 12/1987 | Roehr, Jr. et al. |
| 4,719,917 A | 1/1988 | Barrows et al. |
| 4,727,308 A | 2/1988 | Huljak et al. |
| 4,728,020 A | 3/1988 | Green et al. |
| 4,728,876 A | 3/1988 | Mongeon et al. |
| 4,729,260 A | 3/1988 | Dudden |
| 4,730,726 A | 3/1988 | Holzwarth |
| 4,741,336 A | 5/1988 | Failla et al. |
| 4,743,214 A | 5/1988 | Tai-Cheng |
| 4,747,820 A | 5/1988 | Hornlein et al. |
| 4,750,902 A | 6/1988 | Wuchinich et al. |
| 4,752,024 A | 6/1988 | Green et al. |
| 4,754,909 A | 7/1988 | Barker et al. |
| 4,767,044 A | 8/1988 | Green |
| 4,773,420 A | 9/1988 | Green |
| 4,777,780 A | 10/1988 | Holzwarth |
| 4,787,387 A | 11/1988 | Burbank, III et al. |
| 4,790,225 A | 12/1988 | Moody et al. |
| 4,805,617 A | 2/1989 | Bedi et al. |
| 4,805,823 A | 2/1989 | Rothfuss |
| 4,809,695 A | 3/1989 | Gwathmey et al. |
| 4,815,460 A | 3/1989 | Porat et al. |
| 4,817,847 A | 4/1989 | Redtenbacher et al. |
| 4,819,853 A | 4/1989 | Green |
| 4,821,939 A | 4/1989 | Green |
| 4,827,911 A | 5/1989 | Broadwin et al. |
| 4,830,855 A | 5/1989 | Stewart |
| 4,834,720 A | 5/1989 | Blinkhorn |
| 4,844,068 A | 7/1989 | Arata et al. |
| 4,848,637 A | 7/1989 | Pruitt |
| 4,856,078 A | 8/1989 | Konopka |
| 4,865,030 A | 9/1989 | Polyak |
| 4,868,530 A | 9/1989 | Ahs |
| 4,869,414 A | 9/1989 | Green et al. |
| 4,869,415 A | 9/1989 | Fox |
| 4,873,977 A | 10/1989 | Avant et al. |
| 4,875,486 A | 10/1989 | Rapoport et al. |
| 4,880,015 A | 11/1989 | Nierman |
| 4,890,613 A | 1/1990 | Golden et al. |
| 4,892,244 A | 1/1990 | Fox et al. |
| 4,893,622 A | 1/1990 | Green et al. |
| 4,896,678 A | 1/1990 | Ogawa |
| 4,900,303 A | 2/1990 | Lemelson |
| 4,903,697 A | 2/1990 | Resnick et al. |
| 4,915,100 A | 4/1990 | Green |
| 4,930,503 A | 6/1990 | Pruitt |
| 4,930,674 A | 6/1990 | Barak |
| 4,931,047 A | 6/1990 | Broadwin et al. |
| 4,932,960 A | 6/1990 | Green et al. |
| 4,933,843 A | 6/1990 | Scheller et al. |
| 4,938,408 A | 7/1990 | Bedi et al. |
| 4,941,623 A | 7/1990 | Pruitt |
| 4,943,182 A | 7/1990 | Hoblingre |
| 4,944,443 A | 7/1990 | Oddsen et al. |
| 4,951,860 A | 8/1990 | Peters et al. |
| 4,955,959 A | 9/1990 | Tompkins et al. |
| 4,965,709 A | 10/1990 | Ngo |
| 4,973,274 A | 11/1990 | Hirukawa |
| 4,978,049 A | 12/1990 | Green |
| 4,978,333 A | 12/1990 | Broadwin et al. |
| 4,986,808 A | 1/1991 | Broadwin et al. |
| 4,988,334 A | 1/1991 | Hornlein et al. |
| 5,002,543 A | 3/1991 | Bradshaw et al. |
| 5,002,553 A | 3/1991 | Shiber |
| 5,005,754 A | 4/1991 | Van Overloop |
| 5,009,661 A | 4/1991 | Michelson |
| 5,014,899 A | 5/1991 | Presty et al. |
| 5,015,227 A | 5/1991 | Broadwin et al. |
| 5,018,515 A | 5/1991 | Gilman |
| 5,018,657 A | 5/1991 | Pedlick et al. |
| 5,024,671 A | 6/1991 | Tu et al. |
| 5,027,834 A | 7/1991 | Pruitt |
| 5,031,814 A | 7/1991 | Tompkins et al. |
| 5,035,040 A | 7/1991 | Kerrigan et al. |
| 5,038,109 A | 8/1991 | Goble et al. |
| 5,040,715 A | 8/1991 | Green et al. |
| 5,042,707 A | 8/1991 | Taheri |
| 5,061,269 A | 10/1991 | Muller |
| 5,062,563 A | 11/1991 | Green et al. |
| 5,065,929 A | 11/1991 | Schulze et al. |
| 5,071,052 A | 12/1991 | Rodak et al. |
| 5,071,430 A | 12/1991 | de Salis et al. |
| 5,074,454 A | 12/1991 | Peters |
| 5,079,006 A | 1/1992 | Urquhart |
| 5,080,556 A | 1/1992 | Carreno |
| 5,083,695 A | 1/1992 | Foslien et al. |
| 5,084,057 A | 1/1992 | Green et al. |
| 5,088,979 A | 2/1992 | Filipi et al. |
| 5,088,997 A | 2/1992 | Delahuerga et al. |
| 5,094,247 A | 3/1992 | Hernandez et al. |
| 5,100,420 A | 3/1992 | Green et al. |
| 5,104,025 A | 4/1992 | Main et al. |
| 5,104,397 A | 4/1992 | Vasconcelos et al. |
| 5,106,008 A | 4/1992 | Tompkins et al. |
| 5,108,368 A | 4/1992 | Hammerslag et al. |
| 5,111,987 A | 5/1992 | Moeinzadeh et al. |
| 5,116,349 A | 5/1992 | Aranyi |
| 5,122,156 A | 6/1992 | Granger et al. |

(56) References Cited

U.S. PATENT DOCUMENTS

| | | |
|---|---|---|
| 5,124,990 A | 6/1992 | Williamson |
| 5,129,570 A | 7/1992 | Schulze et al. |
| 5,137,198 A | 8/1992 | Nobis et al. |
| 5,139,513 A | 8/1992 | Segato |
| 5,141,144 A | 8/1992 | Foslien et al. |
| 5,142,932 A | 9/1992 | Moya et al. |
| 5,155,941 A | 10/1992 | Takahashi et al. |
| 5,156,315 A | 10/1992 | Green et al. |
| 5,156,609 A | 10/1992 | Nakao et al. |
| 5,156,614 A | 10/1992 | Green et al. |
| 5,158,567 A | 10/1992 | Green |
| 330,699 A | 11/1992 | Gill |
| 5,163,598 A | 11/1992 | Peters et al. |
| 5,171,247 A | 12/1992 | Hughett et al. |
| 5,171,249 A | 12/1992 | Stefanchik et al. |
| 5,171,253 A | 12/1992 | Klieman et al. |
| 5,188,111 A | 2/1993 | Yates et al. |
| 5,190,517 A | 3/1993 | Zieve et al. |
| 5,190,544 A | 3/1993 | Chapman et al. |
| 5,190,560 A | 3/1993 | Woods et al. |
| 5,192,288 A | 3/1993 | Thompson et al. |
| 5,195,968 A | 3/1993 | Lundquist et al. |
| 5,197,648 A | 3/1993 | Gingold |
| 5,197,649 A | 3/1993 | Bessler et al. |
| 5,197,966 A | 3/1993 | Sommerkamp |
| 5,200,280 A | 4/1993 | Karasa |
| 5,205,459 A | 4/1993 | Brinkerhoff et al. |
| 5,207,697 A | 5/1993 | Carusillo et al. |
| 5,209,747 A | 5/1993 | Knoepfler |
| 5,211,649 A | 5/1993 | Kohler et al. |
| 5,211,655 A | 5/1993 | Hasson |
| 5,217,457 A | 6/1993 | Delahuerga et al. |
| 5,217,478 A | 6/1993 | Rexroth |
| 5,219,111 A | 6/1993 | Bilotti et al. |
| 5,221,036 A | 6/1993 | Takase |
| 5,221,281 A | 6/1993 | Klicek |
| 5,222,963 A | 6/1993 | Brinkerhoff et al. |
| 5,222,975 A | 6/1993 | Crainich |
| 5,222,976 A | 6/1993 | Yoon |
| 5,223,675 A | 6/1993 | Taft |
| 5,234,447 A | 8/1993 | Kaster et al. |
| 5,236,440 A | 8/1993 | Hlavacek |
| 5,239,981 A | 8/1993 | Anapliotis |
| 5,240,163 A | 8/1993 | Stein et al. |
| 5,242,457 A | 9/1993 | Akopov et al. |
| 5,244,462 A | 9/1993 | Delahuerga et al. |
| 5,246,156 A | 9/1993 | Rothfuss et al. |
| 5,246,443 A | 9/1993 | Mai |
| 5,253,793 A | 10/1993 | Green et al. |
| 5,258,009 A | 11/1993 | Conners |
| 5,258,012 A | 11/1993 | Luscombe et al. |
| 5,259,366 A | 11/1993 | Reydel et al. |
| 5,259,835 A | 11/1993 | Clark et al. |
| 5,260,637 A | 11/1993 | Pizzi |
| 5,263,629 A | 11/1993 | Trumbull et al. |
| 5,263,973 A | 11/1993 | Cook |
| 5,264,218 A | 11/1993 | Rogozinski |
| 5,268,622 A | 12/1993 | Philipp |
| 5,271,543 A | 12/1993 | Grant et al. |
| 5,271,544 A | 12/1993 | Fox et al. |
| RE34,519 E | 1/1994 | Fox et al. |
| 5,275,323 A | 1/1994 | Schulze et al. |
| 5,275,608 A | 1/1994 | Forman et al. |
| 5,279,416 A | 1/1994 | Malec et al. |
| 5,281,216 A | 1/1994 | Klicek |
| 5,282,806 A | 2/1994 | Haber et al. |
| 5,282,829 A | 2/1994 | Hermes |
| 5,284,128 A | 2/1994 | Hart |
| 5,285,381 A | 2/1994 | Iskarous et al. |
| 5,285,945 A | 2/1994 | Brinkerhoff et al. |
| 5,289,963 A | 3/1994 | McGarry et al. |
| 5,290,271 A | 3/1994 | Jernberg |
| 5,292,053 A | 3/1994 | Bilotti et al. |
| 5,297,714 A | 3/1994 | Kramer |
| 5,304,204 A | 4/1994 | Bregen |
| 5,307,976 A | 5/1994 | Olson et al. |
| 5,309,387 A | 5/1994 | Mori et al. |
| 5,309,927 A | 5/1994 | Welch |
| 5,312,023 A | 5/1994 | Green et al. |
| 5,312,024 A | 5/1994 | Grant et al. |
| 5,312,329 A | 5/1994 | Beaty et al. |
| 5,314,424 A | 5/1994 | Nicholas |
| 5,314,445 A | 5/1994 | Heidmueller née Degwitz et al. |
| 5,314,466 A | 5/1994 | Stern et al. |
| 5,318,221 A | 6/1994 | Green et al. |
| 5,330,487 A | 7/1994 | Thornton et al. |
| 5,330,502 A | 7/1994 | Hassler et al. |
| 5,332,142 A | 7/1994 | Robinson et al. |
| 5,333,422 A | 8/1994 | Warren et al. |
| 5,333,772 A | 8/1994 | Rothfuss et al. |
| 5,333,773 A | 8/1994 | Main et al. |
| 5,334,183 A | 8/1994 | Wuchinich |
| 5,336,232 A | 8/1994 | Green et al. |
| 5,339,799 A | 8/1994 | Kami et al. |
| 5,341,724 A | 8/1994 | Vatel |
| 5,341,810 A | 8/1994 | Dardel |
| 5,342,381 A | 8/1994 | Tidemand |
| 5,342,395 A | 8/1994 | Jarrett et al. |
| 5,342,396 A | 8/1994 | Cook |
| 5,343,391 A | 8/1994 | Mushabac |
| 5,344,060 A | 9/1994 | Gravener et al. |
| 5,344,454 A | 9/1994 | Clarke et al. |
| 5,346,504 A | 9/1994 | Ortiz et al. |
| 5,348,259 A | 9/1994 | Blanco et al. |
| 5,350,388 A | 9/1994 | Epstein |
| 5,350,391 A | 9/1994 | Iacovelli |
| 5,350,400 A | 9/1994 | Esposito et al. |
| 5,352,229 A | 10/1994 | Goble et al. |
| 5,352,235 A | 10/1994 | Koros et al. |
| 5,352,238 A | 10/1994 | Green et al. |
| 5,354,303 A | 10/1994 | Spaeth et al. |
| 5,356,006 A | 10/1994 | Alpern et al. |
| 5,358,506 A | 10/1994 | Green et al. |
| 5,358,510 A | 10/1994 | Luscombe et al. |
| 5,359,231 A | 10/1994 | Flowers et al. |
| D352,780 S | 11/1994 | Glaeser et al. |
| 5,360,305 A | 11/1994 | Kerrigan |
| 5,360,428 A | 11/1994 | Hutchinson, Jr. |
| 5,364,001 A | 11/1994 | Bryan |
| 5,364,003 A | 11/1994 | Williamson, IV |
| 5,366,133 A | 11/1994 | Geiste |
| 5,366,134 A | 11/1994 | Green et al. |
| 5,366,479 A | 11/1994 | McGarry et al. |
| 5,368,015 A | 11/1994 | Wilk |
| 5,368,592 A | 11/1994 | Stern et al. |
| 5,370,645 A | 12/1994 | Klicek et al. |
| 5,372,124 A | 12/1994 | Takayama et al. |
| 5,372,596 A | 12/1994 | Klicek et al. |
| 5,372,602 A | 12/1994 | Burke |
| 5,374,277 A | 12/1994 | Hassler |
| 5,376,095 A | 12/1994 | Ortiz |
| 5,379,933 A | 1/1995 | Green et al. |
| 5,381,649 A | 1/1995 | Webb |
| 5,381,782 A | 1/1995 | DeLaRama et al. |
| 5,382,247 A | 1/1995 | Cimino et al. |
| 5,383,880 A | 1/1995 | Hooven |
| 5,383,881 A | 1/1995 | Green et al. |
| 5,383,888 A | 1/1995 | Zvenyatsky et al. |
| 5,383,895 A | 1/1995 | Holmes et al. |
| 5,389,098 A | 2/1995 | Tsuruta et al. |
| 5,389,104 A | 2/1995 | Hahnen et al. |
| 5,391,180 A | 2/1995 | Tovey et al. |
| 5,392,979 A | 2/1995 | Green et al. |
| 5,395,030 A | 3/1995 | Kuramoto et al. |
| 5,395,033 A | 3/1995 | Byrne et al. |
| 5,395,034 A | 3/1995 | Allen et al. |
| 5,395,312 A | 3/1995 | Desai |
| 5,395,384 A | 3/1995 | Duthoit |
| 5,397,046 A | 3/1995 | Savage et al. |
| 5,397,324 A | 3/1995 | Carroll et al. |
| 5,403,312 A | 4/1995 | Yates et al. |
| 5,405,072 A | 4/1995 | Zlock et al. |
| 5,405,073 A | 4/1995 | Porter |
| 5,405,344 A | 4/1995 | Williamson et al. |

(56) References Cited

U.S. PATENT DOCUMENTS

| | | |
|---|---|---|
| 5,405,360 A | 4/1995 | Tovey |
| 5,407,293 A | 4/1995 | Crainich |
| 5,408,409 A | 4/1995 | Glassman et al. |
| 5,409,498 A | 4/1995 | Braddock et al. |
| 5,411,481 A | 5/1995 | Allen et al. |
| 5,411,508 A | 5/1995 | Bessler et al. |
| 5,413,107 A | 5/1995 | Oakley et al. |
| 5,413,267 A | 5/1995 | Solyntjes et al. |
| 5,413,268 A | 5/1995 | Green et al. |
| 5,413,272 A | 5/1995 | Green et al. |
| 5,413,573 A | 5/1995 | Koivukangas |
| 5,415,334 A | 5/1995 | Williamson, IV et al. |
| 5,415,335 A | 5/1995 | Knodell, Jr. |
| 5,417,203 A | 5/1995 | Tovey et al. |
| 5,417,361 A | 5/1995 | Williamson, IV |
| 5,421,829 A | 6/1995 | Olichney et al. |
| 5,422,567 A | 6/1995 | Matsunaga |
| 5,423,471 A | 6/1995 | Mastri et al. |
| 5,423,809 A | 6/1995 | Klicek |
| 5,425,745 A | 6/1995 | Green et al. |
| 5,431,322 A | 7/1995 | Green et al. |
| 5,431,654 A | 7/1995 | Nic |
| 5,431,668 A | 7/1995 | Burbank, III et al. |
| 5,433,721 A | 7/1995 | Hooven et al. |
| 5,437,681 A | 8/1995 | Meade et al. |
| 5,438,302 A | 8/1995 | Goble |
| 5,439,155 A | 8/1995 | Viola |
| 5,439,156 A | 8/1995 | Grant et al. |
| 5,439,479 A | 8/1995 | Shichman et al. |
| 5,441,191 A | 8/1995 | Linden |
| 5,441,193 A | 8/1995 | Gravener |
| 5,441,483 A | 8/1995 | Avitall |
| 5,441,494 A | 8/1995 | Ortiz |
| 5,444,113 A | 8/1995 | Sinclair et al. |
| 5,445,155 A | 8/1995 | Sieben |
| 5,445,304 A | 8/1995 | Plyley et al. |
| 5,445,644 A | 8/1995 | Pietrafitta et al. |
| 5,447,265 A | 9/1995 | Vidal et al. |
| 5,447,417 A | 9/1995 | Kuhl et al. |
| 5,447,513 A | 9/1995 | Davison et al. |
| 5,449,355 A | 9/1995 | Rhum et al. |
| 5,449,365 A | 9/1995 | Green et al. |
| 5,449,370 A | 9/1995 | Vaitekunas |
| 5,452,836 A | 9/1995 | Huitema et al. |
| 5,452,837 A | 9/1995 | Williamson, IV et al. |
| 5,454,378 A | 10/1995 | Palmer et al. |
| 5,454,827 A | 10/1995 | Aust et al. |
| 5,456,401 A | 10/1995 | Green et al. |
| 5,458,579 A | 10/1995 | Chodorow et al. |
| 5,462,215 A | 10/1995 | Viola et al. |
| 5,464,013 A | 11/1995 | Lemelson |
| 5,464,144 A | 11/1995 | Guy et al. |
| 5,464,300 A | 11/1995 | Crainich |
| 5,465,894 A | 11/1995 | Clark et al. |
| 5,465,895 A | 11/1995 | Knodel et al. |
| 5,465,896 A | 11/1995 | Allen et al. |
| 5,466,020 A | 11/1995 | Page et al. |
| 5,467,911 A | 11/1995 | Tsuruta et al. |
| 5,468,253 A | 11/1995 | Bezwada et al. |
| 5,470,006 A | 11/1995 | Rodak |
| 5,470,007 A | 11/1995 | Plyley et al. |
| 5,470,009 A | 11/1995 | Rodak |
| 5,470,010 A | 11/1995 | Rothfuss et al. |
| 5,472,132 A | 12/1995 | Savage et al. |
| 5,472,442 A | 12/1995 | Klicek |
| 5,473,204 A | 12/1995 | Temple |
| 5,474,057 A | 12/1995 | Makower et al. |
| 5,474,223 A | 12/1995 | Viola et al. |
| 5,474,566 A | 12/1995 | Alesi et al. |
| 5,476,206 A | 12/1995 | Green et al. |
| 5,476,479 A | 12/1995 | Green et al. |
| 5,478,003 A | 12/1995 | Green et al. |
| 5,478,354 A | 12/1995 | Tovey et al. |
| 5,480,089 A | 1/1996 | Blewett |
| 5,480,409 A | 1/1996 | Riza |
| 5,482,197 A | 1/1996 | Green et al. |
| 5,484,095 A | 1/1996 | Green et al. |
| 5,484,398 A | 1/1996 | Stoddard |
| 5,484,451 A | 1/1996 | Akopov et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,489,256 A | 2/1996 | Adair |
| 5,496,312 A | 3/1996 | Klicek |
| 5,496,317 A | 3/1996 | Goble et al. |
| 5,497,933 A | 3/1996 | DeFonzo et al. |
| 5,501,654 A | 3/1996 | Failla et al. |
| 5,503,320 A | 4/1996 | Webster et al. |
| 5,503,635 A | 4/1996 | Sauer et al. |
| 5,503,638 A | 4/1996 | Cooper et al. |
| 5,505,363 A | 4/1996 | Green et al. |
| 5,507,426 A | 4/1996 | Young et al. |
| 5,509,596 A | 4/1996 | Green et al. |
| 5,509,916 A | 4/1996 | Taylor |
| 5,511,564 A | 4/1996 | Wilk |
| 5,514,129 A | 5/1996 | Smith |
| 5,514,157 A | 5/1996 | Nicholas et al. |
| 5,518,163 A | 5/1996 | Hooven |
| 5,518,164 A | 5/1996 | Hooven |
| 5,520,678 A | 5/1996 | Heckele et al. |
| 5,520,700 A | 5/1996 | Beyar et al. |
| 5,522,817 A | 6/1996 | Sander et al. |
| 5,522,831 A | 6/1996 | Sleister et al. |
| 5,527,320 A | 6/1996 | Carruthers et al. |
| 5,529,235 A | 6/1996 | Boiarski et al. |
| D372,086 S | 7/1996 | Grasso et al. |
| 5,531,305 A | 7/1996 | Roberts et al. |
| 5,531,744 A | 7/1996 | Nardella et al. |
| 5,533,521 A | 7/1996 | Granger |
| 5,533,581 A | 7/1996 | Barth et al. |
| 5,533,661 A | 7/1996 | Main et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,541,376 A | 7/1996 | Ladtkow et al. |
| 5,542,594 A | 8/1996 | McKean et al. |
| 5,542,949 A | 8/1996 | Yoon |
| 5,543,119 A | 8/1996 | Sutter et al. |
| 5,547,117 A | 8/1996 | Hamblin et al. |
| 5,549,583 A | 8/1996 | Sanford et al. |
| 5,549,621 A | 8/1996 | Bessler et al. |
| 5,549,627 A | 8/1996 | Kieturakis |
| 5,549,628 A | 8/1996 | Cooper et al. |
| 5,549,637 A | 8/1996 | Crainich |
| 5,551,622 A | 9/1996 | Yoon |
| 5,553,675 A | 9/1996 | Pitzen et al. |
| 5,553,765 A | 9/1996 | Knodel et al. |
| 5,554,148 A | 9/1996 | Aebischer et al. |
| 5,554,169 A | 9/1996 | Green et al. |
| 5,556,416 A | 9/1996 | Clark et al. |
| 5,558,665 A | 9/1996 | Kieturakis |
| 5,558,671 A | 9/1996 | Yates |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,690 A | 10/1996 | Green et al. |
| 5,562,701 A | 10/1996 | Huitema et al. |
| 5,562,702 A | 10/1996 | Huitema et al. |
| 5,563,481 A | 10/1996 | Krause |
| 5,564,615 A | 10/1996 | Bishop et al. |
| 5,569,161 A | 10/1996 | Ebling et al. |
| 5,569,270 A | 10/1996 | Weng |
| 5,569,284 A | 10/1996 | Young et al. |
| 5,571,090 A | 11/1996 | Sherts |
| 5,571,100 A | 11/1996 | Goble et al. |
| 5,571,116 A | 11/1996 | Bolanos et al. |
| 5,571,285 A | 11/1996 | Chow et al. |
| 5,573,543 A | 11/1996 | Akopov et al. |
| 5,574,431 A | 11/1996 | McKeown et al. |

(56) References Cited

U.S. PATENT DOCUMENTS

| | | |
|---|---|---|
| 5,575,054 A | 11/1996 | Klinzing et al. |
| 5,575,789 A | 11/1996 | Bell et al. |
| 5,575,799 A | 11/1996 | Bolanos et al. |
| 5,575,803 A | 11/1996 | Cooper et al. |
| 5,575,805 A | 11/1996 | Li |
| 5,577,654 A | 11/1996 | Bishop |
| 5,579,978 A | 12/1996 | Green et al. |
| 5,580,067 A | 12/1996 | Hamblin et al. |
| 5,582,611 A | 12/1996 | Tsuruta et al. |
| 5,582,617 A | 12/1996 | Klieman et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,591,170 A | 1/1997 | Spievack et al. |
| 5,591,187 A | 1/1997 | Dekel |
| 5,597,107 A | 1/1997 | Knodel et al. |
| 5,599,151 A | 2/1997 | Daum et al. |
| 5,599,279 A | 2/1997 | Slotman et al. |
| 5,599,344 A | 2/1997 | Paterson |
| 5,599,350 A | 2/1997 | Schulze et al. |
| 5,599,852 A | 2/1997 | Scopelianos et al. |
| 5,601,224 A | 2/1997 | Bishop et al. |
| 5,601,573 A | 2/1997 | Fogelberg et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,607,095 A | 3/1997 | Smith et al. |
| 5,607,433 A | 3/1997 | Polla et al. |
| 5,607,450 A | 3/1997 | Zvenyatsky et al. |
| 5,609,285 A | 3/1997 | Grant et al. |
| 5,609,601 A | 3/1997 | Kolesa et al. |
| 5,611,709 A | 3/1997 | McAnulty |
| 5,613,966 A | 3/1997 | Makower et al. |
| 5,615,820 A | 4/1997 | Viola |
| 5,618,294 A | 4/1997 | Aust et al. |
| 5,618,303 A | 4/1997 | Marlow et al. |
| 5,618,307 A | 4/1997 | Donlon et al. |
| 5,619,992 A | 4/1997 | Guthrie et al. |
| 5,620,289 A | 4/1997 | Curry |
| 5,620,452 A | 4/1997 | Yoon |
| 5,624,398 A | 4/1997 | Smith et al. |
| 5,624,452 A | 4/1997 | Yates |
| 5,626,587 A | 5/1997 | Bishop et al. |
| 5,626,595 A | 5/1997 | Sklar et al. |
| 5,628,446 A | 5/1997 | Geiste et al. |
| 5,628,743 A | 5/1997 | Cimino |
| 5,628,745 A | 5/1997 | Bek |
| 5,630,539 A | 5/1997 | Plyley et al. |
| 5,630,540 A | 5/1997 | Blewett |
| 5,630,541 A | 5/1997 | Williamson, IV et al. |
| 5,630,782 A | 5/1997 | Adair |
| 5,632,432 A | 5/1997 | Schulze et al. |
| 5,632,433 A | 5/1997 | Grant et al. |
| 5,634,584 A | 6/1997 | Okorocha et al. |
| 5,636,779 A | 6/1997 | Palmer |
| 5,636,780 A | 6/1997 | Green et al. |
| 5,639,008 A | 6/1997 | Gallagher et al. |
| 5,643,291 A | 7/1997 | Pier et al. |
| 5,645,209 A | 7/1997 | Green et al. |
| 5,647,526 A | 7/1997 | Green et al. |
| 5,647,869 A | 7/1997 | Goble et al. |
| 5,649,937 A * | 7/1997 | Bito .................. A61B 17/1285 606/139 |
| 5,649,956 A | 7/1997 | Jensen et al. |
| 5,651,491 A | 7/1997 | Heaton et al. |
| 5,653,373 A | 8/1997 | Green et al. |
| 5,653,374 A | 8/1997 | Young et al. |
| 5,653,677 A | 8/1997 | Okada et al. |
| 5,653,721 A | 8/1997 | Knodel et al. |
| 5,655,698 A | 8/1997 | Yoon |
| 5,657,429 A | 8/1997 | Wang et al. |
| 5,657,921 A | 8/1997 | Young et al. |
| 5,658,238 A | 8/1997 | Suzuki et al. |
| 5,658,281 A | 8/1997 | Heard |
| 5,658,300 A | 8/1997 | Bito et al. |
| 5,658,307 A | 8/1997 | Exconde |
| 5,662,258 A | 9/1997 | Knodel et al. |
| 5,662,260 A | 9/1997 | Yoon |
| 5,662,662 A | 9/1997 | Bishop et al. |
| 5,665,085 A | 9/1997 | Nardella |
| 5,667,517 A | 9/1997 | Hooven |
| 5,667,526 A | 9/1997 | Levin |
| 5,667,527 A | 9/1997 | Cook |
| 5,669,544 A | 9/1997 | Schulze et al. |
| 5,669,904 A | 9/1997 | Platt, Jr. et al. |
| 5,669,907 A | 9/1997 | Platt, Jr. et al. |
| 5,669,918 A | 9/1997 | Balazs et al. |
| 5,673,840 A | 10/1997 | Schulze et al. |
| 5,673,841 A | 10/1997 | Schulze et al. |
| 5,673,842 A | 10/1997 | Bittner et al. |
| 5,674,286 A | 10/1997 | D'Alessio et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,683,349 A | 11/1997 | Makower et al. |
| 5,685,474 A | 11/1997 | Seeber |
| 5,686,090 A | 11/1997 | Schilder et al. |
| 5,688,270 A | 11/1997 | Yates et al. |
| 5,690,269 A | 11/1997 | Bolanos et al. |
| 5,692,668 A | 12/1997 | Schulze et al. |
| 5,693,020 A | 12/1997 | Rauh |
| 5,693,042 A | 12/1997 | Boiarski et al. |
| 5,693,051 A | 12/1997 | Schulze et al. |
| 5,695,494 A | 12/1997 | Becker |
| 5,695,502 A | 12/1997 | Pier et al. |
| 5,695,504 A | 12/1997 | Gifford, III et al. |
| 5,695,524 A | 12/1997 | Kelley et al. |
| 5,697,542 A | 12/1997 | Knodel et al. |
| 5,697,543 A | 12/1997 | Burdorff |
| 5,697,909 A | 12/1997 | Eggers et al. |
| 5,697,943 A | 12/1997 | Sauer et al. |
| 5,700,270 A | 12/1997 | Peyser et al. |
| 5,702,387 A | 12/1997 | Arts et al. |
| 5,702,408 A | 12/1997 | Wales et al. |
| 5,702,409 A | 12/1997 | Rayburn et al. |
| 5,704,087 A | 1/1998 | Strub |
| 5,704,534 A | 1/1998 | Huitema et al. |
| 5,706,997 A | 1/1998 | Green et al. |
| 5,706,998 A | 1/1998 | Plyley et al. |
| 5,707,392 A | 1/1998 | Kortenbach |
| 5,709,334 A | 1/1998 | Sorrentino et al. |
| 5,709,680 A | 1/1998 | Yates et al. |
| 5,709,706 A | 1/1998 | Kienzle et al. |
| 5,711,472 A | 1/1998 | Bryan |
| 5,712,460 A | 1/1998 | Carr et al. |
| 5,713,128 A | 2/1998 | Schrenk et al. |
| 5,713,505 A | 2/1998 | Huitema |
| 5,713,895 A | 2/1998 | Lontine et al. |
| 5,713,896 A | 2/1998 | Nardella |
| 5,713,920 A | 2/1998 | Bezwada et al. |
| 5,715,987 A | 2/1998 | Kelley et al. |
| 5,715,988 A | 2/1998 | Palmer |
| 5,716,366 A | 2/1998 | Yates |
| 5,718,359 A | 2/1998 | Palmer et al. |
| 5,718,360 A | 2/1998 | Green et al. |
| 5,718,548 A | 2/1998 | Cotellessa |
| 5,718,714 A | 2/1998 | Livneh |
| 5,720,744 A | 2/1998 | Eggleston et al. |
| D393,067 S | 3/1998 | Geary et al. |
| 5,725,536 A | 3/1998 | Oberlin et al. |
| 5,725,554 A | 3/1998 | Simon et al. |
| 5,728,110 A | 3/1998 | Vidal et al. |
| 5,728,121 A | 3/1998 | Bimbo et al. |
| 5,730,758 A | 3/1998 | Allgeyer |
| 5,732,821 A | 3/1998 | Stone et al. |
| 5,732,871 A | 3/1998 | Clark et al. |
| 5,732,872 A | 3/1998 | Bolduc et al. |
| 5,733,308 A | 3/1998 | Daugherty et al. |
| 5,735,445 A | 4/1998 | Vidal et al. |
| 5,735,848 A | 4/1998 | Yates et al. |

(56) References Cited

U.S. PATENT DOCUMENTS

| | | |
|---|---|---|
| 5,735,874 A | 4/1998 | Measamer et al. |
| 5,738,474 A | 4/1998 | Blewett |
| 5,738,648 A | 4/1998 | Lands et al. |
| 5,743,456 A | 4/1998 | Jones et al. |
| 5,747,953 A | 5/1998 | Philipp |
| 5,749,889 A | 5/1998 | Bacich et al. |
| 5,749,893 A | 5/1998 | Vidal et al. |
| 5,752,644 A | 5/1998 | Bolanos et al. |
| 5,752,965 A | 5/1998 | Francis et al. |
| 5,755,717 A | 5/1998 | Yates et al. |
| 5,758,814 A | 6/1998 | Gallagher et al. |
| 5,762,255 A | 6/1998 | Chrisman et al. |
| 5,762,256 A | 6/1998 | Mastri et al. |
| 5,766,188 A | 6/1998 | Igaki |
| 5,766,205 A | 6/1998 | Zvenyatsky et al. |
| 5,769,748 A | 6/1998 | Eyerly et al. |
| 5,769,892 A | 6/1998 | Kingwell |
| 5,772,379 A | 6/1998 | Evensen |
| 5,772,578 A | 6/1998 | Heimberger et al. |
| 5,772,659 A | 6/1998 | Becker et al. |
| 5,776,130 A | 7/1998 | Buysse et al. |
| 5,778,939 A | 7/1998 | Hok-Yin |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,749 A | 7/1998 | Riza |
| 5,782,859 A | 7/1998 | Nicholas et al. |
| 5,784,934 A | 7/1998 | Izumisawa |
| 5,785,232 A | 7/1998 | Vidal et al. |
| 5,785,647 A | 7/1998 | Tompkins et al. |
| 5,787,897 A | 8/1998 | Kieturakis |
| 5,792,135 A | 8/1998 | Madhani et al. |
| 5,792,165 A | 8/1998 | Klieman et al. |
| 5,794,834 A | 8/1998 | Hamblin et al. |
| 5,796,188 A | 8/1998 | Bays |
| 5,797,536 A | 8/1998 | Smith et al. |
| 5,797,537 A | 8/1998 | Oberlin et al. |
| 5,797,538 A | 8/1998 | Heaton et al. |
| 5,797,906 A | 8/1998 | Rhum et al. |
| 5,797,959 A | 8/1998 | Castro et al. |
| 5,799,857 A | 9/1998 | Robertson et al. |
| 5,800,379 A | 9/1998 | Edwards |
| 5,800,423 A | 9/1998 | Jensen |
| 5,806,676 A | 9/1998 | Wasgien |
| 5,807,376 A | 9/1998 | Viola et al. |
| 5,807,378 A | 9/1998 | Jensen et al. |
| 5,807,393 A | 9/1998 | Williamson, IV et al. |
| 5,809,441 A | 9/1998 | McKee |
| 5,810,721 A | 9/1998 | Mueller et al. |
| 5,810,811 A | 9/1998 | Yates et al. |
| 5,810,846 A | 9/1998 | Virnich et al. |
| 5,810,855 A | 9/1998 | Rayburn et al. |
| 5,813,813 A | 9/1998 | Daum et al. |
| 5,814,055 A | 9/1998 | Knodel et al. |
| 5,814,057 A | 9/1998 | Oi et al. |
| 5,816,471 A | 10/1998 | Plyley et al. |
| 5,817,084 A | 10/1998 | Jensen |
| 5,817,091 A | 10/1998 | Nardella et al. |
| 5,817,093 A | 10/1998 | Williamson, IV et al. |
| 5,817,109 A | 10/1998 | McGarry et al. |
| 5,817,119 A | 10/1998 | Klieman et al. |
| 5,820,009 A | 10/1998 | Melling et al. |
| 5,823,066 A | 10/1998 | Huitema et al. |
| 5,824,333 A | 10/1998 | Scopelianos et al. |
| 5,826,776 A | 10/1998 | Schulze et al. |
| 5,827,271 A | 10/1998 | Buysse et al. |
| 5,827,298 A | 10/1998 | Hart et al. |
| 5,829,662 A | 11/1998 | Allen et al. |
| 5,833,690 A | 11/1998 | Yates et al. |
| 5,833,695 A | 11/1998 | Yoon |
| 5,833,696 A | 11/1998 | Whitfield et al. |
| 5,836,503 A | 11/1998 | Ehrenfels et al. |
| 5,836,960 A | 11/1998 | Kolesa et al. |
| 5,839,639 A | 11/1998 | Sauer et al. |
| 5,843,021 A | 12/1998 | Edwards et al. |
| 5,843,096 A | 12/1998 | Igaki et al. |
| 5,843,097 A | 12/1998 | Mayenberger et al. |
| 5,843,122 A | 12/1998 | Riza |
| 5,843,132 A | 12/1998 | Ilvento |
| 5,843,169 A | 12/1998 | Taheri |
| 5,846,254 A | 12/1998 | Schulze et al. |
| 5,849,011 A | 12/1998 | Jones et al. |
| 5,849,023 A | 12/1998 | Mericle |
| 5,855,311 A | 1/1999 | Hamblin et al. |
| 5,855,583 A | 1/1999 | Wang et al. |
| 5,860,581 A | 1/1999 | Robertson et al. |
| 5,860,975 A | 1/1999 | Goble et al. |
| 5,865,361 A | 2/1999 | Milliman et al. |
| 5,868,760 A | 2/1999 | McGuckin, Jr. |
| 5,871,135 A | 2/1999 | Williamson IV et al. |
| 5,873,885 A | 2/1999 | Weidenbenner |
| 5,876,401 A | 3/1999 | Schulze et al. |
| 5,878,193 A | 3/1999 | Wang et al. |
| 5,878,607 A | 3/1999 | Nunes et al. |
| 5,878,937 A | 3/1999 | Green et al. |
| 5,878,938 A | 3/1999 | Bittner et al. |
| 5,891,160 A | 4/1999 | Williamson, IV et al. |
| 5,893,506 A | 4/1999 | Powell |
| 5,893,835 A | 4/1999 | Witt et al. |
| 5,893,878 A | 4/1999 | Pierce |
| 5,894,979 A | 4/1999 | Powell |
| 5,897,552 A | 4/1999 | Edwards et al. |
| 5,897,562 A | 4/1999 | Bolanos et al. |
| 5,899,914 A | 5/1999 | Zirps et al. |
| 5,901,895 A | 5/1999 | Heaton et al. |
| 5,902,312 A | 5/1999 | Frater et al. |
| 5,903,117 A | 5/1999 | Gregory |
| 5,904,647 A | 5/1999 | Ouchi |
| 5,904,693 A | 5/1999 | Dicesare et al. |
| 5,904,702 A | 5/1999 | Ek et al. |
| 5,906,625 A | 5/1999 | Bito et al. |
| 5,908,402 A | 6/1999 | Blythe |
| 5,908,427 A | 6/1999 | McKean et al. |
| 5,911,353 A | 6/1999 | Bolanos et al. |
| 5,915,616 A | 6/1999 | Viola et al. |
| 5,916,225 A | 6/1999 | Kugel |
| 5,918,791 A | 7/1999 | Sorrentino et al. |
| 5,919,198 A | 7/1999 | Graves, Jr. et al. |
| 5,921,956 A | 7/1999 | Grinberg et al. |
| 5,928,256 A | 7/1999 | Riza |
| 5,931,847 A | 8/1999 | Bittner et al. |
| 5,931,853 A | 8/1999 | McEwen et al. |
| 5,937,951 A | 8/1999 | Izuchukwu et al. |
| 5,938,667 A | 8/1999 | Peyser et al. |
| 5,941,442 A | 8/1999 | Geiste et al. |
| 5,941,890 A | 8/1999 | Voegele et al. |
| 5,944,172 A | 8/1999 | Hannula |
| 5,944,715 A | 8/1999 | Goble et al. |
| 5,947,984 A | 9/1999 | Whipple |
| 5,948,030 A | 9/1999 | Miller et al. |
| 5,951,516 A | 9/1999 | Bunyan |
| 5,951,552 A | 9/1999 | Long et al. |
| 5,951,574 A | 9/1999 | Stefanchik et al. |
| 5,951,581 A | 9/1999 | Saadat et al. |
| 5,954,259 A | 9/1999 | Viola et al. |
| 5,964,394 A | 10/1999 | Robertson |
| 5,964,774 A | 10/1999 | McKean et al. |
| 5,971,916 A | 10/1999 | Koren |
| 5,973,221 A | 10/1999 | Collyer et al. |
| 5,977,746 A | 11/1999 | Hershberger et al. |
| 5,984,949 A | 11/1999 | Levin |
| 5,988,479 A | 11/1999 | Palmer |
| 5,997,528 A | 12/1999 | Bisch et al. |
| 5,997,552 A | 12/1999 | Person et al. |
| 6,001,108 A | 12/1999 | Wang et al. |
| 6,003,517 A | 12/1999 | Sheffield et al. |
| 6,004,319 A | 12/1999 | Goble et al. |
| 6,004,335 A | 12/1999 | Vaitekunas et al. |
| 6,010,054 A | 1/2000 | Johnson et al. |
| 6,010,513 A | 1/2000 | Törmälä et al. |
| 6,012,494 A | 1/2000 | Balazs |
| 6,013,076 A | 1/2000 | Goble et al. |

(56) References Cited

U.S. PATENT DOCUMENTS

| | | |
|---|---|---|
| 6,015,406 A | 1/2000 | Goble et al. |
| 6,015,417 A | 1/2000 | Reynolds, Jr. |
| 6,017,322 A | 1/2000 | Snoke et al. |
| 6,017,354 A | 1/2000 | Culp et al. |
| 6,017,356 A | 1/2000 | Frederick et al. |
| 6,018,227 A | 1/2000 | Kumar et al. |
| 6,022,352 A | 2/2000 | Vandewalle |
| 6,024,741 A | 2/2000 | Williamson, IV et al. |
| 6,024,748 A | 2/2000 | Manzo et al. |
| 6,024,764 A * | 2/2000 | Schroeppel ............ A61F 2/04 264/296 |
| 6,027,501 A | 2/2000 | Goble et al. |
| 6,032,849 A | 3/2000 | Mastri et al. |
| 6,033,378 A | 3/2000 | Lundquist et al. |
| 6,033,399 A | 3/2000 | Gines |
| 6,033,427 A | 3/2000 | Lee |
| 6,037,724 A | 3/2000 | Buss et al. |
| 6,037,927 A | 3/2000 | Rosenberg |
| 6,039,733 A | 3/2000 | Buysse et al. |
| 6,039,734 A | 3/2000 | Goble |
| 6,042,601 A | 3/2000 | Smith |
| 6,045,560 A | 4/2000 | McKean et al. |
| 6,047,861 A | 4/2000 | Vidal et al. |
| 6,049,145 A | 4/2000 | Austin et al. |
| 6,050,472 A | 4/2000 | Shibata |
| 6,050,990 A | 4/2000 | Tankovich et al. |
| 6,050,996 A | 4/2000 | Schmaltz et al. |
| 6,053,390 A | 4/2000 | Green et al. |
| 6,053,922 A | 4/2000 | Krause et al. |
| RE36,720 E | 5/2000 | Green et al. |
| 6,056,735 A | 5/2000 | Okada et al. |
| 6,056,746 A | 5/2000 | Goble et al. |
| 6,062,360 A | 5/2000 | Shields |
| 6,063,095 A | 5/2000 | Wang et al. |
| 6,063,097 A | 5/2000 | Oi et al. |
| 6,063,098 A | 5/2000 | Houser et al. |
| 6,065,679 A | 5/2000 | Levie et al. |
| 6,065,919 A | 5/2000 | Peck |
| 6,066,132 A | 5/2000 | Chen et al. |
| 6,068,627 A | 5/2000 | Orszulak et al. |
| 6,071,233 A | 6/2000 | Ishikawa et al. |
| 6,074,386 A | 6/2000 | Goble et al. |
| 6,074,401 A | 6/2000 | Gardiner et al. |
| 6,077,286 A | 6/2000 | Cuschieri et al. |
| 6,079,606 A | 6/2000 | Milliman et al. |
| 6,080,181 A | 6/2000 | Jensen et al. |
| 6,082,577 A | 7/2000 | Coates et al. |
| 6,083,191 A | 7/2000 | Rose |
| 6,083,234 A | 7/2000 | Nicholas et al. |
| 6,083,242 A | 7/2000 | Cook |
| 6,086,544 A | 7/2000 | Hibner et al. |
| 6,086,600 A | 7/2000 | Kortenbach |
| 6,090,106 A | 7/2000 | Goble et al. |
| 6,093,186 A | 7/2000 | Goble |
| 6,099,537 A | 8/2000 | Sugai et al. |
| 6,099,551 A | 8/2000 | Gabbay |
| 6,102,271 A | 8/2000 | Longo et al. |
| 6,104,304 A | 8/2000 | Clark et al. |
| 6,106,511 A | 8/2000 | Jensen |
| 6,109,500 A | 8/2000 | Alli et al. |
| 6,117,148 A | 9/2000 | Ravo et al. |
| 6,117,158 A | 9/2000 | Measamer et al. |
| 6,119,913 A | 9/2000 | Adams et al. |
| 6,120,433 A | 9/2000 | Mizuno et al. |
| 6,120,462 A | 9/2000 | Hibner et al. |
| 6,123,241 A | 9/2000 | Walter et al. |
| H1904 H | 10/2000 | Yates et al. |
| 6,126,058 A | 10/2000 | Adams et al. |
| 6,126,670 A | 10/2000 | Walker et al. |
| 6,131,789 A | 10/2000 | Schulze et al. |
| 6,131,790 A | 10/2000 | Piraka |
| 6,132,368 A | 10/2000 | Cooper |
| 6,139,546 A | 10/2000 | Koenig et al. |
| 6,149,660 A | 11/2000 | Laufer et al. |
| 6,152,935 A | 11/2000 | Kammerer et al. |
| 6,155,473 A | 12/2000 | Tompkins et al. |
| 6,156,056 A | 12/2000 | Kearns et al. |
| 6,159,146 A | 12/2000 | El Gazayerli |
| 6,159,200 A | 12/2000 | Verdura et al. |
| 6,159,224 A | 12/2000 | Yoon |
| 6,162,208 A | 12/2000 | Hipps |
| 6,162,537 A | 12/2000 | Martin et al. |
| 6,165,175 A | 12/2000 | Wampler et al. |
| 6,165,184 A | 12/2000 | Verdura et al. |
| 6,165,188 A | 12/2000 | Saadat et al. |
| 6,168,605 B1 | 1/2001 | Measamer et al. |
| 6,171,305 B1 | 1/2001 | Sherman |
| 6,171,316 B1 | 1/2001 | Kovac et al. |
| 6,171,330 B1 | 1/2001 | Benchetrit |
| 6,174,308 B1 | 1/2001 | Goble et al. |
| 6,174,309 B1 | 1/2001 | Wrublewski et al. |
| 6,175,290 B1 | 1/2001 | Forsythe et al. |
| 6,179,195 B1 | 1/2001 | Adams et al. |
| 6,179,776 B1 | 1/2001 | Adams et al. |
| 6,181,105 B1 | 1/2001 | Cutolo et al. |
| 6,182,673 B1 | 2/2001 | Kindermann et al. |
| 6,187,003 B1 | 2/2001 | Buysse et al. |
| 6,190,386 B1 | 2/2001 | Rydell |
| 6,193,129 B1 | 2/2001 | Bittner et al. |
| 6,197,042 B1 | 3/2001 | Ginn et al. |
| 6,200,330 B1 | 3/2001 | Benderev et al. |
| 6,202,914 B1 | 3/2001 | Geiste et al. |
| 6,206,897 B1 | 3/2001 | Jamiolkowski et al. |
| 6,206,904 B1 | 3/2001 | Ouchi |
| 6,210,403 B1 | 4/2001 | Klicek |
| 6,213,999 B1 | 4/2001 | Platt, Jr. et al. |
| 6,214,028 B1 | 4/2001 | Yoon et al. |
| 6,220,368 B1 | 4/2001 | Ark et al. |
| 6,223,100 B1 | 4/2001 | Green |
| 6,223,835 B1 | 5/2001 | Habedank et al. |
| 6,224,617 B1 | 5/2001 | Saadat et al. |
| 6,228,081 B1 | 5/2001 | Goble |
| 6,228,083 B1 | 5/2001 | Lands et al. |
| 6,228,084 B1 | 5/2001 | Kirwan, Jr. |
| 6,231,565 B1 | 5/2001 | Tovey et al. |
| 6,234,178 B1 | 5/2001 | Goble et al. |
| 6,241,139 B1 | 6/2001 | Milliman et al. |
| 6,241,140 B1 | 6/2001 | Adams et al. |
| 6,241,723 B1 | 6/2001 | Heim et al. |
| 6,245,084 B1 | 6/2001 | Mark et al. |
| 6,248,116 B1 | 6/2001 | Chevillon et al. |
| 6,248,117 B1 | 6/2001 | Blatter |
| 6,249,076 B1 | 6/2001 | Madden et al. |
| 6,249,105 B1 | 6/2001 | Andrews et al. |
| 6,250,532 B1 | 6/2001 | Green et al. |
| 6,258,107 B1 | 7/2001 | Balázs et al. |
| 6,261,286 B1 | 7/2001 | Goble et al. |
| 6,264,086 B1 | 7/2001 | McGuckin, Jr. |
| 6,264,087 B1 | 7/2001 | Whitman |
| 6,270,508 B1 | 8/2001 | Klieman et al. |
| 6,273,876 B1 | 8/2001 | Klima et al. |
| 6,273,897 B1 | 8/2001 | Dalessandro et al. |
| 6,277,114 B1 | 8/2001 | Bullivant et al. |
| 6,293,942 B1 | 9/2001 | Goble et al. |
| 6,296,640 B1 | 10/2001 | Wampler et al. |
| 6,302,311 B1 | 10/2001 | Adams et al. |
| 6,305,891 B1 | 10/2001 | Burlingame |
| 6,306,134 B1 | 10/2001 | Goble et al. |
| 6,306,149 B1 | 10/2001 | Meade |
| 6,309,403 B1 | 10/2001 | Minor et al. |
| 6,315,184 B1 | 11/2001 | Whitman |
| 6,320,123 B1 | 11/2001 | Reimers |
| 6,322,494 B1 | 11/2001 | Bullivant et al. |
| 6,324,339 B1 | 11/2001 | Hudson et al. |
| 6,325,799 B1 | 12/2001 | Goble |
| 6,325,810 B1 | 12/2001 | Hamilton et al. |
| 6,330,965 B1 | 12/2001 | Milliman et al. |
| 6,331,181 B1 | 12/2001 | Tierney et al. |
| 6,331,761 B1 | 12/2001 | Kumar et al. |
| 6,333,029 B1 | 12/2001 | Vyakarnam et al. |
| 6,334,860 B1 | 1/2002 | Dorn |
| 6,334,861 B1 | 1/2002 | Chandler et al. |
| 6,336,926 B1 | 1/2002 | Goble |
| 6,338,737 B1 | 1/2002 | Toledano |

(56) References Cited

U.S. PATENT DOCUMENTS

| | | |
|---|---|---|
| 6,343,731 B1 | 2/2002 | Adams et al. |
| 6,346,077 B1 | 2/2002 | Taylor et al. |
| 6,352,503 B1 | 3/2002 | Matsui et al. |
| 6,352,532 B1 | 3/2002 | Kramer et al. |
| 6,355,699 B1 | 3/2002 | Vyakarnam et al. |
| 6,356,072 B1 | 3/2002 | Chass |
| 6,358,224 B1 | 3/2002 | Tims et al. |
| 6,364,877 B1 | 4/2002 | Goble et al. |
| 6,364,888 B1 | 4/2002 | Niemeyer et al. |
| 6,370,981 B2 | 4/2002 | Watarai |
| 6,373,152 B1 | 4/2002 | Wang et al. |
| 6,383,201 B1 | 5/2002 | Dong |
| 6,387,113 B1 | 5/2002 | Hawkins et al. |
| 6,387,114 B2 | 5/2002 | Adams |
| 6,391,038 B2 | 5/2002 | Vargas et al. |
| 6,392,854 B1 | 5/2002 | O'Gorman |
| 6,398,781 B1 | 6/2002 | Goble et al. |
| 6,398,797 B2 | 6/2002 | Bombard et al. |
| 6,402,766 B2 | 6/2002 | Bowman et al. |
| 6,406,440 B1 | 6/2002 | Stefanchik |
| 6,406,472 B1 | 6/2002 | Jensen |
| 6,409,724 B1 | 6/2002 | Penny et al. |
| H2037 H | 7/2002 | Yates et al. |
| 6,413,274 B1 | 7/2002 | Pedros |
| 6,416,486 B1 | 7/2002 | Wampler |
| 6,416,509 B1 | 7/2002 | Goble et al. |
| 6,419,695 B1 | 7/2002 | Gabbay |
| 6,423,079 B1 | 7/2002 | Blake, III |
| RE37,814 E | 8/2002 | Allgeyer |
| 6,428,070 B1 | 8/2002 | Takanashi et al. |
| 6,429,611 B1 | 8/2002 | Li |
| 6,430,298 B1 | 8/2002 | Kettl et al. |
| 6,432,065 B1 | 8/2002 | Burdorff et al. |
| 6,436,097 B1 | 8/2002 | Nardella |
| 6,436,107 B1 | 8/2002 | Wang et al. |
| 6,436,110 B2 | 8/2002 | Bowman et al. |
| 6,436,122 B1 | 8/2002 | Frank et al. |
| 6,439,439 B1 | 8/2002 | Rickard et al. |
| 6,439,446 B1 | 8/2002 | Perry et al. |
| 6,440,146 B2 | 8/2002 | Nicholas et al. |
| 6,441,577 B2 | 8/2002 | Blumenkranz et al. |
| 6,443,973 B1 | 9/2002 | Whitman |
| 6,447,518 B1 | 9/2002 | Krause et al. |
| 6,447,864 B2 | 9/2002 | Johnson et al. |
| 6,450,391 B1 | 9/2002 | Kayan et al. |
| 6,450,989 B2 | 9/2002 | Dubrul et al. |
| 6,454,781 B1 | 9/2002 | Witt et al. |
| 6,468,275 B1 | 10/2002 | Wampler et al. |
| 6,471,106 B1 | 10/2002 | Reining |
| 6,471,659 B2 | 10/2002 | Eggers et al. |
| 6,478,210 B2 | 11/2002 | Adams et al. |
| 6,482,200 B2 | 11/2002 | Shippert |
| 6,485,490 B2 | 11/2002 | Wampler et al. |
| 6,485,667 B1 | 11/2002 | Tan |
| 6,488,196 B1 | 12/2002 | Fenton, Jr. |
| 6,488,197 B1 | 12/2002 | Whitman |
| 6,491,201 B1 | 12/2002 | Whitman |
| 6,491,690 B1 | 12/2002 | Goble et al. |
| 6,491,701 B2 | 12/2002 | Tierney et al. |
| 6,492,785 B1 | 12/2002 | Kasten et al. |
| 6,494,896 B1 | 12/2002 | D'Alessio et al. |
| 6,498,480 B1 | 12/2002 | Manara |
| 6,500,176 B1 | 12/2002 | Truckai et al. |
| 6,500,194 B2 | 12/2002 | Benderev et al. |
| 6,503,257 B2 | 1/2003 | Grant et al. |
| 6,503,259 B2 | 1/2003 | Huxel et al. |
| 6,505,768 B2 | 1/2003 | Whitman |
| 6,510,854 B2 | 1/2003 | Goble |
| 6,511,468 B1 | 1/2003 | Cragg et al. |
| 6,512,360 B1 | 1/2003 | Goto et al. |
| 6,517,528 B1 | 2/2003 | Pantages et al. |
| 6,517,535 B2 | 2/2003 | Edwards |
| 6,517,565 B1 | 2/2003 | Whitman et al. |
| 6,517,566 B1 | 2/2003 | Hovland et al. |
| 6,522,101 B2 | 2/2003 | Malackowski |
| 6,527,782 B2 | 3/2003 | Hogg et al. |
| 6,527,785 B2 | 3/2003 | Sancoff et al. |
| 6,533,157 B1 | 3/2003 | Whitman |
| 6,533,784 B2 | 3/2003 | Truckai et al. |
| 6,535,764 B2 | 3/2003 | Imran et al. |
| 6,543,456 B1 | 4/2003 | Freeman |
| 6,545,384 B1 | 4/2003 | Pelrine et al. |
| 6,547,786 B1 | 4/2003 | Goble |
| 6,550,546 B2 | 4/2003 | Thurler et al. |
| 6,551,333 B2 | 4/2003 | Kuhns et al. |
| 6,554,861 B2 | 4/2003 | Knox et al. |
| 6,555,770 B2 | 4/2003 | Kawase |
| 6,558,378 B2 | 5/2003 | Sherman et al. |
| 6,558,379 B1 | 5/2003 | Batchelor et al. |
| 6,565,560 B1 | 5/2003 | Goble et al. |
| 6,566,619 B2 | 5/2003 | Gillman et al. |
| 6,569,085 B2 | 5/2003 | Kortenbach et al. |
| 6,569,171 B2 | 5/2003 | DeGuillebon et al. |
| 6,578,751 B2 | 6/2003 | Hartwick |
| 6,582,427 B1 | 6/2003 | Goble et al. |
| 6,582,441 B1 | 6/2003 | He et al. |
| 6,583,533 B2 | 6/2003 | Pelrine et al. |
| 6,585,144 B2 | 7/2003 | Adams et al. |
| 6,587,750 B2 | 7/2003 | Gerbi et al. |
| 6,588,643 B2 | 7/2003 | Bolduc et al. |
| 6,588,931 B2 | 7/2003 | Betzner et al. |
| 6,589,164 B1 | 7/2003 | Flaherty |
| 6,592,538 B1 | 7/2003 | Hotchkiss et al. |
| 6,592,597 B2 | 7/2003 | Grant et al. |
| 6,596,296 B1 | 7/2003 | Nelson et al. |
| 6,596,304 B1 | 7/2003 | Bayon et al. |
| 6,596,432 B2 | 7/2003 | Kawakami et al. |
| D478,665 S | 8/2003 | Isaacs et al. |
| D478,986 S | 8/2003 | Johnston et al. |
| 6,601,749 B2 | 8/2003 | Sullivan et al. |
| 6,602,252 B2 | 8/2003 | Mollenauer |
| 6,602,262 B2 | 8/2003 | Griego et al. |
| 6,605,078 B2 | 8/2003 | Adams |
| 6,605,669 B2 | 8/2003 | Awokola et al. |
| 6,607,475 B2 | 8/2003 | Doyle et al. |
| 6,611,793 B1 | 8/2003 | Burnside et al. |
| 6,613,069 B2 | 9/2003 | Boyd et al. |
| 6,616,686 B2 | 9/2003 | Coleman et al. |
| 6,619,529 B2 | 9/2003 | Green et al. |
| 6,620,166 B1 | 9/2003 | Wenstrom, Jr. et al. |
| 6,626,834 B2 | 9/2003 | Dunne et al. |
| 6,629,630 B2 | 10/2003 | Adams |
| 6,629,974 B2 | 10/2003 | Penny et al. |
| 6,629,988 B2 | 10/2003 | Weadock |
| 6,635,838 B1 | 10/2003 | Kornelson |
| 6,636,412 B2 | 10/2003 | Smith |
| 6,638,108 B2 | 10/2003 | Tachi |
| 6,638,285 B2 | 10/2003 | Gabbay |
| 6,638,297 B1 | 10/2003 | Huitema |
| RE38,335 E | 11/2003 | Aust et al. |
| 6,641,528 B2 | 11/2003 | Torii |
| 6,644,532 B2 | 11/2003 | Green et al. |
| 6,645,201 B1 | 11/2003 | Utley et al. |
| 6,646,307 B1 | 11/2003 | Yu et al. |
| 6,648,816 B2 | 11/2003 | Irion et al. |
| 6,652,595 B1 | 11/2003 | Nicolo |
| D484,243 S | 12/2003 | Ryan et al. |
| D484,595 S | 12/2003 | Ryan et al. |
| D484,596 S | 12/2003 | Ryan et al. |
| 6,656,177 B2 | 12/2003 | Truckai et al. |
| 6,656,193 B2 | 12/2003 | Grant et al. |
| 6,663,623 B1 | 12/2003 | Oyama et al. |
| 6,663,641 B1 | 12/2003 | Kovac et al. |
| 6,666,854 B1 | 12/2003 | Lange |
| 6,666,875 B1 | 12/2003 | Sakurai et al. |
| 6,667,825 B2 | 12/2003 | Lu et al. |
| 6,669,073 B2 | 12/2003 | Milliman et al. |
| 6,671,185 B2 | 12/2003 | Duval |
| D484,977 S | 1/2004 | Ryan et al. |
| 6,676,660 B2 | 1/2004 | Wampler et al. |
| 6,679,269 B2 | 1/2004 | Swanson |
| 6,679,410 B2 | 1/2004 | Würsch et al. |
| 6,681,978 B2 | 1/2004 | Geiste et al. |
| 6,681,979 B2 | 1/2004 | Whitman |

(56) References Cited

U.S. PATENT DOCUMENTS

| | | |
|---|---|---|
| 6,682,527 B2 | 1/2004 | Strul |
| 6,682,528 B2 | 1/2004 | Frazier et al. |
| 6,685,727 B2 | 2/2004 | Fisher et al. |
| 6,689,153 B1 | 2/2004 | Skiba |
| 6,692,507 B2 | 2/2004 | Pugsley et al. |
| 6,695,198 B2 | 2/2004 | Adams et al. |
| 6,695,199 B2 | 2/2004 | Whitman |
| 6,695,774 B2 | 2/2004 | Hale et al. |
| 6,697,048 B2 | 2/2004 | Rosenberg et al. |
| 6,698,643 B2 | 3/2004 | Whitman |
| 6,699,235 B2 | 3/2004 | Wallace et al. |
| 6,704,210 B1 | 3/2004 | Myers |
| 6,705,503 B1 | 3/2004 | Pedicini et al. |
| 6,709,445 B2 | 3/2004 | Boebel et al. |
| 6,712,773 B1 | 3/2004 | Viola |
| 6,716,223 B2 | 4/2004 | Leopold et al. |
| 6,716,232 B1 | 4/2004 | Vidal et al. |
| 6,716,233 B1 | 4/2004 | Whitman |
| 6,722,552 B2 | 4/2004 | Fenton, Jr. |
| 6,723,087 B2 | 4/2004 | O'Neill et al. |
| 6,723,091 B2 | 4/2004 | Goble et al. |
| 6,726,697 B2 | 4/2004 | Nicholas et al. |
| 6,726,706 B2 | 4/2004 | Dominguez |
| 6,729,119 B2 | 5/2004 | Schnipke et al. |
| 6,736,825 B2 | 5/2004 | Blatter et al. |
| 6,736,854 B2 | 5/2004 | Vadurro et al. |
| 6,740,030 B2 | 5/2004 | Martone et al. |
| 6,747,121 B2 | 6/2004 | Gogolewski |
| 6,749,560 B1 | 6/2004 | Konstorum et al. |
| 6,752,768 B2 | 6/2004 | Burdorff et al. |
| 6,752,816 B2 | 6/2004 | Culp et al. |
| 6,755,195 B1 | 6/2004 | Lemke et al. |
| 6,755,338 B2 | 6/2004 | Hahnen et al. |
| 6,758,846 B2 | 7/2004 | Goble et al. |
| 6,761,685 B2 | 7/2004 | Adams et al. |
| 6,762,339 B1 | 7/2004 | Klun et al. |
| 6,764,445 B2 | 7/2004 | Ramans et al. |
| 6,767,352 B2 | 7/2004 | Field et al. |
| 6,767,356 B2 | 7/2004 | Kanner et al. |
| 6,769,590 B2 | 8/2004 | Vresh et al. |
| 6,769,594 B2 | 8/2004 | Orban, III |
| 6,770,027 B2 | 8/2004 | Banik et al. |
| 6,770,070 B1 | 8/2004 | Balbierz |
| 6,770,072 B1 | 8/2004 | Truckai et al. |
| 6,773,409 B2 | 8/2004 | Truckai et al. |
| 6,773,438 B1 | 8/2004 | Knodel et al. |
| 6,775,575 B2 | 8/2004 | Bommannan et al. |
| 6,777,838 B2 | 8/2004 | Miekka et al. |
| 6,780,151 B2 | 8/2004 | Grabover et al. |
| 6,780,180 B1 | 8/2004 | Goble et al. |
| 6,783,524 B2 | 8/2004 | Anderson et al. |
| 6,786,382 B1 | 9/2004 | Hoffman |
| 6,786,864 B2 | 9/2004 | Matsuura et al. |
| 6,786,896 B2 | 9/2004 | Madhani et al. |
| 6,788,018 B1 | 9/2004 | Blumenkranz |
| 6,790,173 B2 | 9/2004 | Saadat et al. |
| 6,793,652 B1 | 9/2004 | Whitman et al. |
| 6,793,661 B2 | 9/2004 | Hamilton et al. |
| 6,793,663 B2 | 9/2004 | Kneifel et al. |
| 6,802,843 B2 | 10/2004 | Truckai et al. |
| 6,805,273 B2 | 10/2004 | Bilotti et al. |
| 6,806,808 B1 | 10/2004 | Watters et al. |
| 6,808,525 B2 | 10/2004 | Latterell et al. |
| 6,814,741 B2 | 11/2004 | Bowman et al. |
| 6,817,508 B1 | 11/2004 | Racenet et al. |
| 6,817,509 B2 | 11/2004 | Geiste et al. |
| 6,817,974 B2 | 11/2004 | Cooper et al. |
| 6,818,018 B1 | 11/2004 | Sawhney |
| 6,820,791 B2 | 11/2004 | Adams |
| 6,821,273 B2 | 11/2004 | Mollenauer |
| 6,821,282 B2 | 11/2004 | Perry et al. |
| 6,821,284 B2 | 11/2004 | Sturtz et al. |
| 6,827,246 B2 | 12/2004 | Sullivan et al. |
| 6,827,712 B2 | 12/2004 | Tovey et al. |
| 6,827,725 B2 | 12/2004 | Batchelor et al. |
| 6,828,902 B2 | 12/2004 | Casden |
| 6,830,174 B2 | 12/2004 | Hillstead et al. |
| 6,831,629 B2 | 12/2004 | Nakamura et al. |
| 6,832,998 B2 | 12/2004 | Goble |
| 6,834,001 B2 | 12/2004 | Myono |
| 6,835,173 B2 | 12/2004 | Couvillon, Jr. |
| 6,835,199 B2 | 12/2004 | McGuckin, Jr. et al. |
| 6,835,336 B2 | 12/2004 | Watt |
| 6,837,846 B2 | 1/2005 | Jaffe et al. |
| 6,837,883 B2 | 1/2005 | Moll et al. |
| 6,838,493 B2 | 1/2005 | Williams et al. |
| 6,840,423 B2 | 1/2005 | Adams et al. |
| 6,843,403 B2 | 1/2005 | Whitman |
| 6,843,789 B2 | 1/2005 | Goble |
| 6,843,793 B2 | 1/2005 | Brock et al. |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,850,817 B1 | 2/2005 | Green |
| 6,853,879 B2 | 2/2005 | Sunaoshi |
| 6,858,005 B2 | 2/2005 | Ohline et al. |
| RE38,708 E | 3/2005 | Bolanos et al. |
| 6,861,142 B1 | 3/2005 | Wilkie et al. |
| 6,863,694 B1 | 3/2005 | Boyce et al. |
| 6,866,178 B2 | 3/2005 | Adams et al. |
| 6,866,671 B2 | 3/2005 | Tierney et al. |
| 6,867,248 B1 | 3/2005 | Martin et al. |
| 6,869,430 B2 | 3/2005 | Balbierz et al. |
| 6,869,435 B2 | 3/2005 | Blake, III |
| 6,872,214 B2 | 3/2005 | Sonnenschein et al. |
| 6,874,669 B2 | 4/2005 | Adams et al. |
| 6,877,647 B2 | 4/2005 | Green et al. |
| 6,878,106 B1 | 4/2005 | Herrmann |
| 6,889,116 B2 | 5/2005 | Jinno |
| 6,893,435 B2 | 5/2005 | Goble |
| 6,899,538 B2 | 5/2005 | Matoba |
| 6,905,057 B2 | 6/2005 | Swayze et al. |
| 6,905,497 B2 | 6/2005 | Truckai et al. |
| 6,905,498 B2 | 6/2005 | Hooven |
| 6,908,472 B2 | 6/2005 | Wiener et al. |
| 6,911,033 B2 | 6/2005 | de Guillebon et al. |
| 6,911,916 B1 | 6/2005 | Wang et al. |
| 6,913,579 B2 | 7/2005 | Truckai et al. |
| 6,913,608 B2 | 7/2005 | Liddicoat et al. |
| 6,913,613 B2 | 7/2005 | Schwarz et al. |
| 6,921,397 B2 | 7/2005 | Corcoran et al. |
| 6,921,412 B1 | 7/2005 | Black et al. |
| 6,923,093 B2 | 8/2005 | Ullah |
| 6,923,803 B2 | 8/2005 | Goble |
| 6,926,716 B2 | 8/2005 | Baker et al. |
| 6,929,641 B2 | 8/2005 | Goble et al. |
| 6,929,644 B2 | 8/2005 | Truckai et al. |
| 6,931,830 B2 | 8/2005 | Liao |
| 6,932,218 B2 | 8/2005 | Kosann et al. |
| 6,932,810 B2 | 8/2005 | Ryan |
| 6,936,042 B2 | 8/2005 | Wallace et al. |
| 6,936,948 B2 | 8/2005 | Bell et al. |
| 6,939,358 B2 | 9/2005 | Palacios et al. |
| 6,942,662 B2 | 9/2005 | Goble et al. |
| 6,945,444 B2 | 9/2005 | Gresham et al. |
| 6,945,981 B2 | 9/2005 | Donofrio et al. |
| 6,953,138 B1 | 10/2005 | Dworak et al. |
| 6,953,139 B2 | 10/2005 | Milliman et al. |
| 6,958,035 B2 | 10/2005 | Friedman et al. |
| 6,959,851 B2 | 11/2005 | Heinrich |
| 6,959,852 B2 | 11/2005 | Shelton, IV et al. |
| 6,960,107 B1 | 11/2005 | Schaub et al. |
| 6,960,163 B2 | 11/2005 | Ewers et al. |
| 6,960,220 B2 | 11/2005 | Marino et al. |
| 6,962,587 B2 | 11/2005 | Johnson et al. |
| 6,963,792 B1 | 11/2005 | Green |
| 6,964,363 B2 | 11/2005 | Wales et al. |
| 6,966,907 B2 | 11/2005 | Goble |
| 6,966,909 B2 | 11/2005 | Marshall et al. |
| 6,971,988 B2 | 12/2005 | Orban, III |
| 6,972,199 B2 | 12/2005 | Lebouitz et al. |
| 6,974,462 B2 | 12/2005 | Sater |
| 6,978,921 B2 | 12/2005 | Shelton, IV et al. |

(56) References Cited

U.S. PATENT DOCUMENTS

| | | |
|---|---|---|
| 6,978,922 B2 | 12/2005 | Bilotti et al. |
| 6,981,628 B2 | 1/2006 | Wales |
| 6,981,941 B2 | 1/2006 | Whitman et al. |
| 6,981,978 B2 | 1/2006 | Gannoe |
| 6,984,203 B2 | 1/2006 | Tartaglia et al. |
| 6,984,231 B2 | 1/2006 | Goble et al. |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,990,796 B2 | 1/2006 | Schnipke et al. |
| 6,993,413 B2 | 1/2006 | Sunaoshi |
| 6,994,708 B2 | 2/2006 | Manzo |
| 6,995,729 B2 | 2/2006 | Govari et al. |
| 6,997,931 B2 | 2/2006 | Sauer et al. |
| 6,998,816 B2 | 2/2006 | Wieck et al. |
| 7,000,818 B2 | 2/2006 | Shelton, IV et al. |
| 7,000,819 B2 | 2/2006 | Swayze et al. |
| 7,001,380 B2 | 2/2006 | Goble |
| 7,001,408 B2 | 2/2006 | Knodel et al. |
| 7,008,435 B2 | 3/2006 | Cummins |
| 7,009,039 B2 | 3/2006 | Yayon et al. |
| 7,011,657 B2 | 3/2006 | Truckai et al. |
| 7,018,357 B2 | 3/2006 | Emmons |
| 7,018,390 B2 | 3/2006 | Turovskiy et al. |
| 7,021,669 B1 | 4/2006 | Lindermeir et al. |
| 7,025,743 B2 | 4/2006 | Mann et al. |
| 7,029,435 B2 | 4/2006 | Nakao |
| 7,029,439 B2 | 4/2006 | Roberts et al. |
| 7,032,798 B2 | 4/2006 | Whitman et al. |
| 7,032,799 B2 | 4/2006 | Viola et al. |
| 7,033,356 B2 | 4/2006 | Latterell et al. |
| 7,036,680 B1 | 5/2006 | Flannery |
| 7,037,344 B2 | 5/2006 | Kagan et al. |
| 7,041,102 B2 | 5/2006 | Truckai et al. |
| 7,041,868 B2 | 5/2006 | Greene et al. |
| 7,043,852 B2 | 5/2006 | Hayashida et al. |
| 7,044,350 B2 | 5/2006 | Kameyama et al. |
| 7,044,352 B2 | 5/2006 | Shelton, IV et al. |
| 7,044,353 B2 | 5/2006 | Mastri et al. |
| 7,048,687 B1 | 5/2006 | Reuss et al. |
| 7,048,745 B2 | 5/2006 | Tierney et al. |
| 7,052,494 B2 | 5/2006 | Goble et al. |
| 7,052,499 B2 | 5/2006 | Steger et al. |
| 7,055,730 B2 | 6/2006 | Ehrenfels et al. |
| 7,055,731 B2 | 6/2006 | Shelton, IV et al. |
| 7,056,284 B2 | 6/2006 | Martone et al. |
| 7,056,330 B2 | 6/2006 | Gayton |
| 7,059,331 B2 | 6/2006 | Adams et al. |
| 7,059,508 B2 | 6/2006 | Shelton, IV et al. |
| 7,063,671 B2 | 6/2006 | Couvillon, Jr. |
| 7,063,712 B2 | 6/2006 | Vargas et al. |
| 7,066,879 B2 | 6/2006 | Fowler et al. |
| 7,066,944 B2 | 6/2006 | Laufer et al. |
| 7,067,038 B2 | 6/2006 | Trokhan et al. |
| 7,070,083 B2 | 7/2006 | Jankowski |
| 7,070,559 B2 | 7/2006 | Adams et al. |
| 7,070,597 B2 | 7/2006 | Truckai et al. |
| 7,071,287 B2 | 7/2006 | Rhine et al. |
| 7,075,770 B1 | 7/2006 | Smith |
| 7,077,856 B2 | 7/2006 | Whitman |
| 7,080,769 B2 | 7/2006 | Vresh et al. |
| 7,081,114 B2 | 7/2006 | Rashidi |
| 7,083,073 B2 | 8/2006 | Yoshie et al. |
| 7,083,075 B2 | 8/2006 | Swayze et al. |
| 7,083,571 B2 | 8/2006 | Wang et al. |
| 7,083,615 B2 | 8/2006 | Peterson et al. |
| 7,083,619 B2 | 8/2006 | Truckai et al. |
| 7,083,620 B2 | 8/2006 | Jahns et al. |
| 7,087,054 B2 | 8/2006 | Truckai et al. |
| 7,087,071 B2 | 8/2006 | Nicholas et al. |
| 7,090,637 B2 | 8/2006 | Danitz et al. |
| 7,090,673 B2 | 8/2006 | Dycus et al. |
| 7,090,683 B2 | 8/2006 | Brock et al. |
| 7,090,684 B2 | 8/2006 | McGuckin, Jr. et al. |
| 7,094,202 B2 | 8/2006 | Nobis et al. |
| 7,094,247 B2 | 8/2006 | Monassevitch et al. |
| 7,097,089 B2 | 8/2006 | Marczyk |
| 7,097,644 B2 | 8/2006 | Long |
| 7,097,650 B2 | 8/2006 | Weller et al. |
| 7,098,794 B2 | 8/2006 | Lindsay et al. |
| 7,100,949 B2 | 9/2006 | Williams et al. |
| 7,101,394 B2 | 9/2006 | Hamm et al. |
| 7,104,741 B2 | 9/2006 | Krohn |
| 7,108,695 B2 | 9/2006 | Witt et al. |
| 7,108,701 B2 | 9/2006 | Evens et al. |
| 7,108,709 B2 | 9/2006 | Cummins |
| 7,111,769 B2 | 9/2006 | Wales et al. |
| 7,112,214 B2 | 9/2006 | Peterson et al. |
| RE39,358 E | 10/2006 | Goble |
| 7,114,642 B2 | 10/2006 | Whitman |
| 7,118,582 B1 | 10/2006 | Wang et al. |
| 7,121,446 B2 | 10/2006 | Arad et al. |
| 7,122,028 B2 | 10/2006 | Looper et al. |
| 7,125,409 B2 | 10/2006 | Truckai et al. |
| 7,126,303 B2 | 10/2006 | Farritor et al. |
| 7,126,879 B2 | 10/2006 | Snyder |
| 7,128,253 B2 | 10/2006 | Mastri et al. |
| 7,128,254 B2 | 10/2006 | Shelton, IV et al. |
| 7,128,748 B2 | 10/2006 | Mooradian et al. |
| 7,131,445 B2 | 11/2006 | Amoah |
| 7,133,601 B2 | 11/2006 | Phillips et al. |
| 7,134,587 B2 | 11/2006 | Schwemberger et al. |
| 7,137,980 B2 | 11/2006 | Buysse et al. |
| 7,137,981 B2 | 11/2006 | Long |
| 7,139,016 B2 | 11/2006 | Squilla et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,147,139 B2 | 12/2006 | Schwemberger et al. |
| 7,147,140 B2 | 12/2006 | Wukusick et al. |
| 7,147,637 B2 | 12/2006 | Goble |
| 7,147,650 B2 | 12/2006 | Lee |
| 7,150,748 B2 | 12/2006 | Ebbutt et al. |
| 7,153,300 B2 | 12/2006 | Goble |
| 7,155,316 B2 | 12/2006 | Sutherland et al. |
| 7,156,863 B2 | 1/2007 | Sonnenschein et al. |
| 7,159,750 B2 | 1/2007 | Racenet et al. |
| 7,160,296 B2 | 1/2007 | Pearson et al. |
| 7,160,299 B2 | 1/2007 | Baily |
| 7,161,036 B2 | 1/2007 | Oikawa et al. |
| 7,166,133 B2 | 1/2007 | Evans et al. |
| 7,168,604 B2 | 1/2007 | Milliman et al. |
| 7,172,104 B2 | 2/2007 | Scirica et al. |
| 7,172,593 B2 | 2/2007 | Trieu et al. |
| 7,179,223 B2 | 2/2007 | Motoki et al. |
| 7,179,267 B2 | 2/2007 | Nolan et al. |
| 7,182,239 B1 | 2/2007 | Myers |
| 7,182,763 B2 | 2/2007 | Nardella |
| 7,183,737 B2 | 2/2007 | Kitagawa |
| 7,188,758 B2 | 3/2007 | Viola et al. |
| 7,189,207 B2 | 3/2007 | Viola |
| 7,195,627 B2 | 3/2007 | Amoah et al. |
| 7,199,537 B2 | 4/2007 | Okamura et al. |
| 7,202,653 B2 | 4/2007 | Pai |
| 7,204,835 B2 | 4/2007 | Latterell et al. |
| 7,207,233 B2 | 4/2007 | Wadge |
| 7,207,471 B2 | 4/2007 | Heinrich et al. |
| 7,207,472 B2 | 4/2007 | Wukusick et al. |
| 7,207,556 B2 | 4/2007 | Saitoh et al. |
| 7,208,005 B2 | 4/2007 | Frecker et al. |
| 7,210,609 B2 | 5/2007 | Leiboff et al. |
| 7,211,081 B2 | 5/2007 | Goble |
| 7,211,084 B2 | 5/2007 | Goble et al. |
| 7,211,092 B2 | 5/2007 | Hughett |
| 7,211,979 B2 | 5/2007 | Khatib et al. |
| 7,213,736 B2 | 5/2007 | Wales et al. |
| 7,214,224 B2 | 5/2007 | Goble |
| 7,215,517 B2 | 5/2007 | Takamatsu |
| 7,217,285 B2 | 5/2007 | Vargas et al. |
| 7,220,260 B2 | 5/2007 | Fleming et al. |

(56) References Cited

U.S. PATENT DOCUMENTS

| | | |
|---|---|---|
| 7,220,272 B2 | 5/2007 | Weadock |
| 7,225,963 B2 | 6/2007 | Scirica |
| 7,225,964 B2 | 6/2007 | Mastri et al. |
| 7,234,624 B2 | 6/2007 | Gresham et al. |
| 7,235,089 B1 | 6/2007 | McGuckin, Jr. |
| 7,235,302 B2 | 6/2007 | Jing et al. |
| 7,237,708 B1 | 7/2007 | Guy et al. |
| 7,238,195 B2 | 7/2007 | Viola |
| 7,238,901 B2 | 7/2007 | Kim et al. |
| 7,241,288 B2 | 7/2007 | Braun |
| 7,246,734 B2 | 7/2007 | Shelton, IV |
| 7,247,161 B2 | 7/2007 | Johnston et al. |
| 7,249,267 B2 | 7/2007 | Chapuis |
| 7,252,660 B2 | 8/2007 | Kunz |
| 7,255,696 B2 | 8/2007 | Goble et al. |
| 7,256,695 B2 | 8/2007 | Hamel et al. |
| 7,258,262 B2 | 8/2007 | Mastri et al. |
| 7,258,546 B2 | 8/2007 | Beier et al. |
| 7,260,431 B2 | 8/2007 | Libbus et al. |
| 7,265,374 B2 | 9/2007 | Lee et al. |
| 7,267,679 B2 | 9/2007 | McGuckin, Jr. et al. |
| 7,273,483 B2 | 9/2007 | Wiener et al. |
| 7,278,562 B2 | 10/2007 | Mastri et al. |
| 7,278,563 B1 | 10/2007 | Green |
| 7,278,949 B2 | 10/2007 | Bader |
| 7,278,994 B2 | 10/2007 | Goble |
| 7,282,048 B2 | 10/2007 | Goble et al. |
| 7,286,850 B2 | 10/2007 | Frielink et al. |
| 7,287,682 B1 | 10/2007 | Ezzat et al. |
| 7,293,685 B2 | 11/2007 | Ehrenfels et al. |
| 7,295,893 B2 | 11/2007 | Sunaoshi |
| 7,295,907 B2 | 11/2007 | Lu et al. |
| 7,296,722 B2 | 11/2007 | Ivanko |
| 7,296,724 B2 | 11/2007 | Green et al. |
| 7,297,149 B2 | 11/2007 | Vitali et al. |
| 7,300,373 B2 | 11/2007 | Jinno et al. |
| 7,300,450 B2 | 11/2007 | Vleugels et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,303,502 B2 | 12/2007 | Thompson |
| 7,303,556 B2 | 12/2007 | Metzger |
| 7,306,597 B2 | 12/2007 | Manzo |
| 7,308,998 B2 | 12/2007 | Mastri et al. |
| 7,322,859 B2 | 1/2008 | Evans |
| 7,322,975 B2 | 1/2008 | Goble et al. |
| 7,322,994 B2 | 1/2008 | Nicholas et al. |
| 7,324,572 B2 | 1/2008 | Chang |
| 7,326,203 B2 | 2/2008 | Papineau et al. |
| 7,326,213 B2 | 2/2008 | Benderev et al. |
| 7,328,828 B2 | 2/2008 | Ortiz et al. |
| 7,328,829 B2 | 2/2008 | Arad et al. |
| 7,330,004 B2 | 2/2008 | DeJonge et al. |
| 7,331,340 B2 | 2/2008 | Barney |
| 7,334,717 B2 | 2/2008 | Rethy et al. |
| 7,334,718 B2 | 2/2008 | McAlister et al. |
| 7,335,199 B2 | 2/2008 | Goble et al. |
| 7,336,048 B2 | 2/2008 | Lohr |
| 7,336,184 B2 | 2/2008 | Smith et al. |
| 7,338,513 B2 | 3/2008 | Lee et al. |
| 7,341,591 B2 | 3/2008 | Grinberg |
| 7,343,920 B2 | 3/2008 | Toby et al. |
| 7,344,532 B2 | 3/2008 | Goble et al. |
| 7,344,533 B2 | 3/2008 | Pearson et al. |
| 7,346,344 B2 | 3/2008 | Fontaine |
| 7,348,763 B1 | 3/2008 | Reinhart et al. |
| RE40,237 E | 4/2008 | Bilotti et al. |
| 7,351,258 B2 | 4/2008 | Ricotta et al. |
| 7,354,447 B2 | 4/2008 | Shelton, IV et al. |
| 7,354,502 B2 | 4/2008 | Polat et al. |
| 7,357,287 B2 | 4/2008 | Shelton, IV et al. |
| 7,357,806 B2 | 4/2008 | Rivera et al. |
| 7,361,195 B2 | 4/2008 | Schwartz et al. |
| 7,364,060 B2 | 4/2008 | Milliman |
| 7,364,061 B2 | 4/2008 | Swayze et al. |
| 7,377,918 B2 | 5/2008 | Amoah |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,384,417 B2 | 6/2008 | Cucin |
| 7,386,365 B2 | 6/2008 | Nixon |
| 7,386,730 B2 | 6/2008 | Uchikubo |
| 7,388,217 B2 | 6/2008 | Buschbeck et al. |
| 7,388,484 B2 | 6/2008 | Hsu |
| 7,391,173 B2 | 6/2008 | Schena |
| 7,396,356 B2 | 7/2008 | Mollenauer |
| 7,397,364 B2 | 7/2008 | Govari |
| 7,398,907 B2 | 7/2008 | Racenet et al. |
| 7,398,908 B2 | 7/2008 | Holsten et al. |
| 7,400,752 B2 | 7/2008 | Zacharias |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,404,822 B2 | 7/2008 | Viart et al. |
| 7,407,074 B2 | 8/2008 | Ortiz et al. |
| 7,407,075 B2 | 8/2008 | Holsten et al. |
| 7,407,076 B2 | 8/2008 | Racenet et al. |
| 7,407,077 B2 | 8/2008 | Ortiz et al. |
| 7,407,078 B2 | 8/2008 | Shelton, IV et al. |
| 7,410,086 B2 | 8/2008 | Ortiz et al. |
| 7,413,563 B2 | 8/2008 | Corcoran et al. |
| 7,416,101 B2 | 8/2008 | Shelton, IV et al. |
| 7,418,078 B2 | 8/2008 | Blanz et al. |
| RE40,514 E | 9/2008 | Mastri et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,136 B1 | 9/2008 | Marczyk |
| 7,422,138 B2 | 9/2008 | Bilotti et al. |
| 7,422,139 B2 | 9/2008 | Shelton, IV et al. |
| 7,424,965 B2 | 9/2008 | Racenet et al. |
| 7,427,607 B2 | 9/2008 | Suzuki |
| 7,431,188 B1 | 10/2008 | Marczyk |
| 7,431,189 B2 | 10/2008 | Shelton, IV et al. |
| 7,431,694 B2 | 10/2008 | Stefanchik et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,209 B1 | 10/2008 | Hess et al. |
| 7,438,718 B2 | 10/2008 | Milliman et al. |
| 7,439,354 B2 | 10/2008 | Lenges et al. |
| 7,441,684 B2 | 10/2008 | Shelton, IV et al. |
| 7,441,685 B1 | 10/2008 | Boudreaux |
| 7,442,201 B2 | 10/2008 | Pugsley et al. |
| 7,443,547 B2 | 10/2008 | Moreno et al. |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,455,682 B2 | 11/2008 | Viola |
| 7,461,767 B2 | 12/2008 | Viola et al. |
| 7,462,187 B2 | 12/2008 | Johnston et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,467,849 B2 | 12/2008 | Silverbrook et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,253 B2 | 1/2009 | Dycus et al. |
| 7,473,263 B2 | 1/2009 | Johnston et al. |
| 7,476,237 B2 | 1/2009 | Taniguchi et al. |
| 7,479,608 B2 | 1/2009 | Smith |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,485,133 B2 | 2/2009 | Cannon et al. |
| 7,485,142 B2 | 2/2009 | Milo |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,494,499 B2 | 2/2009 | Nagase et al. |

(56) References Cited

U.S. PATENT DOCUMENTS

| | | | |
|---|---|---|---|
| 7,494,501 B2 | 2/2009 | Ahlberg et al. |
| 7,500,979 B2 | 3/2009 | Hueil et al. |
| 7,501,198 B2 | 3/2009 | Barlev et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,507,202 B2 | 3/2009 | Schoellhorn |
| 7,510,107 B2 | 3/2009 | Timm et al. |
| 7,510,566 B2 | 3/2009 | Jacobs et al. |
| 7,513,408 B2 | 4/2009 | Shelton, IV et al. |
| 7,517,356 B2 | 4/2009 | Heinrich |
| 7,524,320 B2 | 4/2009 | Tierney et al. |
| 7,530,984 B2 | 5/2009 | Sonnenschein et al. |
| 7,530,985 B2 | 5/2009 | Takemoto et al. |
| 7,533,906 B2 | 5/2009 | Luettgen et al. |
| 7,534,259 B2 | 5/2009 | Lashinski et al. |
| 7,540,867 B2 | 6/2009 | Jinno et al. |
| 7,542,807 B2 | 6/2009 | Bertolero et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,549,563 B2 | 6/2009 | Mather et al. |
| 7,549,564 B2 | 6/2009 | Boudreaux |
| 7,549,998 B2 | 6/2009 | Braun |
| 7,552,854 B2 | 6/2009 | Wixey et al. |
| 7,556,185 B2 | 7/2009 | Viola |
| 7,556,186 B2 | 7/2009 | Milliman |
| 7,556,647 B2 | 7/2009 | Drews et al. |
| 7,559,449 B2 | 7/2009 | Viola |
| 7,559,450 B2 | 7/2009 | Wales et al. |
| 7,559,452 B2 | 7/2009 | Wales et al. |
| 7,559,937 B2 | 7/2009 | de la Torre et al. |
| 7,562,910 B2 | 7/2009 | Kertesz et al. |
| 7,563,862 B2 | 7/2009 | Sieg et al. |
| 7,565,993 B2 | 7/2009 | Milliman et al. |
| 7,566,300 B2 | 7/2009 | Devierre et al. |
| 7,567,045 B2 | 7/2009 | Fristedt |
| 7,568,603 B2 | 8/2009 | Shelton, IV et al. |
| 7,568,604 B2 | 8/2009 | Ehrenfels et al. |
| 7,568,619 B2 | 8/2009 | Todd et al. |
| 7,575,144 B2 | 8/2009 | Ortiz et al. |
| 7,583,063 B2 | 9/2009 | Dooley |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,591,783 B2 | 9/2009 | Boulais et al. |
| 7,591,818 B2 | 9/2009 | Bertolero et al. |
| 7,597,229 B2 | 10/2009 | Boudreaux et al. |
| 7,597,230 B2 | 10/2009 | Racenet et al. |
| 7,597,693 B2 | 10/2009 | Garrison |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,611,474 B2 | 11/2009 | Hibner et al. |
| 7,615,003 B2 | 11/2009 | Stefanchik et al. |
| 7,615,067 B2 | 11/2009 | Lee et al. |
| 7,617,961 B2 | 11/2009 | Viola |
| 7,624,902 B2 | 12/2009 | Marczyk et al. |
| 7,624,903 B2 | 12/2009 | Green et al. |
| 7,625,370 B2 | 12/2009 | Hart et al. |
| 7,631,793 B2 | 12/2009 | Rethy et al. |
| 7,631,794 B2 | 12/2009 | Rethy et al. |
| 7,635,074 B2 | 12/2009 | Olson et al. |
| 7,637,409 B2 | 12/2009 | Marczyk |
| 7,637,410 B2 | 12/2009 | Marczyk |
| 7,638,958 B2 | 12/2009 | Philipp et al. |
| 7,641,091 B2 | 1/2010 | Olson et al. |
| 7,641,092 B2 | 1/2010 | Kruszynski et al. |
| 7,641,093 B2 | 1/2010 | Doll et al. |
| 7,641,095 B2 | 1/2010 | Viola |
| 7,644,783 B2 | 1/2010 | Roberts et al. |
| 7,644,848 B2 | 1/2010 | Swayze et al. |
| 7,645,230 B2 | 1/2010 | Mikkaichi et al. |
| 7,648,519 B2 | 1/2010 | Lee et al. |
| 7,650,185 B2 | 1/2010 | Maile et al. |
| 7,651,017 B2 | 1/2010 | Ortiz et al. |
| 7,651,498 B2 | 1/2010 | Shifrin et al. |
| 7,654,431 B2 | 2/2010 | Hueil et al. |
| 7,655,288 B2 | 2/2010 | Bauman et al. |
| 7,656,131 B2 | 2/2010 | Embrey et al. |
| 7,658,311 B2 | 2/2010 | Boudreaux |
| 7,658,312 B2 | 2/2010 | Vidal et al. |
| 7,659,219 B2 * | 2/2010 | Biran ............... A61L 31/146 424/422 |
| 7,662,161 B2 | 2/2010 | Briganti et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,674,253 B2 | 3/2010 | Fisher et al. |
| 7,674,255 B2 | 3/2010 | Braun |
| 7,674,263 B2 | 3/2010 | Ryan |
| 7,674,270 B2 | 3/2010 | Layer |
| 7,682,307 B2 | 3/2010 | Danitz et al. |
| 7,682,367 B2 | 3/2010 | Shah et al. |
| 7,686,201 B2 | 3/2010 | Csiky |
| 7,686,804 B2 | 3/2010 | Johnson et al. |
| 7,686,826 B2 | 3/2010 | Lee et al. |
| 7,688,028 B2 | 3/2010 | Phillips et al. |
| 7,691,098 B2 | 4/2010 | Wallace et al. |
| 7,691,103 B2 | 4/2010 | Fernandez et al. |
| 7,691,106 B2 | 4/2010 | Schenberger et al. |
| 7,694,865 B2 | 4/2010 | Scirica |
| 7,695,485 B2 | 4/2010 | Whitman et al. |
| 7,699,204 B2 | 4/2010 | Viola |
| 7,699,835 B2 | 4/2010 | Lee et al. |
| 7,699,844 B2 | 4/2010 | Utley et al. |
| 7,699,846 B2 | 4/2010 | Ryan |
| 7,699,856 B2 | 4/2010 | Van Wyk et al. |
| 7,699,859 B2 | 4/2010 | Bombard et al. |
| 7,699,860 B2 | 4/2010 | Huitema et al. |
| 7,703,653 B2 | 4/2010 | Shah et al. |
| 7,708,180 B2 | 5/2010 | Murray et al. |
| 7,708,181 B2 | 5/2010 | Cole et al. |
| 7,708,758 B2 | 5/2010 | Lee et al. |
| 7,712,182 B2 | 5/2010 | Zeiler et al. |
| 7,714,239 B2 | 5/2010 | Smith |
| 7,717,312 B2 | 5/2010 | Beetel |
| 7,717,313 B2 | 5/2010 | Criscuolo et al. |
| 7,717,846 B2 | 5/2010 | Zirps et al. |
| 7,718,180 B2 | 5/2010 | Karp |
| 7,718,556 B2 | 5/2010 | Matsuda et al. |
| 7,721,930 B2 | 5/2010 | McKenna et al. |
| 7,721,931 B2 | 5/2010 | Shelton, IV et al. |
| 7,721,933 B2 | 5/2010 | Ehrenfels et al. |
| 7,721,934 B2 | 5/2010 | Shelton, IV et al. |
| 7,721,936 B2 | 5/2010 | Shalton, IV et al. |
| 7,722,527 B2 | 5/2010 | Bouchier et al. |
| 7,722,607 B2 | 5/2010 | Dumbauld et al. |
| 7,722,610 B2 | 5/2010 | Viola et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,727,954 B2 | 6/2010 | McKay |
| 7,729,742 B2 | 6/2010 | Govari |
| 7,731,072 B2 | 6/2010 | Timm et al. |
| 7,731,073 B2 | 6/2010 | Wixey et al. |
| 7,731,724 B2 | 6/2010 | Huitema et al. |
| 7,735,703 B2 | 6/2010 | Morgan et al. |
| 7,736,374 B2 | 6/2010 | Vaughan et al. |
| 7,738,971 B2 | 6/2010 | Swayze et al. |
| 7,740,159 B2 | 6/2010 | Shelton, IV et al. |
| 7,742,036 B2 | 6/2010 | Grant et al. |
| 7,743,960 B2 | 6/2010 | Whitman et al. |
| 7,744,624 B2 | 6/2010 | Bettuchi |
| 7,744,627 B2 | 6/2010 | Orban, III et al. |

(56) References Cited

U.S. PATENT DOCUMENTS

| | | |
|---|---|---|
| 7,744,628 B2 | 6/2010 | Viola |
| 7,748,587 B2 | 7/2010 | Haramiishi et al. |
| 7,749,204 B2 | 7/2010 | Dhanaraj et al. |
| 7,751,870 B2 | 7/2010 | Whitman |
| 7,753,245 B2 | 7/2010 | Boudreaux et al. |
| 7,753,246 B2 | 7/2010 | Scirica |
| 7,753,904 B2 | 7/2010 | Shelton, IV et al. |
| 7,758,612 B2 | 7/2010 | Shipp |
| 7,766,207 B2 | 8/2010 | Mather et al. |
| 7,766,209 B2 | 8/2010 | Baxter, III et al. |
| 7,766,210 B2 | 8/2010 | Shelton, IV et al. |
| 7,766,821 B2 | 8/2010 | Brunnen et al. |
| 7,766,894 B2 | 8/2010 | Weitzner et al. |
| 7,770,773 B2 | 8/2010 | Whitman et al. |
| 7,770,774 B2 | 8/2010 | Mastri et al. |
| 7,770,775 B2 | 8/2010 | Shelton, IV et al. |
| 7,770,776 B2 | 8/2010 | Chen et al. |
| 7,771,396 B2 | 8/2010 | Stefanchik et al. |
| 7,772,720 B2 | 8/2010 | McGee et al. |
| 7,776,037 B2 | 8/2010 | Odom |
| 7,776,060 B2 | 8/2010 | Mooradian et al. |
| 7,778,004 B2 | 8/2010 | Nerheim et al. |
| 7,780,054 B2 | 8/2010 | Wales |
| 7,780,055 B2 | 8/2010 | Scirica et al. |
| 7,780,663 B2 | 8/2010 | Yates et al. |
| 7,780,685 B2 | 8/2010 | Hunt et al. |
| 7,784,662 B2 | 8/2010 | Wales et al. |
| 7,784,663 B2 | 8/2010 | Shelton, IV |
| 7,787,256 B2 | 8/2010 | Chan et al. |
| 7,789,875 B2 | 9/2010 | Brock et al. |
| 7,789,883 B2 | 9/2010 | Takashino et al. |
| 7,789,889 B2 | 9/2010 | Zubik et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,799,044 B2 | 9/2010 | Johnston et al. |
| 7,799,965 B2 | 9/2010 | Patel et al. |
| 7,803,151 B2 | 9/2010 | Whitman |
| 7,806,891 B2 | 10/2010 | Nowlin et al. |
| 7,810,690 B2 | 10/2010 | Bilotti et al. |
| 7,810,691 B2 | 10/2010 | Boyden et al. |
| 7,810,692 B2 | 10/2010 | Hall et al. |
| 7,810,693 B2 | 10/2010 | Broehl et al. |
| 7,815,092 B2 | 10/2010 | Whitman et al. |
| 7,815,565 B2 | 10/2010 | Stefanchik et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,884 B2 | 10/2010 | Lee et al. |
| 7,819,886 B2 | 10/2010 | Whitfield et al. |
| 7,823,592 B2 | 11/2010 | Bettuchi et al. |
| 7,823,760 B2 | 11/2010 | Zemlok et al. |
| 7,824,401 B2 | 11/2010 | Manzo et al. |
| 7,824,426 B2 | 11/2010 | Racenet et al. |
| 7,828,189 B2 | 11/2010 | Holsten et al. |
| 7,828,794 B2 | 11/2010 | Sartor |
| 7,828,808 B2 | 11/2010 | Hinman et al. |
| 7,831,292 B2 | 11/2010 | Quaid et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,833,234 B2 | 11/2010 | Bailly et al. |
| 7,836,400 B2 | 11/2010 | May et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,837,694 B2 | 11/2010 | Tethrake et al. |
| 7,838,789 B2 | 11/2010 | Stoffers et al. |
| 7,841,503 B2 | 11/2010 | Sonnenschein et al. |
| 7,842,025 B2 | 11/2010 | Coleman et al. |
| 7,842,028 B2 | 11/2010 | Lee |
| 7,845,533 B2 | 12/2010 | Marczyk et al. |
| 7,845,534 B2 | 12/2010 | Viola et al. |
| 7,845,535 B2 | 12/2010 | Scircia |
| 7,845,536 B2 | 12/2010 | Viola et al. |
| 7,845,537 B2 | 12/2010 | Shelton, IV et al. |
| 7,846,149 B2 | 12/2010 | Jankowski |
| 7,850,642 B2 | 12/2010 | Moll et al. |
| 7,850,982 B2 | 12/2010 | Stopek et al. |
| 7,854,736 B2 | 12/2010 | Ryan |
| 7,857,183 B2 | 12/2010 | Shelton, IV |
| 7,857,185 B2 | 12/2010 | Swayze et al. |
| 7,857,186 B2 | 12/2010 | Baxter, III et al. |
| 7,857,813 B2 | 12/2010 | Schmitz et al. |
| 7,861,906 B2 | 1/2011 | Doll et al. |
| 7,862,579 B2 | 1/2011 | Ortiz et al. |
| 7,866,525 B2 | 1/2011 | Scirica |
| 7,866,527 B2 | 1/2011 | Hall et al. |
| 7,866,528 B2 | 1/2011 | Olson et al. |
| 7,870,989 B2 | 1/2011 | Viola et al. |
| 7,871,418 B2 | 1/2011 | Thompson et al. |
| 7,879,070 B2 | 2/2011 | Ortiz et al. |
| 7,883,465 B2 | 2/2011 | Donofrio et al. |
| 7,886,951 B2 | 2/2011 | Hessler |
| 7,886,952 B2 | 2/2011 | Scirica et al. |
| 7,887,530 B2 | 2/2011 | Zemlok et al. |
| 7,887,535 B2 | 2/2011 | Lands et al. |
| 7,891,531 B1 | 2/2011 | Ward |
| 7,891,532 B2 | 2/2011 | Mastri et al. |
| 7,892,245 B2 | 2/2011 | Liddicoat et al. |
| 7,893,586 B2 | 2/2011 | West et al. |
| 7,896,214 B2 | 3/2011 | Farascioni |
| 7,896,215 B2 | 3/2011 | Adams et al. |
| 7,896,877 B2 | 3/2011 | Hall et al. |
| 7,896,895 B2 | 3/2011 | Boudreaux et al. |
| 7,900,805 B2 | 3/2011 | Shelton, IV et al. |
| 7,905,380 B2 | 3/2011 | Shelton, IV et al. |
| 7,905,381 B2 | 3/2011 | Baxter, III et al. |
| 7,905,889 B2 | 3/2011 | Catanese, III et al. |
| 7,905,902 B2 | 3/2011 | Huitema et al. |
| 7,909,191 B2 | 3/2011 | Baker et al. |
| 7,909,220 B2 | 3/2011 | Viola |
| 7,909,221 B2 | 3/2011 | Viola et al. |
| 7,913,891 B2 | 3/2011 | Doll et al. |
| 7,913,893 B2 | 3/2011 | Mastri et al. |
| 7,914,543 B2 | 3/2011 | Roth et al. |
| 7,914,551 B2 | 3/2011 | Ortiz et al. |
| 7,918,230 B2 | 4/2011 | Whitman et al. |
| 7,918,376 B1 | 4/2011 | Knodel et al. |
| 7,918,377 B2 | 4/2011 | Measamer et al. |
| 7,918,848 B2 | 4/2011 | Lau et al. |
| 7,918,867 B2 | 4/2011 | Dana et al. |
| 7,922,061 B2 | 4/2011 | Shelton, IV et al. |
| 7,922,063 B2 | 4/2011 | Zemlok et al. |
| 7,922,743 B2 | 4/2011 | Heinrich et al. |
| 7,923,144 B2 | 4/2011 | Kohn et al. |
| 7,926,691 B2 | 4/2011 | Viola et al. |
| 7,927,328 B2 | 4/2011 | Orszulak et al. |
| 7,928,281 B2 | 4/2011 | Augustine |
| 7,930,065 B2 | 4/2011 | Larkin et al. |
| 7,931,660 B2 | 4/2011 | Aranyi et al. |
| 7,931,695 B2 | 4/2011 | Ringeisen |
| 7,934,630 B2 | 5/2011 | Shelton, Iv et al. |
| 7,934,631 B2 | 5/2011 | Balbierz et al. |
| 7,935,773 B2 | 5/2011 | Hadba et al. |
| 7,938,307 B2 | 5/2011 | Bettuchi |
| 7,941,865 B2 | 5/2011 | Seman, Jr. et al. |
| 7,942,303 B2 | 5/2011 | Shah |
| 7,942,890 B2 | 5/2011 | D'Agostino et al. |
| 7,944,175 B2 | 5/2011 | Mori et al. |
| 7,945,792 B2 | 5/2011 | Cherpantier |
| 7,950,560 B2 | 5/2011 | Zemlok et al. |
| 7,950,561 B2 | 5/2011 | Aranyi |
| 7,951,071 B2 | 5/2011 | Whitman et al. |
| 7,951,166 B2 | 5/2011 | Orban, Iii et al. |
| 7,954,682 B2 | 6/2011 | Giordano et al. |
| 7,954,684 B2 | 6/2011 | Boudreaux |
| 7,954,686 B2 | 6/2011 | Baxter, Iii et al. |
| 7,954,687 B2 | 6/2011 | Zemlok et al. |
| 7,955,257 B2 | 6/2011 | Frasier et al. |
| 7,955,322 B2 | 6/2011 | Devengenzo et al. |
| 7,955,380 B2 | 6/2011 | Chu et al. |

(56) References Cited

U.S. PATENT DOCUMENTS

| | | |
|---|---|---|
| 7,959,050 B2 | 6/2011 | Smith et al. |
| 7,959,051 B2 | 6/2011 | Smith et al. |
| 7,959,052 B2 | 6/2011 | Sonnenschein et al. |
| 7,963,432 B2 | 6/2011 | Knodel et al. |
| 7,963,433 B2 | 6/2011 | Whitman et al. |
| 7,963,963 B2 | 6/2011 | Francischelli et al. |
| 7,963,964 B2 | 6/2011 | Santilli et al. |
| 7,966,799 B2 | 6/2011 | Morgan et al. |
| 7,967,178 B2 | 6/2011 | Scirica et al. |
| 7,967,179 B2 | 6/2011 | Olson et al. |
| 7,967,180 B2 | 6/2011 | Scirica |
| 7,967,181 B2 | 6/2011 | Viola et al. |
| 7,967,839 B2 | 6/2011 | Flock et al. |
| 7,972,298 B2 | 7/2011 | Wallace et al. |
| 7,980,443 B2 | 7/2011 | Scheib et al. |
| 7,987,405 B2 | 7/2011 | Turner et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,757 B2 | 8/2011 | Wheeler et al. |
| 7,993,360 B2 | 8/2011 | Hacker et al. |
| 7,994,670 B2 | 8/2011 | Ji |
| 7,997,468 B2 | 8/2011 | Farascioni |
| 7,997,469 B2 | 8/2011 | Olson et al. |
| 8,002,696 B2 | 8/2011 | Suzuki |
| 8,002,784 B2 | 8/2011 | Jinno et al. |
| 8,002,785 B2 | 8/2011 | Weiss et al. |
| 8,002,795 B2 | 8/2011 | Beetel |
| 8,006,365 B2 | 8/2011 | Levin et al. |
| 8,006,885 B2 | 8/2011 | Marczyk |
| 8,006,889 B2 | 8/2011 | Adams et al. |
| 8,007,511 B2 | 8/2011 | Brock et al. |
| 8,011,550 B2 | 9/2011 | Aranyi et al. |
| 8,011,551 B2 | 9/2011 | Marczyk et al. |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,016,176 B2 | 9/2011 | Kasvikis et al. |
| 8,016,177 B2 | 9/2011 | Bettuchi et al. |
| 8,016,178 B2 | 9/2011 | Olson et al. |
| 8,016,855 B2 | 9/2011 | Whitman et al. |
| 8,016,858 B2 | 9/2011 | Whitman |
| 8,016,881 B2 | 9/2011 | Furst |
| 8,020,742 B2 | 9/2011 | Marczyk |
| 8,020,743 B2 | 9/2011 | Shelton, Iv |
| 8,021,375 B2 | 9/2011 | Aldrich et al. |
| 8,025,199 B2 | 9/2011 | Whitman et al. |
| 8,028,883 B2 | 10/2011 | Stopek |
| 8,028,884 B2 | 10/2011 | Sniffin et al. |
| 8,028,885 B2 | 10/2011 | Smith et al. |
| 8,034,077 B2 | 10/2011 | Smith et al. |
| 8,034,363 B2 | 10/2011 | Li et al. |
| 8,037,591 B2 | 10/2011 | Spivey et al. |
| 8,038,045 B2 | 10/2011 | Bettuchi et al. |
| 8,038,046 B2 | 10/2011 | Smith et al. |
| 8,038,686 B2 | 10/2011 | Huitema et al. |
| 8,043,207 B2 | 10/2011 | Adams |
| 8,043,328 B2 | 10/2011 | Hahnen et al. |
| 8,044,536 B2 | 10/2011 | Nguyen et al. |
| 8,047,236 B2 | 11/2011 | Perry |
| 8,048,503 B2 | 11/2011 | Farnsworth et al. |
| 8,056,787 B2 | 11/2011 | Boudreaux et al. |
| 8,056,788 B2 | 11/2011 | Mastri et al. |
| 8,057,508 B2 | 11/2011 | Shelton, Iv |
| 8,058,771 B2 | 11/2011 | Giordano et al. |
| 8,060,250 B2 | 11/2011 | Reiland et al. |
| 8,061,576 B2 | 11/2011 | Cappola |
| 8,062,330 B2 | 11/2011 | Prommersberger et al. |
| 8,063,619 B2 | 11/2011 | Zhu et al. |
| 8,066,167 B2 | 11/2011 | Measamer et al. |
| 8,066,168 B2 | 11/2011 | Vidal et al. |
| D650,074 S | 12/2011 | Hunt et al. |
| 8,070,033 B2 | 12/2011 | Milliman et al. |
| 8,070,035 B2 | 12/2011 | Holsten et al. |
| 8,070,743 B2 | 12/2011 | Kagan et al. |
| 8,075,571 B2 | 12/2011 | Vitali et al. |
| 8,079,950 B2 | 12/2011 | Stern et al. |
| 8,080,004 B2 | 12/2011 | Downey et al. |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,084,001 B2 | 12/2011 | Burns et al. |
| 8,085,013 B2 | 12/2011 | Wei et al. |
| 8,087,563 B2 | 1/2012 | Milliman et al. |
| 8,089,509 B2 | 1/2012 | Chatenever et al. |
| 8,091,756 B2 | 1/2012 | Viola |
| 8,092,443 B2 | 1/2012 | Bischoff |
| 8,092,932 B2 | 1/2012 | Phillips et al. |
| 8,096,458 B2 | 1/2012 | Hessler |
| 8,097,017 B2 | 1/2012 | Viola |
| 8,100,310 B2 | 1/2012 | Zemlok |
| 8,100,872 B2 | 1/2012 | Patel |
| 8,102,278 B2 | 1/2012 | Deck et al. |
| 8,105,350 B2 | 1/2012 | Lee et al. |
| 8,107,925 B2 | 1/2012 | Natsuno et al. |
| 8,108,072 B2 | 1/2012 | Zhao et al. |
| 8,109,426 B2 | 2/2012 | Milliman et al. |
| 8,110,208 B1 | 2/2012 | Hen |
| 8,113,405 B2 | 2/2012 | Milliman |
| 8,113,410 B2 | 2/2012 | Hall et al. |
| 8,114,100 B2 | 2/2012 | Smith et al. |
| 8,122,128 B2 | 2/2012 | Burke, Ii et al. |
| 8,123,103 B2 | 2/2012 | Milliman |
| 8,123,766 B2 | 2/2012 | Bauman et al. |
| 8,123,767 B2 | 2/2012 | Bauman et al. |
| 8,125,168 B2 | 2/2012 | Johnson et al. |
| 8,127,975 B2 | 3/2012 | Olson et al. |
| 8,127,976 B2 | 3/2012 | Scirica et al. |
| 8,128,624 B2 | 3/2012 | Couture et al. |
| 8,128,643 B2 | 3/2012 | Aranyi et al. |
| 8,128,645 B2 | 3/2012 | Sonnenschein et al. |
| 8,132,703 B2 | 3/2012 | Milliman et al. |
| 8,132,706 B2 | 3/2012 | Marczyk et al. |
| 8,134,306 B2 | 3/2012 | Drader et al. |
| 8,136,712 B2 | 3/2012 | Zingman |
| 8,136,713 B2 | 3/2012 | Hathaway et al. |
| 8,137,339 B2 | 3/2012 | Jinno et al. |
| 8,140,417 B2 | 3/2012 | Shibata |
| 8,141,762 B2 | 3/2012 | Bedi et al. |
| 8,141,763 B2 | 3/2012 | Milliman |
| 8,142,425 B2 | 3/2012 | Eggers |
| 8,146,790 B2 | 4/2012 | Milliman |
| 8,147,485 B2 | 4/2012 | Wham et al. |
| 8,152,041 B2 | 4/2012 | Kostrzewski |
| 8,154,239 B2 | 4/2012 | Katsuki et al. |
| 8,157,145 B2 | 4/2012 | Shelton, Iv et al. |
| 8,157,148 B2 | 4/2012 | Scirica |
| 8,157,151 B2 | 4/2012 | Ingmanson et al. |
| 8,157,152 B2 | 4/2012 | Holsten et al. |
| 8,157,153 B2 | 4/2012 | Shelton, Iv et al. |
| 8,157,793 B2 | 4/2012 | Omori et al. |
| 8,161,977 B2 | 4/2012 | Shelton, Iv et al. |
| 8,162,138 B2 | 4/2012 | Bettenhausen et al. |
| 8,162,197 B2 | 4/2012 | Mastri et al. |
| 8,167,185 B2 | 5/2012 | Shelton, Iv et al. |
| 8,167,895 B2 | 5/2012 | D'Agostino et al. |
| 8,167,898 B1 | 5/2012 | Schaller et al. |
| 8,170,241 B2 | 5/2012 | Roe et al. |
| 8,172,120 B2 | 5/2012 | Boyden et al. |
| 8,172,122 B2 | 5/2012 | Kasvikis et al. |
| 8,172,124 B2 | 5/2012 | Shelton, Iv et al. |
| 8,177,797 B2 | 5/2012 | Shimoji et al. |
| 8,179,705 B2 | 5/2012 | Chapuis |
| 8,180,458 B2 | 5/2012 | Kane et al. |
| 8,181,840 B2 | 5/2012 | Milliman |
| 8,186,555 B2 | 5/2012 | Shelton, Iv et al. |
| 8,186,560 B2 | 5/2012 | Hess et al. |
| 8,191,752 B2 | 6/2012 | Scirica |
| 8,192,460 B2 | 6/2012 | Orban, Iii et al. |
| 8,196,795 B2 | 6/2012 | Moore et al. |
| 8,196,796 B2 | 6/2012 | Shelton, Iv et al. |
| 8,201,720 B2 | 6/2012 | Hessler |
| 8,201,721 B2 | 6/2012 | Zemlok et al. |
| 8,205,779 B2 | 6/2012 | Ma et al. |

(56) References Cited

U.S. PATENT DOCUMENTS

| | | |
|---|---|---|
| 8,205,780 B2 | 6/2012 | Sorrentino et al. |
| 8,205,781 B2 | 6/2012 | Baxter, Iii et al. |
| 8,210,411 B2 | 7/2012 | Yates et al. |
| 8,210,414 B2 | 7/2012 | Bettuchi et al. |
| 8,210,415 B2 | 7/2012 | Ward |
| 8,210,416 B2 | 7/2012 | Milliman et al. |
| 8,211,125 B2 | 7/2012 | Spivey |
| 8,214,019 B2 | 7/2012 | Govari et al. |
| 8,215,531 B2 | 7/2012 | Shelton, Iv et al. |
| 8,215,533 B2 | 7/2012 | Viola et al. |
| 8,220,468 B2 | 7/2012 | Cooper et al. |
| 8,220,688 B2 | 7/2012 | Laurent et al. |
| 8,220,690 B2 | 7/2012 | Hess et al. |
| 8,221,424 B2 | 7/2012 | Cha |
| 8,225,799 B2 | 7/2012 | Bettuchi |
| 8,226,715 B2 | 7/2012 | Hwang et al. |
| 8,227,946 B2 | 7/2012 | Kim |
| 8,228,048 B2 | 7/2012 | Spencer |
| 8,231,040 B2 | 7/2012 | Zemlok et al. |
| 8,231,041 B2 | 7/2012 | Marczyk et al. |
| 8,231,042 B2 | 7/2012 | Hessler et al. |
| 8,231,043 B2 | 7/2012 | Tarinelli et al. |
| 8,236,010 B2 | 8/2012 | Ortiz et al. |
| 8,241,271 B2 | 8/2012 | Millman et al. |
| 8,241,308 B2 | 8/2012 | Kortenbach et al. |
| 8,241,322 B2 | 8/2012 | Whitman et al. |
| 8,245,594 B2 | 8/2012 | Rogers et al. |
| 8,245,898 B2 | 8/2012 | Smith et al. |
| 8,245,899 B2 | 8/2012 | Swensgard et al. |
| 8,245,900 B2 | 8/2012 | Scirica |
| 8,245,901 B2 | 8/2012 | Stopek |
| 8,246,637 B2 | 8/2012 | Viola et al. |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,257,251 B2 | 9/2012 | Shelton, IV et al. |
| 8,257,356 B2 | 9/2012 | Bleich et al. |
| 8,257,391 B2 | 9/2012 | Orban, Iii et al. |
| 8,262,655 B2 | 9/2012 | Ghabrial et al. |
| 8,267,300 B2 | 9/2012 | Boudreaux |
| 8,267,924 B2 | 9/2012 | Zemlok et al. |
| 8,267,946 B2 | 9/2012 | Whitfield et al. |
| 8,267,951 B2 | 9/2012 | Whayne et al. |
| 8,269,121 B2 | 9/2012 | Smith |
| 8,272,553 B2 | 9/2012 | Mastri et al. |
| 8,272,554 B2 | 9/2012 | Whitman et al. |
| 8,273,404 B2 | 9/2012 | Dave et al. |
| 8,276,801 B2 | 10/2012 | Zemlok et al. |
| 8,276,802 B2 | 10/2012 | Kostrzewski |
| 8,277,473 B2 | 10/2012 | Sunaoshi et al. |
| 8,281,973 B2 | 10/2012 | Wenchell et al. |
| 8,281,974 B2 | 10/2012 | Hessler et al. |
| 8,282,654 B2 | 10/2012 | Ferrari et al. |
| 8,286,845 B2 | 10/2012 | Perry et al. |
| 8,287,561 B2 | 10/2012 | Nunez et al. |
| 8,292,147 B2 | 10/2012 | Viola |
| 8,292,150 B2 | 10/2012 | Bryant |
| 8,292,151 B2 | 10/2012 | Viola |
| 8,292,152 B2 | 10/2012 | Milliman et al. |
| 8,292,155 B2 | 10/2012 | Shelton, Iv et al. |
| 8,292,157 B2 | 10/2012 | Smith et al. |
| 8,292,888 B2 | 10/2012 | Whitman |
| 8,298,161 B2 | 10/2012 | Vargas |
| 8,298,677 B2 | 10/2012 | Wiesner et al. |
| 8,302,323 B2 | 11/2012 | Fortier et al. |
| 8,308,040 B2 | 11/2012 | Huang et al. |
| 8,308,042 B2 | 11/2012 | Aranyi |
| 8,308,046 B2 | 11/2012 | Prommersberger |
| 8,308,659 B2 | 11/2012 | Scheibe et al. |
| 8,313,496 B2 | 11/2012 | Sauer et al. |
| 8,313,509 B2 | 11/2012 | Kostrzewski |
| 8,317,070 B2 | 11/2012 | Hueil et al. |
| 8,317,071 B1 | 11/2012 | Knodel |
| 8,317,074 B2 | 11/2012 | Ortiz et al. |
| 8,317,790 B2 | 11/2012 | Bell et al. |
| 8,319,002 B2 | 11/2012 | Daniels et al. |
| 8,322,455 B2 | 12/2012 | Shelton, IV et al. |
| 8,322,589 B2 | 12/2012 | Boudreaux |
| 8,322,590 B2 | 12/2012 | Patel et al. |
| 8,323,789 B2 | 12/2012 | Rozhin et al. |
| 8,328,061 B2 | 12/2012 | Kasvikis |
| 8,328,062 B2 | 12/2012 | Viola |
| 8,328,063 B2 | 12/2012 | Milliman et al. |
| 8,328,064 B2 | 12/2012 | Racenet et al. |
| 8,328,802 B2 | 12/2012 | Deville et al. |
| 8,328,823 B2 | 12/2012 | Aranyi et al. |
| 8,333,313 B2 | 12/2012 | Boudreaux et al. |
| 8,333,764 B2 | 12/2012 | Francischelli et al. |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,348,123 B2 | 1/2013 | Scirica et al. |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,348,972 B2 | 1/2013 | Soltz et al. |
| 8,353,437 B2 | 1/2013 | Boudreaux |
| 8,353,438 B2 | 1/2013 | Baxter, III et al. |
| 8,353,439 B2 | 1/2013 | Baxter, III et al. |
| 8,356,740 B1 | 1/2013 | Knodel |
| 8,357,144 B2 | 1/2013 | Whitman et al. |
| 8,360,296 B2 | 1/2013 | Zingman |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,361,501 B2 | 1/2013 | Ditizio et al. |
| 8,365,973 B1 | 2/2013 | White et al. |
| 8,365,975 B1 | 2/2013 | Manoux et al. |
| 8,365,976 B2 | 2/2013 | Hess et al. |
| 8,366,559 B2 | 2/2013 | Papenfuss et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,372,094 B2 | 2/2013 | Bettuchi et al. |
| 8,376,865 B2 | 2/2013 | Forster et al. |
| 8,377,044 B2 | 2/2013 | Coe et al. |
| 8,388,633 B2 | 3/2013 | Rousseau et al. |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,971 B2 | 3/2013 | Yates et al. |
| 8,398,633 B2 | 3/2013 | Mueller |
| 8,398,673 B2 | 3/2013 | Hinchliffe et al. |
| 8,403,138 B2 | 3/2013 | Weisshaupt et al. |
| 8,403,198 B2 | 3/2013 | Sorrentino et al. |
| 8,403,832 B2 | 3/2013 | Cunningham et al. |
| 8,403,945 B2 | 3/2013 | Whitfield et al. |
| 8,408,439 B2 | 4/2013 | Huang et al. |
| 8,408,442 B2 | 4/2013 | Racenet et al. |
| 8,409,079 B2 | 4/2013 | Okamoto et al. |
| 8,409,174 B2 | 4/2013 | Omori |
| 8,409,222 B2 | 4/2013 | Whitfield et al. |
| 8,409,223 B2 | 4/2013 | Sorrentino et al. |
| 8,413,870 B2 | 4/2013 | Pastorelli et al. |
| 8,413,871 B2 | 4/2013 | Racenet et al. |
| 8,413,872 B2 | 4/2013 | Patel |
| 8,414,577 B2 | 4/2013 | Boudreaux et al. |
| 8,418,909 B2 | 4/2013 | Kostrzewski |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,424,741 B2 | 4/2013 | McGuckin, Jr. et al. |
| 8,425,600 B2 | 4/2013 | Maxwell |
| 8,430,292 B2 | 4/2013 | Patel et al. |
| 8,430,892 B2 | 4/2013 | Bindra et al. |
| 8,430,898 B2 | 4/2013 | Wiener et al. |
| 8,439,246 B1 | 5/2013 | Knodel |
| 8,444,036 B2 | 5/2013 | Shelton, IV |
| 8,444,549 B2 | 5/2013 | Viola et al. |

(56) References Cited

U.S. PATENT DOCUMENTS

| | | |
|---|---|---|
| 8,453,904 B2 | 6/2013 | Eskaros et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,912 B2 | 6/2013 | Mastri et al. |
| 8,453,914 B2 | 6/2013 | Laurent et al. |
| 8,454,628 B2 | 6/2013 | Smith et al. |
| 8,457,757 B2 | 6/2013 | Cauller et al. |
| 8,459,520 B2 | 6/2013 | Giordano et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,464,924 B2 | 6/2013 | Gresham et al. |
| 8,464,925 B2 | 6/2013 | Hull et al. |
| 8,465,502 B2 | 6/2013 | Zergiebel |
| 8,469,973 B2 | 6/2013 | Meade et al. |
| 8,474,677 B2 | 7/2013 | Woodard, Jr. et al. |
| 8,475,453 B2 | 7/2013 | Marczyk et al. |
| 8,475,474 B2 | 7/2013 | Bombard et al. |
| 8,479,969 B2 | 7/2013 | Shelton, IV |
| 8,480,703 B2 | 7/2013 | Nicholas et al. |
| 8,485,412 B2 | 7/2013 | Shelton, IV et al. |
| 8,485,413 B2 | 7/2013 | Scheib et al. |
| 8,490,853 B2 | 7/2013 | Criscuolo et al. |
| 8,491,581 B2 | 7/2013 | Deville et al. |
| 8,496,156 B2 | 7/2013 | Sniffin et al. |
| 8,496,683 B2 | 7/2013 | Prommersberger et al. |
| 8,499,992 B2 | 8/2013 | Whitman et al. |
| 8,499,993 B2 | 8/2013 | Shelton, IV et al. |
| 8,500,762 B2 | 8/2013 | Sholev et al. |
| 8,506,557 B2 | 8/2013 | Zemlok et al. |
| 8,506,580 B2 | 8/2013 | Zergiebel et al. |
| 8,506,581 B2 | 8/2013 | Wingardner, III et al. |
| 8,511,308 B2 | 8/2013 | Hecox et al. |
| 8,512,359 B2 | 8/2013 | Whitman et al. |
| 8,517,239 B2 | 8/2013 | Scheib et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,521,273 B2 | 8/2013 | Kliman |
| 8,523,043 B2 | 9/2013 | Ullrich et al. |
| 8,523,881 B2 | 9/2013 | Cabiri et al. |
| 8,523,900 B2 | 9/2013 | Jinno et al. |
| 8,529,588 B2 | 9/2013 | Ahlberg et al. |
| 8,529,600 B2 | 9/2013 | Woodard, Jr. et al. |
| 8,529,819 B2 | 9/2013 | Ostapoff et al. |
| 8,534,528 B2 | 9/2013 | Shelton, IV |
| 8,535,304 B2 | 9/2013 | Sklar et al. |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,133 B2 | 9/2013 | Bedi et al. |
| 8,540,733 B2 | 9/2013 | Whitman et al. |
| 8,540,735 B2 | 9/2013 | Mitelberg et al. |
| 8,551,076 B2 | 10/2013 | Duval et al. |
| 8,556,151 B2 | 10/2013 | Viola |
| 8,556,918 B2 | 10/2013 | Bauman et al. |
| 8,561,870 B2 | 10/2013 | Baxter, III et al. |
| 8,561,873 B2 | 10/2013 | Ingmanson et al. |
| 8,567,656 B2 | 10/2013 | Shelton, IV et al. |
| 8,573,461 B2 | 11/2013 | Shelton, IV et al. |
| 8,573,465 B2 | 11/2013 | Shelton, IV |
| 8,574,199 B2 | 11/2013 | Von BÜlow et al. |
| 8,574,263 B2 | 11/2013 | Mueller |
| 8,575,880 B2 | 11/2013 | Grantz |
| 8,579,176 B2 | 11/2013 | Smith et al. |
| 8,579,178 B2 | 11/2013 | Holsten et al. |
| 8,579,897 B2 | 11/2013 | Vakharia et al. |
| 8,579,937 B2 | 11/2013 | Gresham |
| 8,584,919 B2 | 11/2013 | Hueil et al. |
| 8,585,721 B2 | 11/2013 | Kirsch |
| 8,590,762 B2 | 11/2013 | Hess et al. |
| 8,602,287 B2 | 12/2013 | Yates et al. |
| 8,602,288 B2 | 12/2013 | Shelton, IV et al. |
| 8,603,135 B2 | 12/2013 | Mueller |
| 8,608,044 B2 | 12/2013 | Hueil et al. |
| 8,608,045 B2 | 12/2013 | Smith et al. |
| 8,608,046 B2 | 12/2013 | Laurent et al. |
| 8,608,745 B2 | 12/2013 | Guzman et al. |
| 8,613,383 B2 | 12/2013 | Beckman et al. |
| 8,616,431 B2 | 12/2013 | Timm et al. |
| 8,622,274 B2 | 1/2014 | Yates et al. |
| 8,622,275 B2 | 1/2014 | Baxter, III et al. |
| 8,628,518 B2 | 1/2014 | Blumenkranz et al. |
| 8,628,545 B2 | 1/2014 | Cabrera et al. |
| 8,631,987 B2 | 1/2014 | Shelton, IV et al. |
| 8,632,462 B2 | 1/2014 | Yoo et al. |
| 8,632,525 B2 | 1/2014 | Kerr et al. |
| 8,632,535 B2 | 1/2014 | Shelton, IV et al. |
| 8,632,563 B2 | 1/2014 | Nagase et al. |
| 8,636,187 B2 | 1/2014 | Hueil et al. |
| 8,636,736 B2 | 1/2014 | Yates et al. |
| 8,636,766 B2 | 1/2014 | Milliman et al. |
| 8,640,788 B2 | 2/2014 | Dachs, II et al. |
| 8,647,258 B2 | 2/2014 | Aranyi et al. |
| 8,652,120 B2 | 2/2014 | Giordano et al. |
| 8,652,151 B2 | 2/2014 | Lehman et al. |
| 8,657,174 B2 | 2/2014 | Yates et al. |
| 8,657,176 B2 | 2/2014 | Shelton, Iv et al. |
| 8,657,177 B2 | 2/2014 | Scirica et al. |
| 8,657,178 B2 | 2/2014 | Hueil et al. |
| 8,657,482 B2 | 2/2014 | Malackowski et al. |
| 8,662,370 B2 | 3/2014 | Takei |
| 8,663,192 B2 | 3/2014 | Hester et al. |
| 8,668,129 B2 | 3/2014 | Olson |
| 8,668,130 B2 | 3/2014 | Hess et al. |
| 8,672,206 B2 | 3/2014 | Aranyi et al. |
| 8,672,207 B2 | 3/2014 | Shelton, IV et al. |
| 8,672,208 B2 | 3/2014 | Hess et al. |
| 8,673,210 B2 | 3/2014 | Deshays |
| 8,678,263 B2 | 3/2014 | Viola |
| 8,679,093 B2 | 3/2014 | Farra |
| 8,679,098 B2 | 3/2014 | Hart |
| 8,679,137 B2 | 3/2014 | Bauman et al. |
| 8,679,454 B2 | 3/2014 | Guire et al. |
| 8,684,250 B2 | 4/2014 | Bettuchi et al. |
| 8,684,253 B2 | 4/2014 | Giordano et al. |
| 8,685,020 B2 | 4/2014 | Weizman et al. |
| 8,695,866 B2 | 4/2014 | Leimbach et al. |
| 8,696,665 B2 | 4/2014 | Hunt et al. |
| 8,701,958 B2 | 4/2014 | Shelton, IV et al. |
| 8,701,959 B2 | 4/2014 | Shah |
| 8,708,211 B2 | 4/2014 | Zemlok et al. |
| 8,708,213 B2 | 4/2014 | Shelton, IV et al. |
| 8,715,256 B2 | 5/2014 | Greener |
| 8,720,766 B2 | 5/2014 | Hess et al. |
| 8,721,630 B2 | 5/2014 | Ortiz et al. |
| 8,721,666 B2 | 5/2014 | Schroeder et al. |
| 8,727,197 B2 | 5/2014 | Hess et al. |
| 8,727,200 B2 | 5/2014 | Roy |
| 8,728,119 B2 | 5/2014 | Cummins |
| 8,733,613 B2 | 5/2014 | Huitema et al. |
| 8,733,614 B2 | 5/2014 | Ross et al. |
| 8,734,478 B2 | 5/2014 | Widenhouse et al. |
| 8,739,033 B2 | 5/2014 | Rosenberg |
| 8,740,034 B2 | 6/2014 | Morgan et al. |
| 8,740,037 B2 | 6/2014 | Shelton, IV et al. |
| 8,740,038 B2 | 6/2014 | Shelton, IV et al. |
| 8,740,987 B2 | 6/2014 | Geremakis et al. |
| 8,746,529 B2 | 6/2014 | Shelton, IV et al. |
| 8,746,530 B2 | 6/2014 | Giordano et al. |
| 8,746,535 B2 | 6/2014 | Shelton, IV et al. |
| 8,747,238 B2 | 6/2014 | Shelton, IV et al. |
| 8,752,264 B2 | 6/2014 | Ackley et al. |
| 8,752,699 B2 | 6/2014 | Morgan et al. |
| 8,752,747 B2 | 6/2014 | Shelton, IV et al. |
| 8,752,749 B2 | 6/2014 | Moore et al. |
| 8,757,465 B2 | 6/2014 | Woodard, Jr. et al. |
| 8,758,235 B2 | 6/2014 | Jaworek |
| 8,758,391 B2 | 6/2014 | Swayze et al. |
| 8,758,438 B2 | 6/2014 | Boyce et al. |
| 8,763,875 B2 | 7/2014 | Morgan et al. |
| 8,763,877 B2 | 7/2014 | Schall et al. |

(56) References Cited

U.S. PATENT DOCUMENTS

| | | |
|---|---|---|
| 8,763,879 B2 | 7/2014 | Shelton, IV et al. |
| 8,771,169 B2 | 7/2014 | Whitman et al. |
| 8,777,004 B2 | 7/2014 | Shelton, IV et al. |
| 8,783,541 B2 | 7/2014 | Shelton, IV et al. |
| 8,783,542 B2 | 7/2014 | Riestenberg et al. |
| 8,783,543 B2 | 7/2014 | Shelton, IV et al. |
| 8,784,404 B2 | 7/2014 | Doyle et al. |
| 8,784,415 B2 | 7/2014 | Malackowski et al. |
| 8,789,737 B2 | 7/2014 | Hodgkinson et al. |
| 8,789,739 B2 | 7/2014 | Swensgard |
| 8,789,740 B2 | 7/2014 | Baxter, III et al. |
| 8,789,741 B2 | 7/2014 | Baxter, III et al. |
| 8,790,684 B2 | 7/2014 | Dave et al. |
| 8,794,496 B2 | 8/2014 | Scirica |
| 8,794,497 B2 | 8/2014 | Zingman |
| 8,795,276 B2 | 8/2014 | Dietz et al. |
| 8,800,838 B2 | 8/2014 | Shelton, IV |
| 8,800,839 B2 | 8/2014 | Beetel |
| 8,800,841 B2 | 8/2014 | Ellerhorst et al. |
| 8,801,734 B2 | 8/2014 | Shelton, IV et al. |
| 8,801,735 B2 | 8/2014 | Shelton, IV et al. |
| 8,801,752 B2 | 8/2014 | Fortier et al. |
| 8,806,973 B2 | 8/2014 | Ross et al. |
| 8,807,414 B2 | 8/2014 | Ross et al. |
| 8,808,294 B2 | 8/2014 | Fox et al. |
| 8,808,311 B2 | 8/2014 | Heinrich et al. |
| 8,813,866 B2 | 8/2014 | Suzuki |
| 8,814,024 B2 | 8/2014 | Woodard, Jr. et al. |
| 8,814,025 B2 | 8/2014 | Miller et al. |
| 8,820,603 B2 | 9/2014 | Shelton, IV et al. |
| 8,820,605 B2 | 9/2014 | Shelton, IV |
| 8,820,606 B2 | 9/2014 | Hodgkinson |
| 8,820,607 B2 | 9/2014 | Marczyk |
| 8,827,133 B2 | 9/2014 | Shelton, IV et al. |
| 8,827,903 B2 | 9/2014 | Shelton, IV et al. |
| 8,833,632 B2 | 9/2014 | Swensgard |
| 8,840,003 B2 | 9/2014 | Morgan et al. |
| 8,840,603 B2 | 9/2014 | Shelton, IV et al. |
| 8,844,789 B2 | 9/2014 | Shelton, IV et al. |
| 8,851,354 B2 | 10/2014 | Swensgard et al. |
| 8,852,199 B2 | 10/2014 | Deslauriers et al. |
| 8,857,693 B2 | 10/2014 | Schuckmann et al. |
| 8,857,694 B2 | 10/2014 | Shelton, IV et al. |
| 8,858,571 B2 | 10/2014 | Shelton, IV et al. |
| 8,858,590 B2 | 10/2014 | Shelton, IV et al. |
| 8,864,007 B2 | 10/2014 | Widenhouse et al. |
| 8,864,009 B2 | 10/2014 | Shelton, IV et al. |
| 8,870,050 B2 | 10/2014 | Hodgkinson |
| 8,875,971 B2 | 11/2014 | Hall et al. |
| 8,875,972 B2 | 11/2014 | Weisenburgh, IV et al. |
| 8,876,857 B2 | 11/2014 | Burbank |
| 8,893,946 B2 | 11/2014 | Boudreaux et al. |
| 8,893,949 B2 | 11/2014 | Shelton, IV et al. |
| 8,899,463 B2 | 12/2014 | Schall et al. |
| 8,899,464 B2 | 12/2014 | Hueil et al. |
| 8,899,465 B2 | 12/2014 | Shelton, IV et al. |
| 8,899,466 B2 | 12/2014 | Baxter, III et al. |
| 8,905,977 B2 | 12/2014 | Shelton et al. |
| 8,911,426 B2 | 12/2014 | Coppeta et al. |
| 8,911,471 B2 | 12/2014 | Spivey et al. |
| 8,920,438 B2 | 12/2014 | Aranyi et al. |
| 8,925,782 B2 | 1/2015 | Shelton, IV |
| 8,925,783 B2 | 1/2015 | Zemlok et al. |
| 8,925,788 B2 | 1/2015 | Hess et al. |
| 8,926,598 B2 | 1/2015 | Mollere et al. |
| 8,931,682 B2 | 1/2015 | Timm et al. |
| 8,936,614 B2 | 1/2015 | Allen, IV |
| 8,939,343 B2 | 1/2015 | Milliman et al. |
| 8,939,344 B2 | 1/2015 | Olson et al. |
| 8,955,732 B2 | 2/2015 | Zemlok et al. |
| 8,956,342 B1 | 2/2015 | Russo et al. |
| 8,960,520 B2 | 2/2015 | McCuen |
| 8,960,521 B2 | 2/2015 | Kostrzewski |
| 8,961,504 B2 | 2/2015 | Hoarau et al. |
| 8,967,443 B2 | 3/2015 | McCuen |
| 8,967,446 B2 | 3/2015 | Beardsley et al. |
| 8,968,276 B2 | 3/2015 | Zemlok et al. |
| 8,968,312 B2 | 3/2015 | Marczyk et al. |
| 8,968,337 B2 | 3/2015 | Whitfield et al. |
| 8,968,340 B2 | 3/2015 | Chowaniec et al. |
| 8,970,507 B2 | 3/2015 | Holbein et al. |
| 8,973,803 B2 | 3/2015 | Hall et al. |
| 8,973,804 B2 | 3/2015 | Hess et al. |
| 8,978,954 B2 | 3/2015 | Shelton, IV et al. |
| 8,978,955 B2 | 3/2015 | Aronhalt et al. |
| 8,978,956 B2 | 3/2015 | Schall et al. |
| 8,979,890 B2 | 3/2015 | Boudreaux |
| 8,982,195 B2 | 3/2015 | Claus et al. |
| 8,991,676 B2 | 3/2015 | Hess et al. |
| 8,991,677 B2 | 3/2015 | Moore et al. |
| 8,992,422 B2 | 3/2015 | Spivey et al. |
| 8,992,565 B2 | 3/2015 | Brisson et al. |
| 8,996,165 B2 | 3/2015 | Wang et al. |
| 8,998,058 B2 | 4/2015 | Moore et al. |
| 9,005,230 B2 | 4/2015 | Yates et al. |
| 9,011,471 B2 | 4/2015 | Timm et al. |
| 9,016,540 B2 | 4/2015 | Whitman et al. |
| 9,016,542 B2 | 4/2015 | Shelton, IV et al. |
| 9,017,331 B2 | 4/2015 | Fox |
| 9,017,371 B2 | 4/2015 | Whitman et al. |
| 9,023,014 B2 | 5/2015 | Chowaniec et al. |
| 9,027,817 B2 | 5/2015 | Milliman et al. |
| 9,028,494 B2 | 5/2015 | Shelton, IV et al. |
| 9,028,495 B2 | 5/2015 | Mueller et al. |
| 9,028,519 B2 | 5/2015 | Yates et al. |
| 9,033,203 B2 | 5/2015 | Woodard, Jr. et al. |
| 9,033,204 B2 | 5/2015 | Shelton, IV et al. |
| 9,038,881 B1 | 5/2015 | Schaller et al. |
| 9,039,690 B2 | 5/2015 | Kersten et al. |
| 9,039,720 B2 | 5/2015 | Madan |
| 9,043,027 B2 | 5/2015 | Durant et al. |
| 9,044,227 B2 | 6/2015 | Shelton, IV et al. |
| 9,044,228 B2 | 6/2015 | Woodard, Jr. et al. |
| 9,044,230 B2 | 6/2015 | Morgan et al. |
| 9,050,083 B2 | 6/2015 | Yates et al. |
| 9,050,084 B2 | 6/2015 | Schmid et al. |
| 9,050,100 B2 | 6/2015 | Yates et al. |
| 9,055,941 B2 | 6/2015 | Schmid et al. |
| 9,055,944 B2 | 6/2015 | Hodgkinson et al. |
| 9,055,961 B2 | 6/2015 | Manzo et al. |
| 9,060,770 B2 | 6/2015 | Shelton, IV et al. |
| 9,072,515 B2 | 7/2015 | Hall et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,084,601 B2 | 7/2015 | Moore et al. |
| 9,084,602 B2 | 7/2015 | Gleiman |
| 9,086,875 B2 | 7/2015 | Harrat et al. |
| 9,089,330 B2 | 7/2015 | Widenhouse et al. |
| 9,095,339 B2 | 8/2015 | Moore et al. |
| 9,095,362 B2 | 8/2015 | Dachs, II et al. |
| 9,096,033 B2 | 8/2015 | Holop et al. |
| 9,099,863 B2 | 8/2015 | Smith et al. |
| 9,101,358 B2 | 8/2015 | Kerr et al. |
| 9,101,385 B2 | 8/2015 | Shelton, IV et al. |
| 9,107,663 B2 | 8/2015 | Swensgard |
| 9,113,862 B2 | 8/2015 | Morgan et al. |
| 9,113,864 B2 | 8/2015 | Morgan et al. |
| 9,113,865 B2 | 8/2015 | Shelton, IV et al. |
| 9,113,873 B2 | 8/2015 | Marczyk et al. |
| 9,113,874 B2 | 8/2015 | Shelton, IV et al. |
| 9,113,880 B2 | 8/2015 | Zemlok et al. |
| 9,113,883 B2 | 8/2015 | Aronhalt et al. |
| 9,113,884 B2 | 8/2015 | Shelton, IV et al. |
| 9,119,657 B2 | 9/2015 | Shelton, IV et al. |
| 9,123,286 B2 | 9/2015 | Park |
| 9,125,654 B2 | 9/2015 | Aronhalt et al. |
| 9,125,662 B2 | 9/2015 | Shelton, IV |
| 9,131,940 B2 | 9/2015 | Huitema et al. |
| 9,131,957 B2 | 9/2015 | Skarbnik et al. |
| 9,138,225 B2 | 9/2015 | Huang et al. |
| 9,149,274 B2 | 10/2015 | Spivey et al. |
| 9,149,325 B2 | 10/2015 | Worrell et al. |
| 9,161,803 B2 | 10/2015 | Yates et al. |

(56) References Cited

U.S. PATENT DOCUMENTS

| | | |
|---|---|---|
| 9,168,038 B2 | 10/2015 | Shelton, IV et al. |
| 9,168,054 B2 | 10/2015 | Turner et al. |
| 9,168,144 B2 | 10/2015 | Rivin et al. |
| 9,179,911 B2 | 11/2015 | Morgan et al. |
| 9,179,912 B2 | 11/2015 | Yates et al. |
| 9,186,143 B2 | 11/2015 | Timm et al. |
| 9,186,148 B2 | 11/2015 | Felder et al. |
| 9,192,380 B2 | 11/2015 | (Tarinelli) Racenet et al. |
| 9,192,384 B2 | 11/2015 | Bettuchi |
| 9,193,045 B2 | 11/2015 | Saur et al. |
| 9,198,661 B2 | 12/2015 | Swensgard |
| 9,198,662 B2 | 12/2015 | Barton et al. |
| 9,204,877 B2 | 12/2015 | Whitman et al. |
| 9,204,878 B2 | 12/2015 | Hall et al. |
| 9,204,879 B2 | 12/2015 | Shelton, IV |
| 9,204,880 B2 | 12/2015 | Baxter, III et al. |
| 9,211,120 B2 | 12/2015 | Scheib et al. |
| 9,211,121 B2 | 12/2015 | Hall et al. |
| 9,211,122 B2 | 12/2015 | Hagerty et al. |
| 9,216,019 B2 | 12/2015 | Schmid et al. |
| 9,220,500 B2 | 12/2015 | Swayze et al. |
| 9,220,501 B2 | 12/2015 | Baxter, III et al. |
| 9,226,750 B2 | 1/2016 | Weir et al. |
| 9,226,751 B2 | 1/2016 | Shelton, IV et al. |
| 9,232,941 B2 | 1/2016 | Mandakolathur Vasudevan et al. |
| 9,232,945 B2 | 1/2016 | Zingman |
| 9,232,979 B2 | 1/2016 | Parihar et al. |
| 9,237,891 B2 | 1/2016 | Shelton, IV |
| 9,241,714 B2 | 1/2016 | Timm et al. |
| 9,259,274 B2 | 2/2016 | Prisco |
| 9,271,799 B2 | 3/2016 | Shelton, IV et al. |
| 9,272,406 B2 | 3/2016 | Aronhalt et al. |
| 9,277,919 B2 | 3/2016 | Timmer et al. |
| 9,277,922 B2 | 3/2016 | Carter et al. |
| 9,282,962 B2 | 3/2016 | Schmid et al. |
| 9,282,966 B2 | 3/2016 | Shelton, IV et al. |
| 9,282,974 B2 | 3/2016 | Shelton, IV |
| 9,283,054 B2 | 3/2016 | Morgan et al. |
| 9,289,206 B2 | 3/2016 | Hess et al. |
| 9,289,207 B2 | 3/2016 | Shelton, IV |
| 9,289,210 B2 | 3/2016 | Baxter, III et al. |
| 9,289,212 B2 | 3/2016 | Shelton, IV et al. |
| 9,289,225 B2 | 3/2016 | Shelton, IV et al. |
| 9,289,256 B2 | 3/2016 | Shelton, IV et al. |
| 9,295,464 B2 | 3/2016 | Shelton, IV et al. |
| 9,301,752 B2 | 4/2016 | Mandakolathur Vasudevan et al. |
| 9,301,753 B2 | 4/2016 | Aldridge et al. |
| 9,301,755 B2 | 4/2016 | Shelton, IV et al. |
| 9,301,759 B2 | 4/2016 | Spivey et al. |
| 9,307,986 B2 | 4/2016 | Hall et al. |
| 9,307,988 B2 | 4/2016 | Shelton, IV |
| 9,308,011 B2 | 4/2016 | Chao et al. |
| 9,314,246 B2 | 4/2016 | Shelton, IV et al. |
| 9,320,518 B2 | 4/2016 | Henderson et al. |
| 9,320,520 B2 | 4/2016 | Shelton, IV et al. |
| 9,320,521 B2 | 4/2016 | Shelton, IV et al. |
| 9,320,523 B2 | 4/2016 | Shelton, IV et al. |
| 9,326,767 B2 | 5/2016 | Koch, Jr. et al. |
| 9,326,768 B2 | 5/2016 | Shelton, IV |
| 9,326,769 B2 | 5/2016 | Shelton, IV et al. |
| 9,326,770 B2 | 5/2016 | Shelton, IV et al. |
| 9,326,771 B2 | 5/2016 | Baxter, III et al. |
| 9,332,974 B2 | 5/2016 | Henderson et al. |
| 9,332,984 B2 | 5/2016 | Weaner et al. |
| 9,332,987 B2 | 5/2016 | Leimbach et al. |
| 9,345,481 B2 | 5/2016 | Hall et al. |
| 9,351,726 B2 | 5/2016 | Leimbach et al. |
| 9,351,727 B2 | 5/2016 | Leimbach et al. |
| 9,351,730 B2 | 5/2016 | Schmid et al. |
| 9,358,003 B2 | 6/2016 | Hall et al. |
| 9,358,005 B2 | 6/2016 | Shelton, IV et al. |
| 9,364,220 B2 | 6/2016 | Williams |
| 9,364,230 B2 | 6/2016 | Shelton, IV et al. |
| 9,364,233 B2 | 6/2016 | Alexander, III et al. |
| 9,364,279 B2 | 6/2016 | Houser et al. |
| 9,370,358 B2 | 6/2016 | Shelton, IV et al. |
| 9,370,364 B2 | 6/2016 | Smith et al. |
| 9,386,983 B2 | 7/2016 | Swensgard et al. |
| 9,386,984 B2 * | 7/2016 | Aronhalt .......... A61B 17/07207 |
| 9,386,988 B2 | 7/2016 | Baxter, III et al. |
| 9,393,015 B2 | 7/2016 | Laurent et al. |
| 9,398,911 B2 | 7/2016 | Auld |
| 9,402,626 B2 | 8/2016 | Ortiz et al. |
| 9,408,604 B2 | 8/2016 | Shelton, IV et al. |
| 9,408,606 B2 | 8/2016 | Shelton, IV |
| 9,414,838 B2 | 8/2016 | Shelton, IV et al. |
| 9,433,419 B2 | 9/2016 | Gonzalez et al. |
| 9,445,813 B2 | 9/2016 | Shelton, IV et al. |
| 9,451,958 B2 | 9/2016 | Shelton, IV et al. |
| 9,480,476 B2 | 11/2016 | Aldridge et al. |
| 9,693,777 B2 * | 7/2017 | Schellin .......... A61B 17/07292 |
| 2001/0025183 A1 | 9/2001 | Shahidi |
| 2001/0044637 A1 | 11/2001 | Jacobs et al. |
| 2002/0014510 A1 | 2/2002 | Richter et al. |
| 2002/0022836 A1 | 2/2002 | Goble et al. |
| 2002/0026126 A1 | 2/2002 | Burdorff et al. |
| 2002/0029032 A1 | 3/2002 | Arkin |
| 2002/0029036 A1 | 3/2002 | Goble et al. |
| 2002/0049472 A1 | 4/2002 | Coleman et al. |
| 2002/0095175 A1 | 7/2002 | Brock et al. |
| 2002/0103494 A1 | 8/2002 | Pacey |
| 2002/0117534 A1 | 8/2002 | Green et al. |
| 2002/0127265 A1 | 9/2002 | Bowman et al. |
| 2002/0128552 A1 | 9/2002 | Nowlin et al. |
| 2002/0134811 A1 | 9/2002 | Napier et al. |
| 2002/0135474 A1 | 9/2002 | Sylliassen |
| 2002/0143340 A1 | 10/2002 | Kaneko |
| 2002/0157481 A1 | 10/2002 | Kogiso et al. |
| 2002/0165541 A1 | 11/2002 | Whitman |
| 2002/0188170 A1 | 12/2002 | Santamore et al. |
| 2002/0193808 A1 | 12/2002 | Belef et al. |
| 2003/0023316 A1 | 1/2003 | Brown et al. |
| 2003/0066858 A1 | 4/2003 | Holgersson |
| 2003/0078647 A1 | 4/2003 | Vallana et al. |
| 2003/0084983 A1 | 5/2003 | Rangachari et al. |
| 2003/0093103 A1 | 5/2003 | Malackowski et al. |
| 2003/0096158 A1 | 5/2003 | Takano et al. |
| 2003/0105478 A1 | 6/2003 | Whitman et al. |
| 2003/0130677 A1 | 7/2003 | Whitman et al. |
| 2003/0139741 A1 | 7/2003 | Goble et al. |
| 2003/0153908 A1 | 8/2003 | Goble et al. |
| 2003/0153968 A1 | 8/2003 | Geis et al. |
| 2003/0163085 A1 | 8/2003 | Tanner et al. |
| 2003/0181900 A1 | 9/2003 | Long |
| 2003/0195387 A1 | 10/2003 | Kortenbach et al. |
| 2003/0205029 A1 | 11/2003 | Chapolini et al. |
| 2003/0216732 A1 | 11/2003 | Truckai et al. |
| 2003/0220660 A1 | 11/2003 | Kortenbach et al. |
| 2003/0236505 A1 | 12/2003 | Bonadio et al. |
| 2003/0236573 A1 * | 12/2003 | Evans .................... A61L 27/12 623/23.58 |
| 2004/0002726 A1 | 1/2004 | Nunez et al. |
| 2004/0006335 A1 | 1/2004 | Garrison |
| 2004/0006340 A1 | 1/2004 | Latterell et al. |
| 2004/0006372 A1 | 1/2004 | Racenet et al. |
| 2004/0006861 A1 | 1/2004 | Haytayan |
| 2004/0030333 A1 | 2/2004 | Goble |
| 2004/0032345 A1 | 2/2004 | Kazuya et al. |
| 2004/0034357 A1 | 2/2004 | Beane et al. |
| 2004/0034369 A1 | 2/2004 | Sauer et al. |
| 2004/0044364 A1 | 3/2004 | DeVries et al. |
| 2004/0068161 A1 | 4/2004 | Couvillon, Jr. |
| 2004/0068224 A1 | 4/2004 | Couvillon, Jr. et al. |
| 2004/0068307 A1 | 4/2004 | Goble |
| 2004/0070369 A1 | 4/2004 | Sakakibara |
| 2004/0073222 A1 | 4/2004 | Koseki |
| 2004/0078037 A1 | 4/2004 | Batchelor et al. |
| 2004/0093024 A1 | 5/2004 | Lousararian et al. |
| 2004/0094597 A1 | 5/2004 | Whitman et al. |
| 2004/0097987 A1 | 5/2004 | Pugsley et al. |
| 2004/0098040 A1 | 5/2004 | Taniguchi et al. |
| 2004/0101822 A1 | 5/2004 | Wiesner et al. |
| 2004/0102783 A1 | 5/2004 | Sutterlin, III et al. |
| 2004/0108357 A1 | 6/2004 | Milliman et al. |

(56) References Cited

U.S. PATENT DOCUMENTS

| | | |
|---|---|---|
| 2004/0110439 A1 | 6/2004 | Chaikof et al. |
| 2004/0111081 A1 | 6/2004 | Whitman et al. |
| 2004/0115022 A1 | 6/2004 | Albertson et al. |
| 2004/0116952 A1 | 6/2004 | Sakurai et al. |
| 2004/0133095 A1 | 7/2004 | Dunki-Jacobs et al. |
| 2004/0143297 A1 | 7/2004 | Ramsey |
| 2004/0147909 A1 | 7/2004 | Johnston et al. |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0181219 A1 | 9/2004 | Goble et al. |
| 2004/0186470 A1 | 9/2004 | Goble et al. |
| 2004/0193189 A1 | 9/2004 | Kortenbach et al. |
| 2004/0199181 A1 | 10/2004 | Knodel et al. |
| 2004/0222268 A1 | 11/2004 | Bilotti et al. |
| 2004/0225186 A1 | 11/2004 | Horne, Jr. et al. |
| 2004/0230214 A1 | 11/2004 | Donofrio et al. |
| 2004/0232201 A1 | 11/2004 | Wenchell et al. |
| 2004/0236352 A1 | 11/2004 | Wang et al. |
| 2004/0243147 A1 | 12/2004 | Lipow |
| 2004/0243151 A1 | 12/2004 | Demmy et al. |
| 2004/0243163 A1 | 12/2004 | Casiano et al. |
| 2004/0243176 A1 | 12/2004 | Hahnen et al. |
| 2004/0247415 A1 | 12/2004 | Mangone, Jr. |
| 2004/0254455 A1 | 12/2004 | Iddan |
| 2004/0254566 A1 | 12/2004 | Plicchi et al. |
| 2004/0254590 A1 | 12/2004 | Hoffman et al. |
| 2004/0254608 A1 | 12/2004 | Huitema et al. |
| 2004/0260315 A1 | 12/2004 | Dell et al. |
| 2004/0267297 A1 | 12/2004 | Malackowski |
| 2004/0267310 A1 | 12/2004 | Racenet et al. |
| 2005/0010158 A1 | 1/2005 | Brugger et al. |
| 2005/0010213 A1 | 1/2005 | Stad et al. |
| 2005/0032511 A1 | 2/2005 | Malone et al. |
| 2005/0033352 A1 | 2/2005 | Zepf et al. |
| 2005/0033357 A1 | 2/2005 | Braun |
| 2005/0048121 A1* | 3/2005 | East .................. A61K 9/0024 424/486 |
| 2005/0054946 A1 | 3/2005 | Krzyzanowski |
| 2005/0059997 A1 | 3/2005 | Bauman et al. |
| 2005/0070929 A1 | 3/2005 | Dalessandro et al. |
| 2005/0075561 A1 | 4/2005 | Golden |
| 2005/0080454 A1 | 4/2005 | Drews et al. |
| 2005/0085693 A1 | 4/2005 | Belson et al. |
| 2005/0090817 A1 | 4/2005 | Phan |
| 2005/0096683 A1 | 5/2005 | Ellins et al. |
| 2005/0103819 A1 | 5/2005 | Racenet et al. |
| 2005/0107814 A1 | 5/2005 | Johnston et al. |
| 2005/0107824 A1 | 5/2005 | Hillstead et al. |
| 2005/0113820 A1 | 5/2005 | Goble et al. |
| 2005/0116673 A1 | 6/2005 | Carl et al. |
| 2005/0119525 A1 | 6/2005 | Takemoto |
| 2005/0119669 A1 | 6/2005 | Demmy |
| 2005/0124855 A1 | 6/2005 | Jaffe et al. |
| 2005/0125009 A1 | 6/2005 | Perry et al. |
| 2005/0125897 A1 | 6/2005 | Wyslucha et al. |
| 2005/0131173 A1 | 6/2005 | McDaniel et al. |
| 2005/0131211 A1 | 6/2005 | Bayley et al. |
| 2005/0131390 A1 | 6/2005 | Heinrich et al. |
| 2005/0131436 A1 | 6/2005 | Johnston et al. |
| 2005/0131437 A1 | 6/2005 | Johnston et al. |
| 2005/0131457 A1 | 6/2005 | Douglas et al. |
| 2005/0137454 A1 | 6/2005 | Saadat et al. |
| 2005/0137455 A1 | 6/2005 | Ewers et al. |
| 2005/0143759 A1 | 6/2005 | Kelly |
| 2005/0143769 A1 | 6/2005 | White et al. |
| 2005/0145675 A1 | 7/2005 | Hartwick et al. |
| 2005/0150928 A1 | 7/2005 | Kameyama et al. |
| 2005/0154258 A1 | 7/2005 | Tartaglia et al. |
| 2005/0154406 A1 | 7/2005 | Bombard et al. |
| 2005/0159184 A1 | 7/2005 | Kerner et al. |
| 2005/0165419 A1 | 7/2005 | Sauer et al. |
| 2005/0165435 A1 | 7/2005 | Johnston et al. |
| 2005/0169974 A1 | 8/2005 | Tenerz et al. |
| 2005/0171522 A1 | 8/2005 | Christopherson |
| 2005/0177181 A1 | 8/2005 | Kagan et al. |
| 2005/0182298 A1 | 8/2005 | Ikeda et al. |
| 2005/0187545 A1 | 8/2005 | Hooven et al. |
| 2005/0187572 A1 | 8/2005 | Johnston et al. |
| 2005/0187576 A1 | 8/2005 | Whitman et al. |
| 2005/0189397 A1 | 9/2005 | Jankowski |
| 2005/0192609 A1 | 9/2005 | Whitman et al. |
| 2005/0192628 A1 | 9/2005 | Viola |
| 2005/0203550 A1 | 9/2005 | Laufer et al. |
| 2005/0216055 A1 | 9/2005 | Scirica et al. |
| 2005/0228224 A1 | 10/2005 | Okada et al. |
| 2005/0240178 A1 | 10/2005 | Morley et al. |
| 2005/0240222 A1 | 10/2005 | Shipp |
| 2005/0245965 A1 | 11/2005 | Orban, III et al. |
| 2005/0251128 A1 | 11/2005 | Amoah |
| 2005/0256452 A1 | 11/2005 | DeMarchi et al. |
| 2005/0256522 A1 | 11/2005 | Francischelli et al. |
| 2005/0261676 A1 | 11/2005 | Hall et al. |
| 2005/0261677 A1 | 11/2005 | Hall et al. |
| 2005/0263563 A1 | 12/2005 | Racenet et al. |
| 2005/0267455 A1 | 12/2005 | Eggers et al. |
| 2005/0267530 A1 | 12/2005 | Cummins |
| 2005/0272973 A1 | 12/2005 | Kawano et al. |
| 2005/0274768 A1 | 12/2005 | Cummins et al. |
| 2005/0283188 A1 | 12/2005 | Loshakove et al. |
| 2005/0283255 A1* | 12/2005 | Geremakis ............ A61F 2/4644 623/23.51 |
| 2006/0004407 A1 | 1/2006 | Hiles et al. |
| 2006/0008787 A1 | 1/2006 | Hayman et al. |
| 2006/0011699 A1 | 1/2006 | Olson et al. |
| 2006/0015009 A1 | 1/2006 | Jaffe et al. |
| 2006/0020247 A1 | 1/2006 | Kagan et al. |
| 2006/0020258 A1 | 1/2006 | Strauss et al. |
| 2006/0020336 A1 | 1/2006 | Liddicoat |
| 2006/0025811 A1 | 2/2006 | Shelton, IV |
| 2006/0025812 A1 | 2/2006 | Shelton, IV |
| 2006/0041188 A1 | 2/2006 | Dirusso et al. |
| 2006/0047275 A1 | 3/2006 | Goble |
| 2006/0047303 A1 | 3/2006 | Ortiz et al. |
| 2006/0047307 A1 | 3/2006 | Ortiz et al. |
| 2006/0049229 A1 | 3/2006 | Milliman et al. |
| 2006/0052825 A1 | 3/2006 | Ransick et al. |
| 2006/0060630 A1 | 3/2006 | Shelton, IV et al. |
| 2006/0064086 A1 | 3/2006 | Odom |
| 2006/0079115 A1 | 4/2006 | Aranyi et al. |
| 2006/0079735 A1 | 4/2006 | Martone et al. |
| 2006/0085031 A1 | 4/2006 | Bettuchi |
| 2006/0085033 A1 | 4/2006 | Criscuolo et al. |
| 2006/0086032 A1 | 4/2006 | Valencic et al. |
| 2006/0087746 A1 | 4/2006 | Lipow |
| 2006/0089535 A1 | 4/2006 | Raz et al. |
| 2006/0100643 A1 | 5/2006 | Laufer et al. |
| 2006/0100649 A1 | 5/2006 | Hart |
| 2006/0108393 A1 | 5/2006 | Heinrich et al. |
| 2006/0111711 A1 | 5/2006 | Goble |
| 2006/0111723 A1 | 5/2006 | Chapolini et al. |
| 2006/0116634 A1 | 6/2006 | Shachar |
| 2006/0122636 A1 | 6/2006 | Bailly et al. |
| 2006/0142772 A1 | 6/2006 | Ralph et al. |
| 2006/0149163 A1 | 7/2006 | Hibner et al. |
| 2006/0161185 A1 | 7/2006 | Saadat et al. |
| 2006/0167471 A1 | 7/2006 | Phillips |
| 2006/0173470 A1 | 8/2006 | Oray et al. |
| 2006/0178556 A1 | 8/2006 | Hasser et al. |
| 2006/0180634 A1 | 8/2006 | Shelton, IV et al. |
| 2006/0185682 A1 | 8/2006 | Marczyk |
| 2006/0200123 A1 | 9/2006 | Ryan |
| 2006/0201989 A1 | 9/2006 | Ojeda |
| 2006/0206100 A1 | 9/2006 | Eskridge et al. |
| 2006/0212069 A1 | 9/2006 | Shelton, IV |
| 2006/0217729 A1 | 9/2006 | Eskridge et al. |
| 2006/0226196 A1 | 10/2006 | Hueil et al. |
| 2006/0235368 A1 | 10/2006 | Oz |
| 2006/0235469 A1 | 10/2006 | Viola |
| 2006/0241655 A1 | 10/2006 | Viola |
| 2006/0241692 A1 | 10/2006 | McGuckin, Jr. et al. |
| 2006/0244460 A1 | 11/2006 | Weaver |
| 2006/0252993 A1 | 11/2006 | Freed et al. |
| 2006/0253069 A1 | 11/2006 | Li et al. |

(56) References Cited

U.S. PATENT DOCUMENTS

| | | |
|---|---|---|
| 2006/0258904 A1 | 11/2006 | Stefanchik et al. |
| 2006/0258910 A1 | 11/2006 | Stefanchik et al. |
| 2006/0259073 A1 | 11/2006 | Miyamoto et al. |
| 2006/0264927 A1 | 11/2006 | Ryan |
| 2006/0264929 A1 | 11/2006 | Goble et al. |
| 2006/0271042 A1 | 11/2006 | Latterell et al. |
| 2006/0271102 A1 | 11/2006 | Bosshard et al. |
| 2006/0278680 A1 | 12/2006 | Viola et al. |
| 2006/0278681 A1 | 12/2006 | Viola et al. |
| 2006/0282064 A1 | 12/2006 | Shimizu et al. |
| 2006/0284730 A1 | 12/2006 | Schmid et al. |
| 2006/0287576 A1 | 12/2006 | Tsuji et al. |
| 2006/0289602 A1 | 12/2006 | Wales et al. |
| 2006/0291981 A1 | 12/2006 | Viola et al. |
| 2007/0010702 A1 | 1/2007 | Wang et al. |
| 2007/0010838 A1 | 1/2007 | Shelton, IV et al. |
| 2007/0023476 A1 | 2/2007 | Whitman et al. |
| 2007/0023477 A1 | 2/2007 | Whitman et al. |
| 2007/0026039 A1 | 2/2007 | Drumheller et al. |
| 2007/0026040 A1 | 2/2007 | Crawley et al. |
| 2007/0027468 A1 | 2/2007 | Wales et al. |
| 2007/0027472 A1 | 2/2007 | Hiles et al. |
| 2007/0027551 A1 | 2/2007 | Farnsworth et al. |
| 2007/0027553 A1* | 2/2007 | Biran ............... A61L 31/146 623/23.74 |
| 2007/0034668 A1 | 2/2007 | Holsten et al. |
| 2007/0049951 A1 | 3/2007 | Menn |
| 2007/0049966 A1 | 3/2007 | Bonadio et al. |
| 2007/0051375 A1 | 3/2007 | Milliman |
| 2007/0055219 A1 | 3/2007 | Whitman et al. |
| 2007/0066981 A1 | 3/2007 | Meagher |
| 2007/0070574 A1 | 3/2007 | Nerheim et al. |
| 2007/0073341 A1 | 3/2007 | Smith et al. |
| 2007/0078328 A1 | 4/2007 | Ozaki et al. |
| 2007/0078484 A1 | 4/2007 | Talarico et al. |
| 2007/0083193 A1 | 4/2007 | Werneth et al. |
| 2007/0084897 A1 | 4/2007 | Shelton, IV et al. |
| 2007/0090788 A1 | 4/2007 | Hansford et al. |
| 2007/0093869 A1 | 4/2007 | Bloom et al. |
| 2007/0102472 A1 | 5/2007 | Shelton, IV |
| 2007/0106113 A1 | 5/2007 | Ravo |
| 2007/0106317 A1 | 5/2007 | Shelton, IV et al. |
| 2007/0118175 A1 | 5/2007 | Butler et al. |
| 2007/0129605 A1 | 6/2007 | Schaaf |
| 2007/0135686 A1 | 6/2007 | Pruitt, Jr. et al. |
| 2007/0135803 A1 | 6/2007 | Belson |
| 2007/0155010 A1 | 7/2007 | Farnsworth et al. |
| 2007/0158358 A1 | 7/2007 | Mason, II et al. |
| 2007/0170225 A1 | 7/2007 | Shelton, IV et al. |
| 2007/0173687 A1 | 7/2007 | Shima et al. |
| 2007/0173806 A1 | 7/2007 | Orszulak et al. |
| 2007/0173813 A1 | 7/2007 | Odom |
| 2007/0175950 A1 | 8/2007 | Shelton, IV et al. |
| 2007/0175951 A1 | 8/2007 | Shelton, IV et al. |
| 2007/0175955 A1 | 8/2007 | Shelton, IV et al. |
| 2007/0179528 A1 | 8/2007 | Soltz et al. |
| 2007/0181632 A1 | 8/2007 | Milliman |
| 2007/0190110 A1 | 8/2007 | Pameijer et al. |
| 2007/0191868 A1 | 8/2007 | Theroux et al. |
| 2007/0194079 A1 | 8/2007 | Hueil et al. |
| 2007/0194082 A1 | 8/2007 | Morgan et al. |
| 2007/0198039 A1 | 8/2007 | Jones et al. |
| 2007/0203510 A1 | 8/2007 | Bettuchi |
| 2007/0213750 A1 | 9/2007 | Weadock |
| 2007/0219571 A1 | 9/2007 | Balbierz et al. |
| 2007/0225562 A1 | 9/2007 | Spivey et al. |
| 2007/0233163 A1 | 10/2007 | Bombard et al. |
| 2007/0239028 A1 | 10/2007 | Houser et al. |
| 2007/0243227 A1 | 10/2007 | Gertner |
| 2007/0244471 A1 | 10/2007 | Malackowski |
| 2007/0246505 A1 | 10/2007 | Pace-Floridia et al. |
| 2007/0249999 A1 | 10/2007 | Sklar et al. |
| 2007/0250113 A1 | 10/2007 | Hegeman et al. |
| 2007/0260278 A1 | 11/2007 | Wheeler et al. |
| 2007/0270784 A1 | 11/2007 | Smith et al. |
| 2007/0270884 A1 | 11/2007 | Smith et al. |
| 2007/0275035 A1 | 11/2007 | Herman et al. |
| 2007/0276409 A1 | 11/2007 | Ortiz et al. |
| 2007/0279011 A1 | 12/2007 | Jones et al. |
| 2007/0286892 A1 | 12/2007 | Herzberg et al. |
| 2007/0287993 A1 | 12/2007 | Hinman et al. |
| 2007/0288044 A1 | 12/2007 | Jinno et al. |
| 2007/0299427 A1 | 12/2007 | Yeung et al. |
| 2008/0003196 A1 | 1/2008 | Jonn et al. |
| 2008/0015598 A1 | 1/2008 | Prommersberger |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0030170 A1 | 2/2008 | Dacquay et al. |
| 2008/0035701 A1 | 2/2008 | Racenet et al. |
| 2008/0041916 A1 | 2/2008 | Milliman et al. |
| 2008/0041917 A1 | 2/2008 | Racenet et al. |
| 2008/0051833 A1 | 2/2008 | Gramuglia et al. |
| 2008/0065153 A1 | 3/2008 | Allard et al. |
| 2008/0071328 A1 | 3/2008 | Haubrich et al. |
| 2008/0078802 A1 | 4/2008 | Hess et al. |
| 2008/0082114 A1 | 4/2008 | McKenna et al. |
| 2008/0082125 A1 | 4/2008 | Murray et al. |
| 2008/0082126 A1 | 4/2008 | Murray et al. |
| 2008/0083808 A1 | 4/2008 | Scirica |
| 2008/0083813 A1 | 4/2008 | Zemlok et al. |
| 2008/0085296 A1 | 4/2008 | Powell et al. |
| 2008/0086078 A1 | 4/2008 | Powell et al. |
| 2008/0091072 A1 | 4/2008 | Omori et al. |
| 2008/0097563 A1 | 4/2008 | Petrie et al. |
| 2008/0108443 A1 | 5/2008 | Jinno et al. |
| 2008/0114250 A1 | 5/2008 | Urbano et al. |
| 2008/0114315 A1 | 5/2008 | Voegele et al. |
| 2008/0114385 A1 | 5/2008 | Byrum et al. |
| 2008/0128469 A1 | 6/2008 | Dalessandro et al. |
| 2008/0129253 A1 | 6/2008 | Shiue et al. |
| 2008/0140115 A1 | 6/2008 | Stopek |
| 2008/0154299 A1 | 6/2008 | Livneh |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0172087 A1 | 7/2008 | Fuchs et al. |
| 2008/0172088 A1 | 7/2008 | Smith et al. |
| 2008/0183193 A1 | 7/2008 | Omori et al. |
| 2008/0185419 A1 | 8/2008 | Smith et al. |
| 2008/0190989 A1 | 8/2008 | Crews et al. |
| 2008/0197167 A1 | 8/2008 | Viola et al. |
| 2008/0200762 A1 | 8/2008 | Stokes et al. |
| 2008/0200835 A1 | 8/2008 | Monson et al. |
| 2008/0200933 A1 | 8/2008 | Bakos et al. |
| 2008/0200949 A1 | 8/2008 | Hiles et al. |
| 2008/0228029 A1 | 9/2008 | Mikkaichi et al. |
| 2008/0241667 A1 | 10/2008 | Kohn et al. |
| 2008/0245841 A1 | 10/2008 | Smith et al. |
| 2008/0249608 A1* | 10/2008 | Dave ..................... A61F 2/91 623/1.16 |
| 2008/0251568 A1 | 10/2008 | Zemlok et al. |
| 2008/0251569 A1 | 10/2008 | Smith et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0281171 A1 | 11/2008 | Fennell et al. |
| 2008/0281254 A1 | 11/2008 | Humayun et al. |
| 2008/0283570 A1 | 11/2008 | Boyden et al. |
| 2008/0287944 A1 | 11/2008 | Pearson et al. |
| 2008/0287988 A1 | 11/2008 | Smith et al. |
| 2008/0290134 A1 | 11/2008 | Bettuchi et al. |
| 2008/0294179 A1 | 11/2008 | Balbierz et al. |
| 2008/0296346 A1 | 12/2008 | Shelton, IV et al. |
| 2008/0297287 A1 | 12/2008 | Shachar et al. |
| 2008/0308602 A1 | 12/2008 | Timm et al. |
| 2008/0308603 A1 | 12/2008 | Shelton, IV et al. |
| 2008/0308608 A1 | 12/2008 | Prommersberger |
| 2008/0314960 A1 | 12/2008 | Marczyk et al. |
| 2008/0315829 A1 | 12/2008 | Jones et al. |
| 2009/0001121 A1 | 1/2009 | Hess et al. |
| 2009/0001130 A1 | 1/2009 | Hess et al. |
| 2009/0004455 A1 | 1/2009 | Gravagna et al. |

(56) References Cited

U.S. PATENT DOCUMENTS

| | | |
|---|---|---|
| 2009/0005809 A1 | 1/2009 | Hess et al. |
| 2009/0012534 A1 | 1/2009 | Madhani et al. |
| 2009/0015195 A1 | 1/2009 | Loth-Krausser |
| 2009/0018553 A1 | 1/2009 | McLean et al. |
| 2009/0020958 A1 | 1/2009 | Soul |
| 2009/0047329 A1 | 2/2009 | Stucky et al. |
| 2009/0048589 A1 | 2/2009 | Takashino et al. |
| 2009/0048612 A1 | 2/2009 | Farritor et al. |
| 2009/0054908 A1 | 2/2009 | Zand et al. |
| 2009/0069842 A1 | 3/2009 | Lee et al. |
| 2009/0076506 A1 | 3/2009 | Baker |
| 2009/0078736 A1 | 3/2009 | Van Lue |
| 2009/0082789 A1 | 3/2009 | Milliman et al. |
| 2009/0088659 A1 | 4/2009 | Graham et al. |
| 2009/0088774 A1 | 4/2009 | Swarup et al. |
| 2009/0090763 A1 | 4/2009 | Zemlok et al. |
| 2009/0092651 A1 | 4/2009 | Shah et al. |
| 2009/0093728 A1 | 4/2009 | Hyde et al. |
| 2009/0099579 A1 | 4/2009 | Nentwick et al. |
| 2009/0099876 A1 | 4/2009 | Whitman |
| 2009/0108048 A1 | 4/2009 | Zemlok et al. |
| 2009/0112229 A1 | 4/2009 | Omori et al. |
| 2009/0114701 A1 | 5/2009 | Zemlok et al. |
| 2009/0119011 A1 | 5/2009 | Kondo et al. |
| 2009/0137952 A1 | 5/2009 | Ramamurthy et al. |
| 2009/0143805 A1 | 6/2009 | Palmer et al. |
| 2009/0143855 A1 | 6/2009 | Weber et al. |
| 2009/0149871 A9 | 6/2009 | Kagan et al. |
| 2009/0157067 A1 | 6/2009 | Kane et al. |
| 2009/0157087 A1 | 6/2009 | Wei et al. |
| 2009/0171147 A1 | 7/2009 | Lee et al. |
| 2009/0177226 A1 | 7/2009 | Reinprecht et al. |
| 2009/0179757 A1 | 7/2009 | Cohn et al. |
| 2009/0188964 A1 | 7/2009 | Orlov |
| 2009/0198272 A1 | 8/2009 | Kerver et al. |
| 2009/0204108 A1 | 8/2009 | Steffen |
| 2009/0204109 A1 | 8/2009 | Grove et al. |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0213685 A1 | 8/2009 | Mak et al. |
| 2009/0234273 A1 | 9/2009 | Intoccia et al. |
| 2009/0242610 A1 | 10/2009 | Shelton, Iv et al. |
| 2009/0247368 A1 | 10/2009 | Chiang |
| 2009/0247901 A1 | 10/2009 | Zimmer |
| 2009/0248007 A1 | 10/2009 | Falkenstein et al. |
| 2009/0248038 A1 | 10/2009 | Blumenkranz et al. |
| 2009/0253959 A1 | 10/2009 | Yoshie et al. |
| 2009/0255974 A1 | 10/2009 | Viola |
| 2009/0255975 A1 | 10/2009 | Zemlok et al. |
| 2009/0255976 A1 | 10/2009 | Marczyk et al. |
| 2009/0255977 A1 | 10/2009 | Zemlok |
| 2009/0255978 A1 | 10/2009 | Viola et al. |
| 2009/0262078 A1 | 10/2009 | Pizzi |
| 2009/0270895 A1 | 10/2009 | Churchill et al. |
| 2009/0277949 A1 | 11/2009 | Viola et al. |
| 2009/0287300 A1* | 11/2009 | Dave .................. A61L 31/06 623/1.42 |
| 2009/0290016 A1 | 11/2009 | Suda |
| 2009/0292283 A1 | 11/2009 | Odom |
| 2009/0308907 A1 | 12/2009 | Nalagatla et al. |
| 2010/0010511 A1 | 1/2010 | Harris et al. |
| 2010/0012704 A1 | 1/2010 | Tarinelli Racenet et al. |
| 2010/0016852 A1 | 1/2010 | Manzo et al. |
| 2010/0016888 A1 | 1/2010 | Calabrese et al. |
| 2010/0023024 A1 | 1/2010 | Zeiner et al. |
| 2010/0036370 A1 | 2/2010 | Mirel et al. |
| 2010/0041945 A1 | 2/2010 | Isbell, Jr. |
| 2010/0049084 A1 | 2/2010 | Nock et al. |
| 2010/0057087 A1 | 3/2010 | Cha |
| 2010/0057107 A1 | 3/2010 | Sorrentino et al. |
| 2010/0069942 A1 | 3/2010 | Shelton, IV |
| 2010/0072254 A1 | 3/2010 | Aranyi et al. |
| 2010/0076483 A1 | 3/2010 | Imuta |
| 2010/0076489 A1 | 3/2010 | Stopek et al. |
| 2010/0081883 A1 | 4/2010 | Murray et al. |
| 2010/0087840 A1* | 4/2010 | Ebersole .......... A61B 17/07207 606/151 |
| 2010/0094289 A1 | 4/2010 | Taylor et al. |
| 2010/0096431 A1 | 4/2010 | Smith et al. |
| 2010/0100124 A1 | 4/2010 | Calabrese et al. |
| 2010/0108740 A1 | 5/2010 | Pastorelli et al. |
| 2010/0108741 A1 | 5/2010 | Hessler et al. |
| 2010/0122339 A1 | 5/2010 | Boccacci |
| 2010/0133317 A1 | 6/2010 | Shelton, IV et al. |
| 2010/0145146 A1 | 6/2010 | Melder |
| 2010/0147921 A1 | 6/2010 | Olson |
| 2010/0147922 A1 | 6/2010 | Olson |
| 2010/0147923 A1 | 6/2010 | D'Agostino et al. |
| 2010/0163598 A1 | 7/2010 | Belzer |
| 2010/0179022 A1 | 7/2010 | Shirokoshi |
| 2010/0179540 A1 | 7/2010 | Marczyk et al. |
| 2010/0180711 A1 | 7/2010 | Kilibarda et al. |
| 2010/0186219 A1 | 7/2010 | Smith |
| 2010/0191292 A1 | 7/2010 | DeMeo et al. |
| 2010/0193566 A1 | 8/2010 | Scheib et al. |
| 2010/0200637 A1 | 8/2010 | Beetel |
| 2010/0204717 A1 | 8/2010 | Knodel |
| 2010/0222901 A1 | 9/2010 | Swayze et al. |
| 2010/0230465 A1 | 9/2010 | Smith et al. |
| 2010/0243707 A1 | 9/2010 | Olson et al. |
| 2010/0243708 A1 | 9/2010 | Aranyi et al. |
| 2010/0249497 A1 | 9/2010 | Peine et al. |
| 2010/0249519 A1 | 9/2010 | Park et al. |
| 2010/0249759 A1 | 9/2010 | Hinman et al. |
| 2010/0258611 A1 | 10/2010 | Smith et al. |
| 2010/0267662 A1 | 10/2010 | Fielder et al. |
| 2010/0268030 A1 | 10/2010 | Viola et al. |
| 2010/0274160 A1 | 10/2010 | Yachi et al. |
| 2010/0276471 A1 | 11/2010 | Whitman |
| 2010/0278891 A1* | 11/2010 | Ringeisen .............. A61B 17/80 424/422 |
| 2010/0292540 A1 | 11/2010 | Hess et al. |
| 2010/0294827 A1 | 11/2010 | Boyden et al. |
| 2010/0298636 A1 | 11/2010 | Castro et al. |
| 2010/0312261 A1 | 12/2010 | Suzuki et al. |
| 2010/0320252 A1 | 12/2010 | Viola et al. |
| 2010/0331856 A1 | 12/2010 | Carlson et al. |
| 2010/0331880 A1 | 12/2010 | Stopek |
| 2011/0003528 A1 | 1/2011 | Lam |
| 2011/0006101 A1 | 1/2011 | Hall et al. |
| 2011/0009890 A1 | 1/2011 | Palmer et al. |
| 2011/0011916 A1 | 1/2011 | Levine |
| 2011/0016960 A1 | 1/2011 | Debrailly |
| 2011/0017799 A1 | 1/2011 | Whitman et al. |
| 2011/0021871 A1 | 1/2011 | Berkelaar |
| 2011/0022032 A1 | 1/2011 | Zemlok et al. |
| 2011/0024477 A1 | 2/2011 | Hall et al. |
| 2011/0024478 A1 | 2/2011 | Shelton, IV |
| 2011/0025311 A1 | 2/2011 | Chauvin et al. |
| 2011/0034910 A1 | 2/2011 | Ross et al. |
| 2011/0034918 A1 | 2/2011 | Reschke |
| 2011/0036887 A1 | 2/2011 | Zemlok et al. |
| 2011/0036890 A1 | 2/2011 | Ma |
| 2011/0036891 A1 | 2/2011 | Zemlok et al. |
| 2011/0045047 A1 | 2/2011 | Bennett et al. |
| 2011/0046666 A1 | 2/2011 | Sorrentino et al. |
| 2011/0046667 A1 | 2/2011 | Culligan et al. |
| 2011/0060356 A1 | 3/2011 | Reschke et al. |
| 2011/0060363 A1 | 3/2011 | Hess et al. |
| 2011/0082538 A1 | 4/2011 | Dahlgren et al. |
| 2011/0084112 A1 | 4/2011 | Kostrzewski |
| 2011/0087276 A1 | 4/2011 | Bedi et al. |
| 2011/0087279 A1 | 4/2011 | Shah et al. |
| 2011/0088921 A1 | 4/2011 | Forgues et al. |
| 2011/0095068 A1 | 4/2011 | Patel |
| 2011/0101065 A1 | 5/2011 | Milliman |
| 2011/0101069 A1 | 5/2011 | Bombard et al. |
| 2011/0112517 A1 | 5/2011 | Peine et al. |

(56) References Cited

U.S. PATENT DOCUMENTS

| | | |
|---|---|---|
| 2011/0114697 A1 | 5/2011 | Baxter, III et al. |
| 2011/0118778 A1 | 5/2011 | Burbank |
| 2011/0121049 A1 | 5/2011 | Malinouskas et al. |
| 2011/0125138 A1 | 5/2011 | Malinouskas et al. |
| 2011/0125176 A1 | 5/2011 | Yates et al. |
| 2011/0144640 A1 | 6/2011 | Heinrich et al. |
| 2011/0147433 A1 | 6/2011 | Shelton, IV et al. |
| 2011/0155786 A1 | 6/2011 | Shelton, IV |
| 2011/0163146 A1 | 7/2011 | Ortiz et al. |
| 2011/0167619 A1 | 7/2011 | Smith et al. |
| 2011/0174099 A1 | 7/2011 | Ross et al. |
| 2011/0174861 A1 | 7/2011 | Shelton, IV et al. |
| 2011/0178536 A1 | 7/2011 | Kostrzewski |
| 2011/0184459 A1 | 7/2011 | Malkowski et al. |
| 2011/0192882 A1 | 8/2011 | Hess et al. |
| 2011/0199225 A1 | 8/2011 | Touchberry et al. |
| 2011/0208093 A1 | 8/2011 | Gross et al. |
| 2011/0210156 A1 | 9/2011 | Smith et al. |
| 2011/0218550 A1 | 9/2011 | Ma |
| 2011/0241597 A1 | 10/2011 | Zhu et al. |
| 2011/0253765 A1 | 10/2011 | Nicholas et al. |
| 2011/0257650 A1 | 10/2011 | Deville et al. |
| 2011/0264119 A1 | 10/2011 | Bayon et al. |
| 2011/0275901 A1 | 11/2011 | Shelton, IV |
| 2011/0276083 A1 | 11/2011 | Shelton, IV et al. |
| 2011/0278343 A1 | 11/2011 | Knodel et al. |
| 2011/0279268 A1 | 11/2011 | Konishi et al. |
| 2011/0282446 A1 | 11/2011 | Schulte et al. |
| 2011/0290851 A1 | 12/2011 | Shelton, IV |
| 2011/0290856 A1 | 12/2011 | Shelton, IV et al. |
| 2011/0293690 A1 | 12/2011 | Griffin et al. |
| 2011/0295295 A1 | 12/2011 | Shelton, IV et al. |
| 2011/0307023 A1 | 12/2011 | Tweden et al. |
| 2011/0313894 A1 | 12/2011 | Dye et al. |
| 2011/0315413 A1 | 12/2011 | Fisher et al. |
| 2012/0004636 A1 | 1/2012 | Lo |
| 2012/0016413 A1 | 1/2012 | Timm et al. |
| 2012/0018326 A1 | 1/2012 | Racenet et al. |
| 2012/0022523 A1 | 1/2012 | Smith et al. |
| 2012/0022630 A1 | 1/2012 | Wübbeling |
| 2012/0029272 A1 | 2/2012 | Shelton, IV et al. |
| 2012/0033360 A1 | 2/2012 | Hsu |
| 2012/0045303 A1 | 2/2012 | Macdonald |
| 2012/0046692 A1 | 2/2012 | Smith et al. |
| 2012/0064483 A1 | 3/2012 | Lint et al. |
| 2012/0074200 A1 | 3/2012 | Schmid et al. |
| 2012/0078071 A1 | 3/2012 | Bohm et al. |
| 2012/0078244 A1 | 3/2012 | Worrell et al. |
| 2012/0078278 A1 | 3/2012 | Bales, Jr. et al. |
| 2012/0080332 A1 | 4/2012 | Shelton, IV et al. |
| 2012/0080336 A1 | 4/2012 | Shelton, IV et al. |
| 2012/0080337 A1 | 4/2012 | Shelton, IV et al. |
| 2012/0080338 A1 | 4/2012 | Shelton, IV et al. |
| 2012/0080340 A1 | 4/2012 | Shelton, IV et al. |
| 2012/0080344 A1 | 4/2012 | Shelton, IV |
| 2012/0080475 A1 | 4/2012 | Smith et al. |
| 2012/0080478 A1 | 4/2012 | Morgan et al. |
| 2012/0080479 A1 | 4/2012 | Shelton, IV |
| 2012/0080481 A1 | 4/2012 | Widenhouse et al. |
| 2012/0080482 A1 | 4/2012 | Schall et al. |
| 2012/0080484 A1 | 4/2012 | Morgan et al. |
| 2012/0080485 A1 | 4/2012 | Woodard, Jr. et al. |
| 2012/0080486 A1 | 4/2012 | Woodard, Jr. et al. |
| 2012/0080488 A1 | 4/2012 | Shelton, IV et al. |
| 2012/0080489 A1 | 4/2012 | Shelton, IV et al. |
| 2012/0080491 A1 | 4/2012 | Shelton, IV et al. |
| 2012/0080493 A1 | 4/2012 | Shelton, IV et al. |
| 2012/0080498 A1 | 4/2012 | Shelton, IV et al. |
| 2012/0080499 A1 | 4/2012 | Schall et al. |
| 2012/0080500 A1 | 4/2012 | Morgan et al. |
| 2012/0080502 A1 | 4/2012 | Morgan et al. |
| 2012/0083835 A1 | 4/2012 | Shelton, IV et al. |
| 2012/0083836 A1 | 4/2012 | Shelton, IV et al. |
| 2012/0089131 A1 | 4/2012 | Zemlok et al. |
| 2012/0110810 A1 | 5/2012 | Houser et al. |
| 2012/0116265 A1 | 5/2012 | Houser et al. |
| 2012/0116367 A1 | 5/2012 | Houser et al. |
| 2012/0116388 A1 | 5/2012 | Houser et al. |
| 2012/0116391 A1 | 5/2012 | Houser et al. |
| 2012/0116395 A1 | 5/2012 | Madan et al. |
| 2012/0123203 A1 | 5/2012 | Riva |
| 2012/0125792 A1 | 5/2012 | Cassivi |
| 2012/0138658 A1 | 6/2012 | Ullrich et al. |
| 2012/0160721 A1 | 6/2012 | Shelton, IV et al. |
| 2012/0175398 A1 | 7/2012 | Sandborn et al. |
| 2012/0187179 A1 | 7/2012 | Gleiman |
| 2012/0209289 A1 | 8/2012 | Duque et al. |
| 2012/0223121 A1 | 9/2012 | Viola et al. |
| 2012/0228355 A1 | 9/2012 | Combrowski et al. |
| 2012/0234895 A1 | 9/2012 | O'Connor et al. |
| 2012/0234897 A1 | 9/2012 | Shelton, IV et al. |
| 2012/0234899 A1 | 9/2012 | Scheib et al. |
| 2012/0241491 A1 | 9/2012 | Aldridge et al. |
| 2012/0241492 A1 | 9/2012 | Shelton, IV et al. |
| 2012/0241493 A1 | 9/2012 | Baxter, III et al. |
| 2012/0241496 A1 | 9/2012 | Mandakolathur Vasudevan et al. |
| 2012/0241497 A1 | 9/2012 | Mandakolathur Vasudevan et al. |
| 2012/0241498 A1 | 9/2012 | Gonzalez et al. |
| 2012/0241499 A1 | 9/2012 | Baxter, III et al. |
| 2012/0241500 A1 | 9/2012 | Timmer et al. |
| 2012/0241501 A1 | 9/2012 | Swayze et al. |
| 2012/0241502 A1 | 9/2012 | Aldridge et al. |
| 2012/0241503 A1 | 9/2012 | Baxter, III et al. |
| 2012/0241505 A1 | 9/2012 | Alexander, III et al. |
| 2012/0248167 A1 | 10/2012 | Flanagan et al. |
| 2012/0248169 A1 | 10/2012 | Widenhouse et al. |
| 2012/0253298 A1 | 10/2012 | Henderson et al. |
| 2012/0253329 A1 | 10/2012 | Zemlok et al. |
| 2012/0265176 A1 | 10/2012 | Braun |
| 2012/0271285 A1 | 10/2012 | Sholev et al. |
| 2012/0273550 A1 | 11/2012 | Scirica |
| 2012/0277780 A1 | 11/2012 | Smith et al. |
| 2012/0283707 A1 | 11/2012 | Giordano et al. |
| 2012/0286021 A1 | 11/2012 | Kostrzewski et al. |
| 2012/0289979 A1 | 11/2012 | Eskaros et al. |
| 2012/0292367 A1 | 11/2012 | Morgan et al. |
| 2012/0296333 A1 | 11/2012 | Twomey |
| 2012/0298719 A1 | 11/2012 | Shelton, IV et al. |
| 2012/0298722 A1 | 11/2012 | Hess et al. |
| 2012/0310255 A1 | 12/2012 | Brisson et al. |
| 2012/0310256 A1 | 12/2012 | Brisson |
| 2012/0312860 A1 | 12/2012 | Ming et al. |
| 2012/0318842 A1 | 12/2012 | Anim et al. |
| 2012/0318844 A1* | 12/2012 | Shelton, IV ..... A61B 17/00491 227/176.1 |
| 2012/0325892 A1 | 12/2012 | Kostrzewski |
| 2013/0012983 A1 | 1/2013 | Kleyman |
| 2013/0018361 A1 | 1/2013 | Bryant |
| 2013/0020375 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0026973 A1 | 1/2013 | Luke et al. |
| 2013/0030608 A1 | 1/2013 | Taylor et al. |
| 2013/0032626 A1 | 2/2013 | Smith et al. |
| 2013/0037596 A1 | 2/2013 | Bear et al. |
| 2013/0046290 A1 | 2/2013 | Palmer et al. |
| 2013/0053851 A1* | 2/2013 | Schmitz ............. A61B 10/0275 606/79 |
| 2013/0060278 A1 | 3/2013 | Bozung et al. |
| 2013/0062391 A1 | 3/2013 | Boudreaux et al. |
| 2013/0075446 A1 | 3/2013 | Wang et al. |
| 2013/0075448 A1 | 3/2013 | Schmid et al. |
| 2013/0075449 A1 | 3/2013 | Schmid et al. |
| 2013/0075450 A1 | 3/2013 | Schmid et al. |
| 2013/0079814 A1 | 3/2013 | Hess et al. |
| 2013/0087597 A1 | 4/2013 | Shelton, IV et al. |
| 2013/0087599 A1 | 4/2013 | Krumanaker et al. |
| 2013/0087602 A1 | 4/2013 | Olson et al. |
| 2013/0090534 A1 | 4/2013 | Burns et al. |
| 2013/0098970 A1 | 4/2013 | Racenet et al. |
| 2013/0103023 A1 | 4/2013 | Monson et al. |
| 2013/0103024 A1 | 4/2013 | Monson et al. |

(56) References Cited

U.S. PATENT DOCUMENTS

| | | |
|---|---|---|
| 2013/0105548 A1 | 5/2013 | Hodgkinson et al. |
| 2013/0116668 A1 | 5/2013 | Shelton, IV et al. |
| 2013/0116669 A1 | 5/2013 | Shelton, IV et al. |
| 2013/0119108 A1 | 5/2013 | Altman et al. |
| 2013/0123822 A1 | 5/2013 | Wellman et al. |
| 2013/0126379 A1 | 5/2013 | Medhal et al. |
| 2013/0131651 A1 | 5/2013 | Strobl et al. |
| 2013/0146641 A1 | 6/2013 | Shelton, IV et al. |
| 2013/0146642 A1 | 6/2013 | Shelton, IV et al. |
| 2013/0146643 A1* | 6/2013 | Schmid .............. A61B 17/0682 227/180.1 |
| 2013/0150832 A1 | 6/2013 | Belson et al. |
| 2013/0153633 A1 | 6/2013 | Casasanta, Jr. et al. |
| 2013/0153634 A1 | 6/2013 | Carter et al. |
| 2013/0153635 A1 | 6/2013 | Hodgkinson |
| 2013/0153636 A1 | 6/2013 | Shelton, IV et al. |
| 2013/0153638 A1 | 6/2013 | Carter et al. |
| 2013/0153641 A1 | 6/2013 | Shelton, IV et al. |
| 2013/0161374 A1 | 6/2013 | Swayze et al. |
| 2013/0168431 A1 | 7/2013 | Zemlok et al. |
| 2013/0172929 A1 | 7/2013 | Hess et al. |
| 2013/0175317 A1 | 7/2013 | Yates et al. |
| 2013/0175322 A1 | 7/2013 | Yates et al. |
| 2013/0186933 A1 | 7/2013 | Shelton, IV et al. |
| 2013/0186934 A1 | 7/2013 | Shelton, IV et al. |
| 2013/0190733 A1 | 7/2013 | Giordano et al. |
| 2013/0190757 A1 | 7/2013 | Yates et al. |
| 2013/0193188 A1 | 8/2013 | Shelton, IV et al. |
| 2013/0193189 A1 | 8/2013 | Swensgard et al. |
| 2013/0197556 A1 | 8/2013 | Shelton, IV et al. |
| 2013/0214025 A1 | 8/2013 | Zemlok et al. |
| 2013/0214030 A1* | 8/2013 | Aronhalt ............ A61B 17/0682 227/176.1 |
| 2013/0221059 A1 | 8/2013 | Racenet et al. |
| 2013/0221063 A1 | 8/2013 | Aronhalt et al. |
| 2013/0221064 A1 | 8/2013 | Aronhalt et al. |
| 2013/0221065 A1 | 8/2013 | Aronhalt et al. |
| 2013/0233905 A1 | 9/2013 | Sorrentino et al. |
| 2013/0233906 A1 | 9/2013 | Hess et al. |
| 2013/0233908 A1 | 9/2013 | Knodel et al. |
| 2013/0238021 A1 | 9/2013 | Gross et al. |
| 2013/0256365 A1 | 10/2013 | Shelton, IV et al. |
| 2013/0256366 A1* | 10/2013 | Shelton, IV ..... A61B 17/07207 227/175.1 |
| 2013/0256367 A1 | 10/2013 | Scheib et al. |
| 2013/0256368 A1 | 10/2013 | Timm et al. |
| 2013/0256369 A1 | 10/2013 | Schmid et al. |
| 2013/0256371 A1 | 10/2013 | Shelton, IV |
| 2013/0256372 A1 | 10/2013 | Baxter, III et al. |
| 2013/0256373 A1 | 10/2013 | Schmid et al. |
| 2013/0256374 A1 | 10/2013 | Shelton, Iv et al. |
| 2013/0256375 A1 | 10/2013 | Shelton, Iv et al. |
| 2013/0256377 A1 | 10/2013 | Schmid et al. |
| 2013/0256378 A1 | 10/2013 | Schmid et al. |
| 2013/0256379 A1 | 10/2013 | Schmid et al. |
| 2013/0256380 A1 | 10/2013 | Schmid et al. |
| 2013/0256382 A1 | 10/2013 | Swayze et al. |
| 2013/0256383 A1 | 10/2013 | Aronhalt et al. |
| 2013/0261648 A1 | 10/2013 | Laurent et al. |
| 2013/0267945 A1 | 10/2013 | Behnke et al. |
| 2013/0270322 A1 | 10/2013 | Scheib et al. |
| 2013/0277412 A1 | 10/2013 | Gresham et al. |
| 2013/0282052 A1 | 10/2013 | Aranyi et al. |
| 2013/0310873 A1 | 11/2013 | Stopek (nee Prommersberger) et al. |
| 2013/0313304 A1 | 11/2013 | Shelton, IV et al. |
| 2013/0313306 A1 | 11/2013 | Shelton, IV et al. |
| 2013/0319706 A1 | 12/2013 | Nicholas et al. |
| 2013/0324981 A1 | 12/2013 | Smith et al. |
| 2013/0324982 A1 | 12/2013 | Smith et al. |
| 2013/0327809 A1 | 12/2013 | Shelton, IV et al. |
| 2013/0327810 A1 | 12/2013 | Swayze et al. |
| 2013/0334283 A1 | 12/2013 | Swayze et al. |
| 2013/0334284 A1 | 12/2013 | Swayze et al. |
| 2013/0334285 A1 | 12/2013 | Swayze et al. |
| 2013/0334286 A1 | 12/2013 | Swayze et al. |
| 2013/0334287 A1 | 12/2013 | Shelton, IV |
| 2013/0334288 A1 | 12/2013 | Shelton, IV |
| 2013/0341374 A1 | 12/2013 | Shelton, IV et al. |
| 2014/0001231 A1 | 1/2014 | Shelton, IV et al. |
| 2014/0001234 A1 | 1/2014 | Shelton, IV et al. |
| 2014/0001237 A1 | 1/2014 | Shelton, IV et al. |
| 2014/0001238 A1 | 1/2014 | Shelton, IV et al. |
| 2014/0001239 A1 | 1/2014 | Shelton, IV et al. |
| 2014/0001240 A1 | 1/2014 | Shelton, IV et al. |
| 2014/0005640 A1 | 1/2014 | Shelton, IV et al. |
| 2014/0005678 A1 | 1/2014 | Shelton, Iv et al. |
| 2014/0005681 A1 | 1/2014 | Gee et al. |
| 2014/0005693 A1 | 1/2014 | Shelton, IV et al. |
| 2014/0005694 A1 | 1/2014 | Shelton, IV et al. |
| 2014/0005702 A1 | 1/2014 | Timm et al. |
| 2014/0005703 A1 | 1/2014 | Stulen et al. |
| 2014/0005718 A1 | 1/2014 | Shelton, IV et al. |
| 2014/0008414 A1 | 1/2014 | Shelton, IV et al. |
| 2014/0012237 A1 | 1/2014 | Pribanic et al. |
| 2014/0012238 A1 | 1/2014 | Chen et al. |
| 2014/0012289 A1 | 1/2014 | Snow et al. |
| 2014/0014705 A1 | 1/2014 | Baxter, III |
| 2014/0015782 A1 | 1/2014 | Kim et al. |
| 2014/0018832 A1 | 1/2014 | Shelton, IV |
| 2014/0025046 A1 | 1/2014 | Williams et al. |
| 2014/0042205 A1 | 2/2014 | Baxter, III et al. |
| 2014/0048580 A1 | 2/2014 | Merchant et al. |
| 2014/0061279 A1 | 3/2014 | Laurent et al. |
| 2014/0061280 A1 | 3/2014 | Ingmanson et al. |
| 2014/0097227 A1 | 4/2014 | Aronhalt et al. |
| 2014/0100558 A1 | 4/2014 | Schmitz et al. |
| 2014/0103093 A1 | 4/2014 | Koch, Jr. et al. |
| 2014/0107640 A1 | 4/2014 | Yates et al. |
| 2014/0110455 A1 | 4/2014 | Ingmanson et al. |
| 2014/0128850 A1 | 5/2014 | Kerr et al. |
| 2014/0138423 A1 | 5/2014 | Whitfield et al. |
| 2014/0151431 A1 | 6/2014 | Hodgkinson et al. |
| 2014/0151433 A1 | 6/2014 | Shelton, IV et al. |
| 2014/0166722 A1 | 6/2014 | Hess et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0171966 A1 | 6/2014 | Giordano et al. |
| 2014/0175152 A1 | 6/2014 | Hess et al. |
| 2014/0175154 A1 | 6/2014 | Shelton, IV et al. |
| 2014/0191014 A1 | 7/2014 | Shelton, IV |
| 2014/0191015 A1 | 7/2014 | Shelton, Iv |
| 2014/0203061 A1 | 7/2014 | Hodgkinson |
| 2014/0205637 A1 | 7/2014 | Widenhouse et al. |
| 2014/0207125 A1 | 7/2014 | Applegate et al. |
| 2014/0207166 A1 | 7/2014 | Shelton, IV et al. |
| 2014/0224686 A1* | 8/2014 | Aronhalt ............ A61B 17/068 206/339 |
| 2014/0224857 A1 | 8/2014 | Schmid |
| 2014/0230595 A1 | 8/2014 | Butt et al. |
| 2014/0232316 A1 | 8/2014 | Philipp |
| 2014/0236184 A1 | 8/2014 | Leimbach et al. |
| 2014/0239036 A1 | 8/2014 | Zerkle et al. |
| 2014/0239038 A1 | 8/2014 | Leimbach et al. |
| 2014/0243865 A1 | 8/2014 | Swayze et al. |
| 2014/0246471 A1 | 9/2014 | Jaworek et al. |
| 2014/0246472 A1 | 9/2014 | Kimsey et al. |
| 2014/0246475 A1 | 9/2014 | Hall et al. |
| 2014/0246478 A1 | 9/2014 | Baber et al. |
| 2014/0246479 A1 | 9/2014 | Baber et al. |
| 2014/0249557 A1 | 9/2014 | Koch, Jr. et al. |
| 2014/0252066 A1 | 9/2014 | Shelton, IV et al. |
| 2014/0252068 A1 | 9/2014 | Shelton, IV et al. |
| 2014/0259591 A1 | 9/2014 | Shelton, IV et al. |
| 2014/0263538 A1 | 9/2014 | Leimbach et al. |
| 2014/0263539 A1 | 9/2014 | Leimbach et al. |
| 2014/0263541 A1 | 9/2014 | Leimbach et al. |
| 2014/0263542 A1 | 9/2014 | Leimbach et al. |
| 2014/0263552 A1 | 9/2014 | Hall et al. |
| 2014/0263554 A1 | 9/2014 | Leimbach et al. |
| 2014/0263558 A1 | 9/2014 | Hausen et al. |
| 2014/0263562 A1 | 9/2014 | Patel et al. |
| 2014/0263564 A1 | 9/2014 | Leimbach et al. |

(56) References Cited

U.S. PATENT DOCUMENTS

| | | |
|---|---|---|
| 2014/0263565 A1 | 9/2014 | Lytle, IV et al. |
| 2014/0263572 A1 | 9/2014 | Shelton, IV et al. |
| 2014/0277017 A1 | 9/2014 | Leimbach et al. |
| 2014/0284371 A1 | 9/2014 | Morgan et al. |
| 2014/0284373 A1 | 9/2014 | Shelton, IV et al. |
| 2014/0291378 A1 | 10/2014 | Shelton, IV et al. |
| 2014/0291379 A1 | 10/2014 | Schellin et al. |
| 2014/0291380 A1 | 10/2014 | Weaner et al. |
| 2014/0291382 A1 | 10/2014 | Lloyd et al. |
| 2014/0291383 A1 | 10/2014 | Spivey et al. |
| 2014/0296873 A1 | 10/2014 | Morgan et al. |
| 2014/0296874 A1 | 10/2014 | Morgan et al. |
| 2014/0299648 A1 | 10/2014 | Shelton, Iv et al. |
| 2014/0303645 A1 | 10/2014 | Morgan et al. |
| 2014/0303646 A1 | 10/2014 | Morgan et al. |
| 2014/0305987 A1 | 10/2014 | Parihar et al. |
| 2014/0305988 A1 | 10/2014 | Boudreaux et al. |
| 2014/0305989 A1 | 10/2014 | Parihar et al. |
| 2014/0305990 A1 | 10/2014 | Shelton, IV et al. |
| 2014/0305991 A1 | 10/2014 | Parihar et al. |
| 2014/0305992 A1 | 10/2014 | Kimsey et al. |
| 2014/0305994 A1 | 10/2014 | Parihar et al. |
| 2014/0309665 A1 | 10/2014 | Parihar et al. |
| 2014/0309666 A1 | 10/2014 | Shelton, IV et al. |
| 2014/0330161 A1 | 11/2014 | Swayze et al. |
| 2014/0339286 A1 | 11/2014 | Motooka et al. |
| 2014/0352463 A1 | 12/2014 | Parihar |
| 2014/0353358 A1 | 12/2014 | Shelton, IV et al. |
| 2014/0367447 A1 | 12/2014 | Woodard, Jr. et al. |
| 2014/0378950 A1 | 12/2014 | Chiu |
| 2015/0008248 A1 | 1/2015 | Giordano et al. |
| 2015/0034696 A1 | 2/2015 | Shelton, IV et al. |
| 2015/0038986 A1 | 2/2015 | Swensgard et al. |
| 2015/0041518 A1 | 2/2015 | Shelton, IV et al. |
| 2015/0053737 A1 | 2/2015 | Leimbach et al. |
| 2015/0053738 A1 | 2/2015 | Morgan et al. |
| 2015/0053739 A1 | 2/2015 | Morgan et al. |
| 2015/0053740 A1 | 2/2015 | Shelton, IV |
| 2015/0053741 A1 | 2/2015 | Shelton, IV et al. |
| 2015/0053742 A1 | 2/2015 | Shelton, IV et al. |
| 2015/0053743 A1 | 2/2015 | Yates et al. |
| 2015/0053744 A1 | 2/2015 | Swayze et al. |
| 2015/0053745 A1 | 2/2015 | Yates et al. |
| 2015/0053746 A1 | 2/2015 | Shelton, IV et al. |
| 2015/0053748 A1 | 2/2015 | Yates et al. |
| 2015/0060518 A1 | 3/2015 | Shelton, IV et al. |
| 2015/0060519 A1 | 3/2015 | Shelton, IV et al. |
| 2015/0060520 A1 | 3/2015 | Shelton, IV et al. |
| 2015/0060521 A1 | 3/2015 | Weisenburgh, IV et al. |
| 2015/0076207 A1 | 3/2015 | Boudreaux et al. |
| 2015/0076208 A1 | 3/2015 | Shelton, IV |
| 2015/0076209 A1 | 3/2015 | Shelton, IV et al. |
| 2015/0076210 A1 | 3/2015 | Shelton, IV et al. |
| 2015/0076212 A1 | 3/2015 | Shelton, IV |
| 2015/0080868 A1 | 3/2015 | Kerr |
| 2015/0083780 A1 | 3/2015 | Shelton, IV et al. |
| 2015/0083781 A1 | 3/2015 | Giordano et al. |
| 2015/0083782 A1 | 3/2015 | Scheib et al. |
| 2015/0083783 A1 | 3/2015 | Shelton, IV et al. |
| 2015/0090759 A1 | 4/2015 | Spivey et al. |
| 2015/0090760 A1 | 4/2015 | Giordano et al. |
| 2015/0090761 A1 | 4/2015 | Giordano et al. |
| 2015/0090762 A1 | 4/2015 | Giordano et al. |
| 2015/0090763 A1 | 4/2015 | Murray et al. |
| 2015/0108199 A1 | 4/2015 | Shelton, IV et al. |
| 2015/0122869 A1 | 5/2015 | Aronhalt et al. |
| 2015/0136830 A1 | 5/2015 | Baxter, III et al. |
| 2015/0136831 A1 | 5/2015 | Baxter, III et al. |
| 2015/0136832 A1 | 5/2015 | Baxter, III et al. |
| 2015/0136833 A1 | 5/2015 | Shelton, IV et al. |
| 2015/0136835 A1 | 5/2015 | Shelton, IV et al. |
| 2015/0157354 A1 | 6/2015 | Bales, Jr. et al. |
| 2015/0173744 A1 | 6/2015 | Shelton, IV et al. |
| 2015/0173745 A1 | 6/2015 | Baxter, III et al. |
| 2015/0173746 A1 | 6/2015 | Baxter, III et al. |
| 2015/0173747 A1 | 6/2015 | Baxter, III et al. |
| 2015/0173749 A1 | 6/2015 | Shelton, IV et al. |
| 2015/0173750 A1 | 6/2015 | Shelton, IV et al. |
| 2015/0173751 A1 | 6/2015 | Shelton, IV et al. |
| 2015/0173755 A1 | 6/2015 | Baxter, III et al. |
| 2015/0173756 A1 | 6/2015 | Baxter, III et al. |
| 2015/0173760 A1 | 6/2015 | Shelton, IV et al. |
| 2015/0173761 A1 | 6/2015 | Shelton, IV et al. |
| 2015/0173762 A1 | 6/2015 | Shelton, IV et al. |
| 2015/0173789 A1 | 6/2015 | Baxter, III et al. |
| 2015/0182220 A1 | 7/2015 | Yates et al. |
| 2015/0182222 A1 | 7/2015 | Swayze et al. |
| 2015/0196295 A1 | 7/2015 | Shelton, IV et al. |
| 2015/0196296 A1 | 7/2015 | Swayze et al. |
| 2015/0196299 A1 | 7/2015 | Swayze et al. |
| 2015/0196347 A1 | 7/2015 | Yates et al. |
| 2015/0196348 A1 | 7/2015 | Yates et al. |
| 2015/0201932 A1 | 7/2015 | Swayze et al. |
| 2015/0201935 A1 | 7/2015 | Weisenburgh, II et al. |
| 2015/0201936 A1 | 7/2015 | Swayze et al. |
| 2015/0201937 A1 | 7/2015 | Swayze et al. |
| 2015/0201938 A1 | 7/2015 | Swayze et al. |
| 2015/0201939 A1 | 7/2015 | Swayze et al. |
| 2015/0201940 A1 | 7/2015 | Swayze et al. |
| 2015/0201941 A1 | 7/2015 | Swayze et al. |
| 2015/0209031 A1 | 7/2015 | Shelton, IV et al. |
| 2015/0209038 A1 | 7/2015 | Shelton, IV et al. |
| 2015/0209039 A1 | 7/2015 | Shelton, IV et al. |
| 2015/0209041 A1 | 7/2015 | Milliman et al. |
| 2015/0223809 A1 | 8/2015 | Scheib et al. |
| 2015/0223816 A1 | 8/2015 | Morgan et al. |
| 2015/0230783 A1 | 8/2015 | Shelton, IV et al. |
| 2015/0230784 A1 | 8/2015 | Shelton, IV et al. |
| 2015/0231409 A1 | 8/2015 | Racenet et al. |
| 2015/0238185 A1 | 8/2015 | Schellin et al. |
| 2015/0238186 A1 | 8/2015 | Aronhalt et al. |
| 2015/0238187 A1 | 8/2015 | Schellin et al. |
| 2015/0238188 A1 | 8/2015 | Vendely et al. |
| 2015/0238191 A1 | 8/2015 | Schellin et al. |
| 2015/0239180 A1 | 8/2015 | Schellin et al. |
| 2015/0265276 A1 | 9/2015 | Huitema et al. |
| 2015/0265357 A1 | 9/2015 | Shelton, IV et al. |
| 2015/0272557 A1 | 10/2015 | Overmyer et al. |
| 2015/0272569 A1 | 10/2015 | Leimbach et al. |
| 2015/0272570 A1 | 10/2015 | Lytle, IV et al. |
| 2015/0272571 A1 | 10/2015 | Leimbach et al. |
| 2015/0272572 A1 | 10/2015 | Overmyer et al. |
| 2015/0272574 A1 | 10/2015 | Leimbach et al. |
| 2015/0272575 A1 | 10/2015 | Leimbach et al. |
| 2015/0272578 A1 | 10/2015 | Leimbach et al. |
| 2015/0272579 A1 | 10/2015 | Leimbach et al. |
| 2015/0272580 A1 | 10/2015 | Leimbach et al. |
| 2015/0272581 A1 | 10/2015 | Leimbach et al. |
| 2015/0272582 A1 | 10/2015 | Leimbach et al. |
| 2015/0272583 A1 | 10/2015 | Leimbach et al. |
| 2015/0277471 A1 | 10/2015 | Leimbach et al. |
| 2015/0280384 A1 | 10/2015 | Leimbach et al. |
| 2015/0280424 A1 | 10/2015 | Leimbach et al. |
| 2015/0282809 A1 | 10/2015 | Shelton, IV et al. |
| 2015/0282810 A1 | 10/2015 | Shelton, IV et al. |
| 2015/0289873 A1 | 10/2015 | Shelton, IV et al. |
| 2015/0289874 A1 | 10/2015 | Leimbach et al. |
| 2015/0297210 A1 | 10/2015 | Widenhouse et al. |
| 2015/0297217 A1 | 10/2015 | Huitema et al. |
| 2015/0297218 A1 | 10/2015 | Shelton, IV et al. |
| 2015/0297219 A1 | 10/2015 | Shelton, IV et al. |
| 2015/0297221 A1 | 10/2015 | Kerr et al. |
| 2015/0297222 A1 | 10/2015 | Huitema et al. |
| 2015/0297223 A1 | 10/2015 | Huitema et al. |
| 2015/0297224 A1 | 10/2015 | Hall et al. |
| 2015/0297225 A1 | 10/2015 | Huitema et al. |
| 2015/0297226 A1 | 10/2015 | Hall et al. |
| 2015/0297227 A1 | 10/2015 | Huitema et al. |
| 2015/0297228 A1 | 10/2015 | Huitema et al. |
| 2015/0297229 A1 | 10/2015 | Schellin et al. |
| 2015/0297230 A1 | 10/2015 | Schellin et al. |
| 2015/0297231 A1 | 10/2015 | Huitema et al. |
| 2015/0297232 A1 | 10/2015 | Huitema et al. |
| 2015/0297233 A1 | 10/2015 | Huitema et al. |

(56) References Cited

U.S. PATENT DOCUMENTS

| | | |
|---|---|---|
| 2015/0297234 A1 | 10/2015 | Schellin et al. |
| 2015/0297235 A1 | 10/2015 | Harris et al. |
| 2015/0297236 A1 | 10/2015 | Harris et al. |
| 2015/0305744 A1 | 10/2015 | Moore et al. |
| 2015/0305745 A1 | 10/2015 | Baxter, III et al. |
| 2015/0313591 A1 | 11/2015 | Baxter, III et al. |
| 2015/0313594 A1 | 11/2015 | Shelton, IV et al. |
| 2015/0327853 A1 | 11/2015 | Aronhalt et al. |
| 2015/0327864 A1 | 11/2015 | Hodgkinson et al. |
| 2015/0335328 A1 | 11/2015 | Shelton, IV et al. |
| 2015/0335329 A1 | 11/2015 | Shelton, IV et al. |
| 2015/0342606 A1 | 12/2015 | Schmid et al. |
| 2015/0342607 A1 | 12/2015 | Shelton, IV et al. |
| 2015/0359536 A1 | 12/2015 | Cropper et al. |
| 2015/0374367 A1 | 12/2015 | Hall et al. |
| 2015/0374368 A1 | 12/2015 | Swayze et al. |
| 2015/0374369 A1 | 12/2015 | Yates et al. |
| 2015/0374374 A1 | 12/2015 | Shelton, IV et al. |
| 2015/0374375 A1 | 12/2015 | Shelton, IV et al. |
| 2015/0374376 A1 | 12/2015 | Shelton, IV |
| 2015/0374377 A1 | 12/2015 | Shelton, IV |
| 2015/0374378 A1 | 12/2015 | Giordano et al. |
| 2015/0374379 A1 | 12/2015 | Shelton, IV |
| 2016/0000430 A1 | 1/2016 | Ming et al. |
| 2016/0000431 A1 | 1/2016 | Giordano et al. |
| 2016/0000432 A1 | 1/2016 | Huang et al. |
| 2016/0000437 A1 | 1/2016 | Giordano et al. |
| 2016/0000438 A1 | 1/2016 | Swayze et al. |
| 2016/0000439 A1 | 1/2016 | Weisenburgh, II et al. |
| 2016/0000440 A1 | 1/2016 | Weisenburgh, II et al. |
| 2016/0000441 A1 | 1/2016 | Shelton, IV et al. |
| 2016/0000442 A1 | 1/2016 | Shelton, IV |
| 2016/0000452 A1 | 1/2016 | Yates et al. |
| 2016/0000453 A1 | 1/2016 | Yates et al. |
| 2016/0000513 A1 | 1/2016 | Shelton, IV et al. |
| 2016/0007992 A1 | 1/2016 | Yates et al. |
| 2016/0008023 A1 | 1/2016 | Yates et al. |
| 2016/0015390 A1 | 1/2016 | Timm et al. |
| 2016/0015391 A1 | 1/2016 | Shelton, IV et al. |
| 2016/0051257 A1 | 2/2016 | Shelton, IV et al. |
| 2016/0058443 A1 | 3/2016 | Yates et al. |
| 2016/0066909 A1 | 3/2016 | Baber et al. |
| 2016/0066910 A1 | 3/2016 | Baber et al. |
| 2016/0066911 A1 | 3/2016 | Baber et al. |
| 2016/0066912 A1 | 3/2016 | Baber et al. |
| 2016/0066913 A1 | 3/2016 | Swayze et al. |
| 2016/0066914 A1 | 3/2016 | Baber et al. |
| 2016/0066915 A1 | 3/2016 | Baber et al. |
| 2016/0066916 A1 | 3/2016 | Overmyer et al. |
| 2016/0069449 A1 | 3/2016 | Kanai et al. |
| 2016/0074038 A1 | 3/2016 | Leimbach et al. |
| 2016/0074040 A1 | 3/2016 | Widenhouse et al. |
| 2016/0089137 A1 | 3/2016 | Hess et al. |
| 2016/0089141 A1 | 3/2016 | Harris et al. |
| 2016/0089142 A1 | 3/2016 | Harris et al. |
| 2016/0089143 A1 | 3/2016 | Harris et al. |
| 2016/0089146 A1 | 3/2016 | Harris et al. |
| 2016/0089147 A1 | 3/2016 | Harris et al. |
| 2016/0089148 A1 | 3/2016 | Harris et al. |
| 2016/0089149 A1 | 3/2016 | Harris et al. |
| 2016/0100837 A1 | 4/2016 | Huang et al. |
| 2016/0106426 A1 | 4/2016 | Shelton, IV et al. |
| 2016/0106427 A1 | 4/2016 | Shelton, IV et al. |
| 2016/0106431 A1 | 4/2016 | Shelton, IV et al. |
| 2016/0113653 A1 | 4/2016 | Zingman |
| 2016/0120544 A1 | 5/2016 | Shelton, IV et al. |
| 2016/0120545 A1 | 5/2016 | Shelton, IV et al. |
| 2016/0120547 A1 | 5/2016 | Schmid et al. |
| 2016/0128694 A1 | 5/2016 | Baxter, III et al. |
| 2016/0135812 A1 | 5/2016 | Shelton, IV et al. |
| 2016/0166256 A1 | 6/2016 | Baxter, III et al. |
| 2016/0174969 A1 | 6/2016 | Kerr et al. |
| 2016/0174970 A1 | 6/2016 | Shelton, IV et al. |
| 2016/0174971 A1 | 6/2016 | Baxter, III et al. |
| 2016/0174972 A1 | 6/2016 | Shelton, IV et al. |
| 2016/0174973 A1 | 6/2016 | Shelton, IV et al. |
| 2016/0174974 A1 | 6/2016 | Schmid et al. |
| 2016/0174975 A1 | 6/2016 | Shelton, IV et al. |
| 2016/0174976 A1 | 6/2016 | Morgan et al. |
| 2016/0174977 A1 | 6/2016 | Lytle, IV et al. |
| 2016/0174978 A1 | 6/2016 | Overmyer et al. |
| 2016/0174983 A1 | 6/2016 | Shelton, IV et al. |
| 2016/0174984 A1 | 6/2016 | Smith et al. |
| 2016/0174985 A1 | 6/2016 | Baxter, III et al. |
| 2016/0183939 A1 | 6/2016 | Shelton, IV et al. |
| 2016/0183943 A1 | 6/2016 | Shelton, IV |
| 2016/0183944 A1 | 6/2016 | Swensgard et al. |
| 2016/0183945 A1 | 6/2016 | Shelton, IV et al. |
| 2016/0183947 A1 | 6/2016 | Shelton, IV et al. |
| 2016/0183948 A1 | 6/2016 | Shelton, IV et al. |
| 2016/0183950 A1 | 6/2016 | Shelton, IV et al. |
| 2016/0184039 A1 | 6/2016 | Shelton, Iv et al. |
| 2016/0192916 A1 | 7/2016 | Shelton, Iv et al. |
| 2016/0192917 A1 | 7/2016 | Shelton, Iv et al. |
| 2016/0192918 A1 | 7/2016 | Shelton, IV et al. |
| 2016/0192929 A1 | 7/2016 | Schmid et al. |
| 2016/0192933 A1 | 7/2016 | Shelton, IV |
| 2016/0192936 A1 | 7/2016 | Leimbach et al. |
| 2016/0192996 A1 | 7/2016 | Spivey et al. |
| 2016/0192997 A1 | 7/2016 | Spivey et al. |
| 2016/0199059 A1 | 7/2016 | Shelton, IV et al. |
| 2016/0199061 A1 | 7/2016 | Shelton, IV et al. |
| 2016/0199063 A1 | 7/2016 | Mandakolathur Vasudevan et al. |
| 2016/0199064 A1 | 7/2016 | Shelton, IV et al. |
| 2016/0199088 A1 | 7/2016 | Shelton, IV et al. |
| 2016/0199089 A1 | 7/2016 | Hess et al. |
| 2016/0199956 A1 | 7/2016 | Shelton, IV et al. |
| 2016/0206309 A1 | 7/2016 | Hess et al. |
| 2016/0206310 A1 | 7/2016 | Shelton, IV |
| 2016/0206314 A1 | 7/2016 | Scheib et al. |
| 2016/0220246 A1 | 8/2016 | Timm et al. |
| 2016/0220247 A1 | 8/2016 | Timm et al. |
| 2016/0220248 A1 | 8/2016 | Timm et al. |
| 2016/0220249 A1 | 8/2016 | Shelton, IV et al. |
| 2016/0220254 A1 | 8/2016 | Baxter, III et al. |
| 2016/0220266 A1 | 8/2016 | Shelton, IV et al. |
| 2016/0220268 A1 | 8/2016 | Shelton, IV et al. |
| 2016/0235403 A1 | 8/2016 | Shelton, IV et al. |
| 2016/0235404 A1 | 8/2016 | Shelton, IV |
| 2016/0235405 A1 | 8/2016 | Shelton, IV et al. |
| 2016/0235406 A1 | 8/2016 | Shelton, IV et al. |
| 2016/0235408 A1 | 8/2016 | Shelton, IV et al. |
| 2016/0235409 A1 | 8/2016 | Shelton, IV et al. |
| 2016/0235494 A1 | 8/2016 | Shelton, IV et al. |
| 2016/0238108 A1 | 8/2016 | Kanai et al. |
| 2016/0242768 A1 | 8/2016 | Moore et al. |
| 2016/0242769 A1 | 8/2016 | Moore et al. |
| 2016/0242770 A1 | 8/2016 | Moore et al. |
| 2016/0242775 A1 | 8/2016 | Shelton, IV et al. |
| 2016/0242776 A1 | 8/2016 | Shelton, IV et al. |
| 2016/0242777 A1 | 8/2016 | Shelton, IV et al. |
| 2016/0242780 A1 | 8/2016 | Shelton, IV et al. |
| 2016/0242781 A1 | 8/2016 | Shelton, IV et al. |
| 2016/0242782 A1 | 8/2016 | Shelton, IV et al. |
| 2016/0242783 A1 | 8/2016 | Shelton, IV et al. |
| 2016/0249908 A1 | 9/2016 | Shelton, IV et al. |
| 2016/0249909 A1 | 9/2016 | Shelton, IV et al. |
| 2016/0249910 A1 | 9/2016 | Shelton, IV et al. |
| 2016/0249911 A1 | 9/2016 | Timm et al. |
| 2016/0249915 A1 | 9/2016 | Beckman et al. |
| 2016/0249916 A1 | 9/2016 | Shelton, IV et al. |
| 2016/0249917 A1 | 9/2016 | Beckman et al. |
| 2016/0249918 A1 | 9/2016 | Shelton, IV et al. |
| 2016/0249919 A1 | 9/2016 | Savage et al. |
| 2016/0249922 A1 | 9/2016 | Morgan et al. |
| 2016/0249927 A1 | 9/2016 | Beckman et al. |
| 2016/0249930 A1 | 9/2016 | Hall et al. |
| 2016/0249945 A1 | 9/2016 | Shelton, IV et al. |
| 2016/0256071 A1 | 9/2016 | Shelton, IV et al. |
| 2016/0256153 A1 | 9/2016 | Shelton, IV et al. |
| 2016/0256154 A1 | 9/2016 | Shelton, IV et al. |
| 2016/0256155 A1 | 9/2016 | Shelton, IV et al. |
| 2016/0256156 A1 | 9/2016 | Shelton, IV et al. |
| 2016/0256160 A1 | 9/2016 | Shelton, IV et al. |

(56) References Cited

U.S. PATENT DOCUMENTS

| | | |
|---|---|---|
| 2016/0256161 A1 | 9/2016 | Overmyer et al. |
| 2016/0256162 A1 | 9/2016 | Shelton, IV et al. |
| 2016/0256163 A1 | 9/2016 | Shelton, IV et al. |
| 2016/0256184 A1 | 9/2016 | Shelton, IV et al. |
| 2016/0256185 A1 | 9/2016 | Shelton, IV et al. |
| 2016/0256186 A1 | 9/2016 | Shelton, IV et al. |
| 2016/0256187 A1 | 9/2016 | Shelton, IV et al. |
| 2016/0256229 A1 | 9/2016 | Morgan et al. |
| 2016/0262745 A1 | 9/2016 | Morgan et al. |
| 2016/0262746 A1 | 9/2016 | Shelton, IV et al. |
| 2016/0262760 A1 | 9/2016 | Shelton, IV et al. |
| 2016/0270780 A1 | 9/2016 | Hall et al. |
| 2016/0287249 A1 | 10/2016 | Alexander, III et al. |
| 2016/0287250 A1 | 10/2016 | Shelton, IV et al. |
| 2016/0287251 A1 | 10/2016 | Shelton, IV et al. |
| 2016/0287253 A1 | 10/2016 | Shelton, IV et al. |
| 2016/0287254 A1 | 10/2016 | Baxter, III et al. |
| 2016/0331375 A1 | 11/2016 | Shelton, IV et al. |

FOREIGN PATENT DOCUMENTS

| | | |
|---|---|---|
| AU | 2012200178 B2 | 7/2013 |
| CA | 2458946 A1 | 3/2003 |
| CA | 2477181 A1 | 4/2004 |
| CA | 2512960 A1 | 1/2006 |
| CA | 2514274 A1 | 1/2006 |
| CA | 2639177 A1 | 2/2009 |
| CA | 2576347 C | 8/2015 |
| CN | 86100996 A | 9/1986 |
| CN | 1163558 A | 10/1997 |
| CN | 2488482 Y | 5/2002 |
| CN | 1424891 A | 6/2003 |
| CN | 1523725 A | 8/2004 |
| CN | 1545154 A | 11/2004 |
| CN | 1634601 A | 7/2005 |
| CN | 2716900 Y | 8/2005 |
| CN | 2738962 Y | 11/2005 |
| CN | 1726874 A | 2/2006 |
| CN | 1726878 A | 2/2006 |
| CN | 1868411 A | 11/2006 |
| CN | 1915180 A | 2/2007 |
| CN | 2868212 Y | 2/2007 |
| CN | 1960679 A | 5/2007 |
| CN | 101011286 A | 8/2007 |
| CN | 101095621 A | 1/2008 |
| CN | 101111196 A | 1/2008 |
| CN | 101137402 A | 3/2008 |
| CN | 101224124 A | 7/2008 |
| CN | 101254126 A | 9/2008 |
| CN | 101507620 A | 8/2009 |
| CN | 101507622 A | 8/2009 |
| CN | 101507623 A | 8/2009 |
| CN | 101507625 A | 8/2009 |
| CN | 101507628 A | 8/2009 |
| CN | 101541251 A | 9/2009 |
| CN | 101626731 A | 1/2010 |
| CN | 101675898 A | 3/2010 |
| CN | 101683280 A | 3/2010 |
| CN | 101868203 A | 10/2010 |
| CN | 101912285 A | 12/2010 |
| CN | 101028205 A | 1/2011 |
| CN | 101934098 A | 5/2011 |
| CN | 102038531 A | 5/2011 |
| CN | 201949071 U | 8/2011 |
| CN | 101336835 B | 9/2011 |
| CN | 102188270 A | 9/2011 |
| CN | 101779977 B | 12/2011 |
| CN | 101534723 B | 1/2012 |
| CN | 101310680 B | 4/2012 |
| CN | 202397539 U | 8/2012 |
| CN | 101317782 B | 10/2012 |
| CN | 101507633 B | 2/2013 |
| CN | 101023879 B | 3/2013 |
| CN | 101327137 B | 6/2013 |
| CN | 101401736 B | 6/2013 |
| CN | 101332110 B | 7/2013 |
| CN | 101683281 B | 1/2014 |
| CN | 103648408 A | 3/2014 |
| CN | 102166129 B | 3/2015 |
| DE | 273689 C | 5/1914 |
| DE | 1775926 A | 1/1972 |
| DE | 3036217 A1 | 4/1982 |
| DE | 3212828 A1 | 11/1982 |
| DE | 3210466 A1 | 9/1983 |
| DE | 3709067 A1 | 9/1988 |
| DE | 4228909 A1 | 3/1994 |
| DE | 9412228 U1 | 9/1994 |
| DE | 19509116 A1 | 9/1996 |
| DE | 19707373 C1 | 2/1998 |
| DE | 19851291 A1 | 1/2000 |
| DE | 19924311 A1 | 11/2000 |
| DE | 69328576 T2 | 1/2001 |
| DE | 20016423 U1 | 2/2001 |
| DE | 10052679 A1 | 5/2001 |
| DE | 20112837 U1 | 10/2001 |
| DE | 20121753 U1 | 4/2003 |
| DE | 10314827 B3 | 4/2004 |
| DE | 10314072 A1 | 10/2004 |
| DE | 202004012389 U1 | 11/2004 |
| DE | 202007003114 U1 | 6/2007 |
| EP | 0000756 A1 | 2/1979 |
| EP | 0122046 A1 | 10/1984 |
| EP | 0070230 B1 | 10/1985 |
| EP | 0156774 A2 | 10/1985 |
| EP | 0033548 B1 | 5/1986 |
| EP | 0077262 B1 | 8/1986 |
| EP | 0189807 A2 | 8/1986 |
| EP | 0129442 B1 | 11/1987 |
| EP | 0276104 A2 | 7/1988 |
| EP | 0379721 B1 | 8/1990 |
| EP | 0178940 B1 | 1/1991 |
| EP | 0178941 B1 | 1/1991 |
| EP | 0169044 B1 | 6/1991 |
| EP | 0248844 B1 | 1/1993 |
| EP | 0539762 A1 | 5/1993 |
| EP | 0545029 A1 | 6/1993 |
| EP | 0548998 A1 | 6/1993 |
| EP | 0277959 B1 | 10/1993 |
| EP | 0591946 A1 | 10/1993 |
| EP | 0233940 B1 | 11/1993 |
| EP | 0261230 B1 | 11/1993 |
| EP | 0639349 A2 | 2/1994 |
| EP | 0324636 B1 | 3/1994 |
| EP | 0593920 A1 | 4/1994 |
| EP | 0594148 A1 | 4/1994 |
| EP | 0427949 B1 | 6/1994 |
| EP | 0523174 B1 | 6/1994 |
| EP | 0600182 A2 | 6/1994 |
| EP | 0310431 B1 | 11/1994 |
| EP | 0375302 B1 | 11/1994 |
| EP | 0376562 B1 | 11/1994 |
| EP | 0630612 A1 | 12/1994 |
| EP | 0630614 A1 | 12/1994 |
| EP | 0634144 A1 | 1/1995 |
| EP | 0646356 A2 | 4/1995 |
| EP | 0646357 A1 | 4/1995 |
| EP | 0505036 B1 | 5/1995 |
| EP | 0653189 A2 | 5/1995 |
| EP | 0669104 A1 | 8/1995 |
| EP | 0387980 B1 | 10/1995 |
| EP | 0511470 B1 | 10/1995 |
| EP | 0674876 A2 | 10/1995 |
| EP | 0679367 A2 | 11/1995 |
| EP | 0392547 B1 | 12/1995 |
| EP | 0685204 A1 | 12/1995 |
| EP | 0364216 B1 | 1/1996 |
| EP | 0699418 A1 | 3/1996 |
| EP | 0702937 A1 | 3/1996 |
| EP | 0488768 B1 | 4/1996 |
| EP | 0705571 A1 | 4/1996 |
| EP | 0528478 B1 | 5/1996 |
| EP | 0711611 A2 | 5/1996 |
| EP | 0484677 B2 | 6/1996 |
| EP | 0541987 B1 | 7/1996 |

(56) References Cited

FOREIGN PATENT DOCUMENTS

| | | |
|---|---|---|
| EP | 0667119 B1 | 7/1996 |
| EP | 0737446 A1 | 10/1996 |
| EP | 0748614 A1 | 12/1996 |
| EP | 0708618 B1 | 3/1997 |
| EP | 0770355 A1 | 5/1997 |
| EP | 0503662 B1 | 6/1997 |
| EP | 0447121 B1 | 7/1997 |
| EP | 0621009 B1 | 7/1997 |
| EP | 0625077 B1 | 7/1997 |
| EP | 0633749 B1 | 8/1997 |
| EP | 0710090 B1 | 8/1997 |
| EP | 0578425 B1 | 9/1997 |
| EP | 0621006 B1 | 10/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0649290 B1 | 3/1998 |
| EP | 0598618 B1 | 9/1998 |
| EP | 0676173 B1 | 9/1998 |
| EP | 0678007 B1 | 9/1998 |
| EP | 0869104 A1 | 10/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0695144 B1 | 12/1998 |
| EP | 0722296 B1 | 12/1998 |
| EP | 0760230 B1 | 2/1999 |
| EP | 0623316 B1 | 3/1999 |
| EP | 0650701 B1 | 3/1999 |
| EP | 0537572 B1 | 6/1999 |
| EP | 0923907 A1 | 6/1999 |
| EP | 0640317 A1 | 9/1999 |
| EP | 0843906 B1 | 3/2000 |
| EP | 0552050 B1 | 5/2000 |
| EP | 0833592 B1 | 5/2000 |
| EP | 0832605 B1 | 6/2000 |
| EP | 0830094 B1 | 9/2000 |
| EP | 1034747 A1 | 9/2000 |
| EP | 1034748 A1 | 9/2000 |
| EP | 0694290 B1 | 11/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1058177 A1 | 12/2000 |
| EP | 1080694 A1 | 3/2001 |
| EP | 1090592 A1 | 4/2001 |
| EP | 1095627 A1 | 5/2001 |
| EP | 0806914 B1 | 9/2001 |
| EP | 0768840 B1 | 12/2001 |
| EP | 0908152 B1 | 1/2002 |
| EP | 0717959 B1 | 2/2002 |
| EP | 0872213 B1 | 5/2002 |
| EP | 0862386 B1 | 6/2002 |
| EP | 0949886 B1 | 9/2002 |
| EP | 1238634 A2 | 9/2002 |
| EP | 0858295 B1 | 12/2002 |
| EP | 0656188 B1 | 1/2003 |
| EP | 0717960 B1 | 2/2003 |
| EP | 1284120 A1 | 2/2003 |
| EP | 1287788 A1 | 3/2003 |
| EP | 0717966 B1 | 4/2003 |
| EP | 0869742 B1 | 5/2003 |
| EP | 0829235 B1 | 6/2003 |
| EP | 0887046 B1 | 7/2003 |
| EP | 1323384 A2 | 7/2003 |
| EP | 0852480 B1 | 8/2003 |
| EP | 0891154 B1 | 9/2003 |
| EP | 0813843 B1 | 10/2003 |
| EP | 0873089 B1 | 10/2003 |
| EP | 0856326 B1 | 11/2003 |
| EP | 1374788 A1 | 1/2004 |
| EP | 0741996 B1 | 2/2004 |
| EP | 0814712 B1 | 2/2004 |
| EP | 1402837 A1 | 3/2004 |
| EP | 0705570 B1 | 4/2004 |
| EP | 0959784 B1 | 4/2004 |
| EP | 1407719 A2 | 4/2004 |
| EP | 1411626 A2 | 4/2004 |
| EP | 1086713 B1 | 5/2004 |
| EP | 0996378 B1 | 6/2004 |
| EP | 1426012 A1 | 6/2004 |
| EP | 0833593 B2 | 7/2004 |
| EP | 1442694 A1 | 8/2004 |
| EP | 0888749 B1 | 9/2004 |
| EP | 0959786 B1 | 9/2004 |
| EP | 1453432 A2 | 9/2004 |
| EP | 1459695 A1 | 9/2004 |
| EP | 1254636 B1 | 10/2004 |
| EP | 1473819 A1 | 11/2004 |
| EP | 1477119 A1 | 11/2004 |
| EP | 1479345 A1 | 11/2004 |
| EP | 1479347 A1 | 11/2004 |
| EP | 1479348 A1 | 11/2004 |
| EP | 0754437 B2 | 12/2004 |
| EP | 1025807 B1 | 12/2004 |
| EP | 1001710 B1 | 1/2005 |
| EP | 1496805 A2 | 1/2005 |
| EP | 1256318 B1 | 2/2005 |
| EP | 1520521 A1 | 4/2005 |
| EP | 1520522 A1 | 4/2005 |
| EP | 1520523 A1 | 4/2005 |
| EP | 1520525 A1 | 4/2005 |
| EP | 1522264 A1 | 4/2005 |
| EP | 1523942 A2 | 4/2005 |
| EP | 1550408 B1 | 7/2005 |
| EP | 1557129 A1 | 7/2005 |
| EP | 1064883 B1 | 8/2005 |
| EP | 1067876 B1 | 8/2005 |
| EP | 0870473 B1 | 9/2005 |
| EP | 1157666 B1 | 9/2005 |
| EP | 0880338 B1 | 10/2005 |
| EP | 1158917 B1 | 11/2005 |
| EP | 1344498 B1 | 11/2005 |
| EP | 0906764 B1 | 12/2005 |
| EP | 1330989 B1 | 12/2005 |
| EP | 0771176 B2 | 1/2006 |
| EP | 1621138 A2 | 2/2006 |
| EP | 1621139 A2 | 2/2006 |
| EP | 1621141 A2 | 2/2006 |
| EP | 1621143 A2 | 2/2006 |
| EP | 1621145 A2 | 2/2006 |
| EP | 1621151 A2 | 2/2006 |
| EP | 1034746 B1 | 3/2006 |
| EP | 1201196 B1 | 3/2006 |
| EP | 1632191 A2 | 3/2006 |
| EP | 1647231 A1 | 4/2006 |
| EP | 1065981 B1 | 5/2006 |
| EP | 1082944 B1 | 5/2006 |
| EP | 1230899 B1 | 5/2006 |
| EP | 1652481 A2 | 5/2006 |
| EP | 1382303 B1 | 6/2006 |
| EP | 1253866 B1 | 7/2006 |
| EP | 1676539 A1 | 7/2006 |
| EP | 1032318 B1 | 8/2006 |
| EP | 1045672 B1 | 8/2006 |
| EP | 1617768 B1 | 8/2006 |
| EP | 1693015 A2 | 8/2006 |
| EP | 1400214 B1 | 9/2006 |
| EP | 1702567 A2 | 9/2006 |
| EP | 1129665 B1 | 11/2006 |
| EP | 1400206 B1 | 11/2006 |
| EP | 1721568 A1 | 11/2006 |
| EP | 1256317 B1 | 12/2006 |
| EP | 1285633 B1 | 12/2006 |
| EP | 1728473 A1 | 12/2006 |
| EP | 1728475 A2 | 12/2006 |
| EP | 1736105 A1 | 12/2006 |
| EP | 1011494 B1 | 1/2007 |
| EP | 1479346 B1 | 1/2007 |
| EP | 1484024 B1 | 1/2007 |

(56) References Cited

FOREIGN PATENT DOCUMENTS

| | | |
|---|---|---|
| EP | 1749485 A1 | 2/2007 |
| EP | 1754445 A2 | 2/2007 |
| EP | 1759812 A1 | 3/2007 |
| EP | 1767157 A1 | 3/2007 |
| EP | 1767163 A1 | 3/2007 |
| EP | 1563792 B1 | 4/2007 |
| EP | 1769756 A1 | 4/2007 |
| EP | 1769758 A1 | 4/2007 |
| EP | 1581128 B1 | 5/2007 |
| EP | 1780825 A1 | 5/2007 |
| EP | 1785097 A2 | 5/2007 |
| EP | 1790293 A2 | 5/2007 |
| EP | 1790294 A1 | 5/2007 |
| EP | 1563793 B1 | 6/2007 |
| EP | 1791473 A2 | 6/2007 |
| EP | 1800610 A1 | 6/2007 |
| EP | 1300117 B1 | 8/2007 |
| EP | 1813199 A1 | 8/2007 |
| EP | 1813200 A2 | 8/2007 |
| EP | 1813201 A1 | 8/2007 |
| EP | 1813202 A1 | 8/2007 |
| EP | 1813203 A2 | 8/2007 |
| EP | 1813207 A1 | 8/2007 |
| EP | 1813209 A1 | 8/2007 |
| EP | 1815950 A1 | 8/2007 |
| EP | 1330991 B1 | 9/2007 |
| EP | 1806103 B1 | 9/2007 |
| EP | 1837041 A1 | 9/2007 |
| EP | 0922435 B1 | 10/2007 |
| EP | 1487359 B1 | 10/2007 |
| EP | 1599146 B1 | 10/2007 |
| EP | 1839596 A1 | 10/2007 |
| EP | 2110083 A2 | 10/2007 |
| EP | 1679096 B1 | 11/2007 |
| EP | 1857057 A2 | 11/2007 |
| EP | 1402821 B1 | 12/2007 |
| EP | 1872727 A1 | 1/2008 |
| EP | 1550410 B1 | 2/2008 |
| EP | 1671593 B1 | 2/2008 |
| EP | 1897502 A1 | 3/2008 |
| EP | 1611856 B1 | 4/2008 |
| EP | 1908417 A2 | 4/2008 |
| EP | 1917929 A1 | 5/2008 |
| EP | 1330201 B1 | 6/2008 |
| EP | 1702568 B1 | 7/2008 |
| EP | 1943955 A2 | 7/2008 |
| EP | 1943957 A2 | 7/2008 |
| EP | 1943959 A1 | 7/2008 |
| EP | 1943962 A2 | 7/2008 |
| EP | 1943964 A1 | 7/2008 |
| EP | 1943976 A2 | 7/2008 |
| EP | 1593337 B1 | 8/2008 |
| EP | 1970014 A1 | 9/2008 |
| EP | 1974678 A2 | 10/2008 |
| EP | 1980213 A2 | 10/2008 |
| EP | 1980214 A2 | 10/2008 |
| EP | 1759645 B1 | 11/2008 |
| EP | 1987780 A2 | 11/2008 |
| EP | 1990014 A2 | 11/2008 |
| EP | 1552795 B1 | 12/2008 |
| EP | 1693008 B1 | 12/2008 |
| EP | 1759640 B1 | 12/2008 |
| EP | 1997439 A2 | 12/2008 |
| EP | 2000101 A2 | 12/2008 |
| EP | 2000102 A2 | 12/2008 |
| EP | 2005894 A2 | 12/2008 |
| EP | 2005897 A2 | 12/2008 |
| EP | 2005901 A1 | 12/2008 |
| EP | 2008595 A2 | 12/2008 |
| EP | 1736104 B1 | 3/2009 |
| EP | 1749486 B1 | 3/2009 |
| EP | 1782743 B1 | 3/2009 |
| EP | 2039302 A2 | 3/2009 |
| EP | 2039308 A2 | 3/2009 |
| EP | 2039316 A2 | 3/2009 |
| EP | 1721576 B1 | 4/2009 |
| EP | 1733686 B1 | 4/2009 |
| EP | 2044890 A1 | 4/2009 |
| EP | 2055243 A2 | 5/2009 |
| EP | 1550409 B1 | 6/2009 |
| EP | 1550413 B1 | 6/2009 |
| EP | 1719461 B1 | 6/2009 |
| EP | 1834594 B1 | 6/2009 |
| EP | 1709911 B1 | 7/2009 |
| EP | 2077093 A2 | 7/2009 |
| EP | 1745748 B1 | 8/2009 |
| EP | 2090231 A1 | 8/2009 |
| EP | 2090237 A1 | 8/2009 |
| EP | 2090241 A1 | 8/2009 |
| EP | 2090244 B1 | 8/2009 |
| EP | 2090245 A1 | 8/2009 |
| EP | 2090254 A1 | 8/2009 |
| EP | 2090256 A2 | 8/2009 |
| EP | 2095777 A2 | 9/2009 |
| EP | 2098170 A2 | 9/2009 |
| EP | 2110082 A1 | 10/2009 |
| EP | 2110084 A2 | 10/2009 |
| EP | 2111803 A2 | 10/2009 |
| EP | 1762190 B8 | 11/2009 |
| EP | 1813208 B1 | 11/2009 |
| EP | 1908426 B1 | 11/2009 |
| EP | 2116195 A1 | 11/2009 |
| EP | 2116197 A2 | 11/2009 |
| EP | 1607050 B1 | 12/2009 |
| EP | 1815804 B1 | 12/2009 |
| EP | 1875870 B1 | 12/2009 |
| EP | 1878395 B1 | 1/2010 |
| EP | 2151204 A1 | 2/2010 |
| EP | 1813211 B1 | 3/2010 |
| EP | 2165656 A2 | 3/2010 |
| EP | 2165660 A2 | 3/2010 |
| EP | 2165664 A1 | 3/2010 |
| EP | 1566150 B1 | 4/2010 |
| EP | 1813206 B1 | 4/2010 |
| EP | 2184014 A2 | 5/2010 |
| EP | 1769754 B1 | 6/2010 |
| EP | 1854416 B1 | 6/2010 |
| EP | 1911408 B1 | 6/2010 |
| EP | 2198787 A1 | 6/2010 |
| EP | 2214610 A1 | 8/2010 |
| EP | 2218409 A1 | 8/2010 |
| EP | 1647286 B1 | 9/2010 |
| EP | 1825821 B1 | 9/2010 |
| EP | 1535565 B1 | 10/2010 |
| EP | 1702570 B1 | 10/2010 |
| EP | 1785098 B1 | 10/2010 |
| EP | 2005896 B1 | 10/2010 |
| EP | 2030578 B1 | 11/2010 |
| EP | 2036505 B1 | 11/2010 |
| EP | 2245993 A2 | 11/2010 |
| EP | 2245994 A1 | 11/2010 |
| EP | 2253280 A1 | 11/2010 |
| EP | 1627605 B1 | 12/2010 |
| EP | 2027811 B1 | 12/2010 |
| EP | 2130498 B1 | 12/2010 |
| EP | 2258282 A2 | 12/2010 |
| EP | 2263568 A2 | 12/2010 |
| EP | 1994890 B1 | 1/2011 |
| EP | 2005900 B1 | 1/2011 |
| EP | 2283780 A2 | 2/2011 |
| EP | 2286738 A2 | 2/2011 |
| EP | 1494595 | 3/2011 |
| EP | 1690502 B1 | 3/2011 |
| EP | 1884201 B1 | 3/2011 |
| EP | 2292153 A1 | 3/2011 |
| EP | 1769755 B1 | 4/2011 |
| EP | 2090240 B1 | 4/2011 |
| EP | 2305135 A1 | 4/2011 |
| EP | 2308388 A1 | 4/2011 |
| EP | 2314254 A2 | 4/2011 |
| EP | 2316345 A1 | 5/2011 |
| EP | 2316366 A2 | 5/2011 |
| EP | 2324776 A2 | 5/2011 |
| EP | 1813205 B1 | 6/2011 |

(56) References Cited

FOREIGN PATENT DOCUMENTS

| | | |
|---|---|---|
| EP | 2090243 B1 | 6/2011 |
| EP | 2329773 A1 | 6/2011 |
| EP | 2090239 B1 | 7/2011 |
| EP | 2340771 A2 | 7/2011 |
| EP | 2353545 A1 | 8/2011 |
| EP | 2361562 A1 | 8/2011 |
| EP | 2377472 A1 | 10/2011 |
| EP | 1836986 B1 | 11/2011 |
| EP | 1908414 B1 | 11/2011 |
| EP | 2153781 B1 | 11/2011 |
| EP | 2389928 A2 | 11/2011 |
| EP | 1847225 B1 | 12/2011 |
| EP | 2397079 A1 | 12/2011 |
| EP | 2399538 A2 | 12/2011 |
| EP | 1785102 B1 | 1/2012 |
| EP | 2415416 A | 2/2012 |
| EP | 2090253 B1 | 3/2012 |
| EP | 2430986 A2 | 3/2012 |
| EP | 1347638 B1 | 5/2012 |
| EP | 1943956 B1 | 5/2012 |
| EP | 2446834 A1 | 5/2012 |
| EP | 2455007 A2 | 5/2012 |
| EP | 2457519 A1 | 5/2012 |
| EP | 2462878 A1 | 6/2012 |
| EP | 2462880 A2 | 6/2012 |
| EP | 1813204 B1 | 7/2012 |
| EP | 2189121 B1 | 7/2012 |
| EP | 2248475 B1 | 7/2012 |
| EP | 2005895 B1 | 8/2012 |
| EP | 2090248 B1 | 8/2012 |
| EP | 2481359 A1 | 8/2012 |
| EP | 2486860 A2 | 8/2012 |
| EP | 2486862 A2 | 8/2012 |
| EP | 1908412 B1 | 9/2012 |
| EP | 1935351 B1 | 9/2012 |
| EP | 2497431 A1 | 9/2012 |
| EP | 1550412 B2 | 10/2012 |
| EP | 1616549 B1 | 10/2012 |
| EP | 2030579 B1 | 10/2012 |
| EP | 2090252 B1 | 10/2012 |
| EP | 2517637 A1 | 10/2012 |
| EP | 2517638 A1 | 10/2012 |
| EP | 2517642 A2 | 10/2012 |
| EP | 2517645 A2 | 10/2012 |
| EP | 2517649 A2 | 10/2012 |
| EP | 2517651 A2 | 10/2012 |
| EP | 2526877 A1 | 11/2012 |
| EP | 2526883 A1 | 11/2012 |
| EP | 1884206 B1 | 3/2013 |
| EP | 2090238 B1 | 4/2013 |
| EP | 2586380 A1 | 5/2013 |
| EP | 2586383 A2 | 5/2013 |
| EP | 2606812 A1 | 6/2013 |
| EP | 1982657 B1 | 7/2013 |
| EP | 2614782 A2 | 7/2013 |
| EP | 2090234 B1 | 9/2013 |
| EP | 2633830 A1 | 9/2013 |
| EP | 2644124 A1 | 10/2013 |
| EP | 2644209 A2 | 10/2013 |
| EP | 2649948 A1 | 10/2013 |
| EP | 2649949 A1 | 10/2013 |
| EP | 2700367 A1 | 2/2014 |
| EP | 2713902 A1 | 4/2014 |
| EP | 1772105 B1 | 5/2014 |
| EP | 2759267 A2 | 7/2014 |
| EP | 2772206 A2 | 9/2014 |
| EP | 2777528 A2 | 9/2014 |
| EP | 2777538 A2 | 9/2014 |
| EP | 2803324 A2 | 11/2014 |
| EP | 2446835 B1 | 1/2015 |
| EP | 2845545 A1 | 3/2015 |
| EP | 2923660 A2 | 9/2015 |
| EP | 2823773 B1 | 4/2016 |
| EP | 2131750 B1 | 5/2016 |
| EP | 2510891 B1 | 6/2016 |
| EP | 1915957 B1 | 8/2016 |
| EP | 2364651 B1 | 11/2016 |
| ES | 2396594 T3 | 2/2013 |
| FR | 459743 A | 11/1913 |
| FR | 999646 A | 2/1952 |
| FR | 2765794 A | 2/1952 |
| FR | 1112936 A | 3/1956 |
| FR | 2598905 A1 | 11/1987 |
| FR | 2689749 B1 | 7/1994 |
| FR | 2815842 A1 | 10/2000 |
| GB | 939929 A | 10/1963 |
| GB | 1210522 A | 10/1970 |
| GB | 1217159 A | 12/1970 |
| GB | 1339394 A | 12/1973 |
| GB | 2024012 A | 1/1980 |
| GB | 2109241 A | 6/1983 |
| GB | 2272159 A | 5/1994 |
| GB | 2284242 A | 5/1995 |
| GB | 2286435 A | 8/1995 |
| GB | 2336214 A | 10/1999 |
| GB | 2425903 A | 11/2006 |
| GB | 2423199 B | 5/2009 |
| GR | 930100110 | 11/1993 |
| JO | H 09-501577 A | 2/1997 |
| JP | S 47-11908 Y1 | 5/1972 |
| JP | S 50-33988 U | 4/1975 |
| JP | S56-112235 A | 9/1981 |
| JP | S 58500053 A | 1/1983 |
| JP | S 58-501360 A | 8/1983 |
| JP | S 59-174920 A | 3/1984 |
| JP | S 60-100955 A | 6/1985 |
| JP | S 60-212152 A | 10/1985 |
| JP | S 61-98249 A | 5/1986 |
| JP | S 61502036 A | 9/1986 |
| JP | S 62-170011 U | 10/1987 |
| JP | S63-59764 A | 3/1988 |
| JP | S 63-147449 A | 6/1988 |
| JP | S 63-203149 A | 8/1988 |
| JP | H02-279149 A | 11/1990 |
| JP | H03-12126 A | 1/1991 |
| JP | H03-18354 A | 1/1991 |
| JP | H 03-78514 U | 8/1991 |
| JP | H 03-85009 U | 8/1991 |
| JP | H04-215747 A | 8/1992 |
| JP | H 04-131860 U | 12/1992 |
| JP | H05-84252 A | 4/1993 |
| JP | H05-123325 A | 5/1993 |
| JP | H06-30945 A | 2/1994 |
| JP | H06-54857 A | 3/1994 |
| JP | H06-63054 A | 3/1994 |
| JP | H 06-26812 U | 4/1994 |
| JP | H06-121798 A | 5/1994 |
| JP | H06-125913 A | 5/1994 |
| JP | H06-197901 A | 7/1994 |
| JP | H06-237937 A | 8/1994 |
| JP | H06-327684 A | 11/1994 |
| JP | H 07-9622 U | 2/1995 |
| JP | H 07-31623 A | 2/1995 |
| JP | H07-47070 A | 2/1995 |
| JP | H07-51273 A | 2/1995 |
| JP | H07-124166 A | 5/1995 |
| JP | H07-163574 A | 6/1995 |
| JP | H07-171163 A | 7/1995 |
| JP | H07-255735 A | 10/1995 |
| JP | H07-285089 A | 10/1995 |
| JP | H07-299074 A | 11/1995 |
| JP | H08-33641 A | 2/1996 |
| JP | H08-33642 A | 2/1996 |
| JP | H08-164141 A | 6/1996 |
| JP | H08-182684 A | 7/1996 |
| JP | H08-507708 Y1 | 8/1996 |
| JP | H08-229050 A | 9/1996 |
| JP | H08-289895 A | 11/1996 |
| JP | H08-336540 A | 12/1996 |
| JP | H08-336544 A | 12/1996 |
| JP | H 09-501081 A | 2/1997 |
| JP | H09-164144 A | 6/1997 |
| JP | H10-113352 A | 5/1998 |
| JP | H10-118090 A | 5/1998 |

(56) References Cited

FOREIGN PATENT DOCUMENTS

| | | |
|---|---|---|
| JP | 10-512469 A | 12/1998 |
| JP | 2000-014632 A | 1/2000 |
| JP | 2000-033071 A | 2/2000 |
| JP | 2000-112002 A | 4/2000 |
| JP | 2000-166932 A | 6/2000 |
| JP | 2000-171730 A | 6/2000 |
| JP | 2000-287987 A | 10/2000 |
| JP | 2000-325303 A | 11/2000 |
| JP | 2001-037763 A | 2/2001 |
| JP | 2001-046384 A | 2/2001 |
| JP | 2001-087272 A | 4/2001 |
| JP | 2001-514541 A | 9/2001 |
| JP | 2001-276091 A | 10/2001 |
| JP | 2001-286477 A | 10/2001 |
| JP | 2001-517473 A | 10/2001 |
| JP | 2002-051974 A | 2/2002 |
| JP | 2002-085415 A | 3/2002 |
| JP | 2002-143078 A | 5/2002 |
| JP | 2002-204801 A | 7/2002 |
| JP | 2002-528161 A | 9/2002 |
| JP | 2002-314298 A | 10/2002 |
| JP | 2002-369820 A | 12/2002 |
| JP | 2002-542186 A | 12/2002 |
| JP | 2003-000603 A | 1/2003 |
| JP | 2003-500153 A | 1/2003 |
| JP | 2003-504104 A | 2/2003 |
| JP | 2003-135473 A | 5/2003 |
| JP | 2003-148903 A | 5/2003 |
| JP | 2003-164066 A | 6/2003 |
| JP | 2003-521301 A | 7/2003 |
| JP | 2003-523251 A | 8/2003 |
| JP | 2003-523254 A | 8/2003 |
| JP | 2003-300416 A | 10/2003 |
| JP | 2004-147701 A | 5/2004 |
| JP | 2004-162035 A | 6/2004 |
| JP | 2004-229976 A | 8/2004 |
| JP | 2004-524076 A | 8/2004 |
| JP | 2004-531280 A | 10/2004 |
| JP | 2004-532084 A | 10/2004 |
| JP | 2004-532676 A | 10/2004 |
| JP | 2004-329624 A | 11/2004 |
| JP | 2004-337617 A | 12/2004 |
| JP | 2004-344662 A | 12/2004 |
| JP | 2004-344663 A | 12/2004 |
| JP | 2005-013573 A | 1/2005 |
| JP | 2005-028147 A | 2/2005 |
| JP | 2005-028148 A | 2/2005 |
| JP | 2005-028149 A | 2/2005 |
| JP | 2005-505309 A | 2/2005 |
| JP | 2005-505322 A | 2/2005 |
| JP | 2005-505334 A | 2/2005 |
| JP | 2005-080702 A | 3/2005 |
| JP | 2005-103280 A | 4/2005 |
| JP | 2005-103281 A | 4/2005 |
| JP | 2005-103293 A | 4/2005 |
| JP | 2005-511131 A | 4/2005 |
| JP | 2005-511137 A | 4/2005 |
| JP | 2005-131163 A | 5/2005 |
| JP | 2005-131164 A | 5/2005 |
| JP | 2005-131173 A | 5/2005 |
| JP | 2005-131211 A | 5/2005 |
| JP | 2005-131212 A | 5/2005 |
| JP | 2005-137423 A | 6/2005 |
| JP | 2005-137919 A | 6/2005 |
| JP | 2005-144183 A | 6/2005 |
| JP | 2005-152416 A | 6/2005 |
| JP | 2005-516714 A | 6/2005 |
| JP | 2005-187954 A | 7/2005 |
| JP | 2005-521109 A | 7/2005 |
| JP | 2005-523105 A | 8/2005 |
| JP | 2005-524474 A | 8/2005 |
| JP | 4461008 B2 | 8/2005 |
| JP | 2005-296412 A | 10/2005 |
| JP | 2005-529675 A | 10/2005 |
| JP | 2005-328882 A | 12/2005 |
| JP | 2005-335432 A | 12/2005 |
| JP | 2005-342267 A | 12/2005 |
| JP | 2006-034975 A | 2/2006 |
| JP | 2006-034977 A | 2/2006 |
| JP | 2006-034978 A | 2/2006 |
| JP | 2006-034980 A | 2/2006 |
| JP | 2006-506106 A | 2/2006 |
| JP | 2006-510879 A | 3/2006 |
| JP | 3791856 B2 | 6/2006 |
| JP | 2006-187649 A | 7/2006 |
| JP | 2006-218297 A | 8/2006 |
| JP | 2006-223872 A | 8/2006 |
| JP | 2006-281405 A | 10/2006 |
| JP | 2006-289064 A | 10/2006 |
| JP | 2006-334412 A | 12/2006 |
| JP | 2006-334417 A | 12/2006 |
| JP | 2006-346445 A | 12/2006 |
| JP | 2007-000634 A | 1/2007 |
| JP | 2007-050253 A | 3/2007 |
| JP | 2007-061628 A | 3/2007 |
| JP | 2007-083051 A | 4/2007 |
| JP | 2007-098130 A | 4/2007 |
| JP | 2007-105481 A | 4/2007 |
| JP | 3906843 B2 | 4/2007 |
| JP | 2007-117725 A | 5/2007 |
| JP | 2007-130471 A | 5/2007 |
| JP | 2007-130479 A | 5/2007 |
| JP | 2007-222615 A | 6/2007 |
| JP | 3934161 B2 | 6/2007 |
| JP | 2007-203047 A | 8/2007 |
| JP | 2007-203049 A | 8/2007 |
| JP | 2007-203051 A | 8/2007 |
| JP | 2007-203055 A | 8/2007 |
| JP | 2007-203057 A | 8/2007 |
| JP | 2007-524435 A | 8/2007 |
| JP | 2007-229448 A | 9/2007 |
| JP | 2007-526026 A | 9/2007 |
| JP | 2007-252916 A | 10/2007 |
| JP | 4001860 B2 | 10/2007 |
| JP | 2007-307373 A | 11/2007 |
| JP | 2007-325922 A | 12/2007 |
| JP | 2008-068073 A | 3/2008 |
| JP | 2008-510515 A | 4/2008 |
| JP | 2008-516669 A | 5/2008 |
| JP | 2008-206967 A | 9/2008 |
| JP | 2008-212637 A | 9/2008 |
| JP | 2008-212638 A | 9/2008 |
| JP | 2008-220956 A | 9/2008 |
| JP | 2009-507526 A | 9/2008 |
| JP | 2008-237881 A | 10/2008 |
| JP | 2008-259860 A | 10/2008 |
| JP | 2008-264535 A | 11/2008 |
| JP | 2008-283459 A | 11/2008 |
| JP | 2008-307393 A | 12/2008 |
| JP | 2009-000531 A | 1/2009 |
| JP | 2009-006137 A | 1/2009 |
| JP | 2009-502351 A | 1/2009 |
| JP | 2009-502352 A | 1/2009 |
| JP | 2009-022742 A | 2/2009 |
| JP | 2009-506799 A | 2/2009 |
| JP | 2009-072595 A | 4/2009 |
| JP | 2009-072599 A | 4/2009 |
| JP | 2009-090113 A | 4/2009 |
| JP | 2009-106752 A | 5/2009 |
| JP | 2009-189821 A | 8/2009 |
| JP | 2009-189823 A | 8/2009 |
| JP | 2009-189836 A | 8/2009 |
| JP | 2009-189837 A | 8/2009 |
| JP | 2009-189838 A | 8/2009 |
| JP | 2009-189847 A | 8/2009 |
| JP | 2009-201998 A | 9/2009 |
| JP | 2009-536082 A | 10/2009 |
| JP | 2009-261944 A | 11/2009 |
| JP | 2009-268908 A | 11/2009 |
| JP | 2009-538684 A | 11/2009 |
| JP | 2009-539420 A | 11/2009 |
| JP | 2009-291604 A | 12/2009 |
| JP | 2010-504808 A | 2/2010 |
| JP | 2010-504809 A | 2/2010 |

(56) References Cited

FOREIGN PATENT DOCUMENTS

| | | |
|---|---|---|
| JP | 2010-504813 A | 2/2010 |
| JP | 2010-504846 A | 2/2010 |
| JP | 2010-505524 A | 2/2010 |
| JP | 2010-069307 A | 4/2010 |
| JP | 2010-069310 A | 4/2010 |
| JP | 2010-075694 A | 4/2010 |
| JP | 2010-075695 A | 4/2010 |
| JP | 2010-088876 A | 4/2010 |
| JP | 2010-098844 A | 4/2010 |
| JP | 2010-142636 A | 7/2010 |
| JP | 2010-214166 A | 9/2010 |
| JP | 4549018 B2 | 9/2010 |
| JP | 2010-279690 A | 12/2010 |
| JP | 2010-540192 A | 12/2010 |
| JP | 2011-005260 A | 1/2011 |
| JP | 2011-504391 A | 2/2011 |
| JP | 2011-072797 A | 4/2011 |
| JP | 2011-078763 A | 4/2011 |
| JP | 2011-524199 A | 9/2011 |
| JP | 4783373 B2 | 9/2011 |
| JP | 2011-251156 A | 12/2011 |
| JP | 2012-040398 A | 3/2012 |
| JP | 2012-517289 A | 8/2012 |
| JP | 5140421 B2 | 2/2013 |
| JP | 5162595 B2 | 3/2013 |
| JP | 2013-128791 A | 7/2013 |
| JP | 5212039 B2 | 7/2013 |
| JP | 6007357 B2 | 10/2013 |
| JP | 5333899 B2 | 11/2013 |
| KR | 20110003229 A | 1/2011 |
| RU | 2008830 C1 | 3/1994 |
| RU | 2052979 C1 | 1/1996 |
| RU | 2098025 C1 | 12/1997 |
| RU | 2141279 C1 | 11/1999 |
| RU | 2144791 C1 | 1/2000 |
| RU | 2181566 C2 | 4/2002 |
| RU | 2187249 C2 | 8/2002 |
| RU | 2189091 C2 | 9/2002 |
| RU | 32984 U1 | 10/2003 |
| RU | 2225170 C2 | 3/2004 |
| RU | 42750 U1 | 12/2004 |
| RU | 61114 U1 | 2/2007 |
| SU | 189517 A | 1/1967 |
| SU | 328636 A | 9/1972 |
| SU | 511939 A1 | 4/1976 |
| SU | 674747 A1 | 7/1979 |
| SU | 886900 A1 | 12/1981 |
| SU | 1009439 A | 4/1983 |
| SU | 1022703 A1 | 6/1983 |
| SU | 1333319 A2 | 8/1987 |
| SU | 1377053 A1 | 2/1988 |
| SU | 1509051 A1 | 9/1989 |
| SU | 1561964 A1 | 5/1990 |
| SU | 1722476 A1 | 5/1990 |
| SU | 1708312 A1 | 1/1992 |
| SU | 1752361 A1 | 3/1992 |
| SU | 1814161 A1 | 5/1993 |
| WO | WO 82/02824 A1 | 9/1982 |
| WO | WO 86/02254 A1 | 4/1986 |
| WO | WO 91/15157 A1 | 10/1991 |
| WO | WO 92/20295 A1 | 11/1992 |
| WO | WO 92/21300 A1 | 12/1992 |
| WO | WO 93/08755 A1 | 5/1993 |
| WO | WO 93/13718 A1 | 7/1993 |
| WO | WO 93/14690 A1 | 8/1993 |
| WO | WO 93/15648 A1 | 8/1993 |
| WO | WO 93/15850 A1 | 8/1993 |
| WO | WO 93/19681 A1 | 10/1993 |
| WO | WO 94/00060 A1 | 1/1994 |
| WO | WO 94/11057 A1 | 5/1994 |
| WO | WO 94/12108 A1 | 6/1994 |
| WO | WO 94/17737 A1 | 8/1994 |
| WO | WO 94/18893 A1 | 9/1994 |
| WO | WO 94/20030 A1 | 9/1994 |
| WO | WO 94/22378 A1 | 10/1994 |
| WO | WO 94/23659 A1 | 10/1994 |
| WO | WO 94/24943 A1 | 11/1994 |
| WO | WO 94/24947 A1 | 11/1994 |
| WO | WO 95/02369 A1 | 1/1995 |
| WO | WO 95/03743 A1 | 2/1995 |
| WO | WO 95/06817 A1 | 3/1995 |
| WO | WO 95/09576 A1 | 4/1995 |
| WO | WO 95/09577 A1 | 4/1995 |
| WO | WO 95/14436 A1 | 6/1995 |
| WO | WO 95/17855 A1 | 7/1995 |
| WO | WO 95/18383 A1 | 7/1995 |
| WO | WO 95/18572 A1 | 7/1995 |
| WO | WO 95/19739 A1 | 7/1995 |
| WO | WO 95/20360 A1 | 8/1995 |
| WO | WO 95/23557 A1 | 9/1995 |
| WO | WO 95/24865 A1 | 9/1995 |
| WO | WO 95/25471 A3 | 9/1995 |
| WO | WO 95/26562 A1 | 10/1995 |
| WO | WO 95/29639 A1 | 11/1995 |
| WO | WO 96/04858 A1 | 2/1996 |
| WO | WO 96/18344 A2 | 6/1996 |
| WO | WO 96/19151 A1 | 6/1996 |
| WO | WO 96/19152 A1 | 6/1996 |
| WO | WO 96/20652 A1 | 7/1996 |
| WO | WO 96/21119 A1 | 7/1996 |
| WO | WO 96/22055 A1 | 7/1996 |
| WO | WO 96/23448 A1 | 8/1996 |
| WO | WO 96/24301 A1 | 8/1996 |
| WO | WO 96/27337 A1 | 9/1996 |
| WO | WO 96/31155 A1 | 10/1996 |
| WO | WO 96/35464 A1 | 11/1996 |
| WO | WO 96/39085 A1 | 12/1996 |
| WO | WO 96/39086 A1 | 12/1996 |
| WO | WO 96/39087 A1 | 12/1996 |
| WO | WO 96/39088 A1 | 12/1996 |
| WO | WO 96/39089 A1 | 12/1996 |
| WO | WO 97/00646 A1 | 1/1997 |
| WO | WO 97/00647 A1 | 1/1997 |
| WO | WO 97/01989 A1 | 1/1997 |
| WO | WO 97/06582 A1 | 2/1997 |
| WO | WO 97/10763 A1 | 3/1997 |
| WO | WO 97/10764 A1 | 3/1997 |
| WO | WO 97/11648 A2 | 4/1997 |
| WO | WO 97/11649 A1 | 4/1997 |
| WO | WO 97/15237 A1 | 5/1997 |
| WO | WO 97/24073 A1 | 7/1997 |
| WO | WO 97/24993 A1 | 7/1997 |
| WO | WO 97/30644 A1 | 8/1997 |
| WO | WO 97/34533 A1 | 9/1997 |
| WO | WO 97/37598 A1 | 10/1997 |
| WO | WO 97/39688 A2 | 10/1997 |
| WO | WO 97/41767 A2 | 11/1997 |
| WO | WO 98/01080 A1 | 1/1998 |
| WO | WO 98/17180 A1 | 4/1998 |
| WO | WO 98/22154 A2 | 5/1998 |
| WO | WO 98/27880 A1 | 7/1998 |
| WO | WO 98/30153 A1 | 7/1998 |
| WO | WO 98/47436 A1 | 10/1998 |
| WO | WO 98/58589 A1 | 12/1998 |
| WO | WO 99/02090 A1 | 1/1999 |
| WO | WO 99/03407 A1 | 1/1999 |
| WO | WO 99/03408 A1 | 1/1999 |
| WO | WO 99/03409 A1 | 1/1999 |
| WO | WO 99/12483 A1 | 3/1999 |
| WO | WO 99/12487 A1 | 3/1999 |
| WO | WO 99/12488 A1 | 3/1999 |
| WO | WO 99/15086 A1 | 4/1999 |
| WO | WO 99/15091 A1 | 4/1999 |
| WO | WO 99/23933 A2 | 5/1999 |
| WO | WO 99/23959 A1 | 5/1999 |
| WO | WO 99/25261 A1 | 5/1999 |
| WO | WO 99/29244 A1 | 6/1999 |
| WO | WO 99/34744 A1 | 7/1999 |
| WO | WO 99/45849 A1 | 9/1999 |
| WO | WO 99/48430 A1 | 9/1999 |
| WO | WO 99/51158 A1 | 10/1999 |
| WO | WO 00/24322 A1 | 5/2000 |
| WO | WO 00/24330 A1 | 5/2000 |
| WO | WO 00/41638 A1 | 7/2000 |

(56) References Cited

FOREIGN PATENT DOCUMENTS

| | | |
|---|---|---|
| WO | WO 00/48506 A1 | 8/2000 |
| WO | WO 00/53112 A2 | 9/2000 |
| WO | WO 00/54653 A1 | 9/2000 |
| WO | WO 00/57796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 00/78222 A1 | 12/2000 |
| WO | WO 01/03587 A1 | 1/2001 |
| WO | WO 01/05702 A1 | 1/2001 |
| WO | WO 01/10482 A1 | 2/2001 |
| WO | WO 01/35845 A1 | 5/2001 |
| WO | WO 01/54594 A1 | 8/2001 |
| WO | WO 01/58371 A1 | 8/2001 |
| WO | WO 01/62158 A2 | 8/2001 |
| WO | WO 01/62161 A1 | 8/2001 |
| WO | WO 01/62162 A1 | 8/2001 |
| WO | WO 01/62163 A1 | 8/2001 |
| WO | WO 01/62164 A2 | 8/2001 |
| WO | WO 01/62169 A2 | 8/2001 |
| WO | WO 01/78605 A2 | 10/2001 |
| WO | WO 01/80757 A2 | 11/2001 |
| WO | WO 01/91646 A1 | 12/2001 |
| WO | WO 02/00121 A1 | 1/2002 |
| WO | WO 02/07608 A2 | 1/2002 |
| WO | WO 02/07618 A1 | 1/2002 |
| WO | WO 02/17799 A1 | 3/2002 |
| WO | WO 02/19920 A1 | 3/2002 |
| WO | WO 02/19932 A1 | 3/2002 |
| WO | WO 02/26143 A1 | 4/2002 |
| WO | WO 02/30297 A2 | 4/2002 |
| WO | WO 02/32322 A2 | 4/2002 |
| WO | WO 02/36028 A1 | 5/2002 |
| WO | WO 02/43571 A2 | 6/2002 |
| WO | WO 02/058568 A1 | 8/2002 |
| WO | WO 02/060328 A1 | 8/2002 |
| WO | WO 02/065933 A2 | 8/2002 |
| WO | WO 02/067785 A2 | 9/2002 |
| WO | WO 02/080781 A2 | 10/2002 |
| WO | WO 02/085218 A2 | 10/2002 |
| WO | WO 02/087586 A1 | 11/2002 |
| WO | WO 02/098302 A1 | 12/2002 |
| WO | WO 03/000138 A2 | 1/2003 |
| WO | WO 03/001329 A2 | 1/2003 |
| WO | WO 03/001986 A2 | 1/2003 |
| WO | WO 03/013363 A1 | 2/2003 |
| WO | WO 03/013372 A2 | 2/2003 |
| WO | WO 03/015604 A2 | 2/2003 |
| WO | WO 03/020106 A2 | 3/2003 |
| WO | WO 03/020139 A2 | 3/2003 |
| WO | WO 03/024339 A1 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/055402 A1 | 7/2003 |
| WO | WO 03/057048 A1 | 7/2003 |
| WO | WO 03/057058 A1 | 7/2003 |
| WO | WO 03/063694 A2 | 8/2003 |
| WO | WO 03/077769 A1 | 9/2003 |
| WO | WO 03/079911 A1 | 10/2003 |
| WO | WO 03/082126 A1 | 10/2003 |
| WO | WO 03/086206 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/004578 A1 | 1/2004 |
| WO | WO 2004/006980 A2 | 1/2004 |
| WO | WO 2004/011037 A2 | 2/2004 |
| WO | WO 2004/014238 A2 | 2/2004 |
| WO | WO 2004/019769 A1 | 3/2004 |
| WO | WO 2004/019803 A1 | 3/2004 |
| WO | WO 2004/021868 A2 | 3/2004 |
| WO | WO 2004/028585 A2 | 4/2004 |
| WO | WO 2004/030554 A1 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/032783 A1 | 4/2004 |
| WO | WO 2004/034875 A2 | 4/2004 |
| WO | WO 2004/047626 A1 | 6/2004 |
| WO | WO 2004/047653 A2 | 6/2004 |
| WO | WO 2004/049956 A2 | 6/2004 |
| WO | WO 2004/050971 A2 | 6/2004 |
| WO | WO 2004/052426 A2 | 6/2004 |
| WO | WO 2004/056276 A1 | 7/2004 |
| WO | WO 2004/056277 A1 | 7/2004 |
| WO | WO 2004/062516 A1 | 7/2004 |
| WO | WO 2004/064600 A2 | 8/2004 |
| WO | WO 2004/078050 A2 | 9/2004 |
| WO | WO 2004/078051 A2 | 9/2004 |
| WO | WO 2004/078236 A2 | 9/2004 |
| WO | WO 2004/086987 A1 | 10/2004 |
| WO | WO 2004/096015 A2 | 11/2004 |
| WO | WO 2004/096057 A2 | 11/2004 |
| WO | WO 2004/103157 A2 | 12/2004 |
| WO | WO 2004/105593 A1 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/042041 A1 | 5/2005 |
| WO | WO 2005/044078 A2 | 5/2005 |
| WO | WO 2005/048809 A1 | 6/2005 |
| WO | WO 2005/055846 A1 | 6/2005 |
| WO | WO 2005/072634 A2 | 8/2005 |
| WO | WO 2005/078892 A1 | 8/2005 |
| WO | WO 2005/079675 A2 | 9/2005 |
| WO | WO 2005/087128 A1 | 9/2005 |
| WO | WO 2005/096954 A2 | 10/2005 |
| WO | WO 2005/112806 A2 | 12/2005 |
| WO | WO 2005/112808 A1 | 12/2005 |
| WO | WO 2005/115251 A1 | 12/2005 |
| WO | WO 2005/115253 A2 | 12/2005 |
| WO | WO 2005/117735 A1 | 12/2005 |
| WO | WO 2005/122936 A1 | 12/2005 |
| WO | WO 2006/023486 A1 | 3/2006 |
| WO | WO 2006/023578 A2 | 3/2006 |
| WO | WO 2006/027014 A1 | 3/2006 |
| WO | WO 2006/028314 A1 | 3/2006 |
| WO | WO 2006/044490 A2 | 4/2006 |
| WO | WO 2006/044581 A2 | 4/2006 |
| WO | WO 2006/044810 A2 | 4/2006 |
| WO | WO 2006/049852 A2 | 5/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/085389 A1 | 8/2006 |
| WO | WO 2006/092563 A1 | 9/2006 |
| WO | WO 2006/092565 A1 | 9/2006 |
| WO | WO 2006/115958 A1 | 11/2006 |
| WO | WO 2006/125940 A1 | 11/2006 |
| WO | WO 2006/132992 A2 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/051000 A2 | 5/2007 |
| WO | WO 2007/059233 A2 | 5/2007 |
| WO | WO 2007/074430 A2 | 7/2007 |
| WO | WO 2007/089603 A2 | 8/2007 |
| WO | WO 2007/098220 A2 | 8/2007 |
| WO | WO 2007/121579 A1 | 11/2007 |
| WO | WO 2007/129121 A1 | 11/2007 |
| WO | WO 2007/131110 A2 | 11/2007 |
| WO | WO 2007/137304 A2 | 11/2007 |
| WO | WO 2007/139734 A2 | 12/2007 |

(56) References Cited

FOREIGN PATENT DOCUMENTS

| WO | WO 2007/142625 A2 | 12/2007 |
|---|---|---|
| WO | WO 2007/145825 A2 | 12/2007 |
| WO | WO 2007/146987 A2 | 12/2007 |
| WO | WO 2007/147439 A1 | 12/2007 |
| WO | WO 2008/020964 A2 | 2/2008 |
| WO | WO 2008/021687 A1 | 2/2008 |
| WO | WO 2008/021969 A2 | 2/2008 |
| WO | WO 2008/039237 A1 | 4/2008 |
| WO | WO 2008/039249 A1 | 4/2008 |
| WO | WO 2008/039270 A1 | 4/2008 |
| WO | WO 2008/045383 A2 | 4/2008 |
| WO | WO 2008/057281 A2 | 5/2008 |
| WO | WO 2008/070763 A1 | 6/2008 |
| WO | WO 2008/080148 A2 | 7/2008 |
| WO | WO 2008/089404 A2 | 7/2008 |
| WO | WO 2008/101080 A1 | 8/2008 |
| WO | WO 2008/101228 A2 | 8/2008 |
| WO | WO 2008/103797 A2 | 8/2008 |
| WO | WO 2008/109123 A2 | 9/2008 |
| WO | WO 2008/109125 A1 | 9/2008 |
| WO | WO 2008/112912 A2 | 9/2008 |
| WO | WO 2008/118728 A1 | 10/2008 |
| WO | WO 2008/118928 A2 | 10/2008 |
| WO | WO 2008/124748 A1 | 10/2008 |
| WO | WO 2008/131357 A1 | 10/2008 |
| WO | WO 2009/005969 A2 | 1/2009 |
| WO | WO 2009/022614 A1 | 2/2009 |
| WO | WO 2009/023851 A1 | 2/2009 |
| WO | WO 2009/033057 A2 | 3/2009 |
| WO | WO 2009/039506 A1 | 3/2009 |
| WO | WO 2009/046394 A1 | 4/2009 |
| WO | WO 2009/066105 A1 | 5/2009 |
| WO | WO 2009/067649 A2 | 5/2009 |
| WO | WO 2009/091497 A2 | 7/2009 |
| WO | WO 2009/120944 A2 | 10/2009 |
| WO | WO 2009/137761 A2 | 11/2009 |
| WO | WO 2009/143092 A1 | 11/2009 |
| WO | WO 2009/143331 A1 | 11/2009 |
| WO | WO 2009/150650 A2 | 12/2009 |
| WO | WO 2009/152307 A1 | 12/2009 |
| WO | WO 2010/028332 A2 | 3/2010 |
| WO | WO 2010/030434 A1 | 3/2010 |
| WO | WO 2010/045425 A1 | 4/2010 |
| WO | WO 2010/050771 A2 | 5/2010 |
| WO | WO 2010/054404 A1 | 5/2010 |
| WO | WO 2010/056714 A1 | 5/2010 |
| WO | WO 2010/063795 A1 | 6/2010 |
| WO | WO 2010/090940 A1 | 8/2010 |
| WO | WO 2010/093333 A1 | 8/2010 |
| WO | WO 2010/098871 A2 | 9/2010 |
| WO | WO 2011/008672 A2 | 1/2011 |
| WO | WO 2011/013103 A1 | 2/2011 |
| WO | WO 2011/044343 A2 | 4/2011 |
| WO | WO 2011/060311 A2 | 5/2011 |
| WO | WO 2011/127137 A1 | 10/2011 |
| WO | WO 2012/006306 A2 | 1/2012 |
| WO | WO 2012/009431 A2 | 1/2012 |
| WO | WO 2012/021671 A1 | 2/2012 |
| WO | WO 2012/040438 A1 | 3/2012 |
| WO | WO 2012/044551 A1 | 4/2012 |
| WO | WO 2012/044554 A1 | 4/2012 |
| WO | WO 2012/044597 A1 | 4/2012 |
| WO | WO 2012/044606 A2 | 4/2012 |
| WO | WO 2012/044820 A1 | 4/2012 |
| WO | WO 2012/044844 A2 | 4/2012 |
| WO | WO 2012/044853 A1 | 4/2012 |
| WO | WO 2012/044854 A1 | 4/2012 |
| WO | WO 2012/058213 A2 | 5/2012 |
| WO | WO 2012/068156 A2 | 5/2012 |
| WO | WO 2012/109760 A1 | 8/2012 |
| WO | WO 2012/127462 A1 | 9/2012 |
| WO | WO 2012/135705 A1 | 10/2012 |
| WO | WO 2012/143913 A2 | 10/2012 |
| WO | WO 2012/148667 A2 | 11/2012 |
| WO | WO 2012/148703 A2 | 11/2012 |
| WO | WO 2012/160163 A1 | 11/2012 |
| WO | WO 2012/166503 A1 | 12/2012 |
| WO | WO 2013/009252 A2 | 1/2013 |
| WO | WO 2013/009699 A2 | 1/2013 |
| WO | WO 2013/036409 A1 | 3/2013 |
| WO | WO 2013/043707 A2 | 3/2013 |
| WO | WO 2013/043717 A1 | 3/2013 |
| WO | WO 2013/043721 A2 | 3/2013 |
| WO | WO 2013/062978 A2 | 5/2013 |
| WO | WO 2013/148762 A2 | 10/2013 |
| WO | WO 2013/167427 A1 | 11/2013 |
| WO | WO 2014/004199 A1 | 1/2014 |
| WO | WO 2014/004294 A2 | 1/2014 |

OTHER PUBLICATIONS

U.S. Appl. No. 13/851,676, filed Mar. 27, 2013.
U.S. Appl. No. 13/851,693, filed Mar. 27, 2013.
U.S. Appl. No. 13/851,684, filed Mar. 27, 2013.
U.S. Appl. No. 14/187,383, filed Feb. 24, 2014.
U.S. Appl. No. 14/187,386, filed Feb. 24, 2014.
U.S. Appl. No. 14/187,385, filed Feb. 24, 2014.
U.S. Appl. No. 14/187,384, filed Feb. 24, 2014.
U.S. Appl. No. 14/187,389, filed Feb. 24, 2014.
International Search Report and Written Opinion for PCT/US2015/015103 dated Nov. 31, 2015 (13 pages).
Disclosed Anonymously, "Motor-Driven Surgical Stapler Improvements," Research Disclosure Database No. 526041, Published: Feb. 2008.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.
B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).
The Sodem Aseptic Battery Transfer Kit, Sodem Systems, (2000), 3 pages.
"Biomedical Coatings," Fort Wayne Metals, Research Products Corporation, obtained online at www.fwmetals.com on Jun. 21, 2010 (1 page).
Van Meer et al., "A Disposable Plastic Compact Wrist for Smart Minimally Invasive Surgical Tools," LAAS/CNRS (Aug. 2005).
Breedveld et al., "A New, Easily Miniaturized Sterrable Endoscope," IEEE Engineering in Medicine and Biology Magazine (Nov./Dec. 2005).
D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).
Datasheet for Panasonic TK Relays Ultra Low Profile 2 A Polarized Relay, Copyright Matsushita Electric Works, Ltd. (Known of at least as early as Aug. 17, 2010), 5 pages.
ASTM procedure D2240-00, "Standard Test Method for Rubber Property-Durometer Hardness," (Published Aug. 2000).
ASTM procedure D2240-05, "Standard Test Method for Rubber Property-Durometer Hardness," (Published Apr. 2010).
Covidien Brochure, "Endo GIA™ Reloads with Tri-Staple™ Technology," (2010), 1 page.
Covidien Brochure, "Endo GIA™ Reloads with Tri-Staple™ Technology and Endo GIA™ Ultra Universal Staplers," (2010), 2 pages.
Covidien Brochure, "Endo GIA™ Black Reload with Tri-Staple ™ Technology," (2012), 2 pages.
Covidien Brochure, "Endo GIA™ Curved Tip Reload with Tri-Staple™ Technology," (2012), 2 pages.
Covidien Brochure, "Endo GIA™ Reloads with Tri-Staple™ Technology," (2010), 2 pages.
Covidien Brochure, "Endo GIA™ Ultra Universal Stapler," (2010), 2 pages.

(56) References Cited

OTHER PUBLICATIONS

Miyata et al., "Biomolecule-Sensitive Hydrogels," Advanced Drug Delivery Reviews, 54 (2002) pp. 79-98.
Jeong et al., "Thermosensitive Sol-Gel Reversible Hydrogels," Advanced Drug Delivery Reviews, 54 (2002) pp. 37-51.
Byrne et al., "Molecular Imprinting Within Hydrogels," Advanced Drug Delivery Reviews, 54 (2002) pp. 149-161.
Qiu et al., "Environment-Sensitive Hydrogels for Drug Delivery," Advanced Drug Delivery Reviews, 53 (2001) pp. 321-339.
Hoffman, "Hydrogels for Biomedical Applications," Advanced Drug Delivery Reviews, 43 (2002) pp. 3-12.
Hoffman, "Hydrogels for Biomedical Applications," Advanced Drug Delivery Reviews, 54 (2002) pp. 3-12.
Peppas, "Physiologically Responsive Hydrogels," Journal of Bioactive and Compatible Polymers, vol. 6 (Jul. 1991) pp. 241-246.
Ebara, "Carbohydrate-Derived Hydrogels and Microgels," Engineered Carbohydrate-Based Materials for Biomedical Applications: Polymers, Surfaes, Dendrirners, Nanoparticles, and Hydrogels, Edited by Ravin Narain, 2011, pp. 337-345.
Peppas, Editor "Hydrogels in Medicine and Pharmacy," vol. I, Fundamentals, CRC Press, 1986.
Matsuda, "Thermodynamics of Formation of Porous Polymeric Membrane from Solutions," Polymer Journal, vol. 23, No. 5, pp. 435-444 (1991).
Young, "Microcellular foams via phase separation," Journal of Vacuum Science & Technology A 4(3), (May/Jun. 1986).
Chen et al., "Elastomeric Biomaterials for Tissue Engineering," Progress in Polymer Science 38 (2013), pp. 584-671.
Pitt et al., "Attachment of Hyaluronan to Metallic Surfaces," J. Biomed. Mater. Res. 68A: pp. 95-106, 2004.
Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).
Solorio et al., "Gelatin Microspheres Crosslinked with Genipin for Local Delivery of Growth Factors," J. Tissue Eng. Regen. Med. (2010), 4(7): pp. 514-523.

http://ninpgan.net/publications/51-100/89.pdf; 2004, Ning Pan, on Uniqueness of Fibrous Materials, Design & Nature II. Eds: Colins, M. and Brebbia, C. WIT Press, Boston, 493-504.
Covidien iDrive™ Ultra in Service Reference Card, "iDrive™ Ultra Powered Stapling Device," (4 pages).
Covidien iDrive™ Ultra Powered Stapling System ibrochure, "The Power of iDrive™ Ultra Powered Stapling System and Tri-Staple™ Technology," (23 pages).
Seils et al., Covidien Summary: Clinical Study "UCONN Biodynamics: Final Report on Results," (2 pages).
Covidien "iDrive™ Ultra Powered Stapling System, A Guide for Surgeons," (6 pages).
Covidien "iDrive™ Ultra Powered Stapling System, Cleaning and Sterilization Guide," (2 pages).
Covidien brochure "iDrive™ Ultra Powered Stapling System," (6 pages).
"Indian Standard: Automotive Vehicles—Brakes and Braking Systems (IS 11852-1:2001)", Mar. 1, 2001.
Fast, Versatile Blackfin Processors Handle Advanced RFID Reader Applications; Analog Dialogue: vol. 40—Sep. 2006; http://www.analog.com/library/analogDialogue/archives/40-09/rfid.pdf; Wayback Machine to Feb. 15, 2012.
Serial Communication Protocol; Michael Lemmon Feb. 1, 2009; http://www3.nd.edu/~lemmon/cou rses/ee224/web-manual/web-manual/lab12/node2.html; Wayback Machine to Apr. 29, 2012.
Allegro MicroSystems, LLC, Automotive Full Bridge MOSFET Driver, A3941-DS, Rev. 5, 21 pages, http://www.allegromicro.com/~/media/Files/Datasheets/A3941-Datasheet.ashx?la=en.
Patrick J. Sweeney: "RFID for Dummies", Mar. 11, 2010, pp. 365-365, XP055150775, ISBN: 978-1-11-805447-5, Retrieved from the Internet: URL: books.google.de/books?isbn=1118054474 [retrieved on Nov. 4, 2014]—book not attached.
Data Sheet of LM4F230H5QR, 2007.
U.S. Appl. No. 12/031,573, filed Feb. 14, 2008.

\* cited by examiner

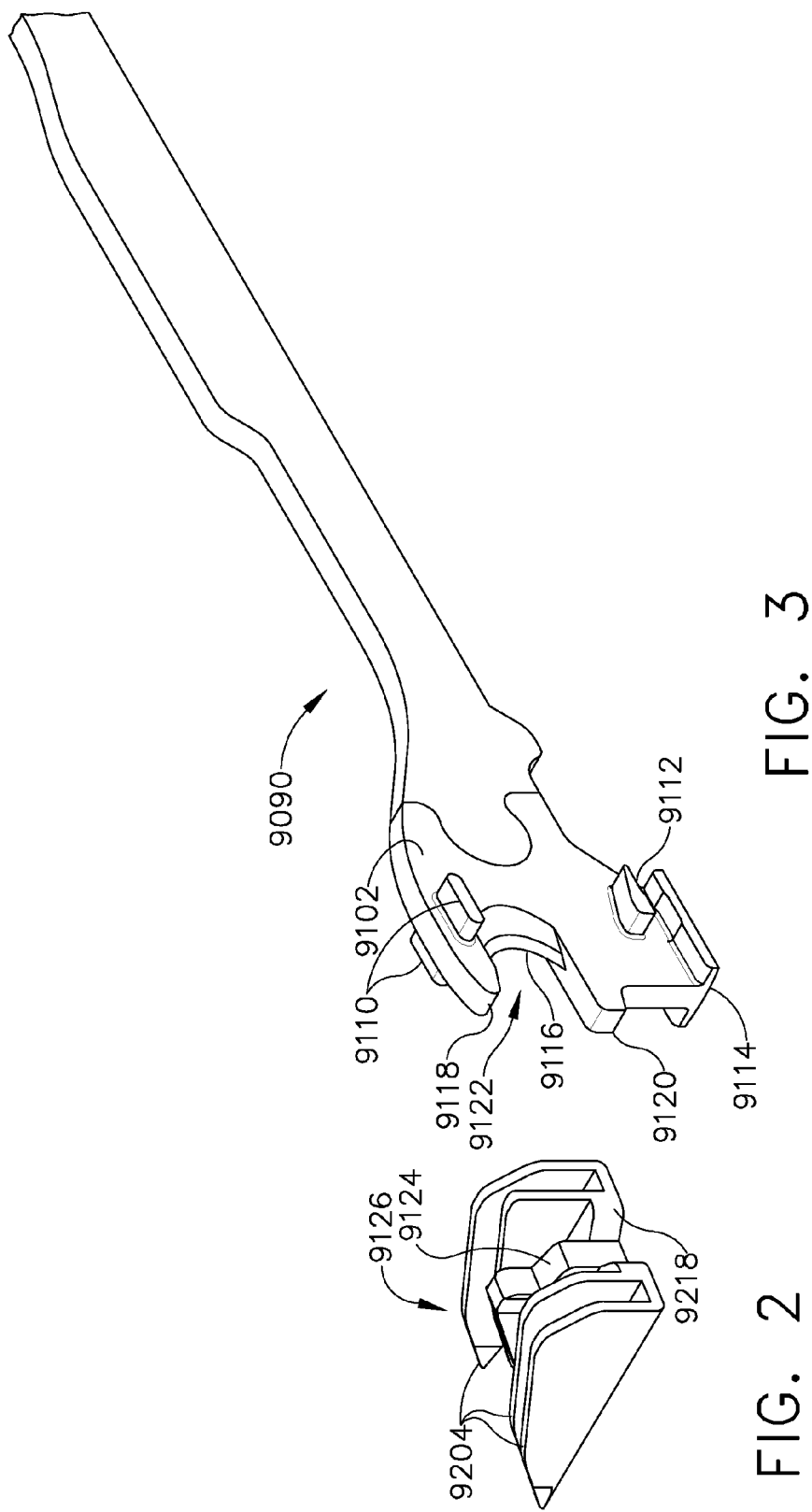

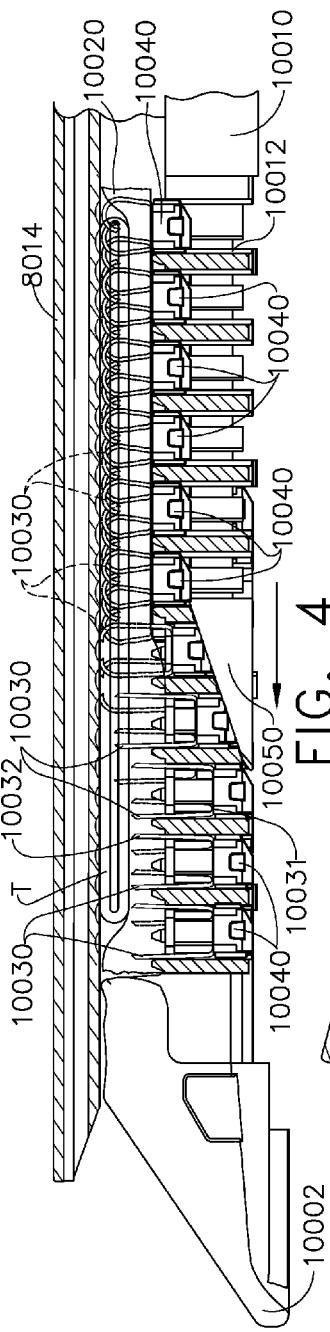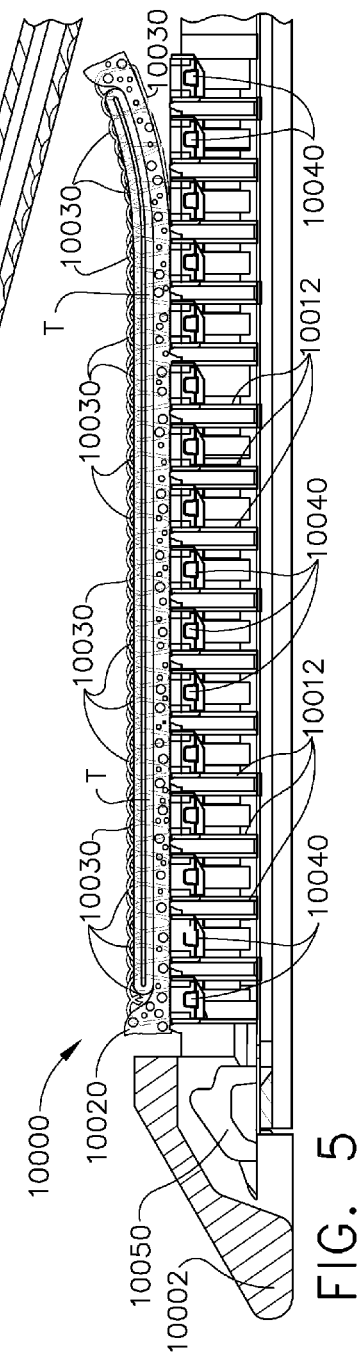

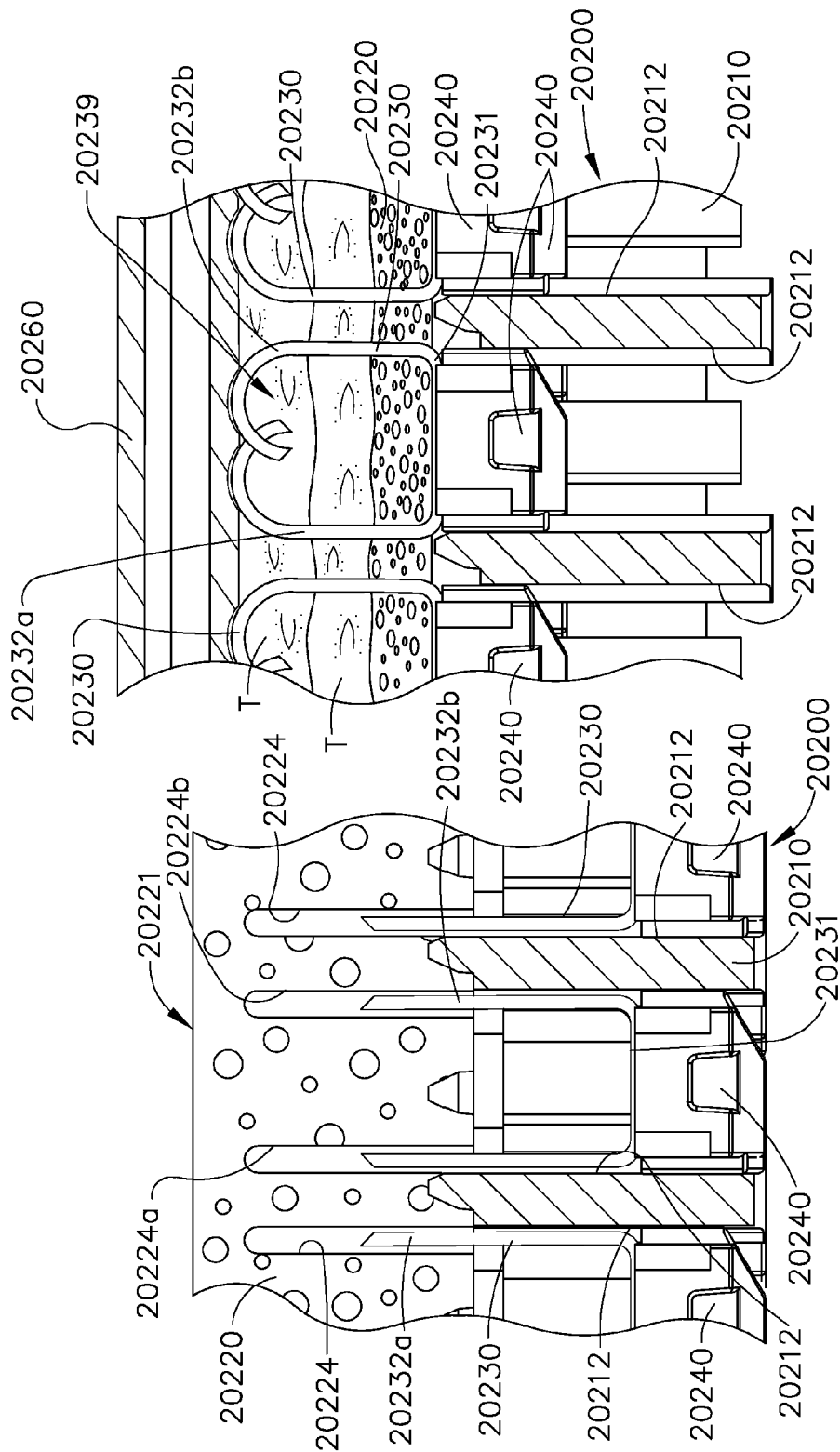

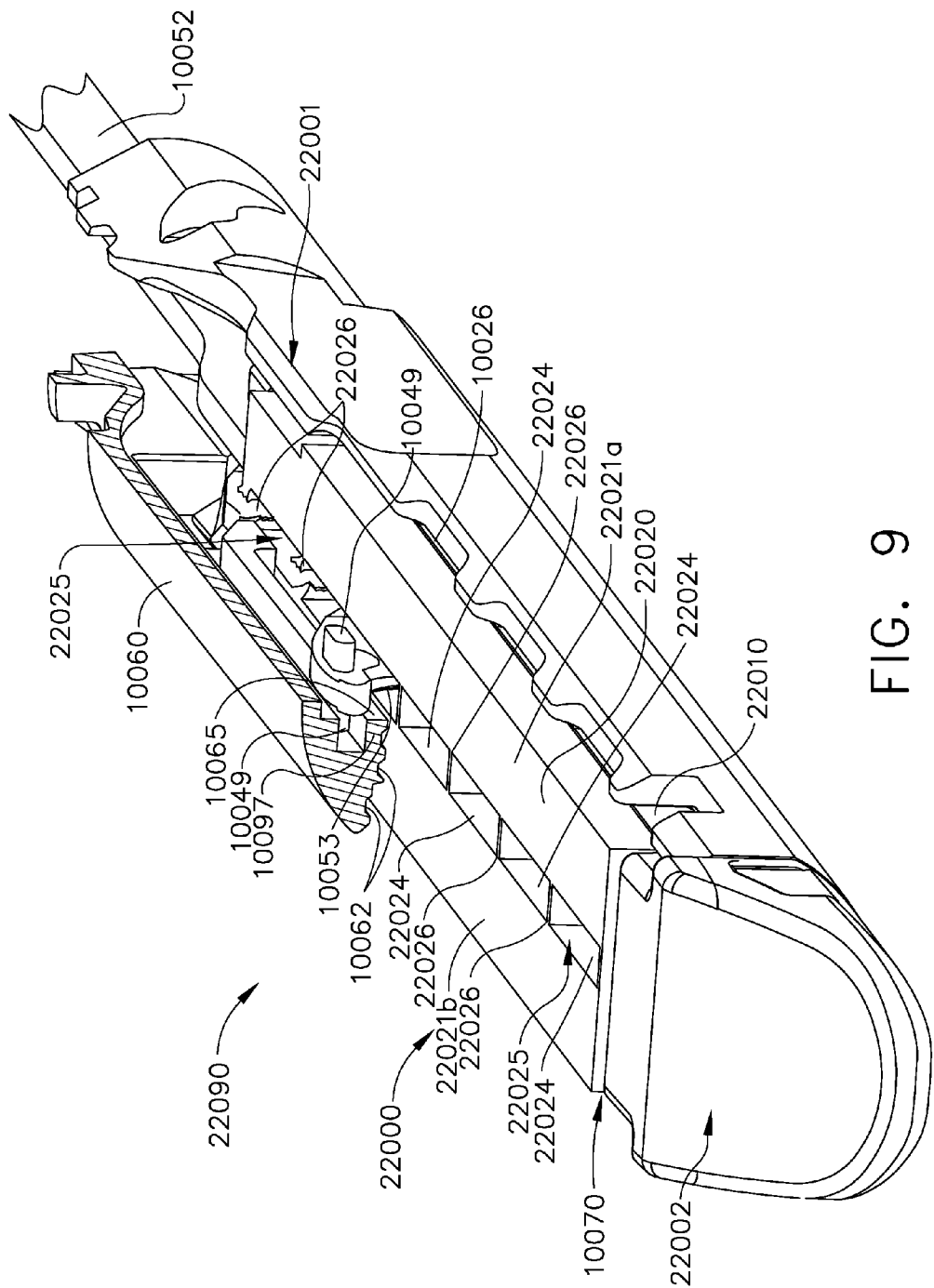

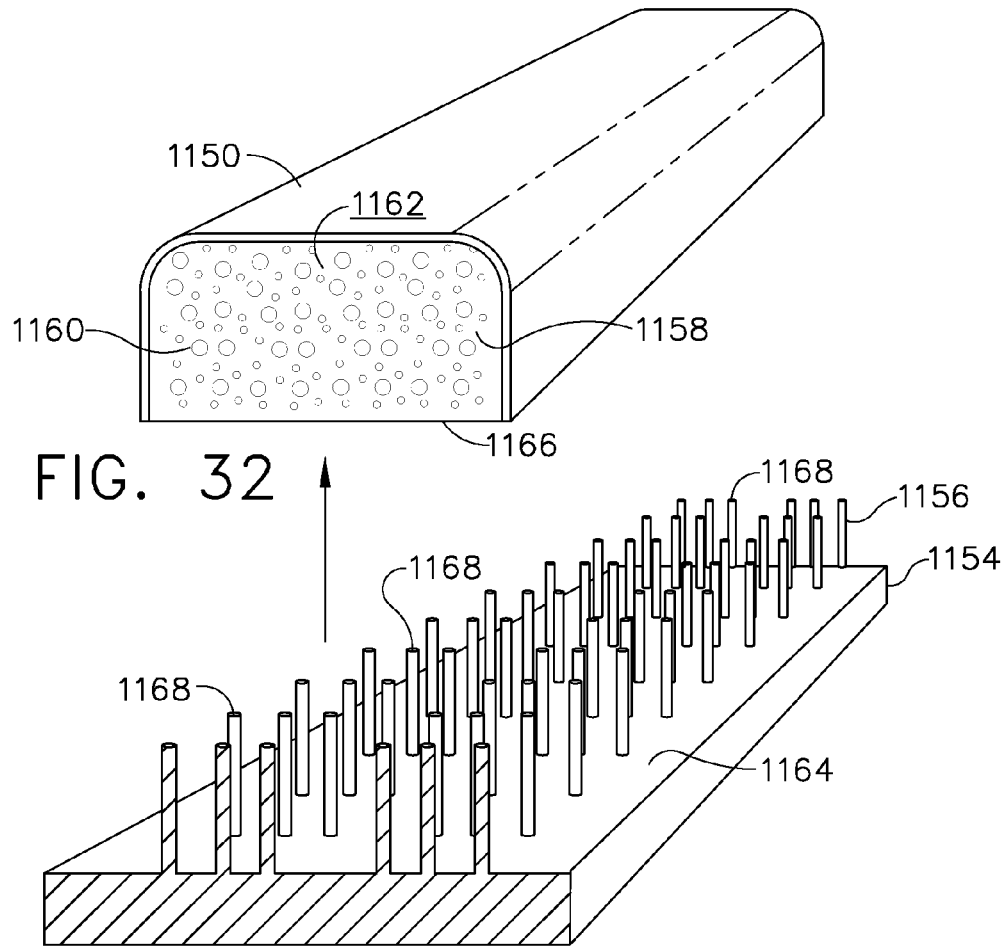
FIG. 32
FIG. 33
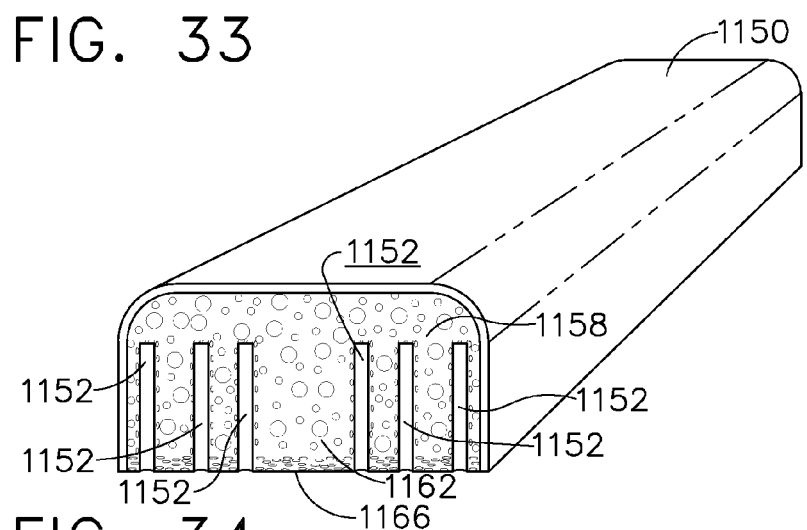
FIG. 34

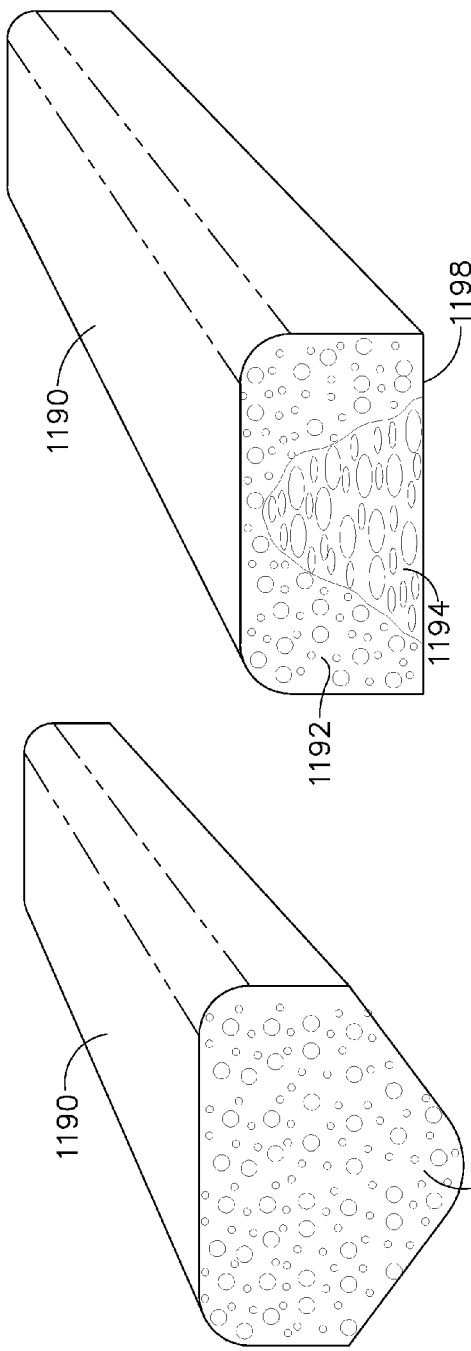
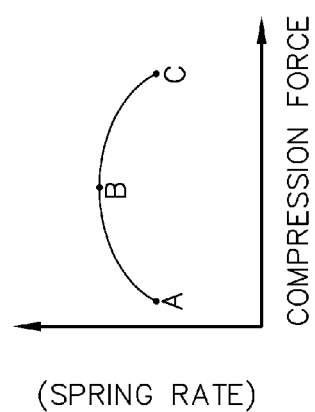
FIG. 38
FIG. 39
FIG. 40

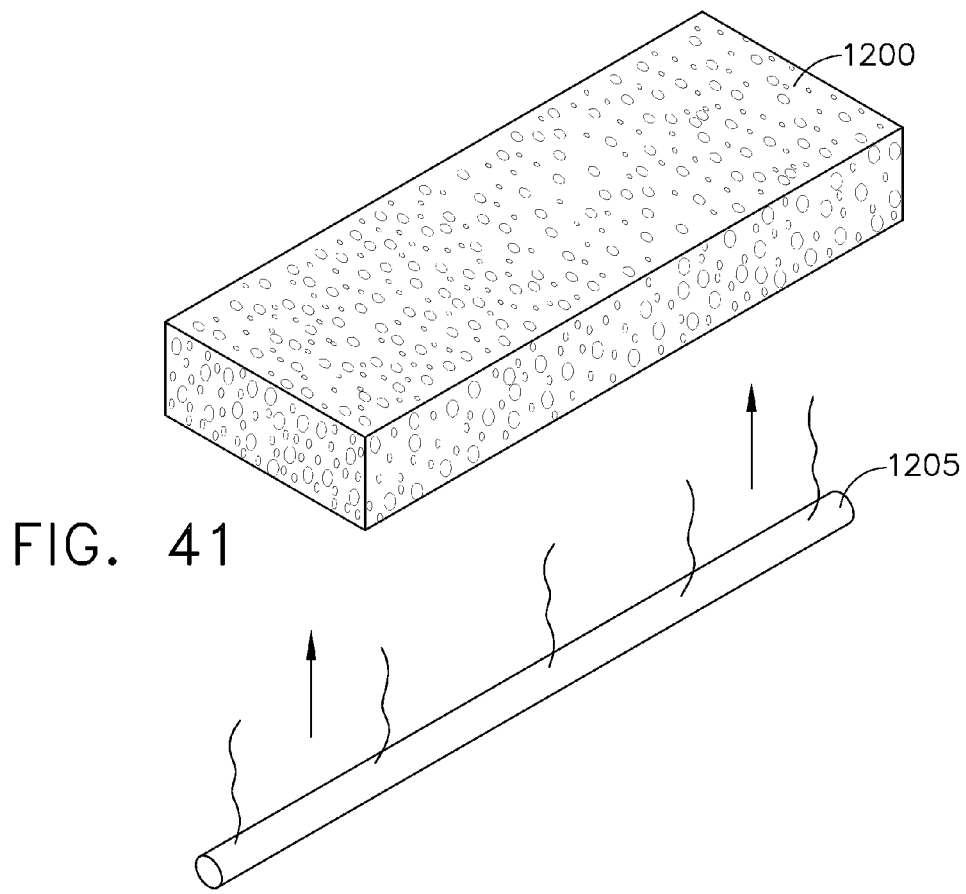
FIG. 41
FIG. 42
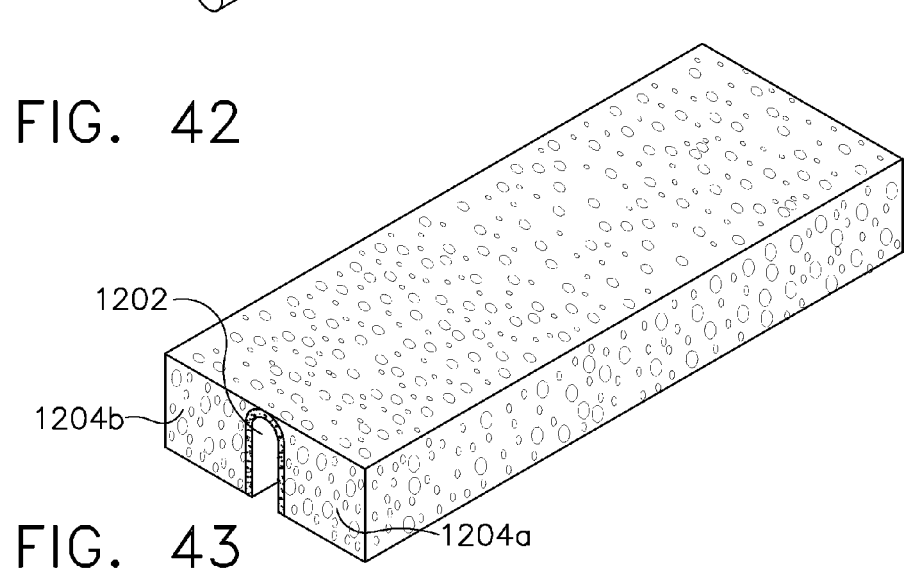
FIG. 43

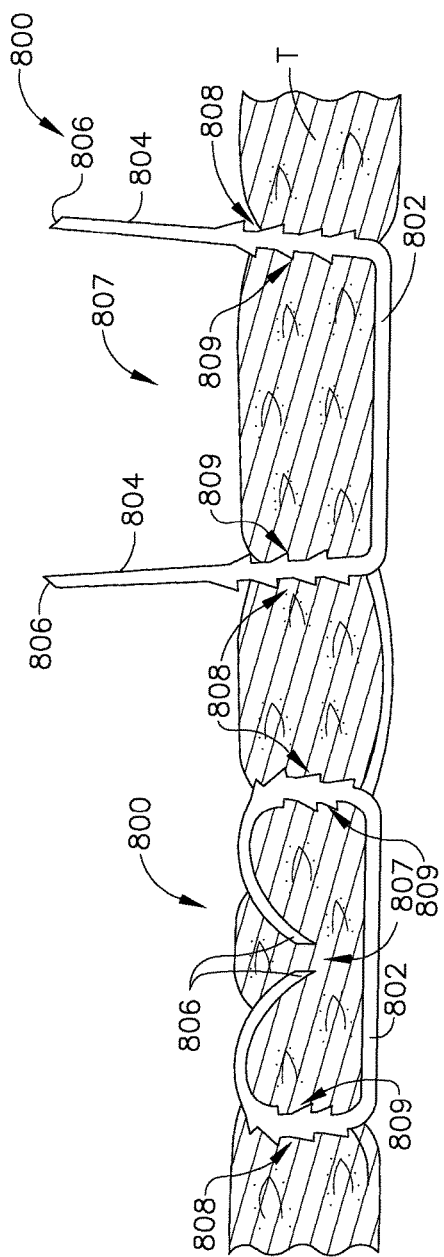
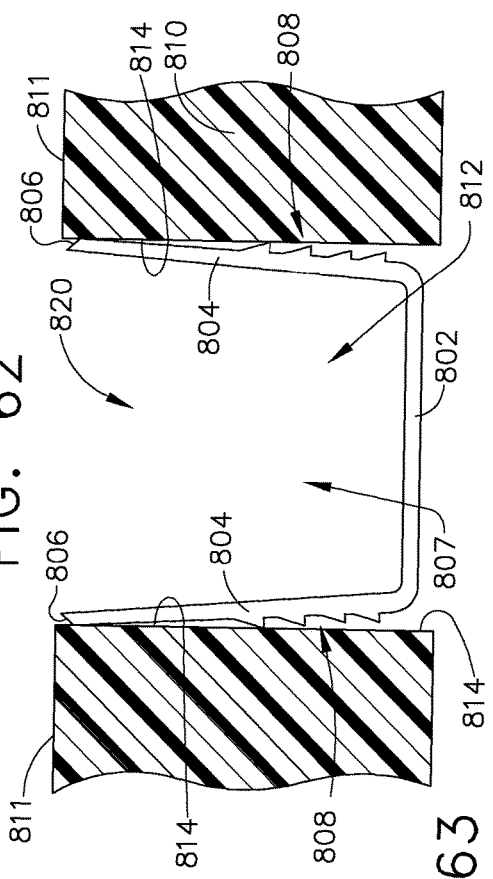
FIG. 62
FIG. 63

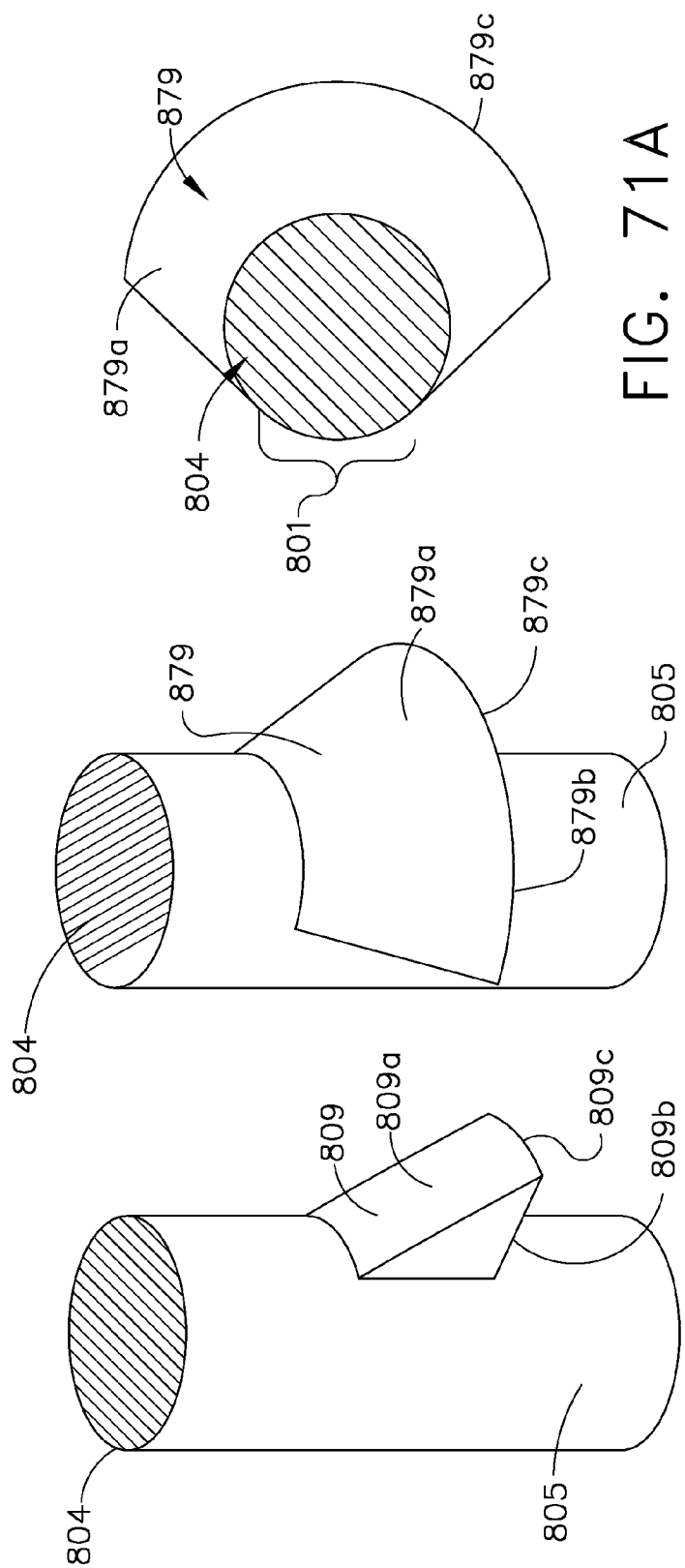

IMPLANTABLE LAYERS AND METHODS FOR MODIFYING THE SHAPE OF THE IMPLANTABLE LAYERS FOR USE WITH A SURGICAL FASTENING INSTRUMENT

BACKGROUND

The present invention relates to surgical instruments and, in various arrangements, to surgical stapling and cutting instruments and staple cartridges therefor that are designed to staple and cut tissue.

BRIEF DESCRIPTION OF THE DRAWINGS

The features and advantages of this invention, and the manner of attaining them, will become more apparent and the invention itself will be better understood by reference to the following description of embodiments of the invention taken in conjunction with the accompanying drawings, wherein:

FIG. 2 is a perspective view of a two-piece knife and firing bar ("E-beam") of the surgical stapling and severing instrument of FIG. 1;

FIG. 3 is a perspective view of a wedge sled of a staple cartridge of a staple applying assembly;

FIG. 4 is a longitudinal cross-sectional view of an anvil in a closed position and a staple cartridge comprising a rigid support portion and a compressible tissue thickness compensator illustrated with staples being moved from an unfired position to a fired position during a first sequence;

FIG. 5 is another cross-sectional view of the anvil and the staple cartridge of FIG. 4 illustrating the anvil in an open position after the firing sequence has been completed;

FIG. 7 is a partial cross-sectional view of the staple cartridge assembly of FIG. 6, illustrating unfired staples positioned in staple cavities of a staple cartridge body and partially embedded in a tissue thickness compensator;

FIG. 8 is a partial cross-sectional view of the staple cartridge assembly of FIG. 6, illustrating fired staples ejected from the staple cavities of the staple cartridge body and formed against an anvil, and further illustrating the tissue thickness compensator and tissue captured within the staple entrapment area of the formed staples;

FIG. 9 is a partial perspective view of an end effector of a surgical fastening instrument illustrated with some portions removed and other portions illustrated in cross-section; moreover, a cutting member of the end effector is illustrated in a partially advanced position;

FIG. 32 is a cross-sectional perspective view of a tissue thickness compensator;

FIG. 33 is a cross-sectional perspective view of a mold for modifying the tissue thickness compensator of FIG. 32;

FIG. 34 is a cross-sectional perspective view of the tissue thickness compensator of FIG. 32 after modification by the mold of FIG. 33;

FIG. 38 is a cross-sectional perspective view of a tissue thickness compensator;

FIG. 39 is a cross-sectional perspective view the tissue thickness compensator of FIG. 38 after modification;

FIG. 40 is a graph illustrating the effect of compression forces on a spring rate of a tissue thickness compensator;

FIG. 41 is a cross-sectional perspective view of a tissue thickness compensator;

FIG. 42 is a cross-sectional perspective view of a space creator for modifying the tissue thickness compensator of FIG. 41;

FIG. 43 is a cross-sectional perspective view of the tissue thickness compensator of FIG. 41 after modification by the space creator of FIG. 42;

FIG. 62 is a diagram depicting a staple comprising a plurality of barbs in accordance with at least one embodiment, wherein the staple is illustrated in an unformed configuration and a deformed configuration;

FIG. 63 is an elevational view of a staple comprising a plurality of barbs in accordance with at least one embodiment, wherein the staple is positioned within a staple cavity in an unfired position;

FIG. 70 is a partial perspective view of a barbed staple leg in accordance with at least one embodiment;

FIG. 71 is a partial perspective view of a barbed staple leg of the staple of FIG. 68;

FIG. 71A is a cross-sectional plan view of the barbed staple leg of FIG. 71;

DETAILED DESCRIPTION

Figure 1:
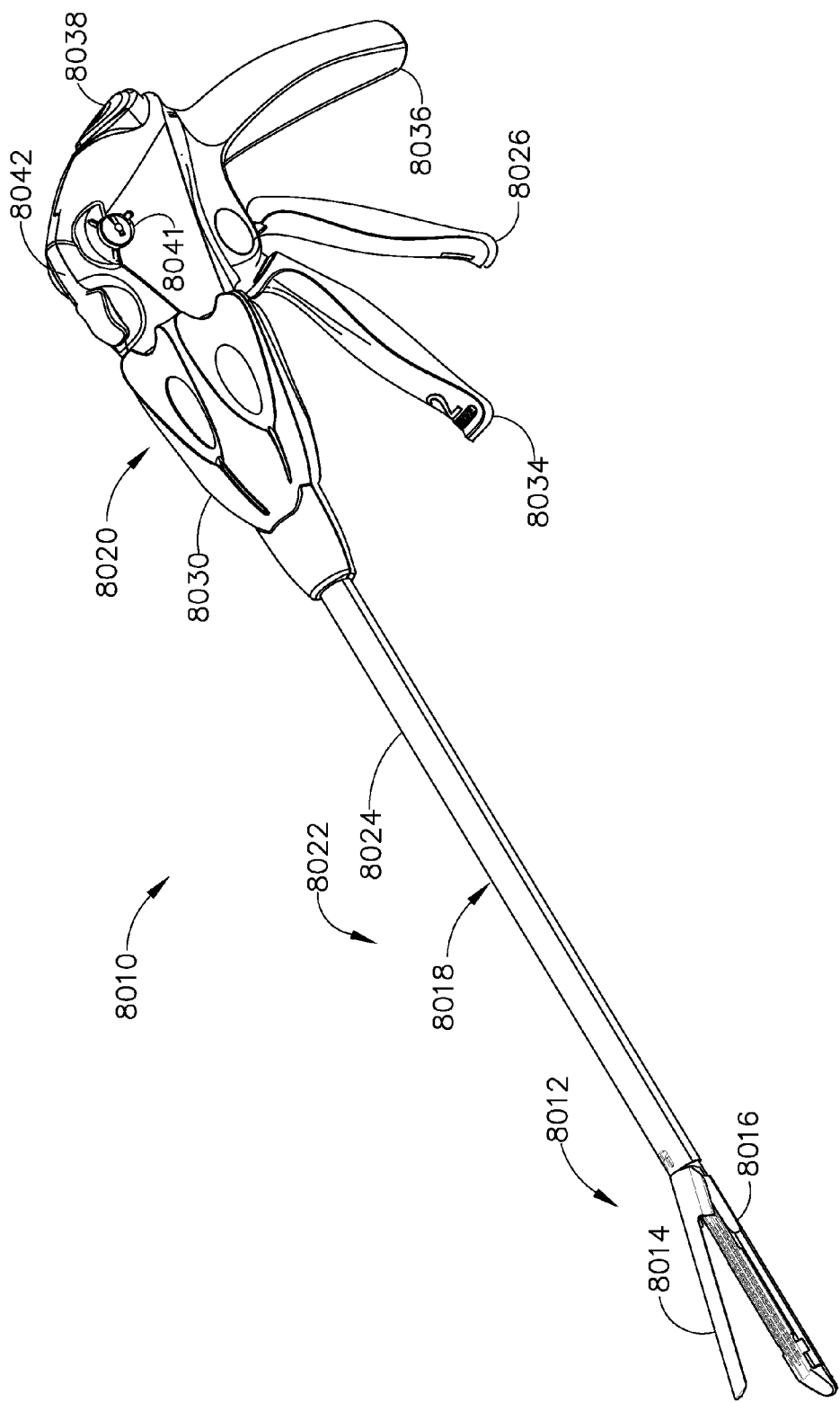
FIG. 1 is a left front perspective view of a surgical stapling and severing instrument with a handle portion.

The Applicant of the present application also owns the U.S. Patent Applications identified below which are each herein incorporated by reference in their respective entirety:

U.S. patent application Ser. No. 12/894,311, entitled SURGICAL INSTRUMENTS WITH RECONFIGURABLE SHAFT SEGMENTS; now U.S. Pat. No. 8,763,877;

U.S. patent application Ser. No. 12/894,340, entitled SURGICAL STAPLE CARTRIDGES SUPPORTING NON-LINEARLY ARRANGED STAPLES AND SURGICAL STAPLING INSTRUMENTS WITH COMMON STAPLE-FORMING POCKETS; now U.S. Pat. No. 8,899,463;

U.S. patent application Ser. No. 12/894,327, entitled JAW CLOSURE ARRANGEMENTS FOR SURGICAL INSTRUMENTS; now U.S. Pat. No. 8,978,956;

U.S. patent application Ser. No. 12/894,351, entitled SURGICAL CUTTING AND FASTENING INSTRUMENTS WITH SEPARATE AND DISTINCT FASTENER DEPLOYMENT AND TISSUE CUTTING SYSTEMS; now U.S. Pat. No. 9,113,864;

U.S. patent application Ser. No. 12/894,338, entitled IMPLANTABLE FASTENER CARTRIDGE HAVING A NON-UNIFORM ARRANGEMENT; now U.S. Pat. No. 8,864,007;

U.S. patent application Ser. No. 12/894,369, entitled IMPLANTABLE FASTENER CARTRIDGE COMPRISING A SUPPORT RETAINER; now U.S. Patent Publication No. 2012/0080344;

U.S. patent application Ser. No. 12/894,312, entitled IMPLANTABLE FASTENER CARTRIDGE COMPRISING MULTIPLE LAYERS; now U.S. Pat. No. 8,925,782;

U.S. patent application Ser. No. 12/894,377, entitled SELECTIVELY ORIENTABLE IMPLANTABLE FASTENER CARTRIDGE; now U.S. Pat. No. 8,393,514;

U.S. patent application Ser. No. 12/894,339, entitled SURGICAL STAPLING INSTRUMENT WITH COMPACT ARTICULATION CONTROL ARRANGEMENT; now U.S. Pat. No. 8,840,003;

U.S. patent application Ser. No. 12/894,360, entitled SURGICAL STAPLING INSTRUMENT WITH A VARIABLE STAPLE FORMING SYSTEM; now U.S. Pat. No. 9,113,862;

U.S. patent application Ser. No. 12/894,322, entitled SURGICAL STAPLING INSTRUMENT WITH INTERCHANGEABLE STAPLE CARTRIDGE ARRANGEMENTS; now U.S. Pat. No. 8,740,034;

U.S. patent application Ser. No. 12/894,350, entitled SURGICAL STAPLE CARTRIDGES WITH DETACHABLE SUPPORT STRUCTURES; now U.S. Patent Publication No. 2012/0080478;

U.S. patent application Ser. No. 12/894,383, entitled IMPLANTABLE FASTENER CARTRIDGE COMPRISING BIOABSORBABLE LAYERS; now U.S. Pat. No. 8,752,699;

U.S. patent application Ser. No. 12/894,389, entitled COMPRESSIBLE FASTENER CARTRIDGE; now U.S. Pat. No. 8,740,037;

U.S. patent application Ser. No. 12/894,345, entitled FASTENERS SUPPORTED BY A FASTENER CARTRIDGE SUPPORT; now U.S. Pat. No. 8,783,542;

U.S. patent application Ser. No. 12/894,306, entitled COLLAPSIBLE FASTENER CARTRIDGE; now U.S. Pat. No. 9,044,227;

U.S. patent application Ser. No. 12/894,318, entitled FASTENER SYSTEM COMPRISING A PLURALITY OF CONNECTED RETENTION MATRIX ELEMENTS; now U.S. Pat. No. 8,814,024;

U.S. patent application Ser. No. 12/894,330, entitled FASTENER SYSTEM COMPRISING A RETENTION MATRIX AND AN ALIGNMENT MATRIX; now U.S. Pat. No. 8,757,465;

U.S. patent application Ser. No. 12/894,361, entitled FASTENER SYSTEM COMPRISING A RETENTION MATRIX; now U.S. Pat. No. 8,529,600;

U.S. patent application Ser. No. 12/894,367, entitled FASTENING INSTRUMENT FOR DEPLOYING A FASTENER SYSTEM COMPRISING A RETENTION MATRIX; now U.S. Pat. No. 9,033,203;

U.S. patent application Ser. No. 12/894,388, entitled FASTENER SYSTEM COMPRISING A RETENTION MATRIX AND A COVER; now U.S. Pat. No. 8,474,677;

U.S. patent application Ser. No. 12/894,376, entitled FASTENER SYSTEM COMPRISING A PLURALITY OF FASTENER CARTRIDGES; now U.S. Pat. No. 9,044,228;

U.S. patent application Ser. No. 13/097,865, entitled SURGICAL STAPLER ANVIL COMPRISING A PLURALITY OF FORMING POCKETS; now U.S. Pat. No. 9,295,464;

U.S. patent application Ser. No. 13/097,936, entitled TISSUE THICKNESS COMPENSATOR FOR A SURGICAL STAPLER; now U.S. Pat. No. 8,657,176;

U.S. patent application Ser. No. 13/097,954, entitled STAPLE CARTRIDGE COMPRISING A VARIABLE THICKNESS COMPRESSIBLE PORTION; now U.S. Patent Publication No. 2012/0080340;

U.S. patent application Ser. No. 13/097,856, entitled STAPLE CARTRIDGE COMPRISING STAPLES POSITIONED WITHIN A COMPRESSIBLE PORTION THEREOF; now U.S. Patent Publication No. 2012/0080336;

U.S. patent application Ser. No. 13/097,928, entitled TISSUE THICKNESS COMPENSATOR COMPRISING DETACHABLE PORTIONS; now U.S. Pat. No. 8,746,535;

U.S. patent application Ser. No. 13/097,891, entitled TISSUE THICKNESS COMPENSATOR FOR A SURGICAL STAPLER COMPRISING AN ADJUSTABLE ANVIL; now U.S. Pat. No. 8,864,009;

U.S. patent application Ser. No. 13/097,948, entitled STAPLE CARTRIDGE COMPRISING AN ADJUSTABLE DISTAL PORTION; now U.S. Pat. No. 8,978,954;

U.S. patent application Ser. No. 13/097,907, entitled COMPRESSIBLE STAPLE CARTRIDGE ASSEMBLY; now U.S. Pat. No. 9,301,755;

U.S. patent application Ser. No. 13/097,861, entitled TISSUE THICKNESS COMPENSATOR COMPRISING PORTIONS HAVING DIFFERENT PROPERTIES; now U.S. Pat. No. 9,113,865;

U.S. patent application Ser. No. 13/097,869, entitled STAPLE CARTRIDGE LOADING ASSEMBLY; now U.S. Pat. No. 8,857,694;

U.S. patent application Ser. No. 13/097,917, entitled COMPRESSIBLE STAPLE CARTRIDGE COMPRISING ALIGNMENT MEMBERS; now U.S. Pat. No. 8,777,004;

U.S. patent application Ser. No. 13/097,873, entitled STAPLE CARTRIDGE COMPRISING A RELEASABLE PORTION; now U.S. Pat. No. 8,740,038;

U.S. patent application Ser. No. 13/097,938, entitled STAPLE CARTRIDGE COMPRISING COMPRESSIBLE DISTORTION RESISTANT COMPONENTS; now U.S. Pat. No. 9,016,542;

U.S. patent application Ser. No. 13/097,924, entitled STAPLE CARTRIDGE COMPRISING A TISSUE THICKNESS COMPENSATOR; now U.S. Pat. No. 9,168,038;

U.S. patent application Ser. No. 13/242,029, entitled SURGICAL STAPLER WITH FLOATING ANVIL; now U.S. Pat. No. 8,893,949;

U.S. patent application Ser. No. 13/242,066, entitled CURVED END EFFECTOR FOR A STAPLING INSTRUMENT; now U.S. Patent Publication No. 2012/0080498;

U.S. patent application Ser. No. 13/242,086, entitled STAPLE CARTRIDGE INCLUDING COLLAPSIBLE DECK; now U.S. Pat. No. 9,055,941;

U.S. patent application Ser. No. 13/241,912, entitled STAPLE CARTRIDGE INCLUDING COLLAPSIBLE DECK ARRANGEMENT; now U.S. Pat. No. 9,050,084;

U.S. patent application Ser. No. 13/241,922, entitled SURGICAL STAPLER WITH STATIONARY STAPLE DRIVERS; now U.S. Pat. No. 9,216,019;

U.S. patent application Ser. No. 13/241,637, entitled SURGICAL INSTRUMENT WITH TRIGGER ASSEMBLY FOR GENERATING MULTIPLE ACTUATION MOTIONS; now U.S. Pat. No. 8,789,741;

U.S. patent application Ser. No. 13/241,629, entitled SURGICAL INSTRUMENT WITH SELECTIVELY ARTICULATABLE END EFFECTOR; now U.S. Patent Publication No. 2012/0074200;

U.S. application Ser. No. 13/433,096, entitled TISSUE THICKNESS COMPENSATOR COMPRISING A PLURALITY OF CAPSULES; now U.S. Pat. No. 9,301,752;

U.S. application Ser. No. 13/433,103, entitled TISSUE THICKNESS COMPENSATOR COMPRISING A PLURALITY OF LAYERS; now U.S. Pat. No. 9,433,419;

U.S. application Ser. No. 13/433,098, entitled EXPANDABLE TISSUE THICKNESS COMPENSATOR; now U.S. Pat. No. 9,301,753;

U.S. application Ser. No. 13/433,102, entitled TISSUE THICKNESS COMPENSATOR COMPRISING A RESERVOIR; now U.S. Pat. No. 9,232,941;

U.S. application Ser. No. 13/433,114, entitled RETAINER ASSEMBLY INCLUDING A TISSUE THICKNESS COMPENSATOR; now U.S. Pat. No. 9,386,988;

U.S. application Ser. No. 13/433,136, entitled TISSUE THICKNESS COMPENSATOR COMPRISING AT LEAST ONE MEDICAMENT; now U.S. Patent Publication No. 2012/0241492;

U.S. application Ser. No. 13/433,141, entitled TISSUE THICKNESS COMPENSATOR COMPRISING CONTROLLED RELEASE AND EXPANSION; now U.S. Patent Publication No. 2012/0241493;

U.S. application Ser. No. 13/433,144, entitled TISSUE THICKNESS COMPENSATOR COMPRISING FIBERS TO PRODUCE A RESILIENT LOAD; now U.S. Pat. No. 9,277,919;

U.S. application Ser. No. 13/433,148, entitled TISSUE THICKNESS COMPENSATOR COMPRISING STRUCTURE TO PRODUCE A RESILIENT LOAD; now U.S. Pat. No. 9,220,500;

U.S. application Ser. No. 13/433,155, entitled TISSUE THICKNESS COMPENSATOR COMPRISING RESILIENT MEMBERS; now U.S. Pat. No. 9,480,476;

U.S. application Ser. No. 13/433,163, entitled METHODS FOR FORMING TISSUE THICKNESS COMPENSATOR ARRANGEMENTS FOR SURGICAL STAPLERS; now U.S. Patent Publication No. 2012/0248169;

U.S. application Ser. No. 13/433,167, entitled TISSUE THICKNESS COMPENSATORS; now U.S. Pat. No. 9,220,501;

U.S. application Ser. No. 13/433,175, entitled LAYERED TISSUE THICKNESS COMPENSATOR; now U.S. Pat. No. 9,332,974;

U.S. application Ser. No. 13/433,179, entitled TISSUE THICKNESS COMPENSATORS FOR CIRCULAR SURGICAL STAPLERS; now U.S. Pat. No. 9,364,233;

U.S. application Ser. No. 13/763,028, entitled ADHESIVE FILM LAMINATE; now U.S. Pat. No. 9,282,962;

U.S. application Ser. No. 13/433,115, entitled TISSUE THICKNESS COMPENSATOR COMPRISING CAPSULES DEFINING A LOW PRESSURE ENVIRONMENT; now U.S. Pat. No. 9,204,880;

U.S. application Ser. No. 13/433,118, entitled TISSUE THICKNESS COMPENSATOR COMPRISED OF A PLURALITY OF MATERIALS; now U.S. Pat. No. 9,414,838;

U.S. application Ser. No. 13/433,135, entitled MOVABLE MEMBER FOR USE WITH A TISSUE THICKNESS COMPENSATOR; now U.S. Pat. No. 9,517,063;

U.S. application Ser. No. 13/433,140, entitled TISSUE THICKNESS COMPENSATOR AND METHOD FOR MAKING THE SAME; now U.S. Pat. No. 9,241,714;

U.S. application Ser. No. 13/433,129, entitled TISSUE THICKNESS COMPENSATOR COMPRISING A PLURALITY OF MEDICAMENTS; now U.S. Pat. No. 9,211,120;

U.S. application Ser. No. 11/216,562, entitled STAPLE CARTRIDGES FOR FORMING STAPLES HAVING DIFFERING FORMED STAPLE HEIGHTS, now U.S. Pat. No. 7,669,746;

U.S. application Ser. No. 11/714,049, entitled SURGICAL STAPLING DEVICE WITH ANVIL HAVING STAPLE FORMING POCKETS OF VARYING DEPTHS, now U.S. Patent Publication No. 2007/0194082;

U.S. application Ser. No. 11/711,979, entitled SURGICAL STAPLING DEVICES THAT PRODUCE FORMED STAPLES HAVING DIFFERENT LENGTHS, now U.S. Pat. No. 8,317,070;

U.S. application Ser. No. 11/711,975, entitled SURGICAL STAPLING DEVICE WITH STAPLE DRIVERS OF DIFFERENT HEIGHT, now U.S. Patent Publication No. 2007/0194079;

U.S. application Ser. No. 11/711,977, entitled SURGICAL STAPLING DEVICE WITH STAPLE DRIVER THAT SUPPORTS MULTIPLE WIRE DIAMETER STAPLES, now U.S. Pat. No. 7,673,781;

U.S. application Ser. No. 11/712,315, entitled SURGICAL STAPLING DEVICE WITH MULTIPLE STACKED ACTUATOR WEDGE CAMS FOR DRIVING STAPLE DRIVERS, now U.S. Pat. No. 7,500,979;

U.S. application Ser. No. 12/038,939, entitled STAPLE CARTRIDGES FOR FORMING STAPLES HAVING DIFFERING FORMED STAPLE HEIGHTS, now U.S. Pat. No. 7,934,630;

U.S. application Ser. No. 13/020,263, entitled SURGICAL STAPLING SYSTEMS THAT PRODUCE FORMED STAPLES HAVING DIFFERENT LENGTHS, now U.S. Pat. No. 8,636,187;

U.S. application Ser. No. 13/118,278, entitled ROBOTICALLY-CONTROLLED SURGICAL STAPLING DEVICES THAT PRODUCE FORMED STAPLES HAVING DIFFERENT LENGTHS, now U.S. Pat. No. 9,237,891;

U.S. application Ser. No. 13/369,629, entitled ROBOTICALLY-CONTROLLED CABLE-BASED SURGICAL END EFFECTORS, now U.S. Pat. No. 8,800,838;

U.S. application Ser. No. 12/695,359, entitled SURGICAL STAPLING DEVICES FOR FORMING STAPLES WITH DIFFERENT FORMED HEIGHTS, now U.S. Pat. No. 8,464,923;

U.S. application Ser. No. 13/072,923, entitled STAPLE CARTRIDGES FOR FORMING STAPLES HAVING DIFFERING FORMED STAPLE HEIGHTS, now U.S. Pat. No. 8,567,656;

U.S. application Ser. No. 13/766,325, entitled LAYER OF MATERIAL FOR A SURGICAL END EFFECTOR; now U.S. Patent Publication No. 2013/0256380;

U.S. application Ser. No. 13/763,078, entitled ANVIL LAYER ATTACHED TO A PROXIMAL END OF AN END EFFECTOR; now U.S. Patent Publication No. 2013/0256383;

U.S. application Ser. No. 13/763,094, entitled LAYER COMPRISING DEPLOYABLE ATTACHMENT MEMBERS; now U.S. Patent Publication No. 2013/0256377;

U.S. application Ser. No. 13/763,106, entitled END EFFECTOR COMPRISING A DISTAL TISSUE ABUTMENT MEMBER; now U.S. Patent Publication No. 2013/0256378;

U.S. application Ser. No. 13/433,147, entitled TISSUE THICKNESS COMPENSATOR COMPRISING CHANNELS; now U.S. Pat. No. 9,351,730;

U.S. application Ser. No. 13/763,112, entitled SURGICAL STAPLING CARTRIDGE WITH LAYER RETENTION FEATURES; now U.S. Patent Publication No. 2013/0256379;

U.S. application Ser. No. 13/763,035, entitled ACTUATOR FOR RELEASING A TISSUE THICKNESS COMPENSATOR FROM A FASTENER CARTRIDGE; now U.S. Patent Publication No. 2013/0214030;

U.S. application Ser. No. 13/763,042, entitled RELEASABLE TISSUE THICKNESS COMPENSATOR AND FASTENER CARTRIDGE HAVING THE SAME; now U.S. Patent Publication No. 2013/0221063;

U.S. application Ser. No. 13/763,048, entitled FASTENER CARTRIDGE COMPRISING A RELEASABLE TISSUE THICKNESS COMPENSATOR; now U.S. Patent Publication No. 2013/0221064;

U.S. application Ser. No. 13/763,054, entitled FASTENER CARTRIDGE COMPRISING A CUTTING MEMBER FOR RELEASING A TISSUE THICKNESS COMPENSATOR, now U.S. Pat. No. 9,272,406;

U.S. application Ser. No. 13/763,065, entitled FASTENER CARTRIDGE COMPRISING A RELEASABLY ATTACHED TISSUE THICKNESS COMPENSATOR; now U.S. Pat. No. 9,566,061;

U.S. application Ser. No. 13/763,021, entitled STAPLE CARTRIDGE COMPRISING A RELEASABLE COVER, now U.S. Pat. No. 9,386,984;

U.S. application Ser. No. 13/763,078, entitled ANVIL LAYER ATTACHED TO A PROXIMAL END OF AN END EFFECTOR; now U.S. Patent Publication No. 2013/0256383;

U.S. application Ser. No. 13/763,095, entitled LAYER ARRANGEMENTS FOR SURGICAL STAPLE CARTRIDGES; now U.S. Patent Publication No. 2013/0161374;

U.S. application Ser. No. 13/463,147, entitled IMPLANTABLE ARRANGEMENTS FOR SURGICAL STAPLE CARTRIDGES; now U.S. Patent Publication No. 2013/0292398;

U.S. application Ser. No. 13/763,192, entitled MULTIPLE THICKNESS IMPLANTABLE LAYERS FOR SURGICAL STAPLING DEVICES; now U.S. Patent Publication No. 2013/0146642;

U.S. application Ser. No. 13/763,161, entitled RELEASABLE LAYER OF MATERIAL AND SURGICAL END EFFECTOR HAVING THE SAME; now U.S. Patent Publication No. 2013/0153641;

U.S. application Ser. No. 13/763,177, entitled ACTUATOR FOR RELEASING A LAYER OF MATERIAL FROM A SURGICAL END EFFECTOR; now U.S. Patent Publication No. 2013/0146641;

U.S. application Ser. No. 13/763,037, entitled STAPLE CARTRIDGE COMPRISING A COMPRESSIBLE PORTION, now U.S. Patent Publication No. 2014/0224857;

U.S. application Ser. No. 13/433,126, entitled TISSUE THICKNESS COMPENSATOR COMPRISING TISSUE INGROWTH FEATURES; now U.S. Pat. No. 9,320,523;

U.S. application Ser. No. 13/433,132, entitled DEVICES AND METHODS FOR ATTACHING TISSUE THICKNESS COMPENSATING MATERIALS TO SURGICAL STAPLING INSTRUMENTS; now U.S. Patent Publication No. 2013/0256373.

U.S. application Ser. No. 13/851,703, entitled FASTENER CARTRIDGE COMPRISING A TISSUE THICKNESS COMPENSATOR INCLUDING OPENINGS THEREIN, now U.S. Pat. No. 9,572,577;

U.S. application Ser. No. 13/851,676, entitled TISSUE THICKNESS COMPENSATOR COMPRISING A CUTTING MEMBER PATH, now U.S. Patent Publication No. 2014/0291379;

U.S. application Ser. No. 13/851,693, entitled FASTENER CARTRIDGE ASSEMBLIES, now U.S. Pat. No. 9,332,984; and U.S. application Ser. No. 13/851,684, entitled FASTENER CARTRIDGE COMPRISING A TISSUE THICKNESS COMPENSATOR AND A GAP SETTING ELEMENT, now U.S. Patent Publication No. 2014/0291380.

Applicant of the present application also owns the following patent applications that were filed on even date herewith and which are each herein incorporated by reference in their respective entireties:

U.S. patent application Ser. No. 14/187,387, entitled STAPLE CARTRIDGE INCLUDING A BARBED STAPLE, now U.S. Patent Publication No. 2014/0166724;

U.S. patent application Ser. No. 14/187,395, entitled STAPLE CARTRIDGE INCLUDING A BARBED STAPLE, now U.S. Patent Publication No. 2014/0166725;

U.S. patent application Ser. No. 14/187,400, entitled STAPLE CARTRIDGE INCLUDING A BARBED STAPLE, now U.S. Patent Publication No. 2014/0166726;

U.S. patent application Ser. No. 14/187,383, entitled IMPLANTABLE LAYERS AND METHODS FOR ALTERING IMPLANTABLE LAYERS FOR USE WITH SURGICAL FASTENING INSTRUMENTS, now U.S. Patent Publication No. 2015/0238185;

U.S. patent application Ser. No. 14/187,386, entitled IMPLANTABLE LAYERS AND METHODS FOR ALTERING ONE OR MORE PROPERTIES OF IMPLANTABLE LAYERS FOR USE WITH FASTENING INSTRUMENTS, now U.S. Patent Publication No. 2015/0239180;

U.S. patent application Ser. No. 14/187,389, entitled IMPLANTABLE LAYER ASSEMBLIES, now U.S. Patent Publication 2015/0238187;

U.S. patent application Ser. No. 14/187,385, entitled IMPLANTABLE LAYERS COMPRISING A PRESSED REGION, now U.S. Patent Publication No. 2015/0238191; and U.S. patent application Ser. No. 14/187,384, entitled FASTENING SYSTEM COMPRISING A FIRING MEMBER LOCKOUT, now U.S. Patent Publication No. 2015/0238186.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the person of ordinary skill in the art will readily appreciate that the various methods and devices disclosed herein can be used in numerous surgical procedures and applications including, for example, in connection with open surgical procedures. As the present Detailed Description proceeds, those of ordinary skill in the art will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongated shaft of a surgical instrument can be advanced.

Turning to the Drawings wherein like numerals denote like components throughout the several views, FIG. 1 illustrates an exemplary surgical stapling and severing instrument 8010 suitable for use with a tissue thickness compensator assembly as described in greater detail below. The surgical stapling and severing instrument 8010 can comprise an anvil 8014 which may be repeatedly opened and closed about its pivotal attachment to an elongate staple channel 8016. A staple applying assembly 8012 may comprise the anvil 8014 and the channel 8016, wherein the assembly 8012 can be proximally attached to an elongate shaft 8018 forming an implement portion 8022. When the staple applying assembly 8012 is closed, or at least substantially closed, the implement portion 8022 can present a sufficiently small cross-section suitable for inserting the staple applying assembly 8012 through a trocar. In various circumstances, the assembly 8012 can be manipulated by a handle 8020 connected to the shaft 8018. The handle 8020 can comprise user controls such as a rotation knob 8030 that rotates the elongate shaft 8018 and the staple applying assembly 8012 about a longitudinal axis of the shaft 8018. A closure trigger 8026, which can pivot in front of a pistol grip 8036 to close the staple applying assembly 8012. A closure release button 8038 can be outwardly presented on the handle 8020 when the closure trigger 8026 is clamped such that the release button 8038 can be depressed to unclamp the closure trigger 8026 and open the staple applying assembly 8012, for example. A firing trigger 8034, which can pivot in front of the closure trigger 8026, can cause the staple applying assembly 8012 to simultaneously sever and staple tissue clamped therein. In various circumstances, multiple firing strokes can be employed using the firing trigger 8034 to reduce the amount of force required to be applied by the surgeon's hand per stroke. In certain embodiments, the handle 8020 can comprise one or more rotatable indicator wheels such as, for example, rotatable indicator wheel 8041 which can indicate the firing progress. A manual firing release lever 8042 can allow the firing system to be retracted before full firing travel has been completed, if desired, and, in addition, the firing release lever 8042 can allow a surgeon, or other clinician, to retract the firing system in the event that the firing system binds and/or fails. Additional details on the surgical stapling and severing instrument 8010 and other surgical stapling and severing instruments suitable for use with the present disclosure are described, for example, in U.S. patent application Ser. No. 13/851,693, entitled FASTENER CARTRIDGE ASSEMBLY, and filed on Mar. 27, 2013, the entire disclosure of which is incorporated herein by reference. Furthermore, powered surgical stapling and severing instruments can also be utilized with the present disclosure. See, for example, U.S. Patent Application Publication No. 2009/0090763 A1, entitled POWERED SURGICAL STAPLING DEVICE, and filed on Aug. 8, 2008, the entire disclosure of which is incorporated herein by reference.

With reference to FIGS. 2 and 3, a firing assembly such as, for example, firing assembly 9090 can be utilized with the surgical stapling and severing instrument 8010 to advance a wedge sled 9126 which comprises a plurality of wedges 9204 configured to deploy staples from the staple applying assembly 8012 into tissue captured between the anvil 8014 and the elongate staple channel 8016. Furthermore, an E-beam 9102 at a distal portion of the firing assembly 9090 may facilitate separate closure and firing as well as spacing of the anvil 8014 from the elongate staple channel 8016 during firing. The E-beam 9102 may include a pair of top pins 9110, a pair of middle pins 9112 which may follow portion 9218 of the wedge sled 9126, and a bottom pin or foot 9114, as well as a sharp cutting edge 9116 which can be configured to sever the captured tissue as the firing assembly 9090 is advanced distally. In addition, integrally formed and proximally projecting top guide 9118 and middle guide 9120 bracketing each vertical end of the cutting edge 9116 may further define a tissue staging area 9122 assisting in guiding tissue to the sharp cutting edge 9116 prior to being severed. The middle guide 9120 may also serve to engage and fire the staple applying assembly 8012 by abutting a stepped central member 9124 of the wedge sled 9126 (FIG. 2) that effects staple formation by the staple applying assembly 8012.

In various circumstances, a staple cartridge can comprise means for compensating for thickness of tissue captured within staples deployed from a staple cartridge. Referring to FIG. 4, a staple cartridge, such as staple cartridge 10000, for example, can be utilized with the surgical stapling and severing instrument 8010 and can include a rigid first portion, such as support portion 10010, for example, and a compressible second portion, such as tissue thickness compensator 10020, for example. The support portion 10010 can comprise a cartridge body and a plurality of staple cavities 10012. A staple 10030, for example, can be removably positioned in each staple cavity 10012. Referring primarily to FIGS. 4 and 5, each staple 10030 can comprise a base 10031 and one or more legs 10032 extending from the base 10031. Prior to the staples 10030 being deployed, the bases 10031 of the staples 10030 can be supported by staple drivers positioned within the support portion 10010 and, concurrently, the legs 10032 of the staples 10030 can be at least partially contained within the staple cavities 10012. In various circumstances, the staples 10030 can be deployed between an unfired position and a fired position such that the legs 10032 move through the tissue thickness compensator 10020, penetrate through a top surface of the tissue thickness compensator 10020, penetrate the tissue T, and contact an anvil positioned opposite the staple cartridge 10000. As the legs 10032 are deformed against the anvil, the legs 10032 of each staple 10030 can capture a portion of the tissue thickness compensator 10020 and a portion of the tissue T within each staple 10030 and apply a compressive force to the tissue. Further to the above, the legs 10032 of each staple 10030 can be deformed downwardly toward the base 10031 of the staple to form a staple entrapment area in which the tissue T and the tissue thickness compensator 10020 can be captured. In various circumstances, the staple entrapment area can be defined between the inner surfaces of the deformed legs 10032 and the inner surface of the base 10031. The size of the entrapment area for a staple can depend on several factors such as the length of the legs, the diameter of the legs, the width of the base, and/or the extent in which the legs are deformed, for example.

In use, further to the above and referring primarily to FIG. 4, an anvil, such as anvil 8014 of the surgical stapling and severing instrument 8010, can be moved into a closed position opposite the staple cartridge 10000 by depressing the closure trigger 8026 to advance the E-beam 9102. The anvil 8014 can position tissue against the tissue thickness compensator 10020 and, in various circumstances, compress the tissue thickness compensator 10020 against the support portion 10010, for example. Once the anvil 8014 has been suitably positioned, the staples 10030 can be deployed, as also illustrated in FIG. 4. In various circumstances, as mentioned above, a staple-firing sled 10050, which is similar in many respects to the sled 9126 (See FIG. 3), can be moved from a proximal end of the staple cartridge 10000 toward a distal end 10002, as illustrated in FIG. 5. As the firing assembly 9090 is advanced, the sled 10050 can contact the staple drivers 10040 and lift the staple drivers 10040 upwardly within the staple cavities 10012. In at least one example, the sled 10050 and the staple drivers 10040 can each comprise one or more ramps, or inclined surfaces, which can co-operate to move the staple drivers 10040 upwardly from their unfired positions. As the staple drivers 10040 are lifted upwardly within their respective staple cavities 10012, the staple drivers 10040 can lift the staples 10030 upwardly such that the staples 10030 can emerge from their staple cavities 10012. In various circumstances, the sled 10050 can move several staples upwardly at the same time as part of a firing sequence.

As discussed above, and referring to FIG. 5, the staple legs 10032 of the staples 10030 can extend into the compensator 10020 beyond the support portion 10010 when the staples 10030 are in their unfired positions. In various circumstances, the tips of the staple legs 10032, or any other portion of the staple legs 10032, may not protrude through a top tissue-contacting surface 10021 of the tissue thickness compensator 10020 when the staples 10030 are in their unfired positions. In certain circumstances, the tips of the staple legs 10032 can comprise sharp tips which can incise and penetrate the tissue thickness compensator 10020.

Figure 6:
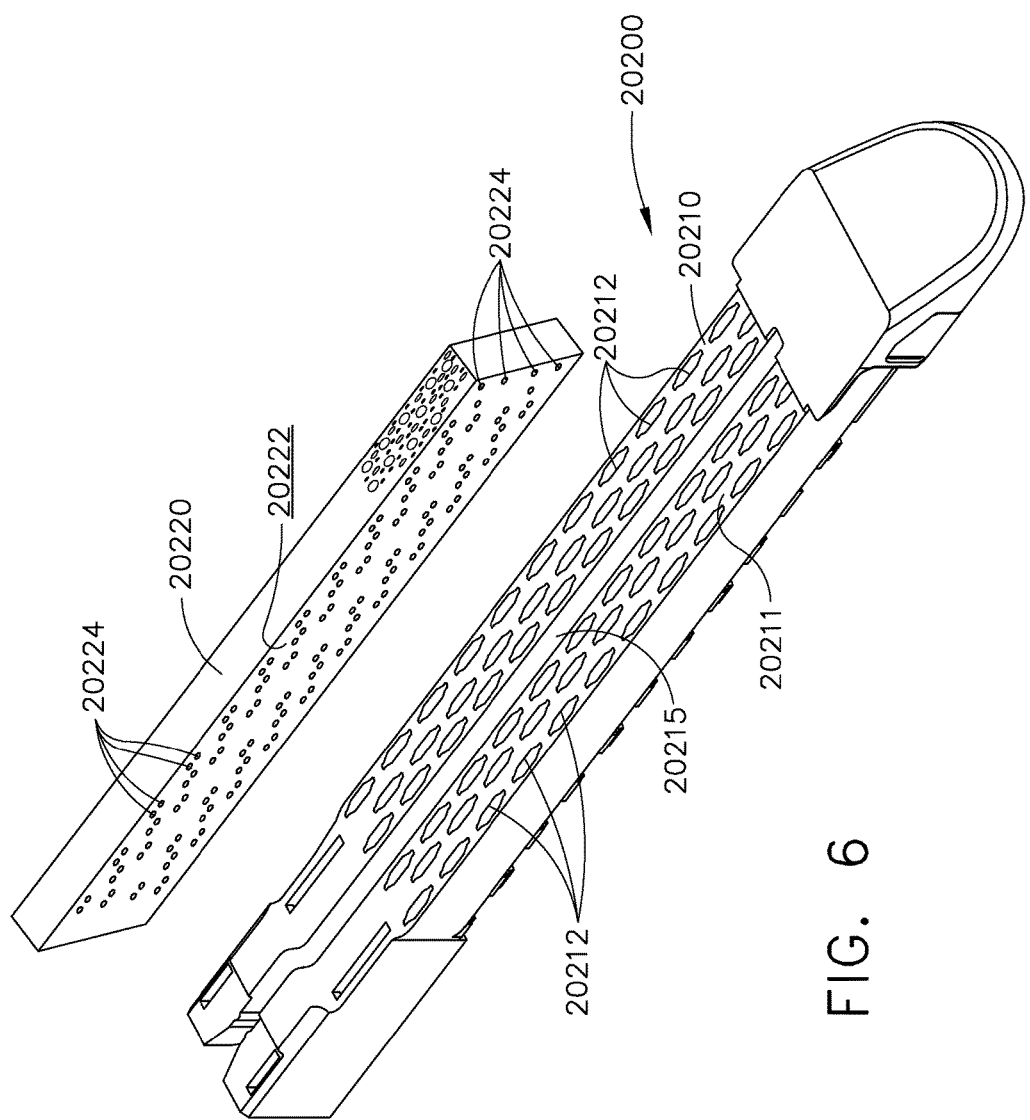
FIG. 6 is an exploded perspective view of a tissue thickness compensator and a staple cartridge assembly.

In various circumstances, it may be preferable to prevent and/or limit frictional forces between a tissue thickness compensator and a staple. Referring now to FIGS. 6-8, a tissue thickness compensator 20220 for use with a staple cartridge assembly 20200 can include a plurality of clearance apertures 20224 extending at least partially through the tissue thickness compensator 20220. In various circumstances, the staple cartridge assembly 20200 can include a staple cartridge body 20210 and a tissue thickness compensator 20220 releasably secured relative to the staple cartridge body 20210. The cartridge body 20210 can include a cartridge deck 20211 and a plurality of staple cavities 20212 defined through the cartridge deck 20211 and into the body of the staple cartridge body 20210, for example. Staples 20230 can be removably positioned in the staple cavities 20212, for example. The tissue thickness compensator 20220 can include a tissue-contacting surface 20221 (FIG. 7) and a deck-contacting surface 20222 (FIG. 6). The deck-contacting surface 20222 can be releasably positioned against the deck 20211 of the cartridge body 20210, for example, and the tissue-contacting surface 20221 can be positioned against tissue T to be stapled, for example. Clearance apertures 20224 can extend through the deck-contacting surface 20222 and into the tissue thickness compensator 20220 and may comprise holes, slits, gaps, bores, openings, and/or cleared pathways, for example, within the tissue thickness compensator 20220.

Referring primarily to FIGS. 7 and 8, staples 20230 can be positioned in the staple cavities 20212 of the cartridge body 20210. Each staple 20230 can include a base 20231 and a pair of staple legs 20232, for example, which can extend from the base 20231. Each staple leg 20232 can extend from opposite ends of the base 20231. Referring primarily to FIG. 7, one or more of the clearance apertures 20224 in the tissue thickness compensator 20220 can include an opening in the deck-contacting surface 20222. The opening of a clearance aperture 20224 can be aligned with a corresponding staple leg 20232 that is positioned in a staple cavity 20212. For example, a single staple leg 20232 can be aligned with the opening of a single clearance aperture 20224 when the tissue thickness compensator 20220 is secured relative to the cartridge body 20210. In certain circumstances, a staple leg 20232 can extend into each clearance aperture 20224, such that at least a portion of the staple 20230 is embedded in the tissue thickness compensator 20220, for example. For example, referring primarily to FIG. 7, a staple 20230 can include a first staple leg 20232*a* and a second staple leg 20232*b*. Furthermore, the tissue thickness compensator 20220 can include a first clearance aperture 20224*a* aligned with the first staple leg 20232*a*, and a second clearance aperture 20224*b* aligned with the second staple leg 20232*b*, for example. Prior to deployment of the staple 20230, the first staple leg 20232*a* can extend partially through the first clearance aperture 20224*a*, and the second staple leg 20232*b* can extend partially through the second clearance aperture 20224*b*, for example. The tissue thickness compensator 20220 can include additional clearance apertures 20224 that are not aligned with staple legs 20232, for example. In certain circumstances, the staple cartridge assembly 20200 can include additional staples 20230 and/or staple legs 20232 that are not aligned with clearance apertures 20224, for example.

The staples 20230 can be moveable from an unfired configuration (FIG. 7) to a fired configuration (FIG. 8). Each staple 20230 can be moved along a staple axis when moving between the unfired configuration and the fired configuration. When in the unfired configuration, the staple legs 20232 can extend from the staple cavities 20212 and into the tissue thickness compensator 20220, for example. The staple legs 20232 can be partially embedded in the tissue thickness compensator 20220 when the staples 20230 are in the unfired configuration, for example. Furthermore, at least a portion of the staple legs 20232 can be aligned with and/or positioned within the clearance apertures 20224 of the tissue thickness compensator 20220 when the staples are in the unfired configuration, for example. In other circumstances, the staple legs 20232 can be positioned entirely within the staple cavity 20212 when in the unfired configuration, and can be aligned with the clearance apertures 20224 positioned above the cartridge deck 20211 (FIG. 6), for example.

The staples 20230 can move from the unfired configuration (FIG. 7) to the fired configuration (FIG. 8) during a firing stroke, as described herein. A staple driver 20240 can be positioned within each staple cavity 20212. The staple driver 20240 within each staple cavity 20212 can be pushed toward the cartridge deck 20211 (FIG. 6), for example, to drive the staple 20230 into tissue T and toward an anvil 20260 (FIG. 8) which can be similar in many respects to other anvils described herein such as, for example, the anvil 8014 (FIG. 1). As each staple 20230 moves from the unfired configuration to the fired configuration, the staple legs 20232 can move through the clearance apertures 20224 in the tissue thickness compensator 20220. The clearance apertures 20224 can have a predefined trajectory within the tissue thickness compensator 20220. For example, the clearance apertures 20224 can extend along an axis that is perpendicular to and/or substantially perpendicular to the tissue-contacting surface 20221 (FIG. 7) and/or the deck-contacting surface 20222 (FIG. 6) of the tissue thickness compensator 20220. In other circumstances, the clearance apertures 20224 can extend along an axis that is oriented at an oblique angle relative to the tissue-contacting surface 20221 and/or the deck-contacting surface 20222 of the tissue thickness compensator 20220, for example. In certain circumstances, a group of the clearance apertures 20224 can be parallel. In some circumstances, all of the clearance apertures 20224 within the tissue thickness compensator 20220 can be parallel, for example. The clearance apertures 20224 can comprise a partially curved trajectory and/or a partially linear trajectory. Other characteristics and features of the clearance apertures 20224 are described in greater detail in U.S. patent application Ser. No. 13/851,693, entitled FASTENER CARTRIDGE ASSEMBLY, and filed on Mar. 27, 2013, the entire disclosure of which is incorporated herein by reference. Methods and techniques for modifying a tissue thickness compensator to include clearance apertures such as, for example, the clearance apertures 20224 are described below in greater detail.

Referring now to FIGS. 9-12, an end effector 22090 of a surgical instrument similar in many respects to the surgical instrument 8010, for example, can comprise a first jaw including a fastener cartridge assembly 22000 and a second jaw including an anvil 10060. The first jaw can include a staple cartridge channel 10070 which can be configured to removably receive the cartridge assembly 22000. Alternatively, the staple cartridge channel 10070 and the cartridge assembly 22000 can comprise an integral unit. In various circumstances, the anvil 10060 can be moved between an open position and a closed position (FIGS. 9-12). In the open position of the anvil 10060, the anvil 10060 can be positioned on a first side of a patient's tissue T (FIGS. 10-12) and the cartridge assembly 22000 can be positioned on a second, or opposite, side of the tissue T, for example. When the anvil 10060 is moved into its closed position, the anvil 10060 can compress the tissue T against the cartridge assembly 22000. Alternatively, the first jaw including the cartridge assembly 22000 can be moved relative to the anvil 10060. A firing member 10052, which is similar in many respects to the firing assembly 9090 (FIG. 3), can be advanced distally from a proximal end 22001 of the cartridge assembly 22000 toward a distal end 22002 of the cartridge assembly 22000 to eject fasteners, such as staples 22030, for example, removably stored in a cartridge body 22010 of the cartridge assembly 22000 as the firing member 10052 is advanced from the proximal end 22001 toward the distal end 22002 of the cartridge assembly 22000.

Further to the above, the staples 22030 can be supported by staple drivers 10040 which are movably positioned within staple cavities 22012 defined in the cartridge body 22010. Moreover, the firing member 10052 can be configured to advance a staple-firing sled 10050 distally within the cartridge body 22010 as the firing member 10052 is moved from the proximal end 22001 toward the distal end 22002. In such circumstances, the staple-firing sled 10050 can be configured to lift the staple drivers 10040, and the staples 22030 supported thereon, toward the anvil 10060. In essence, further to the above, the staple drivers 10040 can move the staples 22030 from an unfired position (FIG. 10) to a fired position (FIGS. 11 and 12) wherein the staples 22030 can contact the anvil 10060 and be deformed between an undeformed configuration (FIG. 10) and a deformed configuration (FIGS. 11 and 12). The anvil 10060 can comprise forming pockets 10062 which can be configured to receive and deform the staples 22030. Staples 22030 can be the same as or similar to staples 10030, for example and/or any other staples disclosed herein, and, as such, staples 22030 are not described in greater detail herein. The reader will note, however, that the staples 22030 can comprise any suitable shape and/or suitable dimensions, such as width and/or height, for example, in their undeformed configuration and/or their deformed configuration. For instance, the staples 22030 can, in certain circumstances, comprise a height which does not extend above a deck surface 22011 of the cartridge body 22010 when the staples 22030 are in their unfired positions while, in other circumstances, the staples 22030 can comprise a height in which the legs of the staples 22030 extend upwardly from the deck surface 22011 when the staples 22030 are in their unfired positions such that the legs of the staples 22030 are at least partially embedded in a tissue thickness compensator 22010 of the cartridge assembly 22000.

With continued reference to the embodiment depicted in FIGS. 9-12, further to the above, the cartridge assembly 22000 can comprise a cartridge body 22010 and a tissue thickness compensator 22020. In various circumstances, the cartridge body 22010 can be similar to the support portion 10010, for example, in many respects and, as a result, many of such respects are not repeated herein for the sake of brevity. Furthermore, the tissue thickness compensator 22020 can be similar to the tissue thickness compensator 10020, for example, in many respects. Further to the above, the firing member 10052 can include a cutting portion 10053 which can be configured to transect the tissue positioned between the anvil 10060 and the tissue thickness compensator 22020 as the firing member 10052 is advanced distally. In various circumstances, as a result, the firing member 10052 can be configured to concurrently fire the staples 22030 to staple the tissue T and cut the tissue T. In certain circumstances, the firing process can at least partially lead the cutting process. Stated another way, the cutting process can lag the firing process. In such circumstances, a portion of the tissue T can be stapled and then incised.

As illustrated in FIGS. 9-12, the cartridge body 22010 can include a cartridge knife slot 22015 which can be configured to receive a portion of the firing member 10052 as the firing member 10052 is advanced distally. Further to the above, the anvil 10060 can include an anvil knife slot 10065 which can be configured to receive a portion of the firing member 10052 as the firing member 10052 is advanced distally. In various circumstances, the tissue thickness compensator 22020 can comprise a tissue thickness compensator knife slot 22025 which can be aligned with the anvil knife slot 10065 and the cartridge knife slot 22015 such that the firing member 10052 can pass through the cartridge knife slot 22015, the anvil knife slot 10065, and the tissue thickness compensator knife slot 22025 simultaneously. In various circumstances, the anvil knife slot 10065 can extend over the tissue thickness compensator knife slot 22025 such that the cutting portion 10053 of the firing member 10052 can pass through the cartridge knife slot 22015, the anvil knife slot 10065, and the tissue thickness compensator knife slot 22025 simultaneously. The tissue thickness compensator knife slot 22025 can define a tissue thickness compensator knife path for the cutting portion 10053 wherein the tissue thickness compensator knife path can be parallel to the anvil knife path and the cartridge knife path. In various circumstances, the tissue thickness compensator knife path can be longitudinal while, in certain circumstances, the tissue thickness compensator knife path can be curved. Further to the above, curved end effectors and curved fastener cartridges are disclosed in U.S. Patent Application Publication No. 2008/0169329. The entire disclosure of U.S. patent application Ser. No. 11/652,164, entitled CURVED END EFFECTOR FOR A SURGICAL STAPLING DEVICE, filed on Jan. 11, 2007, now U.S. Patent Application Publication No. 2008/0169329, is hereby incorporated by reference herein. In such circumstances, a tissue thickness compensator can be curved. In at least one such embodiment, the tissue thickness compensator can be curved to match the curvature of the cartridge body of the fastener cartridge. Methods and techniques for modifying a tissue thickness compensator to include a knife slot such as, for example, the knife slot 22025 are described below.

Further to the above, referring primarily to FIG. 9, the tissue thickness compensator knife slot 22025 can extend between a first stapling portion 22021a which can be stapled by a first group of staples 22030 and a second stapling portion 22021b which can be stapled by a second group of staples 22030. The knife slot 22025 can releasably connect the first stapling portion 22021a to the second stapling portion 22021b. In use, as illustrated in FIG. 9, the cutting portion 10053 can be advanced distally through the knife slot 22025 to transect the knife slot 22025 and separate the first stapling portion 22021a and the second stapling portion 22021b. In certain circumstances, the knife slot 22025 can comprise a plurality of connectors, or bridges, 22026 which can connect the first stapling portion 22021a and the second stapling portion 22021b prior to being transected by the cutting portion 10053. In various circumstances, the connectors 22026 can have the same thickness as the first stapling portion 22021a and/or the second stapling portion 22021b, at least when the tissue thickness compensator 22020 is in an uncompressed state. In at least one such circumstance, the connectors 22026, the first stapling portion 22021a, and/or the second stapling portion 22021b can be unitarily and integrally formed from a flat, or at least substantially flat, piece of material, for example. In various other circumstances, the first stapling portion 22021a can comprise a first thickness, the second stapling portion 22021b can comprise a second thickness, and the connectors 22026 can comprise a third thickness, wherein one or more of the first thickness, the second thickness, and the third thickness can be different than the other thicknesses.

The knife slot 22025 can further comprise apertures, such as apertures 22024, for example, defined therein. For instance, the apertures 22024 can be elongate and can extend longitudinally along the knife slot 22025. In various other circumstances, the apertures in the knife slot 22025 can comprise any suitable arrangement. In certain circumstances, the apertures 22024 can comprise perforations positioned intermediate the connectors 22026 which can be formed utilizing a laser cutting operation, for example. In some circumstances, the apertures 22024 can be cut from a sheet of material to form the tissue thickness compensator 22020 such that the apertures 22024 and the connectors 22026 are arranged in an alternating arrangement, for example. In other instances, the tissue thickness compensator 22020 can be molded with apertures 22024 already formed therein. In various circumstances, one or more of the apertures 22024 can comprise through holes, for example. In various circumstances, one or more of the apertures 22024 can comprise clearance apertures, for example. In certain instances, one or more of the apertures 22024 may not comprise through holes and may instead comprise reductions in the thickness of the knife slot 22025, for example. Methods and techniques for modifying a tissue thickness compensator to include apertures such as, for example, the apertures 22024 are described below.

Further to the above, referring again to FIGS. 9-11, patient tissue can be positioned intermediate the anvil 10060 of the end effector 22090 and the tissue thickness compensator 22020 of the cartridge assembly 22000 when the anvil 10060 is in an open position. When the anvil 10060 is moved into a closed position, a bottom surface, or tissue-contacting surface, 10063 of the anvil 10060 can contact the tissue T and push the tissue T toward a deck surface 22011 of the cartridge body 22010. The tissue T can contact a top surface, or tissue contacting surface, 22021 of the tissue thickness compensator 22020 wherein, when the anvil 10060 is moved into its closed position, the anvil 10060 can press the tissue T against the tissue thickness compensator 22020 and, further to the above, compress the tissue thickness compensator 22020 against the deck surface 22011 of the cartridge body 22010. In various circumstances, the tissue thickness compensator 22020 can comprise a bottom surface 22029 which can abut the deck surface 22011. In some circumstances, a gap may be present between the bottom surface 22029 and the deck surface 22011 before the tissue thickness compensator 22020 is compressed against the cartridge body 22010. In such circumstances, the tissue thickness compensator 22020 may first translate toward the cartridge body 22010 before being compressed thereagainst. When the tissue thickness compensator 22020 is compressed against the cartridge body 22010, in various circumstances, the first stapling portion 22021a and/or the second stapling portion 22021b of the tissue thickness compensator 22020 may move laterally. For instance, the first stapling portion 22021a and/or the second stapling portion 22021b may move laterally away from the cartridge knife slot 22015. In various circumstances, the connectors 22026 can be configured to inhibit such lateral movement between the first stapling portion 22021a and the second stapling portion 22021b. In various circumstances, referring primarily to FIG. 11, the connectors 22026 can be configured to stretch to permit some relative lateral movement between the first stapling portion 22021a and the second stapling portion 22021b when the anvil 10060 is closed. In the event that the anvil 10060 is reopened, the connectors 22026 can be configured to elastically return, or at least substantially return, to their unstretched configuration and, as a result, pull the first stapling portion 22021a and the second stapling portion 22021b laterally back toward their original positions, illustrated in FIG. 10. Moreover, the anvil 10060 can compress the tissue T when the anvil 10060 is moved into its closed position. In such circumstances, the tissue T may at least partially flow into the apertures 22024.

Figure 10:
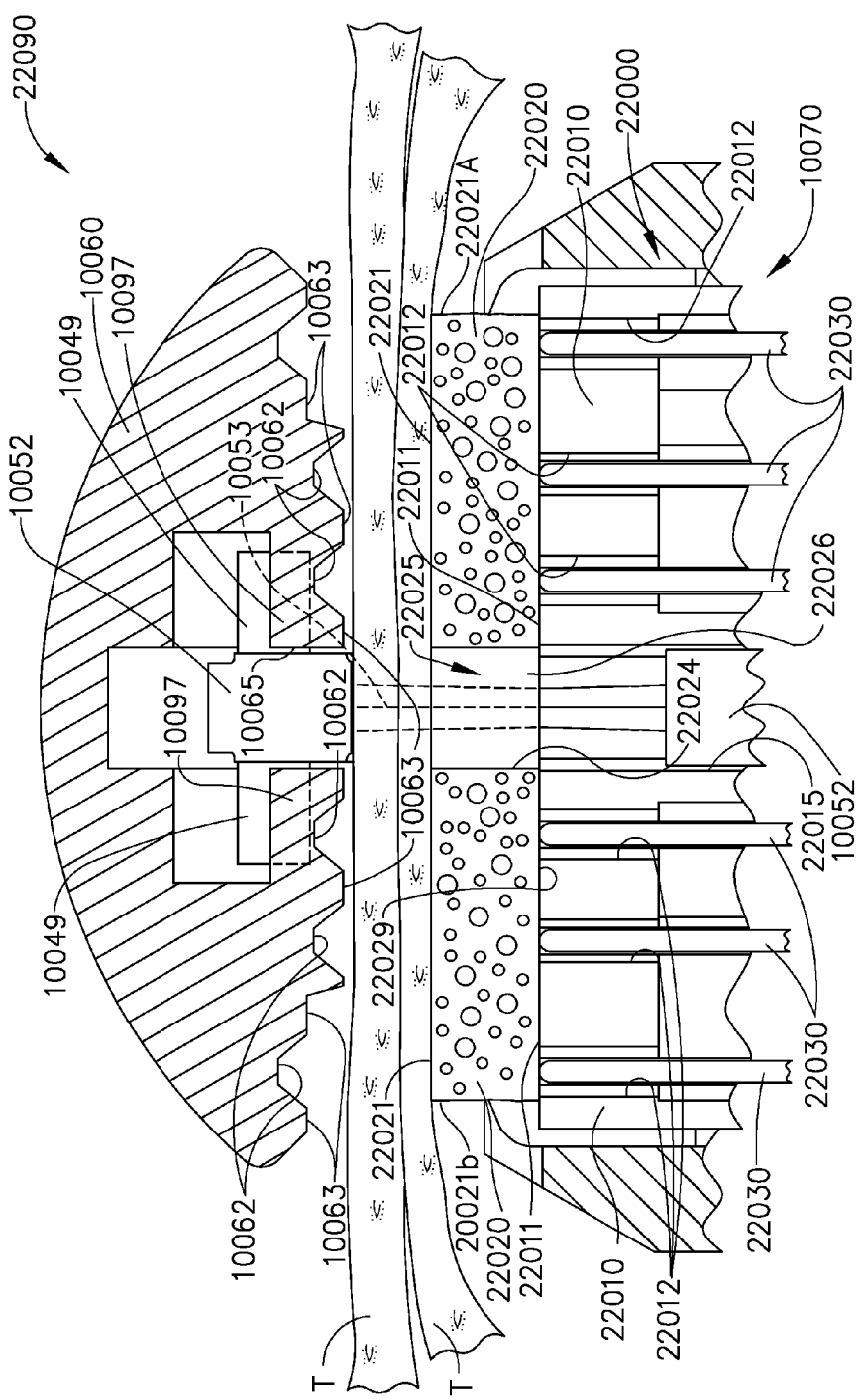
FIG. 10 is a partial cross-sectional end view of the end effector of FIG. 9 illustrated with patient tissue captured between an anvil and a tissue thickness compensator of the end effector; moreover, staples removably stored within a cartridge body of the end effector are illustrated in an unfired position and the cutting member of the end effector is illustrated in an unadvanced position which is proximal to the tissue thickness compensator.
Figure 11:
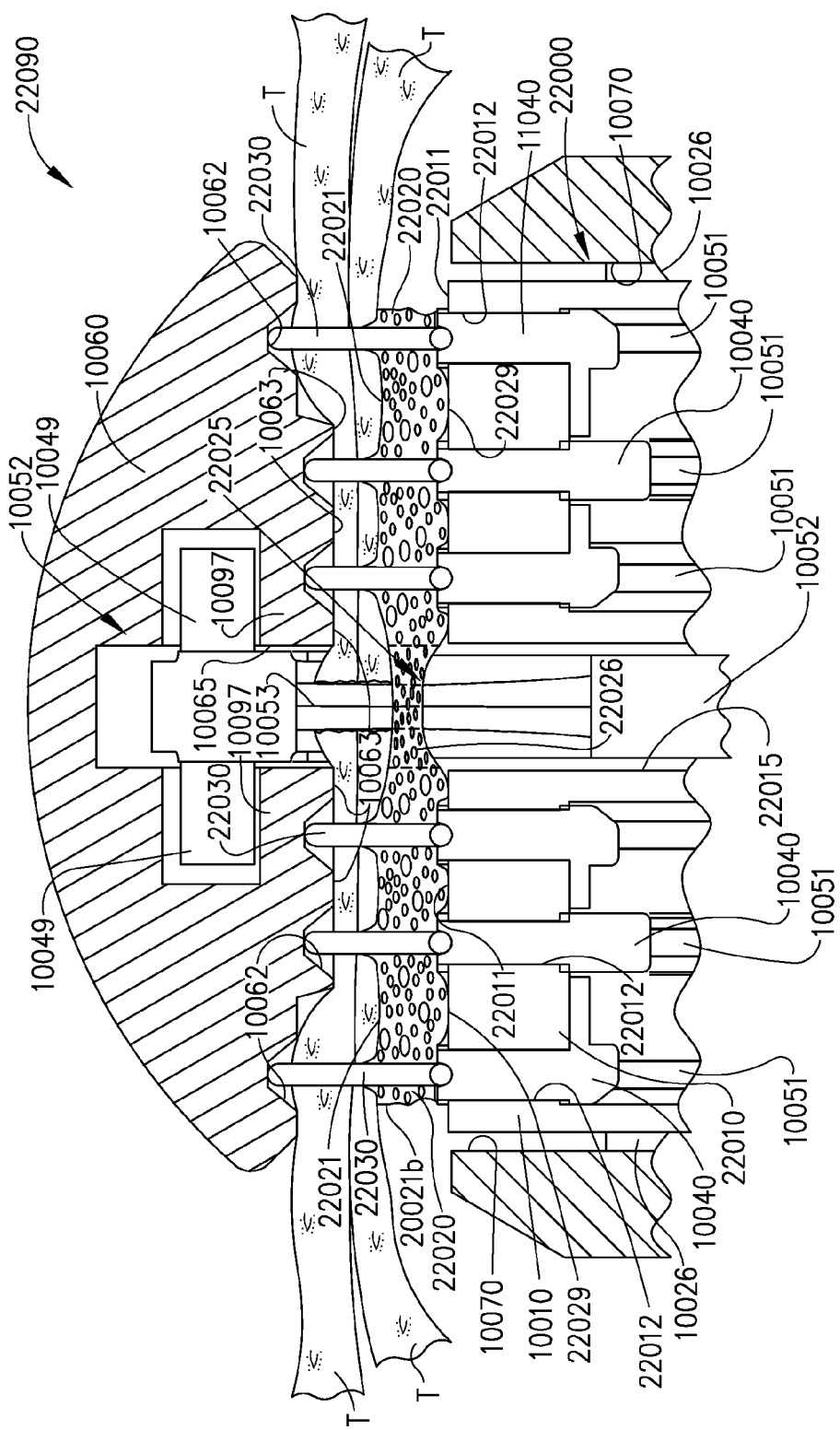
FIG. 11 is a partial cross-sectional end view of the end effector of FIG. 9 illustrated with the staples in a fired position and the cutting member in a partially advanced position in which the patient tissue has been at least partially transected.
Figure 12:
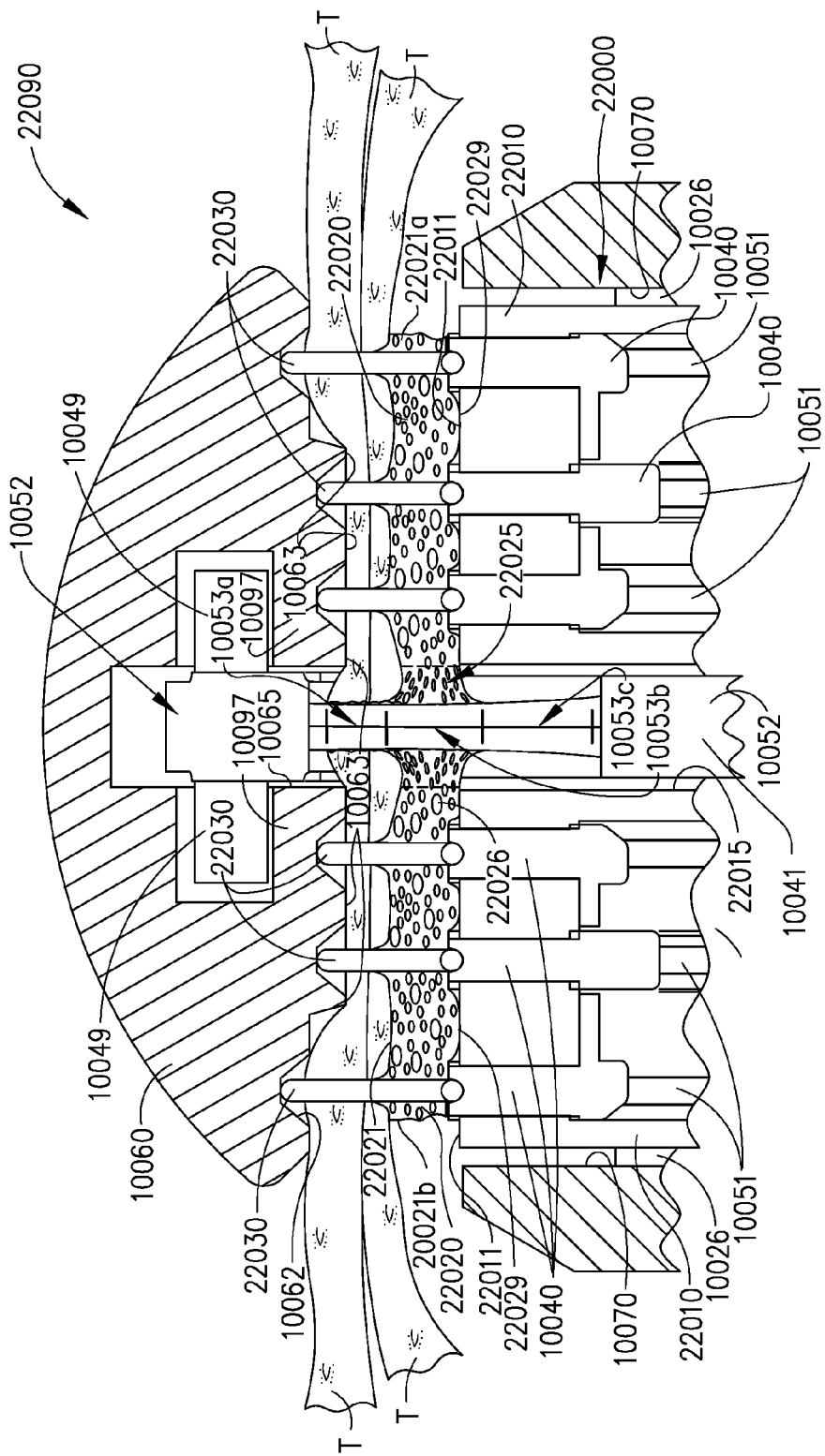
FIG. 12 is a partial cross-sectional end view of the end effector of FIG. 9 illustrated with the staples in a fired position and the cutting member in an advanced position in which at least a portion of the tissue thickness compensator has been transected by the cutting member.

Upon reviewing FIGS. 10-12, the reader will appreciate that the knife slot 22025 of the tissue thickness compensator 22020 comprises less material along the longitudinal length thereof than the first stapling portion 22021a and/or the second stapling portion 22021b. Stated another way, a longitudinal cross-section through the first stapling portion 22021a and/or the second stapling portion 22021b would transect a first amount of material while a longitudinal cross-section through the knife slot 22025 would transect a second amount of material which is less than the first amount of material.

Once the anvil 10060 has been suitably positioned, further to the above, the firing member 10052 can be advanced distally to fire the staples, as illustrated in FIG. 11, and incise the tissue T and the connectors 22026, as illustrated in FIG. 12. Furthermore, the tissue thickness compensator incision force, the tissue incision force, the tissue thickness compensator drag force, and/or the tissue drag force can dull the cutting portion 10053 of the firing member 10052. A dull knife may not be able to transect the tissue T and/or the tissue thickness compensator 22020, for example, according to a preferred manner. With primary reference to FIG. 12, the cutting portion 10053 can comprise a first knife edge zone 10053a, a second knife edge zone 10053b, and/or a third knife edge zone 10053c, for example, wherein the first knife edge zone 10053a is positioned vertically above the second knife edge zone 10053b, and wherein the second knife edge zone 10053b is positioned vertically above the third knife edge zone 10053c, for example. The cutting portion 10053 can comprise any suitable number and/or location of knife edge zones wherein the knife edge zones depicted in FIG. 12 have been selected for the purposes of discussion. Further to the above, the first knife edge zone 10053a can be configured to transect the tissue T while the second knife edge zone 10053b can be configured to transect the tissue thickness compensator 22020. As a result, the first knife edge zone 10053a may experience the tissue incision force and/or the tissue drag force discussed above. Such forces may wear or dull the first knife edge zone 10053a at a first rate. The second knife edge zone 10053b may experience the tissue thickness compensator incision force and/or the tissue thickness compensator drag force discussed above. Such forces may wear or dull the second knife edge zone 10053b at a second rate. In various circumstances, the second rate can be different than the first rate.

Figure 13:
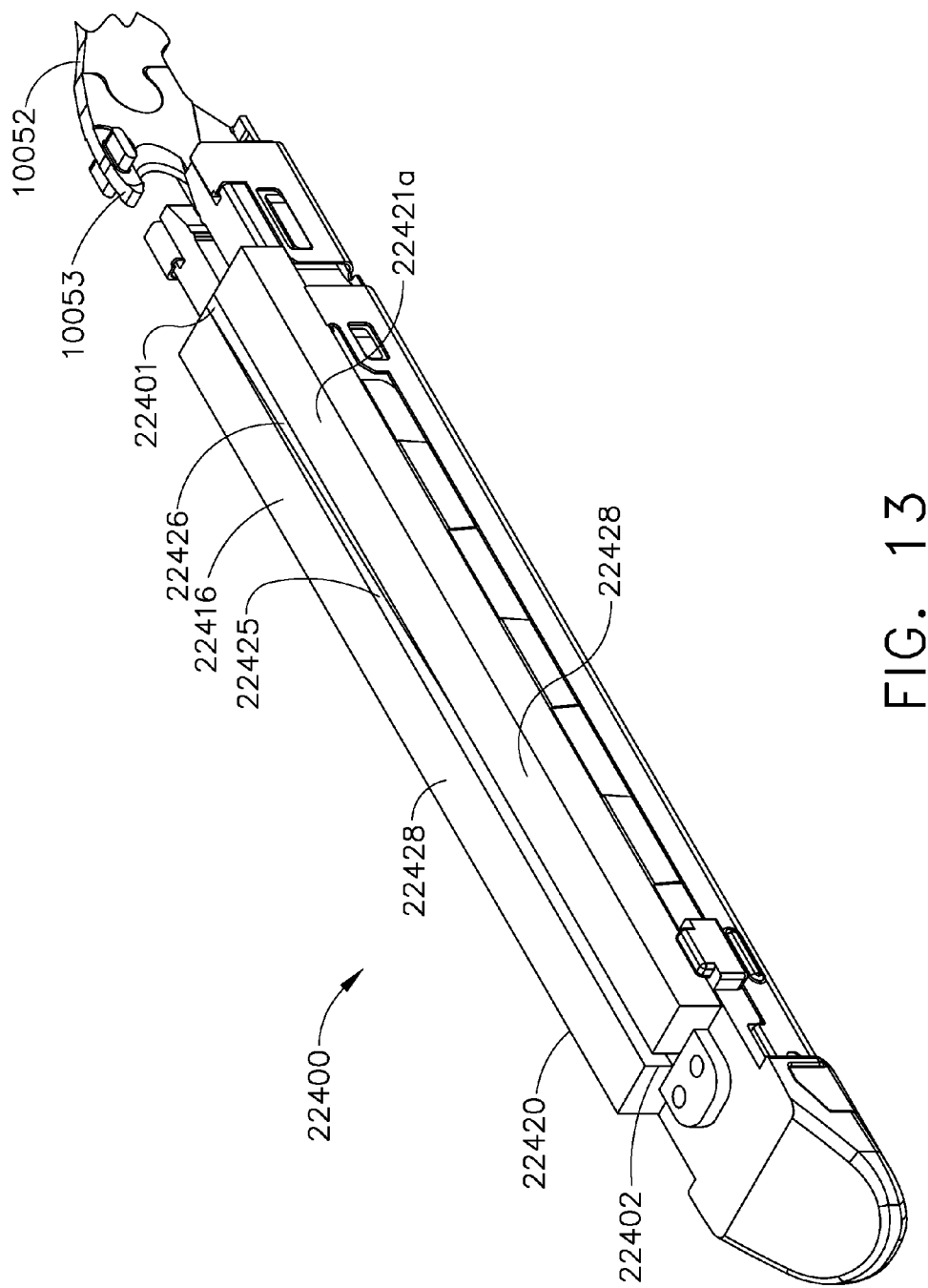
FIG. 13 is a perspective view of a fastener cartridge including a tissue thickness compensator.
Figure 14:
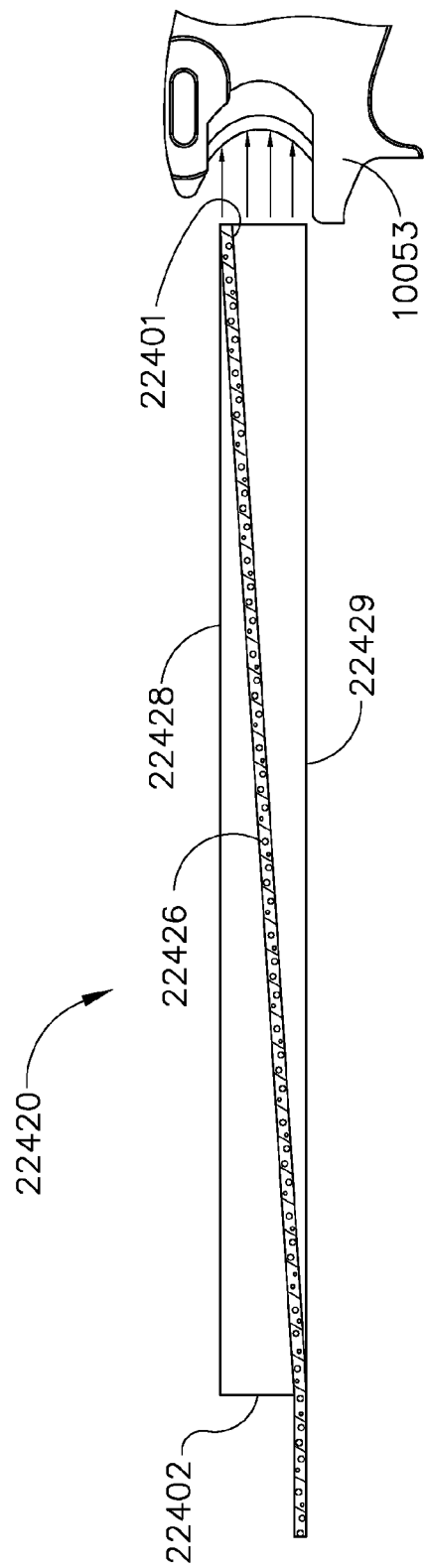
FIG. 14 is a cross-sectional view of the tissue thickness compensator of FIG. 13 illustrating a cutting member positioned relative to a proximal end of the tissue thickness compensator.

Turning now to FIGS. 13 and 14, a fastener cartridge 22400 can comprise a tissue thickness compensator 22420 which can include a first stapling portion 22421a and a second stapling portion 22421b which are connected by a knife slot 22425. The knife slot 22425 can comprise an angled longitudinal connector 22426. The angled longitudinal connector 22426 can extend between a proximal end 22401 of the knife slot 22425 and a distal end 22402 of the knife slot 22425. In some circumstances, the angled longitudinal connector 22426 can extend the entire length of the knife slot 22425 while, in other circumstances, the angled longitudinal connector 22426 can extend less than the length of the knife slot 22425. The angled longitudinal connector 22426 can extend between a top surface 22428 of the tissue thickness compensator 22420 and a bottom surface 22429 of the tissue thickness compensator 22420. In some circumstances, the angled longitudinal connector 22426 can extend the entire distance between the top surface 22428 and the bottom surface 22429 while, in other circumstances, the angled longitudinal connector 22426 can extend less than the distance between the top surface 22428 and the bottom surface 22429. In various circumstances, the proximal end of the longitudinal connector 22426 can extend from the top surface 22428 of the tissue thickness compensator while the distal end of the longitudinal connector 22426 can extend from the bottom surface 22429. Alternatively, the distal end of the longitudinal connector 22426 can extend from the top surface 22428 of the tissue thickness compensator while the proximal end of the longitudinal connector 22426 can extend from the bottom surface 22429. In various circumstances, the longitudinal connector 22426 can comprise a thin bridge (i.e. less than the full thickness of the tissue thickness compensator 22420) or a series of thin bridges that join the first stapling portion 22421a which can be stapled by a first group of staples 22030 to the second stapling portion 22421b which can be stapled by a second group of staples 22030, for example. These thin, angled bridges, and/or the longitudinal connector 22426, could distribute the wear across the second knife edge zone 10053b, rather than concentrating it on one spot. In various circumstances, as a result, the wear occurring on the second knife edge zone 10053b may be equal to, or closer to being equal to, the wear occurring at the first knife edge zone 10053a, for example.

Figure 15:
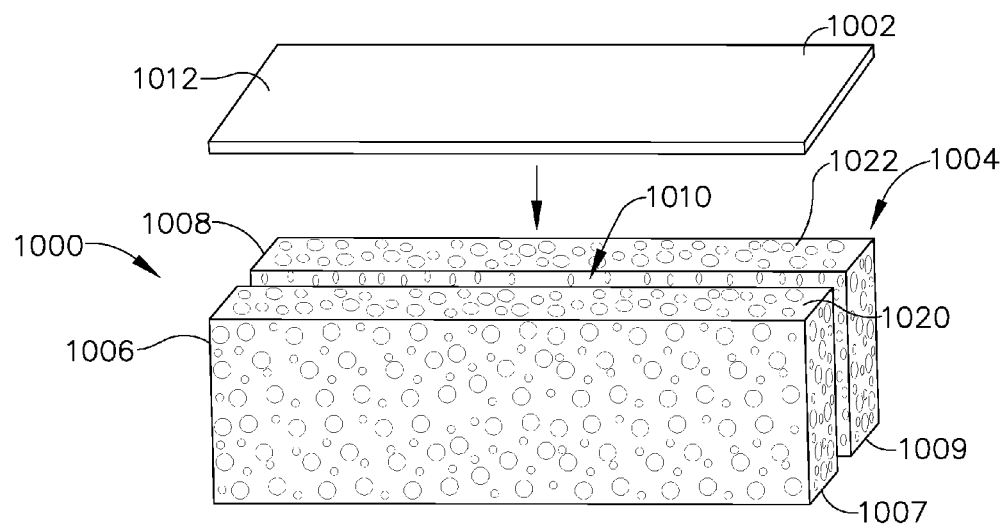
FIG. 15 is an exploded view of a tissue thickness compensator assembly.
Figure 16:
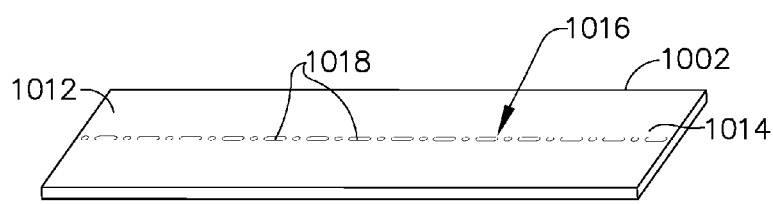
FIG. 16 is a perspective view of layer of a tissue thickness compensator assembly.
Figure 17:
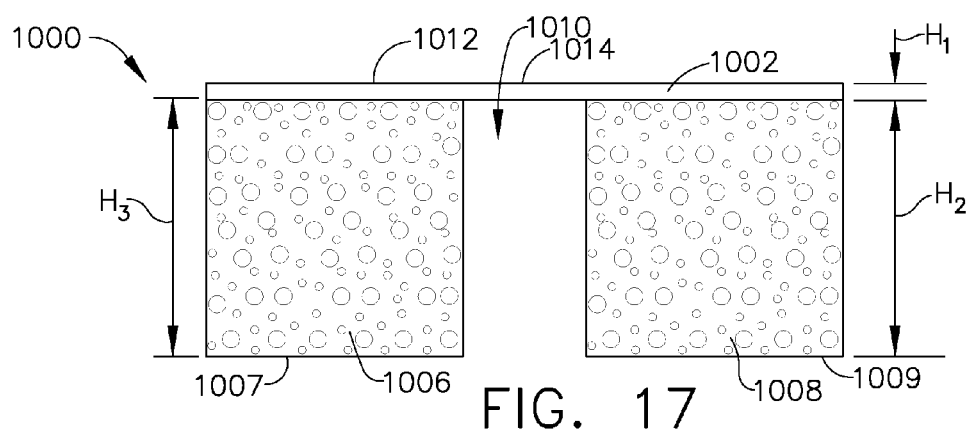
FIG. 17 is a cross-sectional view of the tissue thickness compensator assembly of FIG. 15.

Referring now to FIGS. 15-17, an exemplary tissue thickness compensator assembly 1000 may include a first layer 1002 and a second layer 1004 attachable to the first layer 1002. The tissue thickness compensator assembly 1000 can be utilized with a surgical instrument such as, for example, the surgical instrument 8010 (FIG. 1). In addition, the tissue thickness compensator assembly 1000 can be utilized in a similar manner as and can replace the tissue thickness compensator 22020 of the cartridge assembly 22000 of the end effector 22090 (FIG. 9). For example, the second layer 1004 of the tissue thickness compensator assembly 1000 may include a first portion 1006 which can be positioned on the deck surface 22011 on a first side of the cartridge knife slot 22015 in a similar fashion to the first stapling portion 22021a and a second portion 1008 which can be positioned on the deck surface 22011 on a second side, opposite the first side, of the cartridge knife slot 22015 in a similar fashion to the second stapling portion 22021b (FIGS. 9-11). In various instances, the first portion 1006 and the second portion 1008 of the second layer 1004 can be spaced apart and may comprise a gap 1010 therebetween which can comprise a knife path for the cutting portion 10053 of the firing member 10052 and may extend at least partially over the cartridge knife slot 22015 when the tissue thickness compensator assembly 1000 is assembled with the cartridge end effector 22090. In certain instances, the first layer 1002 can be configured to couple the first portion 1006 and the second portion 1008 and extend at least partially over the gap 1010, as illustrated in FIG. 17, for example.

In use, tissue T can be captured between the anvil 10060 and a tissue contacting surface 1012 of the first layer 1002. As the firing member 10052 is advanced, a first group of staples 20030 can be deployed to staple the first portion 1006 and a second group of staples can be deployed to staple the second portion 1008. The first and second groups of staples can be configured to penetrate through a first deck contacting surface 1007 and a second deck contacting surface 1009, respectively, of the second layer 1004, then through the tissue contacting surface 1012 of the first layer, and then through the captured tissue T to contact the pockets 10062 of the anvil 10060. Furthermore, the advancement of the firing member 10052 can cause the cutting portion 10053 to be advanced distally through the gap 1010 of the tissue thickness compensator assembly 1000. The cutting portion 10053 may transect the first layer 1002 while advancing through the gap 1010 thereby separating the first portion 1006 and the second portion 1008 of the second layer 1004.

Referring again to FIG. 17, the first layer 1002 of the tissue thickness compensator assembly 1000 may comprise a first height H1, the first portion 1006 of the second layer 1004 may comprise a second height H2, and the second portion 1008 of the second layer 1004 may comprise a third height H3. In certain circumstances, as illustrated in FIG. 17, the second height H2 and the third height H3 can be the same or substantially the same. In other circumstances, the second height H2 can be different from the third height H3. In certain circumstances, the first height H1 can be less than the second height H2 and/or the third height H3, as illustrated in FIG. 17. The first layer 1002 of the tissue thickness compensator assembly 1000 may comprise a first density, the first portion 1006 of the second layer 1004 may comprise a second density, and the second portion 1008 of the second layer 1004 may comprise a third density. In certain circumstances, as illustrated in FIG. 17, the second density and the third density can be the same or substantially the same. In other circumstances, the second density can be different from the third density and/or different from the first density of the first layer 1002. The material compositions of the first portion 1006 and the second portion 1008 can be the same, or at least substantially the same. In other circumstances, the material compositions of the first portion 1006 and the second portion 1008 can be different from each other and/or can be different from the material composition of the first layer 1002.

As described above, repeated use of the cutting portion 10053 to cut tissue T and tissue thickness compensator material may dull the cutting portion 10053. To slow the dulling process, it may be desirable to reduce the tissue thickness compensator material that is cut by the cutting portion 10053. An additional benefit can be a reduction in the forces needed to advance the firing member 10052 distally during a firing stroke. In order to reduce the dulling of the cutting portion 10053, the first layer 1002 can be comprised, at least partially, of a thin film, for example. In such circumstances, the first height H1 can be significantly less than the second height H2 and the third height H3, as illustrated in FIG. 17. In certain circumstances, the first layer 1002 may comprise a uniform, or substantially uniform, height therethrough, as illustrated in FIG. 17. In other circumstances, a gap bridging portion 1014 of the first layer 1002 may extend at least partially over the gap 1010 and may be thinner than the remainder of the first layer 1002. The cutting portion 10053 may transect the gap bridging portion 1014 of the first layer 1002 while advancing through the gap 1010 between the first portion 1006 and the second portion 1008 of the second layer 1004 which may reduce the resistance experienced by the cutting portion 10053 and/or slow the dulling of the cutting portion 10053. In any event, the first layer 1002 can be configured to maintain a coupling engagement with the first portion 1006 and the second portion 1008 of the second layer 1004 prior to being transected, and to present the cutting portion 10053 with a reduced resistance as the cutting portion 10053 is advanced to transect the first layer 1002.

To further reduce the dulling of the cutting portion 10053 and/or reduce be resistance experienced by the cutting portion 10053, the gap bridging portion 1014 may comprise a perforated segment 1016 along the knife path defined by the gap 1010, as illustrated in FIG. 16. The perforated segment 1016 can include a plurality of perforations 1018 which can be cut into the first layer 1002 prior to the assembly of the first layer 1002 to the second layer 1004, for example. The perforations 1018 can reduce the interaction between the cutting portion 10053 and the first layer 1002 as the cutting portion 10053 is advanced through the knife path defined by the gap 1010, which may slow the dulling of the cutting portion 10053 and/or reduce the resistance experienced by the cutting portion 10053.

In various circumstances, as described in greater detail below, the tissue thickness compensator assembly 1000 can be comprised of one or more biocompatible materials. In certain circumstance, the first layer 1002 can be comprised of a biocompatible buttress material and/or plastic material, such as polydioxanone (PDS) and/or polyglycolic acid (PGA), for example, and the second layer 1004 can be comprised of a bioabsorbable foam material and/or a compressible haemostatic material, such as oxidized regenerated cellulose (ORC), for example. In certain circumstances, the first layer 1002 can be a thin film comprising a bioabsorbable material such as polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example. In certain circumstances, the first portion 1006 and/or the second portion 1008 of the second layer 1004 can be comprised of a lyophilized foam comprising polylactic acid (PLA) and/or polyglycolic acid (PGA), for example. In certain circumstances, the first portion 1006 and/or the second portion 1008 of the second layer 1004 can be comprised of biocompatible foam which may comprise a porous, open cell foam and/or a porous, closed cell foam.

Referring again to FIGS. 15 and 17, the first layer 1002 can be at least partially disposed over the second layer 1004 such that the second layer 1004 may be positioned between the first layer 1002 and the deck surface 22011 (FIG. 9) when the tissue thickness compensator assembly 1000 is assembled with the end effector 22090 (FIG. 9). In other circumstances, the first layer 1002 can be positioned beneath the first portion 1006 and the second portion 1008 (not shown) such that the first layer 1002 may be positioned between the second layer 1004 and the deck surface 22011 (FIG. 9) when the tissue thickness compensator assembly 1000 is assembled with the end effector 22090 (FIG. 9). In any event, the first layer 1002 can be attached to a first contacting surface 1020 of the first portion 1006 and a second contacting surface 1022 of the second portion 1008 of the second layer 1004. The first layer 1002 can be attached to the second layer 1004 via a thermal pressing process involving the application of heat and/or pressure, as described in greater detail below. In other circumstances, the first layer 1002 can be attached to the second layer 1004 by a biocompatible adhesive material such as a fibrin and/or protein hydrogel, for example. Other means for attaching the first layer 1002 to the second layer 1004 are contemplated by the present disclosure.

Figure 21:
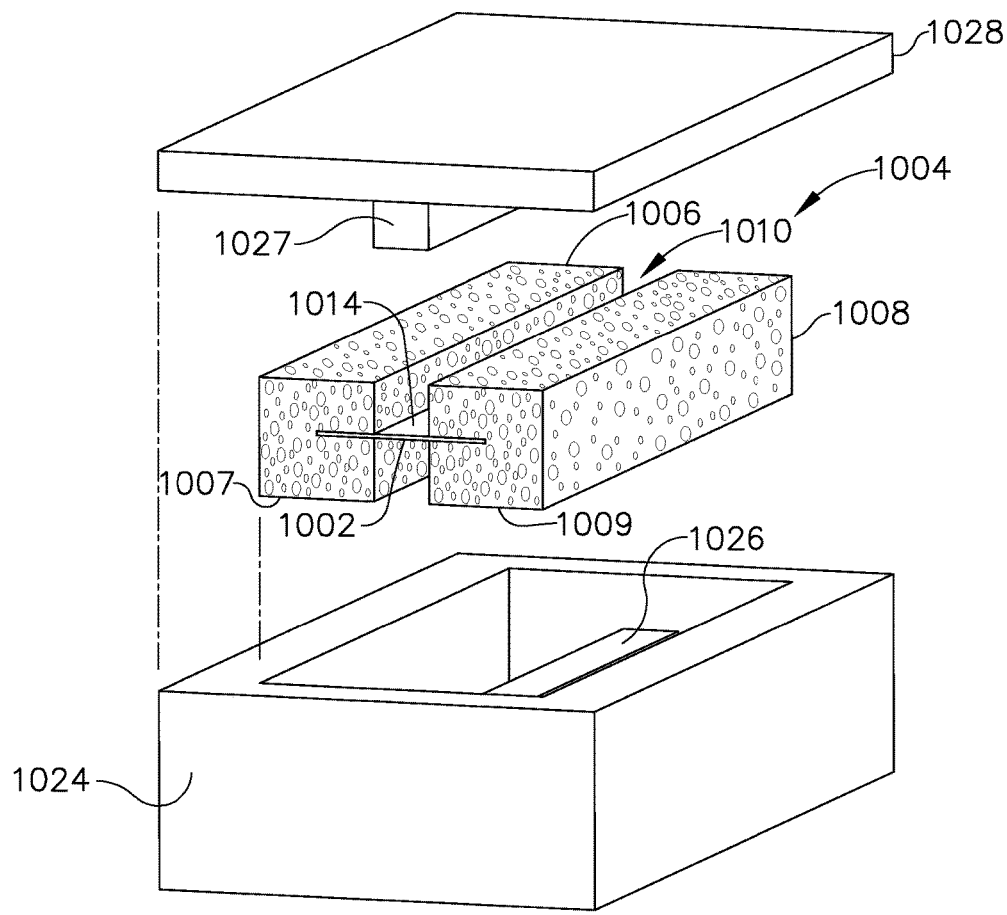
FIG. 21 is a perspective view of a tissue thickness compensator assembly and a mold for assembling the same.
Figure 22:
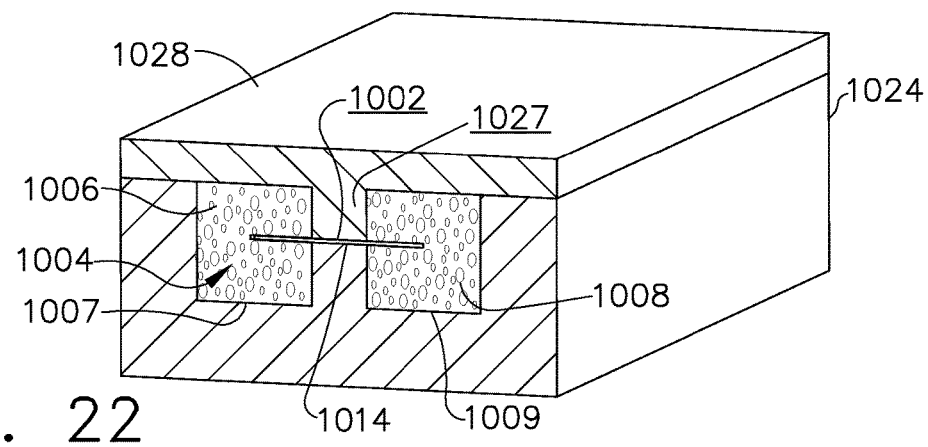
FIG. 22 is a cross-sectional perspective view of the tissue thickness compensator assembly of FIG. 21 and the mold of FIG. 21 for assembling the same.

Referring now to FIGS. 21 and 22, the first layer 1002 can be at least partially embedded into the first portion 1006 and/or the second portion 1008 of the second layer 1004. In such circumstances, the tissue thickness compensator assembly 1000 can be prepared using a mold 1024, for example, as illustrated in FIG. 21. In various instances, an organic solution comprising a polymer such as, for example, polylactic acid (PLA) and/or polyglycolic acid (PGA) can be poured into the mold 1024. The first layer 1002 can be immersed into the organic solution. As illustrated in FIG. 22, a central shelf 1026 and a central beam 1027 of a mold cover 1028 can trap the first layer 1002 therebetween to ensure that the first layer 1002 remains immersed in the organic solution which can then be lyophilized using conventional lyophilization techniques and/or any other suitable techniques, for example. Upon completion of the lyophilization process, and/or any other suitable process, the mold cover 1028 can be removed and the tissue thickness compensator assembly 1000 can be recovered from the mold 1028.

As illustrated in FIG. 21, the first layer 1002 of the tissue thickness compensator 1000 can be partially positioned within the first portion 1006 and the second portion 1008 of the second layer 1004. In certain circumstances, the first layer 1002 can be partially positioned within one of the first portion 1006 and the second portion 1008 and attached to a top surface or a bottom surface of the other one of the first portion 1006 and the second portion 1008.

In certain circumstances, the central beam 1027 and the shelf 1026 can at least partially extend along an axis that is parallel or substantially parallel to the first deck contacting surface 1007 and/or the second deck contacting surface 1009 when the cover 1028 is in a closed configuration with mold 1024, as illustrated in FIG. 22. In such circumstances, the first layer 1002 can be embedded into the first portion 1006 and/or the second portion 1008 such that first layer 1002 is positioned or substantially positioned in a parallel or substantially parallel relationship with the first deck contacting surface 1007 and/or the second deck contacting surface 1009. In other circumstances, although not illustrated, the central beam 1027 and the shelf 1026 can at least partially extend along an axis that is at an oblique angle with the first deck contacting surface 1007 and/or the second deck contacting surface 1008 when the cover 1028 is in a closed configuration with mold 1024. In such circumstances, the first layer 1002 can be embedded into the first portion 1006 and/or the second portion 1008 such that first layer 1002 is positioned or substantially positioned at an oblique angle with respect to the first deck contacting surface 1007 and/or the second deck contacting surface 1009. Other techniques for partially embedding the first layer 1002 into the first portion 1006 and/or the second portion 1008 are contemplated by the present disclosure.

Figure 18:
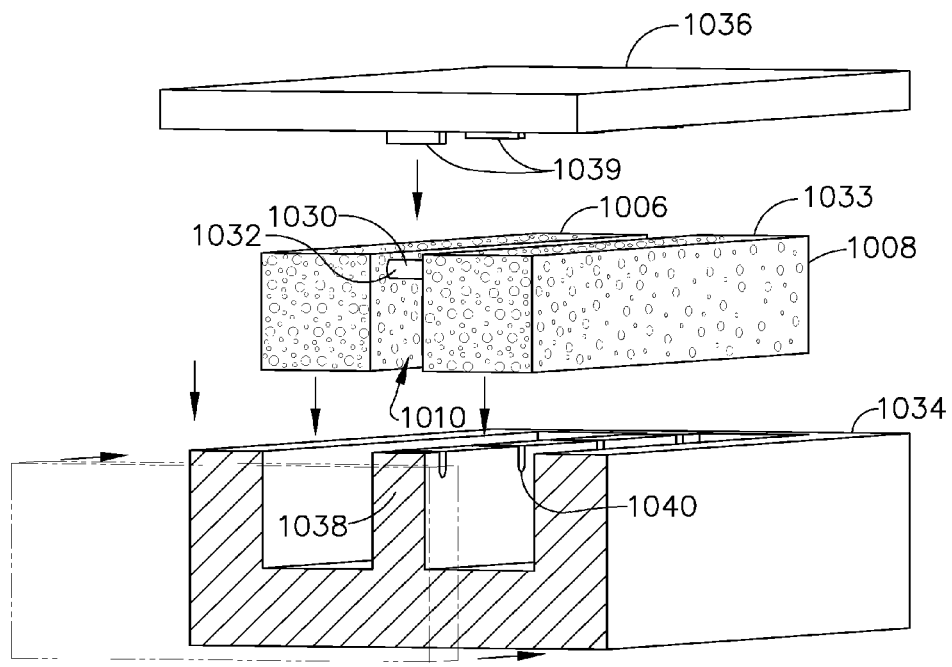
FIG. 18 is a cross-sectional perspective view of an assembled tissue thickness compensator assembly and a mold for assembling the same.
Figure 19:
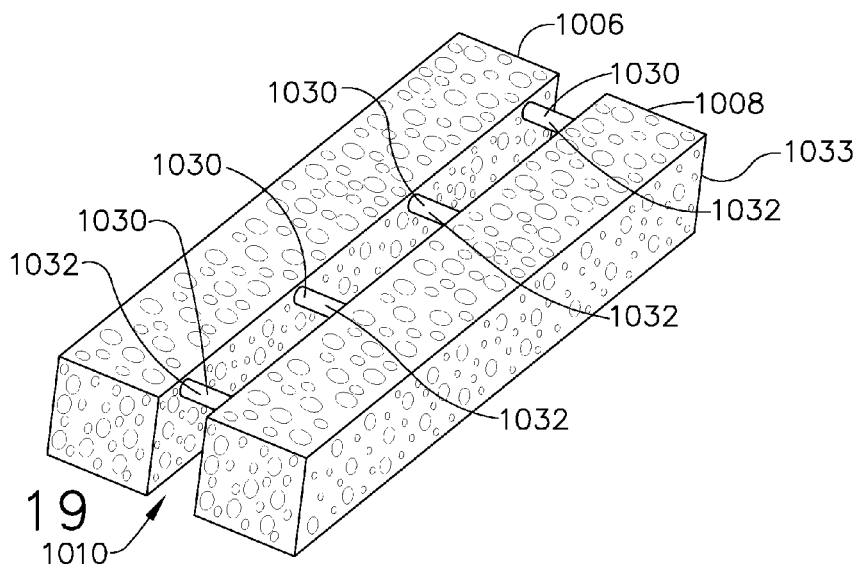
FIG. 19 is a perspective view of the assembled tissue thickness compensator assembly of FIG. 18.

Referring now to FIGS. 18 and 19, a tissue thickness compensator assembly 1033, which is similar in many respects to the tissue thickness compensator assembly 1000 and the tissue thickness compensator 20020, is illustrated. The tissue thickness compensator assembly 1033 can comprise the first portion 1006 and the second portion 1008 which can be spaced apart and separably coupled together by a plurality of bridging members or connectors 1030 which may extend across the gap 1010 between the first portion 1006 and the second portion 1008. In addition, some or all of the connectors 1030 of the tissue thickness compensator assembly 1033 can be partially embedded into the first portion 1006 and the second portion 1008, as illustrated in FIG. 19. Furthermore, some or all of the connectors 1030 can comprise a first end positioned within the first portion 1006, a second end positioned within the second portion 1008, and a gap bridging portion 1032 therebetween. The gap bridging portion 1032 may extend across the gap 1010 between the first portion 1006 and the second portion 1008, as illustrated in FIG. 19. The connectors 1030 can be spaced apart along the length of the gap 1010 to separably couple the first portion 1006 to the second portion 1008.

In certain circumstances, the connectors 1030 can be evenly distributed along an axis extending along the gap 1010, as illustrated in FIG. 19. In other circumstances, although not illustrated, the connectors 1030 can be unevenly distributed along the axis extending along the gap 1010. The cutting portion 10053 can be configured to transect the gap bridging portions 1032 of the connectors 1030 as the cutting portion 10053 is advanced between the first portion 1006 and the second portion 1008 through the knife path defined by the gap 1010. Where the connectors 1030 are unevenly distributed along the axis extending along the first portion 1006 and the second portion, in at least one instance, the connectors 1030 can be disposed in greater frequency and/or in closer proximity to each other at a distal segment of the gap 1010 than at a proximal segment of the gap 1010 such that the cutting portion 10053 may experience an increasing resistance as it is advanced along the knife path defined by the gap 1010. In other circumstances, the connectors 1030 can be disposed in greater frequency and/or in closer proximity to each other at a proximal segment of the gap 1010 than at a distal segment of the gap 1010 such that the cutting portion 10053 may experience a decreasing resistance as it is advanced along the knife path defined by the gap 1010, for example.

In certain circumstances, the connectors 1030 can extend or substantially extend in a single plane which can be parallel or substantially parallel to the first deck contacting portion 1007 and/or the second deck contacting portion 1009, as illustrated in FIG. 19. In other circumstances, although not illustrated, the connectors 1030 can extend or substantially extend along a plurality of planes which can be parallel or substantially parallel to each other and/or to the first deck contacting portion 1007 and/or the second deck contacting portion 1009.

Further to the above, some or all of the gap bridging portions 1032 of the connectors 1030 can be thinner than the remainder of their respective connectors 1030 to present the cutting portion 10053 with a reduced resistance as the cutting portion 10053 is advanced to transect the connectors 1030 while maintaining a coupling engagement with the first portion 1006 and the second portion 1008 of the second layer 1004. For example, some or all the connectors 1030 can comprise a dog-bone shape with thicker ends terminating within the first portion 1006 and the second portion 1008 of the second layer 1004 and thinner central portions extending therebetween. In certain circumstances, the connectors 1030 can each be comprised of a piece of suture which may be comprised of bioabsorbable material such as polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example.

Referring again to FIG. 18, the tissue thickness compensator assembly 1033 can be prepared using a mold 1034. An organic solution comprising a polymer such as, for example, polylactic acid (PLA) and/or polyglycolic acid (PGA) can be poured into the mold 1034. The connectors 1030 can be immersed into the organic solution. As illustrated in FIG. 18, one or more of the connectors 1030 can each be trapped in one or more dedicated slots 1040 on a central shelf 1036 by one or more beams 1039 extending from a mold cover 1038 and configured for mating engagement with the slots 1040 when the mold cover 1038 is in a closed configuration with the mold 1034 to ensure that the connectors 1030 remain immersed in the organic solution. The slots 1040 can be sized to receive or at least partially receive the bridging portions 1032 which can be secured by the beams 1039 when the mold cover 1038 is in the closed configuration with the mold 1034. The ends of the connectors 1030 extending from the gap bridging portions 1032 may freely float in the organic solution. Alternatively, the ends of the connectors 1030 can be secured to sides of the mold 1034, for example. In certain circumstances, the connectors 1030 can be stretched in the organic solution between the sides of the mold 1034. In other circumstances, the connectors 1030 can be loosely held between the sides of the mold 1034 to extend through the organic solution in a non-linear fashion, for example.

Further to the above, in various instances, the organic solution can then be lyophilized using conventional lyophilization techniques and/or any other suitable techniques. Upon completion of the lyophilization process, the mold cover 1036 can be removed and the tissue thickness compensator assembly 1033 can be recovered from the mold 1034. As illustrated in FIG. 19, the resulting tissue thickness compensator assembly 1033 includes connectors 1030 partially positioned within the first portion 1006 and the second portion 1008. Other techniques for partially embedding the connectors 1030 into the first portion 1006 and/or the second portion 1008 are contemplated by the present disclosure. The reader will appreciate that the connectors 1030 can be positioned closer to or further away from the deck contacting surfaces 1007 and 1009 by changing the height of the central shelf 1038 and/or depth of the slots 1040.

Figure 20:
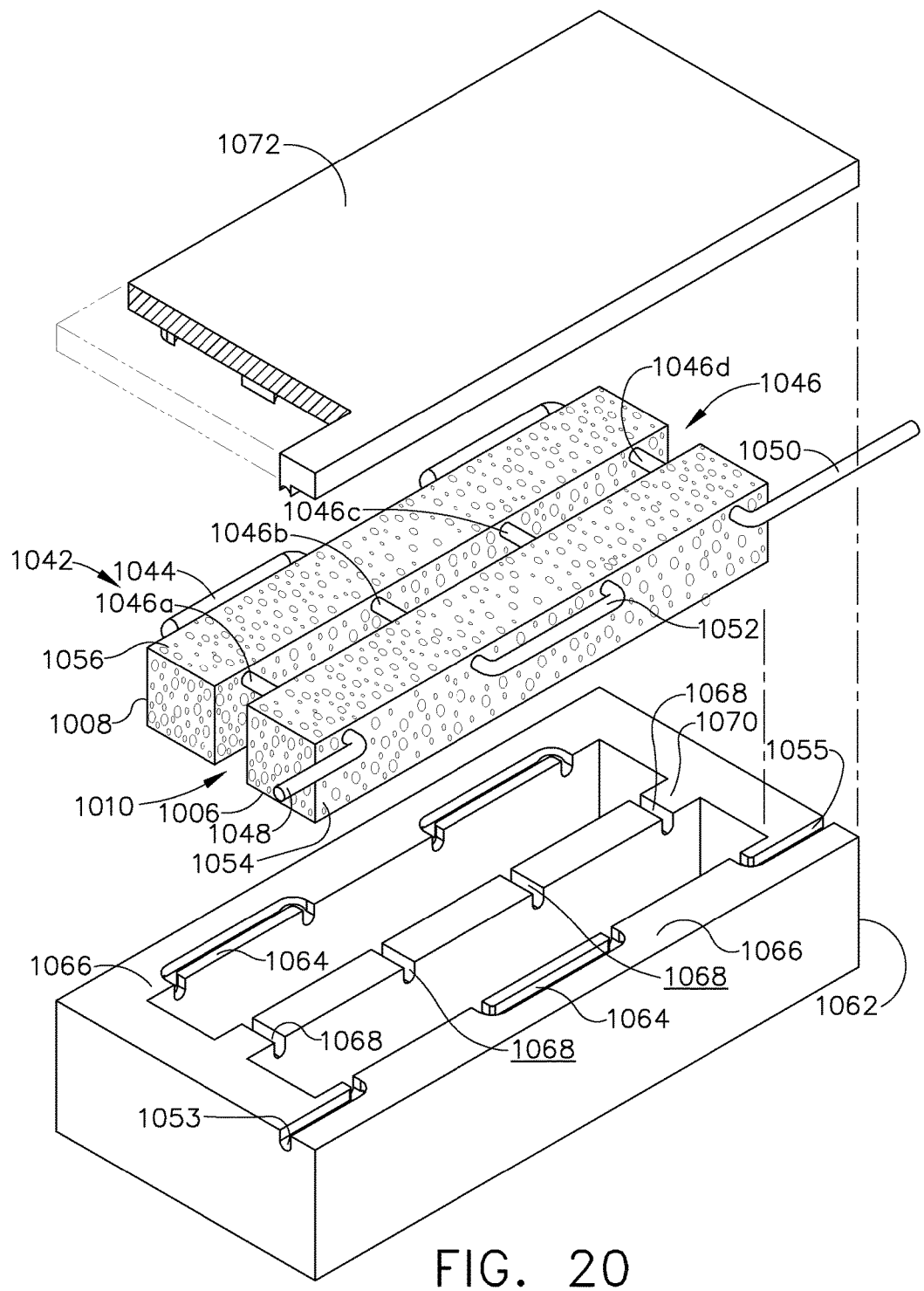
FIG. 20 is a perspective view of a tissue thickness compensator assembly and a mold for assembling the same.

Referring now to FIG. 20, a tissue thickness compensator assembly 1042, which may be similar in many respects to the tissue thickness compensator assembly 1033, the tissue thickness compensator assembly 1000, and/or the tissue thickness compensator 20020, is illustrated. The tissue thickness compensator assembly 1042 may comprise the first portion 1006 and the second portion 1008 which can be spaced apart and separably coupled together by a continuous flexible member 1044 which may form a plurality of bridging members or connectors 1046 which may extend across the gap 1010 between the first portion 1006 and the second portion 1008. The continuous flexible member 1044 may include a first end 1048, a second end 1050, and a flexible portion 1052 extending between the first end 1048 and the second end 1050. The flexible portion 1052 can be configured to extend through the first portion 1006 and the second portion 1008 several times, for example in a zigzag pattern, to form the connectors 1046, as illustrated in FIG. 20. The flexible portion 1052 can be passed in a first direction through a distal segment 1054 of the first portion 1006 and a distal segment 1056 of the second portion 1008 to form a first gap bridging portion 1046a across the gap 1010. The flexible portion 1052 can then be looped and passed in a second direction, opposite the first direction, through the second portion 1008 proximal to the distal segment 1056 and through the first portion 1006 proximal to the distal segment 1054 thereby forming a second gap bridging portion 1046b proximal the first gap bridging portion 1046a. Additional gap bridging portions 1046c and 1046d, for example, can be formed in the same manner across the gap 1010, as illustrated in FIG. 20.

In certain circumstances, the continuous flexible member 1044 can comprise a suture and can be comprised of a suture material such as polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example. In certain circumstances, the tissue thickness compensator assembly 1042 can be assembled after the first portion 1006 and the second portion 1008 are manufactured, for example, via lyophilization. In some circumstances, a needle (not shown) can be attached to the first end 1048 of the continuous flexible member 1044 and can be passed through the first portion 1006 and the second portion 1008, for example in a zigzag pattern, to couple the first portion 1006 to the second portion 1008, as described above. The first end 1048 and/or the second end 1050 of the continuous flexible member 1044 can be secured to the side walls of the first portion 1006 and/or the second portion 1008 by tying in one or more knots at the first end 1048 and/or the second end 1050, for example. The knots may abut against the side walls of the first portion 1006 and/or the second portion 1008 to prevent the flexible portion 1052 from unraveling relative to the first portion 1006 and/or the second portion 1008. In other circumstances, the first portion 1006 and the second portion 1008 of the tissue thickness compensator assembly 1042 can be formed around the continuous flexible member 1044. In such circumstances, as illustrated in FIG. 20, the continuous flexible member 1044 can be disposed in a mold 1062, for example in a zigzag pattern, with slots 1064 defined side walls 1066 and slots 1068 defined in central shelf 1070. An organic solution comprising a polymer such as, for example, polylactic acid (PLA) and/or polyglycolic acid (PGA) can be poured into the mold 1062 until the continuous flexible member 1044 is immersed in the organic solution. A mold cover 1072 can be used to ensure that the continuous flexible member 1044 remains immersed in the organic solution which can then be lyophilized using conventional lyophilization techniques and/or any other suitable techniques. The first end 1048 and the second end 1050 of the continuous flexible member 1044 can be secured at openings 1053 and 1055 of the mold 1062, respectively, by tying in one or more knots at the first end 1048 and the second end 1050 after passing the first end 1048 through the opening 1053 and the second end 1050 through the opening 1055, for example. The knots may abut against the side walls of the mold 1062 to prevent the continuous flexible member 1044 from unraveling relative to the mold 1066. After the tissue thickness compensator has been removed from the mold, in various instances, portions of the continuous flexible member 1044, such as portions 1048, 1050, and/or 1052, for example, can then be cut and removed from the tissue thickness compensator. Other techniques for assembling the tissue thickness compensator assembly 1042 are contemplated by the present disclosure.

In certain circumstances, a tissue thickness compensator assembly such as, for example, the tissue thickness compensator assembly 1042 can be compromised when excessive force or pressure is applied thereto. For instance, pressure can be applied to a tissue thickness compensator assembly such as, for example, the tissue thickness compensator assembly 1042 when the tissue thickness compensator assembly 1042 is loaded onto a staple cartridge such as, for example, the staple cartridge 10000. The tissue thickness compensator assembly 1042 can be equipped with a pressure or force sensitive member that can provide a user with a warning feedback if the pressure experienced by the tissue thickness compensator assembly exceeds a threshold. For example, a pressure or force sensitive film can be attached to the tissue thickness compensator assembly 1042 and can be configured to change color upon experiencing pressure that exceeds the threshold. In certain circumstances, the pressure or force sensitive film can be disposed over the first portion 1006 and/or the second portion 1008 and can be attached thereto via an adhesive, for example. The pressure or force sensitive film can be biocompatible to permit implantation of the pressure or force sensitive film with the tissue thickness compensator assembly 1042 inside a patient.

Figure 23:
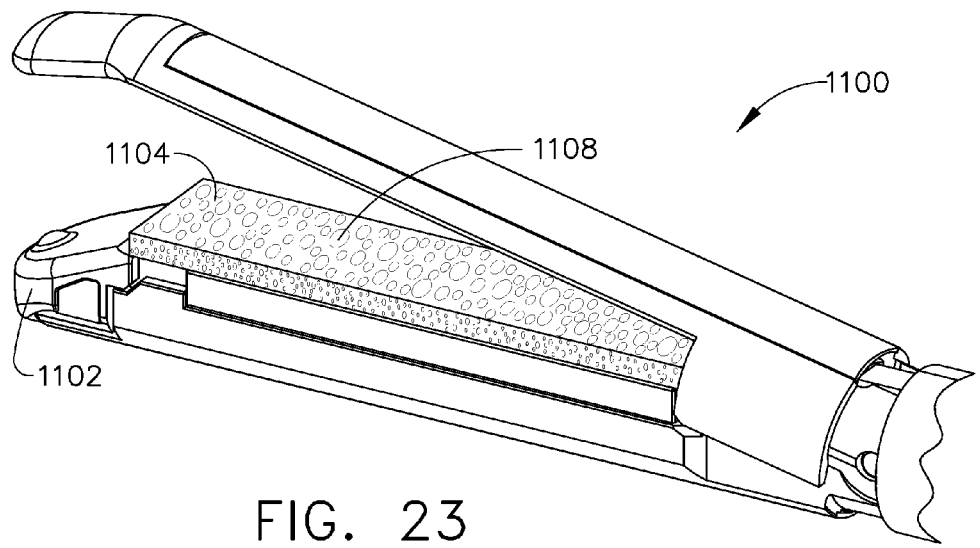
FIG. 23 is a perspective view of an end effector comprising a tissue thickness compensator.
Figure 24:
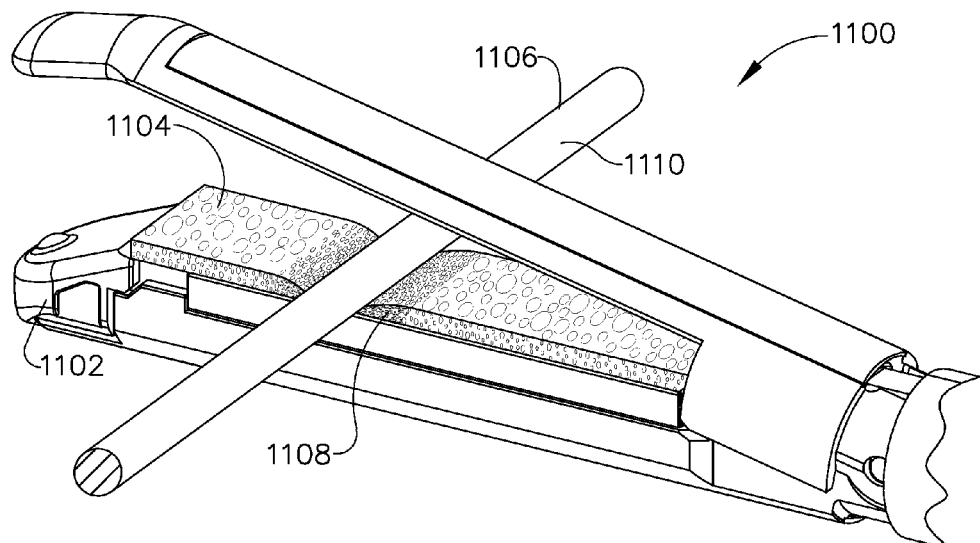
FIG. 24 is a perspective view of the end effector and the tissue thickness compensator of FIG. 23 and a modifying member modifying the tissue thickness compensator.
Figure 25:
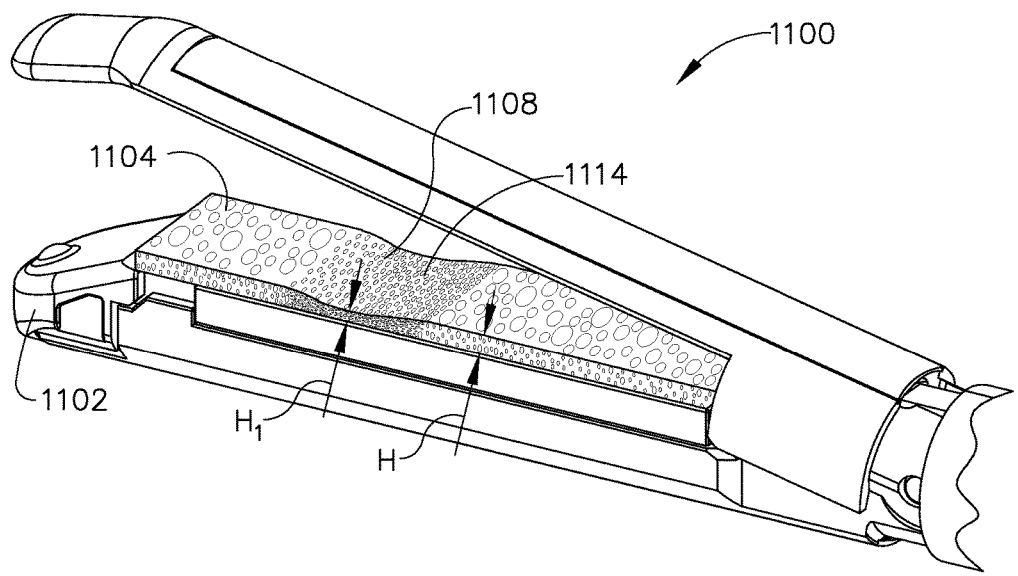
FIG. 25 is a perspective view of the end effector of FIG. 23 comprising the modified tissue thickness compensator of FIG. 24.

Referring now to FIGS. 23-25, a surgical end effector 1100 is illustrated. The end effector 1100 is similar in many respects to various end effectors disclosed elsewhere herein such as, for example, the end effector 22090 (FIG. 9). As illustrated in FIG. 23, the end effector 1100 can include a staple cartridge assembly 1102 which is similar in many respects to the staple cartridge assembly 20200 (FIG. 6), for example. In addition, the end effector 1100 may include a tissue thickness compensator 1104 which is similar in many respects to other tissue thickness compensators disclose elsewhere in this document such as the tissue thickness compensator 22020 (FIG. 9), the tissue thickness compensator 20220 (FIG. 6), and/or the tissue thickness compensator 10020 (FIG. 4), for example.

Further to the above, end effector 1100 can include a tissue thickness compensator 1104 wherein the tissue thickness compensator 1104 can be prepared using conventional lyophilization techniques and/or any other suitable techniques. In at least one example, the tissue thickness compensator 1104 can be prepared by dissolving a polymer such as, for example, polylactic acid (PLA) and/or polyglycolic acid (PGA) in an organic solvent and lyophilizing the solution. The tissue thickness compensator 1104 can be comprised of a biocompatible foam which may comprise a porous, open cell foam and/or a porous, closed cell foam, for example.

Further to the above, the tissue thickness compensator 1104 can be altered or modified for use in a surgical procedure. For example, upon completion of the lyophilization process, the tissue thickness compensator 1104 can be contacted with a modifying member 1106 to modify the tissue thickness compensator 1104 for use in a particular surgical procedure. In certain circumstances, the modification can occur after assembling the tissue thickness compensator 1104 with the end effector 1100, as illustrated in FIGS. 23-35. For example, as illustrated in FIG. 23, the tissue thickness compensator 1104 can be releasably assembled to the cartridge assembly 1102 and modified while assembled with the cartridge assembly 1102. In other circumstances, the modification can occur before assembling the tissue thickness compensator 1104 with the end effector 1100. In at least one example, the modification can be performed as a separate step during manufacturing. In yet another example, the modification may be performed during a surgical procedure.

As described in greater detail below, the modification process can involve modifying a surface or a plurality of surfaces of the tissue thickness compensator 1104. In certain circumstances, the modification process can involve modifying one or more portions of the tissue thickness compensator 1104. One or more portions can be modified in a single modification process. Alternatively, a plurality of portions can each be modified separately in consecutive modification processes. In certain circumstances, the modification process can comprise a thermal pressing process which can be used to change the shape, size, dimensions, and/or porosity of at least a portion of the tissue thickness compensator 1104. Furthermore, the modification process can include means for creating space within one or more portions of the tissue thickness compensator 1104.

Referring again to FIGS. 23-25, in certain circumstances, a portion 1107 (FIG. 23) of the tissue thickness compensator 1104 can be modified by a thermal pressing process which may include transitioning the portion 1107 to a glassy state, engaging the portion 1107 with the modifying member 1106, applying pressure onto the portion 1107 while it is in the glassy state, and allowing the portion 1107 to cool below the glassy state while the modifying member 1106 is still engaged with the portion 1107. The modifying member 1106 may be used to maintain the pressure on the portion 1107 for a time period sufficient to create the resulting modified portion 1108 (FIG. 25). It is note worthy that a material's transition into a glassy state can be a reversible transition from a relatively hard state to a relatively molten or flexible state in response to an increase in the temperature of the material to a glass transition temperature. A glass transition temperature of the material can be a particular temperature or, in some instances, a range of temperatures. The tissue thickness compensator modification process described herein takes advantage of this phenomenon by modifying a tissue thickness compensator while the tissue thickness compensator is in the glassy flexible state and then allowing the tissue thickness compensator to cool below the glass transition temperature while maintaining the modification.

Further to the above, referring again to FIGS. 23-25, the portion 1107 of the tissue thickness compensator 1004 can be transitioned into the glassy state by heating at least the portion 1107 to a temperature greater than or equal to a glass transition temperature of the material from which the portion 1107 is composed but lower than the melting temperature of the same. For example, the tissue thickness compensator 1104 can be comprised of polyglycolic acid (PGA) and in such circumstances, the portion 1107 can be transitioned into the glassy state by heating the portion 1107 to a temperature that is greater than or equal to the glass transition temperature of polyglycolic acid (PGA) but lower than the melting temperature of the same. In various instances, the glass transition temperature of polyglycolic acid (PGA) can be in the range of 35-40° C., for example, and its melting temperature can be in the range of 225-230° C., for example. In at least one example, the portion 1107 of the tissue thickness compensator 1104 can be heated to a temperature that is greater than or equal to 35° C. but lower than 225° C. in order to transition the portion 1107 to the glassy state. In another example, the portion 1107 can be transitioned to the glassy state by heating the portion 1107 to a temperature that is greater than or equal to 40° C. but lower than 200° C., for example.

Further to the above, the modifying member 1106 can then be used to apply pressure onto the portion 1107 while the portion 1107 is in the glassy state. The portion 1107 can be allowed to exit the glassy state by cooling the portion 1107 to a temperature below 35° C., for example. The pressure may be maintained for a time period sufficient to permit the tissue thickness compensator 1104 to retain, or at least partially retain, the modification imposed by the modifying member 1106.

In certain examples, the pressure can be maintained for a period of time from about 30 seconds to about 8 hours, for example, during the time in the glassy state and/or for a period of time from about 30 seconds to about 8 hours, for example, after exiting the glassy state. In at least one example, the pressure can be maintained for approximately 10 minutes during the time in the glassy state and for approximately 10 minutes after exiting the glassy state. Other time periods for maintaining the pressure are contemplated by the present disclosure.

In certain circumstances, the modifying member 1106 can be used to apply pressure onto the portion 1107 before the portion 1107 is transitioned to the glassy state. In certain circumstances, the modifying member 1106 may apply pressure to the portion 1107 while the portion 1107 is heated to reach the glassy state, while the portion 1107 is in the glassy state, and/or while the portion 1107 is transitioned or cooled to a temperature below the glassy state. In certain circumstances, the pressure applied to the portion 1107 can be gradually increased toward a threshold as the temperature of the portion 1107 is gradually increased to transition the portion 1107 toward the glassy state, for example. In certain circumstances, the pressure applied to the portion 1107 can be removed, gradually removed, or at least partially reduced as the portion 1107 exits the glassy state, before the portion 1107 exits the glassy state, and/or after the portion 1107 exits the glassy state.

In certain circumstances, the modifying member 1106 can also be a heat source for transitioning the portion 1107 of the tissue thickness compensator 1104 to the glassy state. For example, the modifying member 1106 can comprise a cylindrical distal portion 1110, as illustrated in FIG. 24, which may include a heating coil (not shown). A user can may energize the heating coil and engage the portion 1107 of the tissue thickness compensator 1104 with the modifying member 1106 to heat the portion 1107 to a temperature that is greater than or equal the glass transition temperature of the material composition of the portion 1107. Upon reaching a desired temperature, the modifying member may be pressed against the portion 1107, as illustrated in FIG. 24. Alternatively, the modifying member may be pressed against the portion 1107 before the modifying member 1106 reaches the desired temperature. As described above, the pressure may be maintained for a time period sufficient to permit the tissue thickness compensator 1104 to retain, or at least partially retain, the modification imposed by the modifying member 1106. In addition, the heating coil of the modifying member 1106 can be turned off to allow the temperature of the portion 1107 to cool below the glass transition temperature. The modifying member can then be removed. In certain circumstances, the pressure applied by the modifying member 1106 can be initiated prior to the portion 1107 entering the glassy state and maintained throughout the glassy state. In some circumstances, the pressure applied by the modifying member 1106 can be removed while the portion 1107 is in the glassy state.

As illustrated in FIGS. 23-25, the modifying member 1106 can be configured to change the shape, size, dimensions, density, spring rate, and/or porosity of the portion 1107 of the tissue thickness compensator 1104. For example, the modified portion 1108 may comprise a substantially concave top surface 1114 with a reduced height H1, while the remainder of the tissue thickness compensator 1104 may retain a substantially flat top surface including an original height H which is greater than the reduced height H1, as illustrated in FIG. 25. As described above, the modifying member 1106 may comprise a cylindrical distal portion 1110. In such circumstances, the curvature of the resulting concave surface 1114 can, in part, depend on the curvature of the cylindrical distal portion 1110 of the modifying member 1106 in contact with the portion 1107 of the tissue thickness compensator 1104 during the modification process. Furthermore, the modified portion 1108 may possess a new lower porosity compared to the unmodified portion 1107 which can result, at least in part, from the compressive forces applied to the portion 1107 by the modifying member 1106 during the modification process, as described above.

Said another way, the pressure applied to the portion 1107 during the modification process may yield a material redistribution wherein a cross-section through the modified portion 1108 may comprise a greater material density than a similar cross section through the portion 1107 prior to the modification process. Furthermore, the modified portion 1108 may comprise a different spring rate from the remainder of the tissue thickness compensator 1104 which can result, in part, from the changes in density and porosity realized by the modified portion 1108 during the modification process, as described in greater detail below. In at least one instance, the spring rate of the modified portion 1108 may be less than or greater than the spring rate of the unmodified portion 1107.

Figure 26:
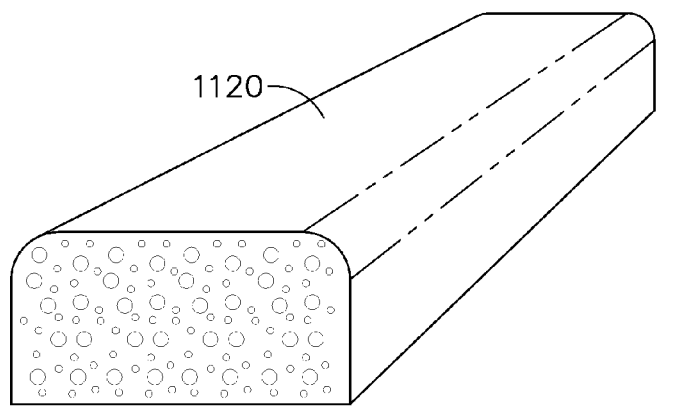
FIG. 26 is a cross-sectional perspective view of a tissue thickness compensator.
Figure 27:
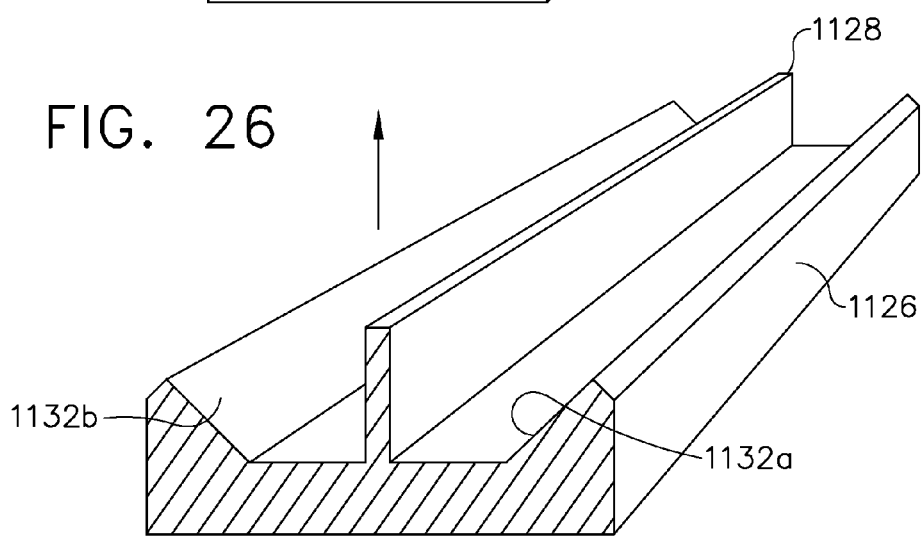
FIG. 27 is a cross-sectional perspective view of a mold for modifying the tissue thickness compensator of FIG. 26.
Figure 28:
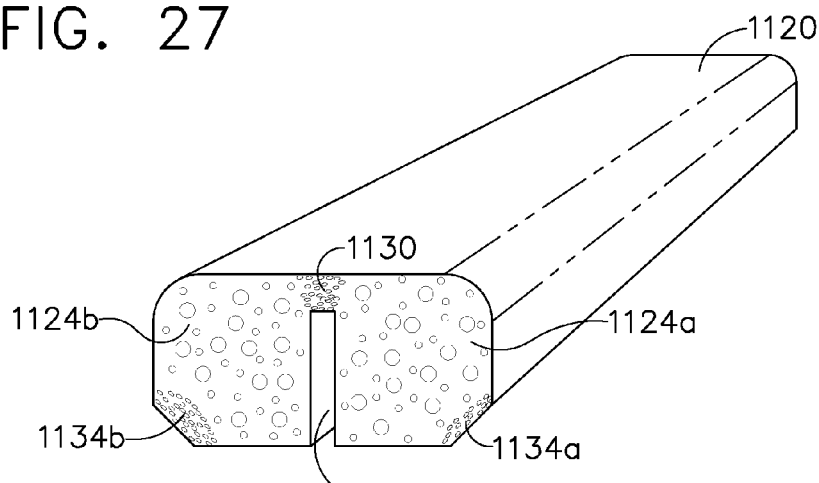
FIG. 28 is a cross-sectional perspective view of the tissue thickness compensator of FIG. 26 after modification by the mold of FIG. 27.
Figure 29:
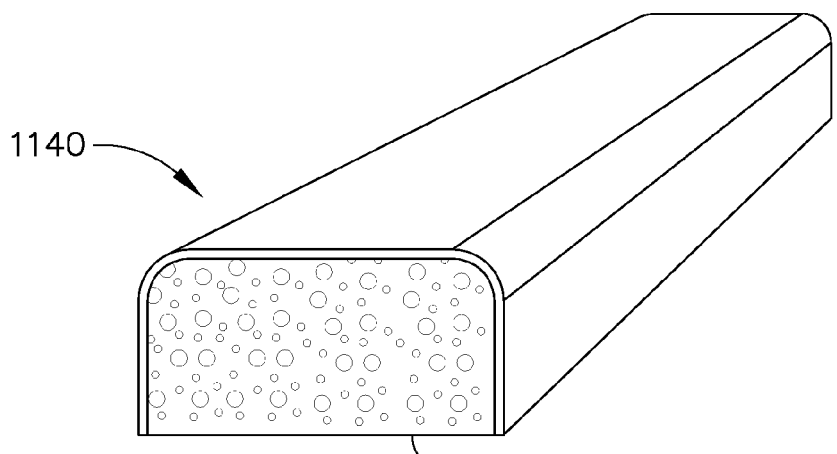
FIG. 29 is a cross-sectional perspective view of a tissue thickness compensator.
Figure 30:
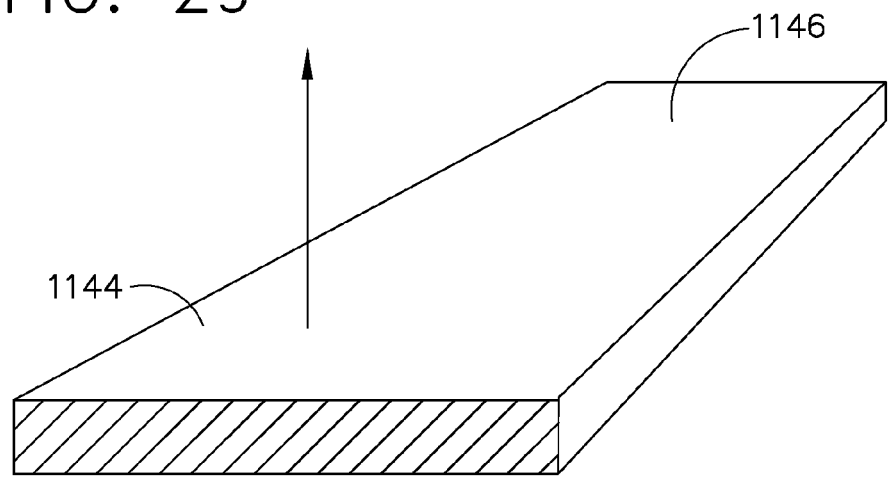
FIG. 30 is a cross-sectional perspective view of a mold for modifying the tissue thickness compensator of FIG. 29.

Referring now to FIGS. 26-34, a tissue thickness compensator can be modified prior to assembly with an end effector such as, for example, the end effector 22090 (FIG. 9). In certain circumstances, as illustrated in FIGS. 27, 30, and 33, a mold can be utilized to modify a tissue thickness compensator using a thermal pressing process, as described above. For example, as illustrated in FIGS. 26-28, a tissue thickness compensator 1120 can be modified to include a longitudinal slot 1122. The tissue thickness compensator 1120 may be similar in many respects to other tissue thickness compensators described elsewhere such as, for example, the tissue thickness compensator 22020 (FIG. 9). For example, like the compensator 22020, the compensator 1120 can be utilized with the end effector 22090. Furthermore, the longitudinal slot 1122 may be similar in many respects to the knife slot 22025. For example, like the knife slot 22025, the slot 1122 may define a tissue thickness compensator knife path for the cutting portion 10053 between a first stapling portion 1124a and a second stapling portion 1124b. Furthermore, the first stapling portion 1124a and the second stapling portion 1124b can be similar in many respects to the first stapling portion 22021a (FIG. 9) and the second stapling portion 22021b (FIG. 9), respectively, of the tissue thickness compensator 22020. In addition, the slot 1122 can be configured to releasably connect the first stapling portion 1124a and the second stapling portion 1124b such that, in use with the end effector 22090, the cutting portion 10053 can be advanced distally through the slot 1122 to transect the slot 1122 and separate the first stapling portion 1124a and the second stapling portion 1124b.

Referring again to FIGS. 26-28, the tissue thickness compensator 1120 can be prepared using traditional lyophilization techniques and/or any other suitable techniques. In addition, the tissue thickness compensator 1120 can be modified or altered to create the slot 1122 therethrough Similar to the tissue thickness compensator 1104, the tissue thickness compensator 1120 can be comprised at least in part of a material comprising a glass transition temperature and can modified by transitioning the material into a glassy state. In one example, the tissue thickness compensator 1120 can be heated in an oven (not shown) to a temperature greater than or equal to the glass transition temperature of the material composition of the tissue thickness compensator 1120 but less than the melting temperature of the same. A mold 1126 comprising a central beam 1128, as illustrated in FIG. 27, can be utilized to create the slot 1122 by inserting the central beam 1128 into the tissue thickness compensator 1120 while the tissue thickness compensator 1120 is in the glassy state. The tissue thickness compensator 1120 can then be allowed to cool to a temperature below the glass transition temperature while the central beam 1128 remains inserted into the tissue thickness compensator 1120. In some instances, the central beam 1128 can be removed from the tissue thickness compensator 1120 while the tissue thickness compensator 1120 is in its glassy state.

In certain circumstances, a cooling medium can be utilized to actively cool the tissue thickness compensator 1120. In some instances, a fan can be used to generate a flow of air over the tissue thickness compensator 1120 while the tissue thickness compensator 1120 is in the mold 1126 and/or after the tissue thickness compensator 1120 has been removed from the mold. In some instances, a refrigeration process can be utilized to cool the tissue thickness compensator 1120 while the tissue thickness compensator 1120 is in the mold 1126 and/or after the tissue thickness compensator 1120 has been removed from the mold. The central beam 1128 can be removed after transitioning the tissue thickness compensator 1120 out of the glassy state. The central beam 1128 can remain inserted into the tissue thickness compensator 1120 for a time period sufficient to permit the tissue thickness compensator 1120 to retain, or at least substantially retain, the space occupied by the central beam 1128. In certain examples, the central beam 1128 can remain inserted for a period of time from about 30 seconds to about 8 hours, for example, during the time in the glassy state and/or for a period of time from about 30 seconds to about 8 hours, for example, after exiting the glassy state. In at least one example, the central beam 1128 can remain inserted for approximately 10 minutes during the time in the glassy state and for approximately 10 minutes after exiting the glassy state. Other time periods for maintaining the central beam 1128 within the tissue thickness compensator 1120 are contemplated by the present disclosure.

Further to the above, as illustrated in FIG. 28, pressure applied by the central beam 1128 during the modification process may yield an increased material density at a portion 1130 of the tissue thickness compensator 1120. The portion 1130 may connect the first stapling portion 1124*a* and a second stapling portion 1124*b* thereby providing additional stability for the slot 1122. In certain circumstances, the mold 1126 may comprise edge modifiers such as, for example, edge modifiers 1132*a* and 1132*b* which can modify the tissue thickness compensator 1120 during the modification process to produce modified edges 1134*a* and 1134*b*, respectively, as illustrated in FIG. 28.

Referring again to FIGS. 26-28, it may be desirable to remove a significant amount of material from the tissue thickness compensator 1120 to create the slot 1122. In such circumstances, the central beam 1128 can be heated to a temperature greater than the melting temperature of the material composition of the tissue thickness compensator 1120. Upon inserting the heated central beam 1128 into the tissue thickness compensator 1120, the central beam 1128 may melt through the tissue thickness compensator 1120 thereby creating a space for the slot 1122 within the tissue thickness compensator 1120, as illustrated in FIG. 28. In certain circumstances, it may be desirable to gradually increase the pressure applied by the central beam 1128 against the tissue thickness compensator 1120 to gradually insert the central beam 1128 into the tissue thickness compensator 1120.

Figure 31:
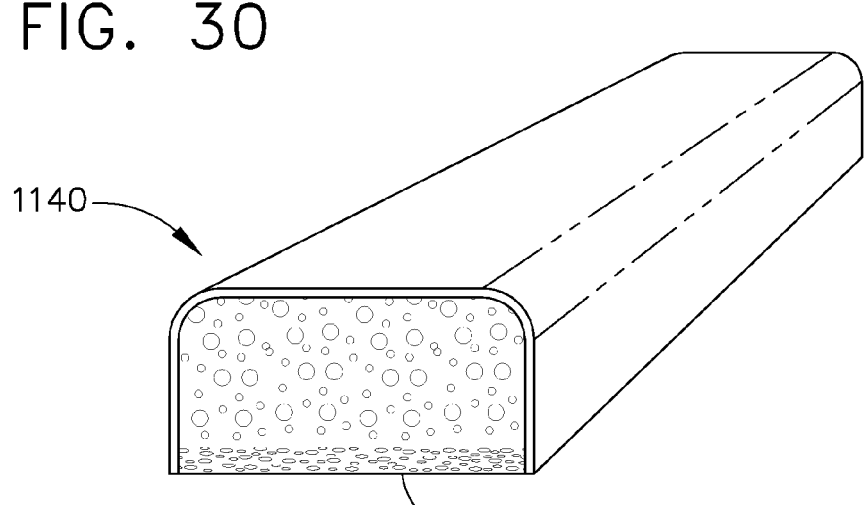
FIG. 31 is a cross-sectional perspective view of the tissue thickness compensator of FIG. 29 after modification by the mold of FIG. 30.

In certain circumstances, it can be desirable to increase material density of one or more surfaces of a tissue thickness compensator. As illustrated in FIGS. 29-31, a tissue thickness compensator 1140 can be modified or altered such that a surface 1142 of the tissue thickness compensator 1140 may comprise a higher material density than the remainder of the tissue thickness compensator 1140, which can be achieved, in certain circumstances, post lyophilization. The tissue thickness compensator 1140 may be similar in many respects to other tissue thickness compensators described elsewhere such as, for example, the tissue thickness compensator 22020 (FIG. 9) and/or the tissue thickness compensator 1120 (FIG. 26). A surface modifier 1144 can be utilized to modify the surface 1142 of the tissue thickness compensator 1140 using a thermal pressing process which is similar in many respects to the thermal pressing processes used to modify the tissue thickness compensator 1104 and/or the tissue thickness compensator 1120, as described above. For example, the tissue thickness compensator 1140 can be comprised at least in part of a material comprising a glass transition temperature and can be modified after being transitioned into a glassy state.

As described above, a tissue thickness compensator such as, for example, the tissue thickness compensator 1140 can be transitioned to the glassy state where it is heated to a temperature greater than or equal to the glass transition temperature of the material composition of the tissue thickness compensator 1140 but less than the melting temperature of the same. The surface modifier 1144 can be pressed against the surface 1142 while the tissue thickness compensator 1140 is in the glassy state. The pressure applied by the surface modifier 1144 may compress the surface 1142 thereby increasing the material density of the surface 1142. The increase in material density can be retained by the surface 1142 by allowing the surface 1142 to cool to a temperature below the glass transition temperature.

In certain instances, the pressure applied by the surface modifier 1144 against the surface 1142 can be maintained for a period of time from about 30 seconds to about 8 hours, for example, during the time in the glassy state and/or for a period of time from about 30 seconds to about 8 hours, for example, after exiting the glassy state. In at least one example, the pressure can be maintained for approximately 10 minutes during the time in the glassy state and for approximately 10 minutes after exiting the glassy state. Other time periods for maintaining the pressure applied by the surface modifier 1144 against the surface 1142 are contemplated by the present disclosure.

In some instances, a fan can be used to generate a flow of air over the tissue thickness compensator 1140 while the tissue thickness compensator 1140 is in contact with the modifier 1144 and/or after the tissue thickness compensator 1140 has been removed from the modifier 1144. In some instances, a refrigeration process can be utilized to cool the tissue thickness compensator 1140 while the tissue thickness compensator 1140 is in contact with the modifier 1144 and/or after the tissue thickness compensator 1140 has been removed from the modifier 1144. Upon transitioning the tissue thickness compensator 1140 out of the glassy state, in various instances, the surface modifier 1144 can be disengaged from the tissue thickness compensator 1140. In certain circumstances, the surface modifier 1144 can include a heating element which can be utilized to increase the temperature of the surface 1142 to a temperature greater than or equal to the glass transition temperature of the material composition of the tissue thickness compensator 1140, as described above.

Referring again to FIG. 30, the surface modifier 1144 may comprise a flat, or at least substantially flat, contacting surface 1146 for contacting the surface 1142, for example. In other circumstances, the contacting surface 1146 may comprise various textures such as, for example, protrusions which can extend into the surface 1142 of the tissue thickness compensator 1140 during the modification process. In certain circumstances, the surface modifier 1144 can be used to apply pressure onto the surface 1142 of the tissue thickness compensator 1140 before the tissue thickness compensator 1140 is transitioned to the glassy state. In certain circumstances, the surface modifier 1144 may apply pressure to the surface 1142 while the tissue thickness compensator 1140 is heated to reach the glassy state, while the tissue thickness compensator 1140 is in the glassy state, and/or while the tissue thickness compensator 1140 is transitioned or cooled to a temperature below the glassy state. In certain circumstances, the pressure applied by the surface modifier 1144 to the surface 1142 can be gradually increased toward a threshold as the temperature of the tissue thickness compensator 1140 is gradually increased to transition the tissue thickness compensator 1140 toward the glassy state, for example. In certain circumstances, the pressure applied to the surface 1142 can be removed, gradually removed, or at least partially reduced as the tissue thickness compensator 1140 exits the glassy state, before the tissue thickness compensator 1140 exits the glassy state, and/or after the tissue thickness compensator 1140 exits the glassy state.

In certain circumstances, the tissue thickness compensator 1140 can be modified or altered to include a skin or a dense outer layer. In certain circumstances, the resulting skin or dense outer layer may comprise textures such as, for example, protrusions which can extend into the surface 1142 of the tissue thickness compensator 1140. In certain instances, the contacting surface 1146 of the surface modifier 1144 can be heated to a temperature greater than or equal to the melting temperature of the material composition of the tissue thickness compensator 1140. The surface modifier 1144 and/or the tissue thickness compensator 1140 can be moved to bring the surface 1142 of the tissue thickness compensator 1140 into contact with the heated contacting surface 1146 of the surface modifier 1144 thereby melting, or at least substantially melting, the surface 1142. The surface modifier 1144 and the tissue thickness compensator 1140 can then be separated to permit the modified surface 1142 to cool below its melting temperature which may create a skin or a dense outer layer onto the tissue thickness compensator 1140.

In certain instances, the contacting surface 1146 of the surface modifier 1144 can be heated prior to coming in contact with the surface 1142. In other instances, the contacting surface 1146 of the surface modifier 1144 can be heated after coming in contact with the surface 1142.

In certain instances, the contacting surface 1146 of the surface modifier 1144 can remain in contact with the surface 1142 of the tissue thickness compensator 1140 for a time period sufficient to allow the surface 1142 to flow into a desired geometry. Such a time period can range from about 30 seconds to about 8 hours, for example; other time periods are contemplated by the present disclosure. Such a time period can be sufficient to locally affect and/or melt the material of the tissue thickness compensator 1140 and have it flow into a new geometry. As described herein, such a new geometry can be prescribed by the tooling used to make the tissue thickness compensator 1140.

In certain instances, the surface 1142 of the tissue thickness compensator 1140 can be allowed to cool, or can be actively cooled, to a temperature below the melting temperature of the tissue thickness compensator 1140 before separating the surface modifier 1144 from the tissue thickness compensator 1140. In other instances, the surface 1142 of the tissue thickness compensator 1140 can be allowed to cool, or can be actively cooled, to a temperature below the melting temperature of the tissue thickness compensator 1140 after separating the surface modifier 1144 from the tissue thickness compensator 1140.

Further to the above, the modified surface 1142 can comprise a density which is approximately 10% greater than the density of the remainder of the tissue thickness compensator 1140, approximately 20% greater than the density of the remainder of the tissue thickness compensator 1140, approximately 30% greater than the density of the remainder of the tissue thickness compensator 1140, approximately 40% greater than the density of the remainder of the tissue thickness compensator 1140, approximately 50% greater than the density of the remainder of the tissue thickness compensator 1140, approximately 60% greater than the density of the remainder of the tissue thickness compensator 1140, approximately 70% greater than the density of the remainder of the tissue thickness compensator 1140, approximately 80% greater than the density of the remainder of the tissue thickness compensator 1140, approximately 90% greater than the density of the remainder of the tissue thickness compensator 1140, and/or approximately 100% greater than the density of the remainder of the tissue thickness compensator 1140, for example. In various circumstances, the modified surface 1142 can comprise a density which is more than the density of the remainder of the tissue thickness compensator 1140 and less than twice the density of the remainder of the tissue thickness compensator 1140, for example. In various circumstances, the modified surface 1142 can comprise a density which is over twice the density of the remainder of the tissue thickness compensator 1140, for example.

Referring now to FIGS. 32-34, a tissue thickness compensator 1150 can be modified to include a plurality of apertures 1152 which may extend at least partially through the tissue thickness compensator 1150. The tissue thickness compensator 1150 may be similar in many respects to other tissue thickness compensators described herein such as, for example, the tissue thickness compensator 20220 (FIG. 6). Like the compensator 20220, the compensator 1150 can be utilized with the cartridge assembly 20200 (FIG. 6) and the apertures 1152 may be similar in many respects to the clearance apertures 20224 extending at least partially through the tissue thickness compensator 20220. For example, like the apertures 20224, the apertures 1152 can be aligned with corresponding staple legs 20232 (FIG. 7) when the tissue thickness compensator 1150 is assembled with the cartridge assembly 20200 such that the staple legs 20232 may move through the clearance apertures 1152 in the tissue thickness compensator 1150 when the staple legs 20232 move from the unfired configuration to the fired configuration, as described above in greater detail.

Further to the above, referring again to FIGS. 32-34, the tissue thickness compensator 1150 can be prepared using traditional lyophilization techniques and/or any other suitable techniques. In certain circumstances, a polymer having a glass transition temperature such as, for example, polylactic acid (PLA) and/or polyglycolic acid (PGA) can be dissolved in an organic solvent to form a solution which can be lyophilized to produce the tissue thickness compensator 1150. Furthermore, the tissue thickness compensator 1150 can be modified post lyophilization using a thermal pressing process which is similar in many respects to the thermal pressing processes used to modify the tissue thickness compensator 1104, the tissue thickness compensator 1120, and/or the tissue thickness compensator 1140, for example, as described above. For example, the tissue thickness compensator 1150 can be modified to include the apertures 1152 once the tissue thickness compensator 1150 is transitioned to a glassy state.

As described above, a tissue thickness compensator such as, for example, the tissue thickness compensator 1150 can be transitioned to a glassy state by being heated in an oven (not shown) to a temperature greater than or equal to the glass transition temperature of the material composition of the tissue thickness compensator 1150 but less than the melting temperature of the same. A mold 1154 comprising a plurality of posts, dowels, pins, and/or protrusions, for example, such as, for example, needles 1156 can be utilized to create the apertures 1152 by inserting the needles 1156 into the tissue thickness compensator 1150 while the tissue thickness compensator 1150 is in the glassy state. The tissue thickness compensator 1150 can then be allowed to cool to a temperature below the glass transition temperature while the needles 1156 remain inserted into the tissue thickness compensator 1150. In some instances, the needles 1156 can be removed from the tissue thickness compensator 1150 while the tissue thickness compensator 1150 is in the glassy state. In some instances, a fan can be used to generate a flow of air over the tissue thickness compensator 1150 while the tissue thickness compensator 1150 is engaged with the needles 1156 and/or after the tissue thickness compensator 1150 has been disengaged from the needles 1156. In some instances, a refrigeration process can be utilized to cool the tissue thickness compensator 1150 while the tissue thickness compensator 1150 is engaged with the needles 1156 and/or after the tissue thickness compensator 1150 has been disengaged from the needles 1156. In various instances, the needles 1156 can be removed after transitioning the tissue thickness compensator 1150 out of the glassy state. The needles 1156 can remain inserted into the tissue thickness compensator 1150 for a time period sufficient to permit the tissue thickness compensator 1150 to retain, or at least substantially retain, the spaces defining the apertures 1152 which are occupied by the needles 1156.

In certain examples, the needles 1156 can remain inserted for a period of time from about 30 seconds to about 8 hours, for example, during the time in the glassy state and/or for a period of time from about 30 seconds to about 8 hours, for example, after exiting the glassy state. In at least one example, the needles 1156 can remain inserted for approximately 10 minutes during the time in the glassy state and for approximately 10 minutes after exiting the glassy state. Other time periods for maintaining the needles 1156 inserted into the tissue thickness compensator 1150 are contemplated by the present disclosure.

In certain circumstances, the needles 1156 can be removed from the tissue thickness compensator 1150 prior to transitioning the tissue thickness compensator 1150 out of the glassy state. In other circumstances, the needles 1156 can be gradually removed over time. For example, the needles 1156 can be partially removed from the tissue thickness compensator 1150 prior to transitioning the tissue thickness compensator 1150 out of the glassy state. The needles 1156 can then be fully removed from the tissue thickness compensator 1150 after transitioning the tissue thickness compensator 1150 out of the glassy state. The reader will appreciate that the greater the depth of insertion of the needles 1156 into the tissue thickness compensator 1150, the greater the depth of the corresponding apertures 1152 that can be created in the tissue thickness compensator 1150.

Referring again to FIGS. 32-34, in certain instances, the needles 1156 can be heated to a temperature greater than or equal to the melting temperature of the material composition of the tissue thickness compensator 1150. In addition, the needles 1156 can be inserted into the tissue thickness compensator 1150 to create the apertures 1152 by melting, or at least partially melting, through the regions of the tissue thickness compensator 1150 that receive the needles 1156. In various instances, the needles 1156 can be heated prior to their insertion into the tissue thickness compensator 1150. In various instances, the needles 1156 can be heated after their insertion into the tissue thickness compensator 1150. In various instances, the needles 1156 can be gradually heated as the needles 1156 are inserted into the tissue thickness compensator 1150.

In certain instances, the needles 1156 may remain positioned within the tissue thickness compensator 1150 for a period of time sufficient to permit the melted material of the tissue thickness compensator 1150 to flow into a desired geometry. Such a time period can range from about 30 seconds to about 8 hours, for example; other time periods are contemplated by the present disclosure. Such a time period can be sufficient to locally affect and/or melt the material of the tissue thickness compensator 1150 and have it flow into a new geometry. As described herein, such a new geometry can be prescribed by the tooling used to make the tissue thickness compensator 1150.

In certain instances, the tissue thickness compensator 1150 can be allowed to cool, or can be actively cooled, to a temperature below the melting temperature of the tissue thickness compensator 1150 before separating the needles 1156 from the tissue thickness compensator 1150. In other instances, the tissue thickness compensator 1150 can be allowed to cool, or can be actively cooled, to a temperature below the melting temperature of the tissue thickness compensator 1150 after separating the needles 1156 from the tissue thickness compensator 1150.

Referring again to FIGS. 32-34, the needles 1156 can be arranged in rows extending longitudinally along a length of the mold 1154 which may correspond to staple rows in a staple cartridge such as, for example, the staple cartridge assembly 20200 (FIG. 6). For example, as illustrated in FIG. 33, the needles 1156 can are arranged in six rows which can be configured to create six rows of the apertures 1152 that can be configured to receive six rows of the staples 20230 (FIG. 7). In certain circumstances, as illustrated in FIG. 33, the rows of the needles 1156 can be arranged in two groups which are spaced apart and configured to be received in two portions 1158 and 1160 of the tissue thickness compensator 1150 thereby creating two groups of the apertures 1152 separated by an intermediate portion 1162. The intermediate portion 1162 can be positioned, at least partially, over the cartridge knife slot 22015 (FIG. 6), when the tissue thickness compensator 1150 is assembled with staple cartridge assembly 20200. In use, the firing member 10052 (FIG. 10) can be advanced distally to push the staple legs 20232 (FIG. 8) through the apertures 1152 within the portions 1158 and 1160 and advance the cutting portion 10053 (FIG. 10) to transect the intermediate portion 1162 and separate the portions 1158 and 1160.

Referring again to FIGS. 32-34, the apertures 1152 can be configured to extend within the tissue thickness compensator 1150 and terminate at a certain depth within the tissue thickness compensator 1150. The apertures 1152 may comprise uniform depths, as illustrated in FIG. 34. In other circumstances, the apertures 1152 may comprise different depths (not shown). For example, a first row of the apertures 1152 may comprise a first depth and a second row of the apertures 1152 may comprise a second depth different from the first depth and yet a third row of the apertures 1152 may comprise a third depth different from the first depth and the second depth. The depths of the apertures 1152 can be determined, at least in part, by the heights of the corresponding needles 1156. For example, a first row of the needles 1156 comprising a first height and a second row of the needles 1156 comprising second height greater than first height may create a first row of the apertures 1152 comprising a first depth and a second row of the apertures 1152 comprising a second depth which is greater than the first depth.

Referring again to FIGS. 32-34, the needles 1156 can be configured to define a trajectory for the apertures 1152 within the tissue thickness compensator 1150. In certain circumstances, the needles 1156 can extend along an axis that is perpendicular and/or substantially perpendicular to a mold surface 1164 of the mold 1154, as illustrated in FIG. 33. Inserting the needles 1156 into the tissue thickness compensator 1150 while maintaining a parallel relationship between the mold surface 1164 and a surface 1166 of the tissue thickness compensator 1150 may result in defining a perpendicular and/or substantially perpendicular trajectory for the apertures 1152 relative to the surface 1166 of the tissue thickness compensator 1150, as illustrated in FIG. 34. In other circumstances, the needles 1156 can extend from the mold surface 1164 at an oblique angle (not shown) and/or the insertion trajectory of the needles 1156 into the tissue thickness compensator 1150 can be at an angle such that the needles 1156 may define a non-perpendicular trajectory for the apertures 1152 relative to the surface 1166 of the tissue thickness compensator 1150. In certain circumstances, a group of the needles 1156 can be parallel and/or substantially parallel to each other, as illustrated in FIG. 33, resulting in a group of the apertures 1152 that may be parallel and/or substantially parallel to each other, as illustrated in FIG. 24. In other circumstances, although not illustrated, a group of non-parallel needles can extend from the mold surface 1164 and may result in non-parallel apertures when inserted into the tissue thickness compensator 1150. In some circumstances, the needles 1156 can be configured to create apertures within the tissue thickness compensator 1150 that can comprise a partially curved trajectory and/or a partially linear trajectory. For example, the needles 1156 can extend from the mold surface 1164 in a partially curved trajectory and can be inserted into the tissue thickness compensator 1150 to create apertures within the tissue thickness compensator 1150 with a corresponding partially curved trajectory.

Referring again to FIGS. 32-34, some or all of the needles 1156 can comprise blunt distal ends 1168, as illustrated in FIG. 33. In other circumstances, some or all of the needles 1156 can comprise sharp distal ends (not shown). Some or all of the needles 1156 can comprise cylindrical, or at least substantially cylindrical, shapes, for example, as illustrated in FIG. 33. Other shapes are also contemplated by the present disclosure.

In various instances, one or more of the needles 1156 extending from the mold surface 1164 may not be insertable through the full thickness of the tissue thickness compensator 1150. In certain instances, one or more of the needles 1156 extending from the mold surface 1164 can be insertable through the full thickness of the tissue thickness compensator 1150 to create openings an/or holes that extend through the full thickness of the tissue thickness compensator 1150. In certain instances, one or more of the needles 1156 extending from the mold surface 1164 can be inserted through a first side of the tissue thickness compensator 1150 and exited through a second side of the tissue thickness compensator 1150 which may be opposite the first side, for example. In certain instances, one or more of the needles 1156 may comprise a length greater than the full thickness of the tissue thickness compensator 1150 to facilitate the insertion of the one or more needles 1156 through the full thickness of the tissue thickness compensator 1150.

Figure 35:
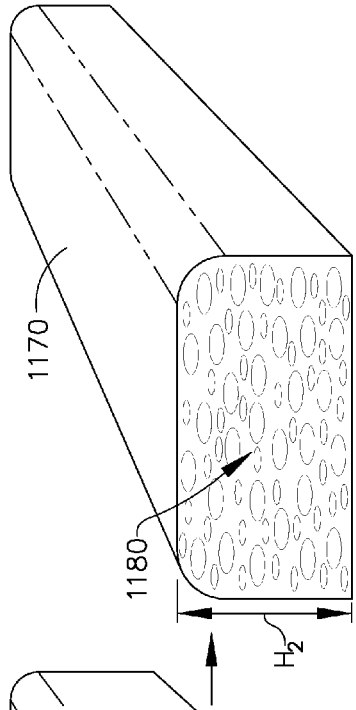
FIG. 35 is a cross-sectional perspective view of a tissue thickness compensator including a first height.
Figure 36:
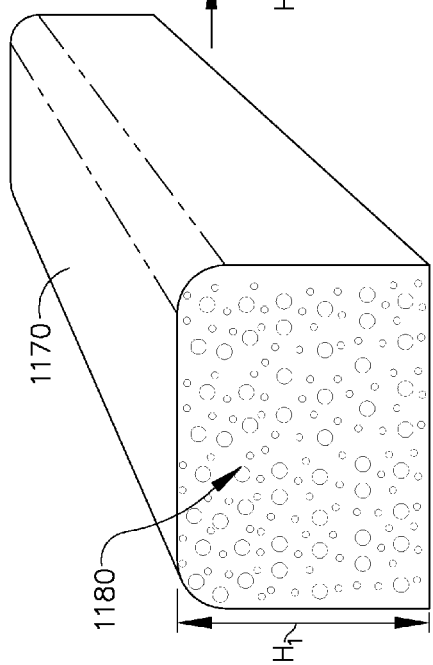
FIG. 36 is a cross-sectional perspective view of the tissue thickness compensator of FIG. 35 after modification to change the first height to a second height.
Figure 37:
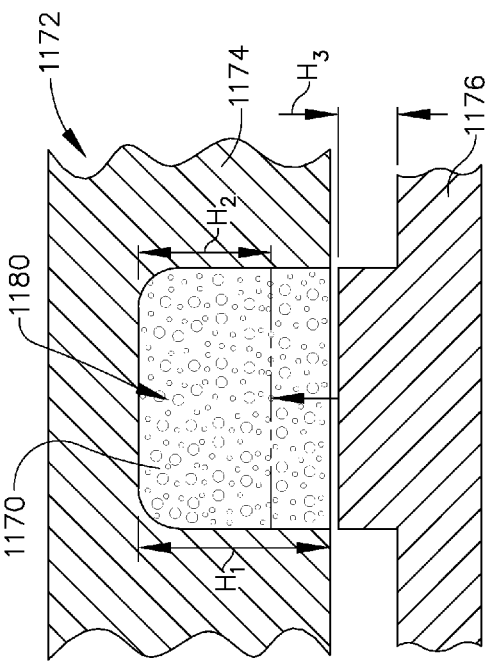
FIG. 37 is a cross-sectional view of a mold for modifying the tissue thickness compensator of FIG. 35.

Referring now to FIGS. 35-37, it may be desirable to resize a tissue thickness compensator. For example, one or more dimensions of a tissue thickness compensator may be adjusted to correspond to dimensions of a staple cartridge in order to provide a better fit to the staple cartridge when the tissue thickness compensator is assembled with the staple cartridge. In certain circumstances, a tissue thickness compensator 1170 can be resized by changing its height from a first height H1, as illustrated in FIG. 35, to a second height H2, as illustrated in FIG. 36. The tissue thickness compensator 1170 may be similar in many respects to other tissue thickness compensators described herein such as, for example, the tissue thickness compensator 22020 (FIG. 9), the tissue thickness compensator 1140 (FIG. 29), and/or the tissue thickness compensator 1150 (FIG. 32). For example, like the compensator 22020, the compensator 1170 can be utilized with the end effector 22090 (FIG. 9).

In various instances, referring again to FIGS. 35-37, the tissue thickness compensator 1170 can be prepared using traditional lyophilization techniques and/or any other suitable techniques. In certain instances, the tissue thickness compensator 1170 can be resized, as illustrated in FIG. 37, using a thermal pressing process and a mold 1172, for example. The mold 1172 may comprise a receiver 1174 configured to receive the tissue thickness compensator 1170 and an adjustment member 1176 which can be partially insertable into the receiver 1174. The tissue thickness compensator 1170 can be resized when the tissue thickness compensator 1170 is transitioned into a glassy state. In one embodiment, the tissue thickness compensator 1170 can be heated in an oven (not shown) to a temperature greater than or equal to a glass transition temperature of the material composition of the tissue thickness compensator 1170 but less than the melting temperature of the same. In another embodiment, the receiver 1174 and/or the adjustment member 1176 may comprise a heating element for transitioning the tissue thickness compensator 1170 to the glassy state. The adjustment member 1176 can then be inserted into the receiver 1174a distance H3, for example, as illustrated in FIG. 37, thereby compressing the tissue thickness compensator 1170 and reducing its height from the first height H1 to the second height H2. In some instances, the adjustment member 1176 can be inserted into the receiver 1174 before the tissue thickness compensator 1170 enters into the glassy state or just as the tissue thickness compensator 1170 enters into the glassy state. The adjustment member 1176 can be held against the tissue thickness compensator 1170 to compress the tissue thickness compensator 1170 for a time period sufficient to permit the tissue thickness compensator 1170 to retain, or at least substantially retain, the second height H2, as illustrated in FIG. 36. The tissue thickness compensator 1170 can then be allowed to cool to a temperature below the glass transition temperature while under compression from the adjustment member 1176. After transitioning the tissue thickness compensator 1170 out of the glassy state, the adjustment member 1176 can be retracted. In some instances, the adjustment member 1176 can be retracted before the tissue thickness compensator 1170 exits the glassy state. In certain circumstances, the above described resizing process can be utilized to change another dimension of the tissue thickness compensator 1170 such as a length or a width of the tissue thickness compensator 1170, for example. In some circumstances, these dimensions can be modified simultaneously or modified sequentially.

In certain examples, the compression from the adjustment member 1176 can be maintained for a period of time from about 30 seconds to about 8 hours, for example, during the time in the glassy state and/or for a period of time from about 30 seconds to about 8 hours, for example, after exiting the glassy state. In at least one example, the compression from the adjustment member 1176 can be maintained for approximately 10 minutes during the time in the glassy state and for approximately 10 minutes after exiting the glassy state. Other time periods for maintaining the compression imposed by the adjustment member 1176 against the tissue thickness compensator 1170 are contemplated by the present disclosure.

In certain circumstances, the adjustment member 1176 can be used to apply pressure onto the tissue thickness compensator 1170 before the tissue thickness compensator 1170 is transitioned to the glassy state. In certain circumstances, the adjustment member 1176 may apply pressure to the tissue thickness compensator 1170 while the tissue thickness compensator 1170 is heated to reach the glassy state, while the tissue thickness compensator 1170 is in the glassy state, and/or while the tissue thickness compensator 1170 is transitioned or cooled to a temperature below the glassy state. In certain circumstances, the pressure applied to the tissue thickness compensator 1170 can be gradually increased toward a threshold as the temperature of the tissue thickness compensator 1170 is gradually transitioned toward the glassy state, for example. In certain circumstances, the pressure applied to the tissue thickness compensator 1170 can be removed, gradually removed, or at least partially reduced as the tissue thickness compensator 1170 exits the glassy state, before the tissue thickness compensator 1170 exits the glassy state, and/or after the tissue thickness compensator 1170 exits the glassy state.

The reader will appreciate that the different molds utilized in the modification processes described above such as, for example, the molds 1144, 1154, and/or 1172 are illustrative examples. Other mold designs and configurations can also be employed to manipulate tissue thickness compensators in a variety of ways. Furthermore, the forces involved in manipulating a tissue thickness compensator need not only be compressive forces. For example, tensile forces can also be utilized to modify, reshape, and/or resize a tissue thickness compensator in similar manners to those described above. For example, the tissue thickness compensator 1170 can be stretched using tensile forces to reduce its height from the first height H1 (FIG. 35) to the second height H2 (FIG. 36), for example, using a modification process that is similar in many respects to the modification processes described above. In certain circumstances, combinations of tensile and compressive forces can be used to manipulate a tissue thickness compensator during a modification process.

Referring again to FIGS. 35-37, it may be desirable to modify the porosity of a tissue thickness compensator for use in a surgical procedure. A tissue thickness compensator may comprise a porous, open cell foam and/or a porous, closed cell foam, for example. Traditional lyophilization techniques may provide some control over a tissue thickness compensator's porosity but such control may not be easily reproducible and may need additional fine adjustments that may not be obtainable by traditional lyophilization techniques. As illustrated in FIGS. 35-37, the height of the tissue thickness compensator 1170 can be changed from the first height H1 (FIG. 35) to the second height H2 (FIG. 36), for example, using the modification process described above. In addition, porosity of the tissue thickness compensator 1170 can also be modified using the same and/or a similar modification process. For example, the tissue thickness compensator 1170 may comprise a first porosity (FIG. 35) prior to the modification process and a second porosity (FIG. 36) after completion of the modification process, as described above. The change in porosity can be attributed, at least in part, to the compressive forces and/or the energy applied to the tissue thickness compensator 1170 by the adjustment member 1176 during the modification process described above.

Further to the above, the tissue thickness compensator 1170 may comprise a plurality of pores 1180. Some or all of the pores 1180 may be altered in position, size, and/or shape, for example, as a result of the modification process described above. For example, one or more of the pores 1180 may comprise a spherical, or substantially spherical, shape prior to the modification process which may be altered to an oval, or substantially oval, shape as a result of the modification process. In at least one example, one or more of the pores 1180 may comprise a first size prior to the modification process and a second size different from the first size as a result of the modification process. In certain circumstances, as described below in greater detail, the porosity changes can be localized to one or more regions or zones of the tissue thickness compensator 1170.

Furthermore, in certain circumstances, the change in porosity of the tissue thickness compensator 1170 may be accompanied by a change in density of the tissue thickness compensator 1170. In other words, as the adjustment member 1176 is advanced against the tissue thickness compensator 1170, compressive forces may reduce space occupied by the tissue thickness compensator 1170 thereby causing material and/or pore redistribution which may yield an increase in the density of the tissue thickness compensator 1170 and/or a reduction in its porosity. In certain circumstances, as described below in greater detail, the density changes can be localized to one or more regions or zones of the tissue thickness compensator 1170.

Further to the above, the change in porosity and/or density of the tissue thickness compensator 1170 may yield a change in the spring rate of the tissue thickness compensator 1170. A tissue thickness compensator's spring rate can influence its ability to compensate for tissue thickness when the tissue thickness compensator is deployed against tissue captured by staples such as, for example, the staples 20230 (FIG. 8), as described above in greater detail. Furthermore, a tissue thickness compensator's spring rate can also influence its ability to apply pressure against tissue captured with the tissue thickness compensator by a staple. In other words, a change in a tissue thickness compensator's spring rate may change the pressure exerted by the tissue thickness compensator against tissue captured by a staple. Since different tissue types may respond more positively to certain pressures, fine control over a tissue thickness compensator's spring rate can be advantageous.

As illustrated in FIGS. 35-37, the tissue thickness compensator 1170 may comprise a first spring rate (FIG. 35) which may be altered or modified to a second spring rate (FIG. 36) different from the first spring rate using the modification process described above. For example, as described above, the adjustment member 1176 can be advanced against the tissue thickness compensator 1170 while the tissue thickness compensator 1170 is in the glassy state. In response, the tissue thickness compensator 1170 may be compressed which may cause a change in the spring rate of the tissue thickness compensator 1170. The adjustment member 1176 can be retained in the advanced position for a period of time sufficient to permit the tissue thickness compensator 1170 to retain, or at least substantially retain, the change in spring rate. In addition, the tissue thickness compensator 1170 can be allowed to cool below the glass transition temperature of its material composition while maintaining the pressure applied by the adjustment member 1176 against the tissue thickness compensator 1170.

In certain instances, the adjustment member 1176 can be maintained in the advanced position against the tissue thickness compensator 1170 for a period of time from about 30 seconds to about 8 hours, for example, during the time in the glassy state and/or for a period of time from about 30 seconds to about 8 hours, for example, after exiting the glassy state. In at least one example, the adjustment member 1176 can be maintained in the advanced position against the tissue thickness compensator 1170 for approximately 10 minutes during the time in the glassy state and for approximately 10 minutes after exiting the glassy state. Other time periods for maintaining the adjustment member 1176 in the advanced position against the tissue thickness compensator 1170 are contemplated by the present disclosure.

In certain circumstances, the adjustment member 1176 can be used to apply pressure onto the tissue thickness compensator 1170 to change the spring rate of the tissue thickness compensator 1170 before the tissue thickness compensator 1170 is transitioned to the glassy state. In certain circumstances, the adjustment member 1176 may apply pressure to the tissue thickness compensator 1170 while the tissue thickness compensator 1170 is heated to reach the glassy state, while the tissue thickness compensator 1170 is in the glassy state, and/or while the tissue thickness compensator 1170 is transitioned or cooled to a temperature below the glassy state. In certain circumstances, the pressure applied to the tissue thickness compensator 1170 can be gradually increased toward a threshold as the temperature of the tissue thickness compensator 1170 is gradually increased to transition the tissue thickness compensator 1170 toward the glassy state, for example. In certain circumstances, the pressure applied to the tissue thickness compensator 1170 can be removed, gradually removed, or at least partially reduced as the tissue thickness compensator 1170 exits the glassy state, before the tissue thickness compensator 1170 exits the glassy state, and/or after the tissue thickness compensator 1170 exits the glassy state.

Referring again to FIGS. 35-40, the tissue thickness compensator 1170 may be manufactured with a native spring rate using traditional lyophilization techniques and/or any other suitable techniques. As described above, the spring rate of the tissue thickness compensator 1170 can influence its ability to apply pressure against tissue captured with the tissue thickness compensator 1170 by a staple. The modification process described above may be utilized to adjust the native spring rate of the tissue thickness compensator 1170 to adjust its ability to apply pressure against tissue captured with the tissue thickness compensator 1170 by the staple. In certain circumstances, the native spring rate of the tissue thickness compensator 1170 can be increased from a first spring rate at point A (FIG. 40) to a second spring rate including and up to a maximum spring rate at point B (FIG. 40). In certain circumstances, such increase of the spring rate of the tissue thickness compensator 1170 can be achieved by applying compression forces to the tissue thickness compensator 1170 using the adjustment member 1176 while the tissue thickness compensator 1170 is in the glassy state, as explain in the modification process described above. As illustrated in FIG. 40, the point B represents a maximum elastic yield of the tissue thickness compensator 1170. As such, any additional compression applied by the adjustment member 1176 to the tissue thickness compensator 1170 beyond a threshold compression at the point B may produce a decrease in the spring rate of the modified tissue thickness compensator 1170. For example, as illustrated in FIG. 40, the spring rate at the point C is lower than the spring rate at the point B even though the compression force applied by the adjustment member 1176 to the tissue thickness compensator 1170 at point C is greater than the compression force applied at the point B.

As discussed above, one or more processes can be used to affect the spring rate, and/or any other property, of a material used in conjunction with a fastener cartridge and/or a surgical fastening instrument, for example. The spring rate, and/or any other property, of the material may change throughout the modification process or processes. Such a change may be gradual in some circumstances, while in other circumstances, the change may be sudden. In various instances, one or more of the steps of the modification process may cause an increase in the spring rate of the material while one or more steps may cause a decrease in the spring rate of the material. Ultimately, the net change in the spring rate can be measured as a comparison between an original spring rate before the modification process begins and a subsequent spring rate after the modification process has been completed. In various instances, a material may comprise an altered spring rate after the material has been heated and then cooled.

In certain circumstances, it may be desirable to apply one or more of the above described modification processes to a tissue thickness compensator. For example, a first modification process can be utilized to modify porosity of the tissue thickness compensator, as described above with respect to the tissue thickness compensator 1170. A second modification process, following the first modification process, can be utilized to alter a surface of the tissue thickness compensator, as described above with respect to the tissue thickness compensator 1140. Furthermore, a third modification process can be utilized to modify the tissue thickness compensator to include a longitudinal slot similar to the longitudinal slot 1122 of the tissue thickness compensator 1120. In yet a fourth modification process, the tissue thickness compensator can be modified to include apertures similar to the apertures 1152 of the tissue thickness compensator 1150. The reader will appreciate that some of above mentioned modifications can be combined or grouped in a single modification process. For example, a mold can be designed to include the needles 1156 of the mold 1154 and the central beam 1128 of the mold 1126. Other modification arrangements are contemplated by the present disclosure.

Referring now to FIGS. 38 and 39, a tissue thickness compensator such as, for example, tissue thickness compensator 1190 can be altered or modified using one or more of the modification processes described above to include portions with different spring rates, porosities, and/or densities. In certain circumstances, the tissue thickness compensator 1190 can be modified using one or more of the modification processes described above to include a gradient pore morphology (i.e. small pores gradually increasing in size to large pores across the thickness of the tissue thickness compensator 1190 in one direction). Such morphology could be more optimal for tissue in-growth or hemostatic behavior. Further, the gradient could also be compositional with a varying bio-absorption profile. A short term absorption profile may be preferred to address hemostasis while a long term absorption profile may address better tissue healing without leakages.

Referring again to FIGS. 38 and 39, the tissue thickness compensator 1190 may include one or more zone geometries that are different from the remainder of the tissue thickness compensator 1196. For example, as illustrated in FIG. 38, the tissue thickness compensator 1190 may include one or more protruding portions such as, for example, protruding portion 1196. In addition, the tissue thickness compensator 1190 may comprise a uniform, or at least a substantially uniform, first spring rate, first porosity, and/or first density through the tissue thickness compensator 1190 including the one or more zone geometries, as illustrated in FIG. 38. In certain circumstances, the tissue thickness compensator 1190 can be altered or modified using one or more of the modification processes described above to alter or modify the one or more zone geometries and/or to induce localized changes in the first spring rate, the first porosity, and/or the first density, for example. The modified tissue thickness compensator 1190 may comprise one or more modified zones with different spring rates, porosities, and/or densities from other modified zones and/or the first spring rate, the first porosity, and/or the first density, respectively, of the remainder of the tissue thickness compensator 1190. In certain circumstances, the resulting one or more modified zones may correspond to the one or more zone geometries. For example, as illustrated in FIG. 39, the tissue thickness compensator 1190 may be altered or modified to level, or at least substantially level, the protruding portion 1196 and to form a flat, or at least a substantially flat, surface 1198, for example. The modified tissue thickness compensator 1190 may include a first portion 1192 comprising the first spring rate, the first porosity, and/or the first density and a second portion 1194 comprising a second spring rate, a second porosity, and/or a second density, which can be different from the first spring rate, the first porosity, and/or the first density, respectively. The second portion 1194 may correspond to the protruding portion 1196 and can result from the leveling, or at least substantially leveling, of the protruding portion 1196 to form the flat, or at least substantially flat, surface 1198, for example. In certain respects, the geometry of the protruding portion 1196 prior to the modification of the tissue thickness compensator 1190 mirrors, matches, or resembles the geometry of the second portion 1194 after the tissue thickness compensator 1190 has been modified.

Referring again to FIGS. 37-39, the tissue thickness compensator 1190 can be altered or modified using the mold 1172, in a similar manner to the tissue thickness compensator 1170. For example, the tissue thickness compensator 1190 can be heated in the receiver 1174 to a temperature greater than or equal to a glass transition temperature of the material composition of the tissue thickness compensator 1190 but less than the melting temperature of the same. In certain circumstances, the adjustment member 1176 can be advanced against the protruding portion 1196, while the tissue thickness compensator 1190 is in the glassy state, thereby compressing the protruding portion 1196 and rearranging its geometry to form the second portion 1194, as illustrated in FIG. 39. Further to the above, the adjustment member 1176 can be configured to maintain compression against the protruding portion 1196 for a time period sufficient to permit the tissue thickness compensator 1190 to retain, or at least substantially retain, the modification imposed by the adjustment member 1176. The tissue thickness compensator 1190 can be allowed to cool or can be actively cooled to a temperature below its glass transition temperature while under compression from the adjustment member 1176. After transitioning the tissue thickness compensator 1190 out of the glassy state, the adjustment member 1190 can be retracted. The tissue thickness compensator 1190 may retain, or at least substantially retain, the second portion 1194, as illustrated in FIG. 39. In certain circumstances, the adjustment member 1176 may apply pressure onto the protruding portion 1196 while the tissue thickness compensator 1190 is heated to reach the glassy state, while the tissue thickness compensator 1190 is in the glassy state, and/or while the tissue thickness compensator 1190 is transitioned or cooled to a temperature below the glassy state. In certain circumstances, the pressure applied to the protruding portion 1196 of the tissue thickness compensator 1190 can be gradually increased toward a threshold as the temperature of the tissue thickness compensator 1190 is gradually increased to transition the tissue thickness compensator 1190 toward the glassy state, for example. In certain circumstances, the pressure applied to the protruding portion 1196 of the tissue thickness compensator 1190 can be removed, gradually removed, or at least partially reduced as the tissue thickness compensator 1190 exits the glassy state, before the tissue thickness compensator 1190 exits the glassy state, and/or after the tissue thickness compensator 1190 exits the glassy state.

Referring now to FIGS. 41-43, a tissue thickness compensator such as, for example, tissue thickness compensator 1200 can be prepared using traditional lyophilization techniques and/or any other suitable techniques. In addition, the tissue thickness compensator 1200 can be modified or altered for use in a surgical procedure, for example. The tissue thickness compensator 1200 can be similar in many respects to other tissue thickness compensators such as, for example, the tissue thickness compensator 22020 (FIG. 9) and/or the tissue thickness compensator 1120 (FIG. 26). For example, like the tissue thickness compensator 22020, the tissue thickness compensator 1200 can be utilized with the end effector 22090. Furthermore, as illustrated in FIGS. 41-43, the tissue thickness compensator 1200 can be modified to include a longitudinal slot 1202 which, like the knife slot 22025, may define a tissue thickness compensator knife path for the cutting portion 10053 between a first stapling portion 1204a and a second stapling portion 1204b. Furthermore, the first stapling portion 1204a and the second stapling portion 1204b can be similar in many respects to the first stapling portion 22021a (FIG. 9) and the second stapling portion 22021b (FIG. 9) of the tissue thickness compensator 22020. In addition, the slot 1202 can be configured to releasably connect the first stapling portion 1204a and the second stapling portion 1204b such that, in use with the end effector 22090, the cutting portion 10053 can be advanced distally through the slot 1202 to transect the slot 1202 and separate the first stapling portion 1204a and the second stapling portion 1204b.

Referring again to FIGS. 41-43, the tissue thickness compensator 1200 can be modified prior to assembly with an end effector such as, for example, the end effector 22090 (FIG. 9). Alternatively, the tissue thickness compensator 1200 can be modified after it has been assembled with an end effector. As described above, the tissue thickness compensator 1200 can be prepared using traditional lyophilization techniques and/or any other suitable techniques. A space creator 1206 can be utilized to modify the tissue thickness compensator 1200 in a thermal pressing process, as illustrated in FIGS. 41-43. For example, the space creator 1206 can be heated to a temperature greater than or equal to a melting temperature of the material composition of the tissue thickness compensator 1200. The space creator 1206 can then be aligned with and inserted into the tissue thickness compensator 1200 to form the longitudinal slot 1202. The space creator 1206 may melt through the tissue thickness compensator 1200 to create space for the longitudinal slot 1202. The space creator 1206 can be retracted upon reaching a desired depth within the tissue thickness compensator 1200. In certain circumstances, the thermal pressing process can be repeated by reinserting the heated space creator 1206 through the tissue thickness compensator 1200 to widen the space created for the longitudinal slot 1202.

Referring again to FIGS. 41-43, the space creator 1206 may comprise a hot wire. For example, the space creator 1206 may comprise a thin, taut metal wire, which can be made of nichrome or stainless steel, for example, or a thicker wire preformed into a desired shape. The hot wire can be heated via electrical resistance to a desired temperature. As the hot wire of the space creator 1206 is passed through the material of the tissue thickness compensator 1200, the heat from the hot wire may vaporize the material just in advance of contact. In certain circumstances, the hot wire may comprise a cylindrical, or substantially cylindrical, shape, as illustrated in FIG. 42. The depth of the longitudinal slot 1202 can depend, in part, on the insertion depth of the space creator 1206 through the tissue thickness compensator 1200 and the width of the longitudinal slot 1202 can depend, in part, on the diameter of the hot wire of the space creator 1206.

In certain instances, the space creator 1206 can be partially inserted through the full thickness of the tissue thickness compensator. In certain instances, the space creator 1206 can be completely inserted through the full thickness of the tissue thickness compensator 1200 to create openings, holes, and/or slots extending through the full thickness of the tissue thickness compensator 1200. In certain instances, the space creator 1206 may be inserted through a first side of the tissue thickness compensator 1200 and exited through a second side of the tissue thickness compensator 1200 which may be opposite the first side, for example.

Many processes are disclosed herein which utilize thermal energy to modify a tissue thickness compensator. Such processes can be referred to as felting processes. In certain instances, a felting process may also utilize the application of compressive and/or tensile forces to a tissue thickness compensator. In other instances, a felting process may not utilize the application of compressive and/or tensile forces to a tissue thickness compensator. In either event, the felting processes disclosed herein can also be utilized to modify and suitable implantable layer and/or buttress material, for example.

In various circumstances, the tissue thickness compensator assembly may comprise a polymeric composition. The polymeric composition may comprise one or more synthetic polymer and/or one or more non-synthetic polymer. The synthetic polymer may comprise a synthetic absorbable polymer and/or a synthetic non-absorbable polymer. In various circumstances, the polymeric composition may comprise a biocompatible foam, for example. The biocompatible foam may comprise a porous, open cell foam and/or a porous, closed cell foam, for example. The biocompatible foam can have a uniform pore morphology or may have a gradient pore morphology (i.e. small pores gradually increasing in size to large pores across the thickness of the foam in one direction). In various circumstances, the polymeric composition may comprise one or more of a porous scaffold, a porous matrix, a gel matrix, a hydrogel matrix, a solution matrix, a filamentous matrix, a tubular matrix, a composite matrix, a membranous matrix, a biostable polymer, and a biodegradable polymer, and combinations thereof. For example, the tissue thickness compensator assembly may comprise a foam reinforced by a filamentous matrix or may comprise a foam having an additional hydrogel layer that expands in the presence of bodily fluids to further provide the compression on the tissue. In various circumstances, a tissue thickness compensator assembly could also be comprised of a coating on a material and/or a second or third layer that expands in the presence of bodily fluids to further provide the compression on the tissue. Such a layer could be a hydrogel that could be a synthetic and/or naturally derived material and could be either biodurable and/or biodegradable, for example. In certain circumstances, a tissue thickness compensator assembly could be reinforced with fibrous non-woven materials or fibrous mesh type elements, for example, that can provide additional flexibility, stiffness, and/or strength. In various circumstances, a tissue thickness compensator assembly that has a porous morphology which exhibits a gradient structure such as, for example, small pores on one surface and larger pores on the other surface. Such morphology could be more optimal for tissue in-growth or hemostatic behavior. Further, the gradient could be also compositional with a varying bio-absorption profile. A short term absorption profile may be preferred to address hemostasis while a long term absorption profile may address better tissue healing without leakages.

Examples of non-synthetic polymers include, but are not limited to, lyophilized polysaccharide, glycoprotein, elastin, proteoglycan, gelatin, collagen, and oxidized regenerated cellulose (ORC). Examples of synthetic absorbable polymers include, but are not limited to, poly(lactic acid) (PLA), poly(L-lactic acid) (PLLA), polycaprolactone (PCL), polyglycolic acid (PGA), poly(trimethylene carbonate) (TMC), polyethylene terephthalate (PET), polyhydroxyalkanoate (PHA), a copolymer of glycolide and ε-caprolactone (PGCL), a copolymer of glycolide and-trimethylene carbonate, poly(glycerol sebacate) (PGS), polydioxanone, poly(orthoesters), polyanhydrides, polysaccharides, poly (ester-amides), tyrosine-based polyarylates, tyrosine-based polyiminocarbonates, tyrosine-based polycarbonates, poly (D,L-lactide-urethane), poly(B-hydroxybutyrate), poly(E-caprolactone), polyethyleneglycol (PEG), poly[bis(carboxylatophenoxy)phosphazene], poly(amino acids), pseudo-poly (amino acids), absorbable polyurethanes, and combinations thereof. In various circumstances, the polymeric composition may comprise from approximately 50% to approximately 90% by weight of the polymeric composition of PLLA and approximately 50% to approximately 10% by weight of the polymeric composition of PCL, for example. In at least one embodiment, the polymeric composition may comprise approximately 70% by weight of PLLA and approximately 30% by weight of PCL, for example. In various circumstances, the polymeric composition may comprise from approximately 55% to approximately 85% by weight of the polymeric composition of PGA and 15% to 45% by weight of the polymeric composition of PCL, for example. In at least one embodiment, the polymeric composition may comprise approximately 65% by weight of PGA and approximately 35% by weight of PCL, for example. In various circumstances, the polymeric composition may comprise from approximately 90% to approximately 95% by weight of the polymeric composition of PGA and approximately 5% to approximately 10% by weight of the polymeric composition of PLA, for example.

In various circumstances, the synthetic absorbable polymer may comprise a bioabsorbable, biocompatible elastomeric copolymer. Suitable bioabsorbable, biocompatible elastomeric copolymers include but are not limited to copolymers of epsilon-caprolactone and glycolide (preferably having a mole ratio of epsilon-caprolactone to glycolide of from about 30:70 to about 70:30, preferably 35:65 to about 65:35, and more preferably 45:55 to 35:65); elastomeric copolymers of epsilon-caprolactone and lactide, including L-lactide, D-lactide blends thereof or lactic acid copolymers (preferably having a mole ratio of epsilon-caprolactone to lactide of from about 35:65 to about 65:35 and more preferably 45:55 to 30:70) elastomeric copolymers of p-dioxanone (1,4-dioxan-2-one) and lactide including L-lactide, D-lactide and lactic acid (preferably having a mole ratio of p-dioxanone to lactide of from about 40:60 to about 60:40); elastomeric copolymers of epsilon-caprolactone and p-dioxanone (preferably having a mole ratio of epsilon-caprolactone to p-dioxanone of from about 30:70 to about 70:30); elastomeric copolymers of p-dioxanone and trimethylene carbonate (preferably having a mole ratio of p-dioxanone to trimethylene carbonate of from about 30:70 to about 70:30); elastomeric copolymers of trimethylene carbonate and glycolide (preferably having a mole ratio of trimethylene carbonate to glycolide of from about 30:70 to about 70:30); elastomeric copolymer of trimethylene carbonate and lactide including L-lactide, D-lactide, blends thereof or lactic acid copolymers (preferably having a mole ratio of trimethylene carbonate to lactide of from about 30:70 to about 70:30) and blends thereof. In one embodiment, the elastomeric copolymer is a copolymer of glycolide and epsilon-caprolactone. In another embodiment, the elastomeric copolymer is a copolymer of lactide and epsilon-caprolactone.

The disclosures of U.S. Pat. No. 5,468,253, entitled ELASTOMERIC MEDICAL DEVICE, which issued on Nov. 21, 1995, and U.S. Pat. No. 6,325,810, entitled FOAM BUTTRESS FOR STAPLING APPARATUS, which issued on Dec. 4, 2001, are hereby incorporated by reference in their respective entireties.

In various circumstances, the synthetic absorbable polymer may comprise one or more of 90/10 poly(glycolide-L-lactide) copolymer, commercially available from Ethicon, Inc. under the trade designation VICRYL (polyglactic 910), polyglycolide, commercially available from American Cyanamid Co. under the trade designation DEXON, polydioxanone, commercially available from Ethicon, Inc. under the trade designation PDS, poly(glycolide-trimethylene carbonate) random block copolymer, commercially available from American Cyanamid Co. under the trade designation MAXON, 75/25 poly(glycolide-E-caprolactone-poliglecaprolactone 25) copolymer, commercially available from Ethicon under the trade designation MONOCRYL, for example.

Examples of synthetic non-absorbable polymers include, but are not limited to, foamed polyurethane, polypropylene (PP), polyethylene (PE), polycarbonate, polyamides, such as nylon, polyvinylchloride (PVC), polymethylmetacrylate (PMMA), polystyrene (PS), polyester, polyetheretherketone (PEEK), polytetrafluoroethylene (PTFE), polytrifluorochloroethylene (PTFCE), polyvinylfluoride (PVF), fluorinated ethylene propylene (FEP), polyacetal, polysulfone, and combinations thereof. The synthetic non-absorbable polymers may include, but are not limited to, foamed elastomers and porous elastomers, such as, for example, silicone, polyisoprene, and rubber. In various circumstances, the synthetic polymers may comprise expanded polytetrafluoroethylene (ePTFE), commercially available from W. L. Gore & Associates, Inc. under the trade designation GORE-TEX Soft Tissue Patch and co-polyetherester urethane foam commercially available from Polyganics under the trade designation NASOPORE.

The polymeric composition of a tissue thickness compensator assembly may be characterized by percent porosity, pore size, and/or hardness, for example. In various circumstances, the polymeric composition may have a percent porosity from approximately 30% by volume to approximately 99% by volume, for example. In certain circumstances, the polymeric composition may have a percent porosity from approximately 60% by volume to approximately 98% by volume, for example. In various circumstances, the polymeric composition may have a percent porosity from approximately 85% by volume to approximately 97% by volume, for example. In at least one embodiment, the polymeric composition may comprise approximately 70% by weight of PLLA and approximately 30% by weight of PCL, for example, and can comprise approximately 90% porosity by volume, for example. In at least one such embodiment, as a result, the polymeric composition would comprise approximately 10% copolymer by volume. In at least one embodiment, the polymeric composition may comprise approximately 65% by weight of PGA and approximately 35% by weight of PCL, for example, and can have a percent porosity from approximately 93% by volume to approximately 95% by volume, for example. In various circumstances, the polymeric composition may comprise a greater than 85% porosity by volume. The polymeric composition may have a pore size from approximately 5 micrometers to approximately 2000 micrometers, for example. In various circumstances, the polymeric composition may have a pore size between approximately 10 micrometers to approximately 100 micrometers, for example. In at least one such embodiment, the polymeric composition can comprise a copolymer of PGA and PCL, for example. In certain circumstances, the polymeric composition may have a pore size between approximately 100 micrometers to approximately 1000 micrometers, for example. In at least one such embodiment, the polymeric composition can comprise a copolymer of PLLA and PCL, for example. According to certain aspects, the hardness of a polymeric composition may be expressed in terms of the Shore Hardness, which can defined as the resistance to permanent indentation of a material as determined with a durometer, such as a Shore Durometer. In order to assess the durometer value for a given material, a pressure is applied to the material with a durometer indenter foot in accordance with ASTM procedure D2240-00, entitled, "Standard Test Method for Rubber Property-Durometer Hardness", the entirety of which is incorporated herein by reference. The durometer indenter foot may be applied to the material for a sufficient period of time, such as 15 seconds, for example, wherein a reading is then taken from the appropriate scale. Depending on the type of scale being used, a reading of 0 can be obtained when the indenter foot completely penetrates the material, and a reading of 100 can be obtained when no penetration into the material occurs. This reading is dimensionless. In various circumstances, the durometer may be determined in accordance with any suitable scale, such as Type A and/or Type OO scales, for example, in accordance with ASTM D2240-00. In various circumstances, the polymeric composition of a tissue thickness compensator assembly may have a Shore A hardness value from approximately 4 A to approximately 16 A, for example, which is approximately 45 OO to approximately 65 OO on the Shore OO range. In at least one such embodiment, the polymeric composition can comprise a PLLA/PCL copolymer or a PGA/PCL copolymer, for example. In various circumstances, the polymeric composition of a tissue thickness compensator assembly may have a Shore A Hardness value of less than 15 A. In various circumstances, the polymeric composition of a tissue thickness compensator assembly may have a Shore A Hardness value of less than 10 A. In various circumstances, the polymeric composition of a tissue thickness compensator assembly may have a Shore A Hardness value of less than 5 A. In certain circumstances, the polymeric material may have a Shore OO composition value from approximately 35 OO to approximately 75 OO, for example.

In various circumstances, the polymeric composition may have at least two of the above-identified properties. In various circumstances, the polymeric composition may have at least three of the above-identified properties. The polymeric composition may have a porosity from 85% to 97% by volume, a pore size from 5 micrometers to 2000 micrometers, and a Shore A hardness value from 4 A to 16 A and Shore OO hardness value from 45 OO to 65 OO, for example. In at least one embodiment, the polymeric composition may comprise 70% by weight of the polymeric composition of PLLA and 30% by weight of the polymeric composition of PCL having a porosity of 90% by volume, a pore size from 100 micrometers to 1000 micrometers, and a Shore A hardness value from 4 A to 16 A and Shore OO hardness value from 45 OO to 65 OO, for example. In at least one embodiment, the polymeric composition may comprise 65% by weight of the polymeric composition of PGA and 35% by weight of the polymeric composition of PCL having a porosity from 93% to 95% by volume, a pore size from 10 micrometers to 100 micrometers, and a Shore A hardness value from 4 A to 16 A and Shore OO hardness value from 45 OO to 65 OO, for example.

In various circumstances, the polymeric composition may comprise a pharmaceutically active agent. The polymeric composition may release a therapeutically effective amount of the pharmaceutically active agent. In various circumstances, the pharmaceutically active agent may be released as the polymeric composition is desorbed/absorbed. In various circumstances, the pharmaceutically active agent may be released into fluid, such as, for example, blood, passing over or through the polymeric composition. Examples of pharmaceutically active agents may include, but are not limited to, hemostatic agents and drugs, such as, for example, fibrin, thrombin, and oxidized regenerated cellulose (ORC); anti-inflammatory drugs, such as, for example, diclofenac, aspirin, naproxen, sulindac, and hydrocortisone; antibiotic and antimicrobial drug or agents, such as, for example, triclosan, ionic silver, ampicillin, gentamicin, polymyxin B, chloramphenicol; and anticancer agents, such as, for example, cisplatin, mitomycin, adriamycin.

Various methods are disclosed herein for altering a tissue thickness compensator. Such methods could be used to alter any suitable layer for use with a fastener cartridge and/or a surgical fastening instrument, for example. Such a layer can comprise a less than one hundred percent dense composition which can be created utilizing any suitable process. For instance, such processes can include, for example, extruding, injection molding, weaving, lyophilization, gas-foaming, and/or melt-blowing processes. Some processes may produce a foam while other processes may not produce a foam; however, in any event, all such embodiments are contemplated for use with all of the embodiments disclosed herein.

Figure 44:
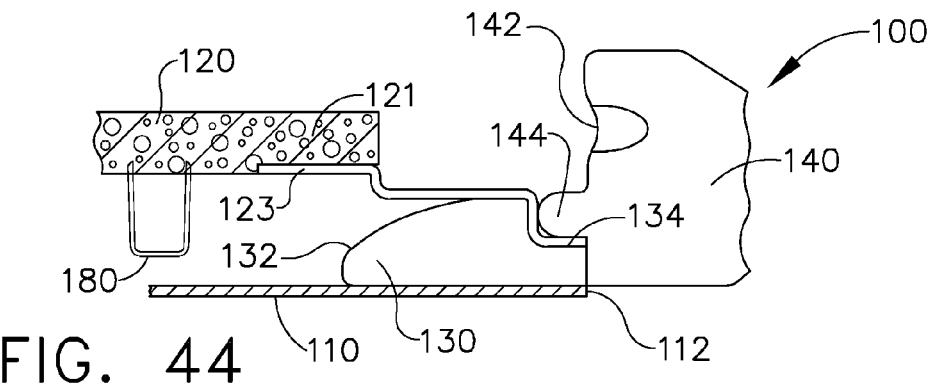
FIG. 44 is a partial cross-sectional elevational view of a fastener cartridge for use with a surgical instrument including a firing member in accordance with at least one embodiment illustrated with portions removed.
Figure 45:
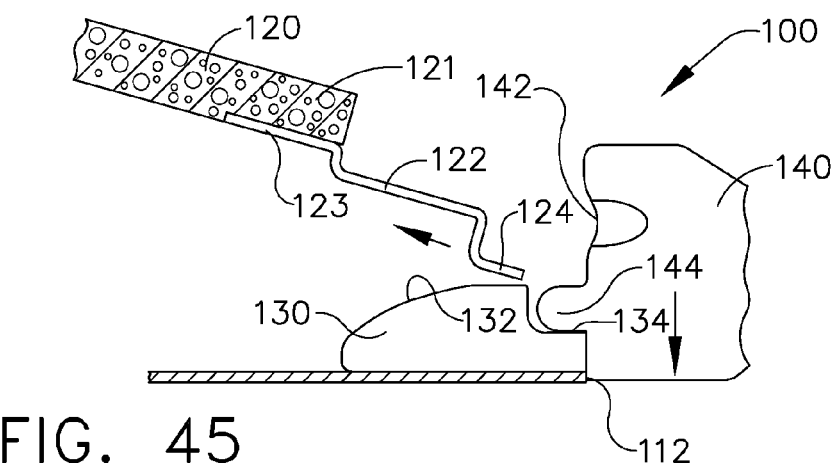
FIG. 45 is a partial cross-sectional elevational view depicting a tissue thickness compensator of the fastener cartridge of FIG. 44 being removed from the fastener cartridge and the firing member of FIG. 44 illustrated in a locked-out condition.
Figure 46:
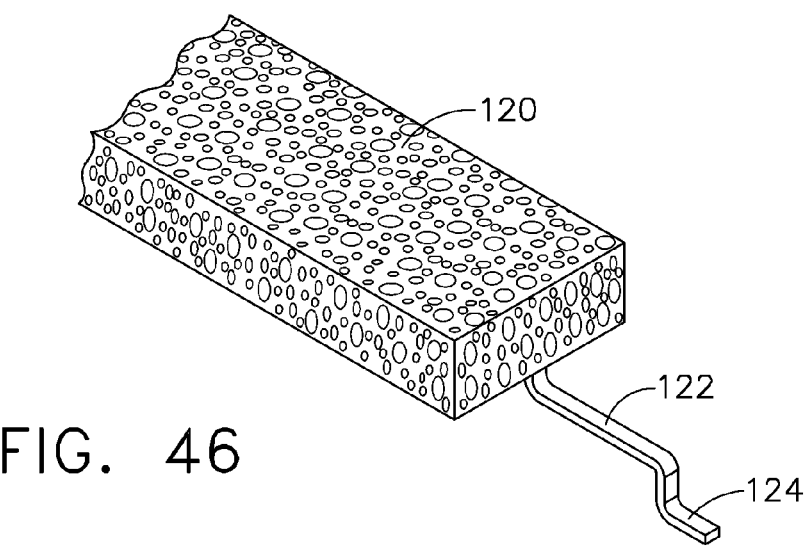
FIG. 46 is a partial perspective view of the tissue thickness compensator of FIG. 45.
Figure 47:
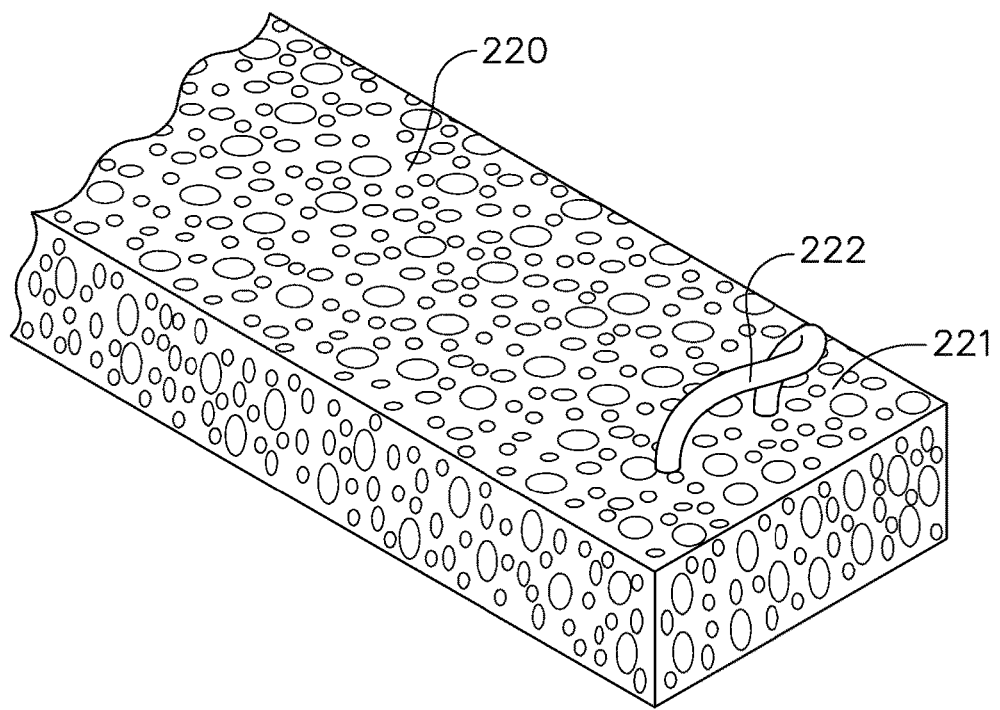
FIG. 47 is a partial perspective view a tissue thickness compensator in accordance with at least one embodiment.

In various embodiments, referring to FIGS. 44-46, an end effector of a surgical fastening instrument, such as end effector 100, for example, can be configured to capture, fasten, and/or incise tissue. The end effector 100 can include a fastener cartridge 110 and, in addition, a firing member 140 which can be advanced through the fastener cartridge 110 to deploy staples removably stored within the staple cartridge 110 into tissue captured within the end effector 100. In various instances, the firing member 140 can be advanced from a proximal position (FIG. 44) toward a distal end of the end effector 100 to simultaneously deploy the staples and transect the tissue. There are some circumstances, however, where it may not be desirable to advance the firing member 140 toward the distal end of the end effector 100. For instance, the fastener cartridge 110 of the end effector 100 can be removable and/or replaceable and, in the event that a fastener cartridge 110 is not positioned within the end effector 100, it may not be desirable for the firing member 140 to be advanced within the end effector 100. In the event that the firing member 140 were to be advanced through the end effector 100 without a fastener cartridge positioned within the end effector 100, a knife edge 142 of the firing member 140 may incise tissue captured within the end effector 100 without simultaneously fastening the tissue. Similarly, in the event that the fastener cartridge positioned within the end effector 100 has been previously used, or expended, and at least some of the fasteners have been deployed from the fastener cartridge, it may not be desirable for the firing member 140 to be advanced within the end effector 100. In the event that the firing member 140 were to be advanced through the end effector 100 with a previously expended fastener cartridge positioned within the end effector 100, the knife edge 142 of the firing member 140 may incise tissue captured within the end effector without simultaneously fastening the tissue. In various embodiments, the end effector 100 can include one or more lockout systems which can prevent the firing member 140 from being advanced distally when a fastener cartridge is not present within the end effector 100 and/or when the fastener cartridge positioned within the end effector 100 has been at least partially expended. Various lockout systems are disclosed in U.S. Pat. No. 6,988,649, entitled SURGICAL STAPLING INSTRUMENT HAVING A SPENT CARTRIDGE LOCKOUT, and issued on Jan. 24, 2006. The entire disclosure of U.S. Pat. No. 6,988,649, entitled SURGICAL STAPLING INSTRUMENT HAVING A SPENT CARTRIDGE LOCKOUT, is incorporated by reference herein.

Referring again to FIGS. 44-46, the fastener cartridge 110 can include a cartridge body and a tissue thickness compensator 120 wherein, further to the above, the tissue thickness compensator 120 can be implanted against tissue captured by the end effector 100 by fasteners removably stored within the cartridge body. The tissue thickness compensator 120 can be positioned above a top surface, or deck, of the cartridge body wherein staples 180 removably stored within staple cavities defined in the cartridge body can be ejected from the staple cavities by a firing member, such as sled 130 and/or firing member 140, for example. In certain embodiments, the fastener cartridge 110 can further include drivers configured to support the staples 180 and transmit the movement of the sled 130 to the staples 180 in order to move the staples 180 between an unfired position and a fired position. In various instances, the staples 180 can be at least partially embedded in the tissue thickness compensator 120 when the staples 180 are in their unfired positions and, in certain instances, the staples 180 can hold the tissue thickness compensator 120 in position over the cartridge deck when the staples 180 are in their unfired position. In the event that the tissue thickness compensator 120 were to be moved relative to the cartridge body and/or the staples 180 prior to deploying the staples 180 into tissue, in some instances, the tissue thickness compensator 120 may move the staples 180 relative to or away from their preferred positions. Moreover, in the event that the tissue thickness compensator 120 were to be removed from the cartridge 110 prior to the staples 180 being deployed, the cartridge 110 may no longer be suitable for its originally intended use. In view of the foregoing, as discussed in greater detail below, the end effector 100 may include a lockout configured to prevent the firing member 140 and/or the sled 130 from being advanced distally to deploy the staples 180 in the event that the tissue thickness compensator 120 is removed from, or becomes at least partially dislodged from, the cartridge body prior to the staples 180 being deployed.

Referring again to FIGS. 44-46, the tissue thickness compensator 120 can comprise, one, a body 121 configured to be captured by the staples 180 and, two, a lockout pin 122 extending from the body 121. In various instances, the lockout pin 122 can include a first end 123 embedded in the body 121 and a second end 124 positioned intermediate the firing member 140 and the sled 130 when the tissue thickness compensator 120 has not been removed from or substantially moved from a suitable position over the cartridge body deck. In such a position, the second end 124 of the lockout pin 122 can be positioned intermediate a shoulder, or shelf, 134 defined on the sled 130 and a protrusion 144 extending distally from the firing bar 140. Stated another way, when the lockout pin 122 is positioned intermediate the sled 130 and the firing bar 140, the lockout pin 122 and the sled 130 can co-operate to support the firing bar 140 in an unlocked position above a lockout shoulder 112 defined in the fastener cartridge 110 such that, when a distal firing force is applied to the firing bar 140, the firing bar 140 can advance the sled 130 distally to fire the staples 180. When the tissue thickness compensator 120 is removed from the cartridge 110 and/or sufficiently dislodged from a desirable position relative to the cartridge body, referring primarily to FIG. 45, the lockout pin 122 may no longer be positioned intermediate the sled 130 and the firing member 140 and/or may otherwise be unable to support the firing member 140 in its unlocked position (FIG. 44). In such circumstances, the firing member 140 may become positioned in a locked position such that the distal advancement of the firing member 140 is prevented by the lockout shoulder 112. In at least one such circumstance, the end effector 100 can further include a biasing member, such as a spring, for example, configured to bias the firing member 140 into its locked condition. In certain circumstances, the biasing member can bias the firing member 140 into contact with the sled 130, for instance, without the lockout pin 122 positioned therebetween which can comprise the locked position of the firing member 140.

As a result of the above, the cartridge 110 may become inoperable if the tissue thickness compensator 120 is prematurely removed from the cartridge 110. In such circumstances, the lockout pin 122 may comprise a fuse which deactivates the cartridge 110 in the event that the tissue thickness compensator 120 is removed before the firing member 140 is advanced distally. In various circumstances, the lockout pin 122 may comprise a key which maintains the cartridge 110 in an unlocked condition when the key is positioned between the sled 130 and the firing member 140 and permits the cartridge 110 to enter into a locked condition in the event that the tissue thickness compensator 120 is removed from the cartridge 110 before the firing member 140 is advanced distally, i.e., before the firing member 140 begins its firing stroke. When the firing member 140 is in its locked-out condition and cannot be advanced distally, the knife edge 142 of the firing member 140 is unable to incise the tissue captured within the end effector 100. Moreover, in such circumstances, the firing member 140 cannot advance the sled 130 distally to fire the staples 180. Thus, the tissue thickness compensator lockout can prevent the tissue captured within the end effector 100 from being incised and stapled when the tissue thickness compensator 120 is not positioned on, or properly positioned on, the cartridge 110. In the event that the firing member 140 is advanced distally before the tissue thickness compensator 120 is removed, or dislodged, the firing member 140 can complete the firing stroke, or at least a portion of the firing stroke, of the end effector 100. In such instances, the sled 130 is advanced distally so that one or more ramps 132 defined on the sled 130 can lift the staples 180 and that a knife edge 142 of the firing member 140 can incise the tissue thickness compensator 120 and/or the tissue captured within the end effector 100. In some circumstances, the firing member 140 can contact the lockout pin 122 and displace it out of the way as the firing member 140 is advanced distally. In such circumstances, the lockout pin 122 can be flexible. In various instances, the lockout pin 122 can be comprised of a bioabsorbable material and/or a biocompatible material, for example. In certain circumstances, the firing member 140 can incise the lockout pin 122 as the firing member 140 is advanced distally. In any event, the purpose of the lockout pin 122 may become obsolete once the firing member 140 has been at least partially advanced. Stated another way, the tissue thickness compensator lockout can serve as an initial check to verify that a tissue thickness compensator is present within the end effector and, once that initial check has been made, the firing stroke of the end effector can proceed.

Referring again to FIGS. 47-50, an end effector 200 can comprise an anvil 260 and, in addition, a fastener cartridge 210 including a cartridge body 214 and a tissue thickness compensator 220 wherein, further to the above, the tissue thickness compensator 220 can be implanted against tissue captured by the end effector 200 by fasteners removably stored within the cartridge body 214. The tissue thickness compensator 220 can be positioned above a top surface, or deck, 211 of the cartridge body 214 wherein staples removably stored within staple cavities defined in the cartridge body 214 can be ejected from the staple cavities by a firing member, such as a sled 230 and/or a firing member 240, for example. In certain embodiments, the fastener cartridge 210 can further include drivers configured to support the staples and transmit the movement of the sled 230 to the staples in order to move the staples between an unfired position and a fired position. In various instances, the staples can be at least partially embedded in the tissue thickness compensator 220 when the staples are in their unfired positions and, in certain instances, the staples can hold the tissue thickness compensator 220 in position when the staples are in their unfired position. In the event that the tissue thickness compensator 220 were to be moved relative to the cartridge body 214 and/or the staples prior to deploying the staples into tissue, in some instances, the tissue thickness compensator 220 may move the staples relative to or away from their preferred positions. Moreover, in the event that the tissue thickness compensator 220 were to be removed from the cartridge 210 prior to the staples being deployed, the cartridge 210 may no longer be suitable for its originally intended use. In view of the foregoing, as discussed in greater detail below, the end effector 200 may include a lockout configured to prevent the firing member 240 and/or the sled 230 from being advanced distally to deploy the staples in the event that the tissue thickness compensator 220 is removed from, or becomes at least partially dislodged from, the cartridge body 214 prior to the staples being deployed.

Figure 48:
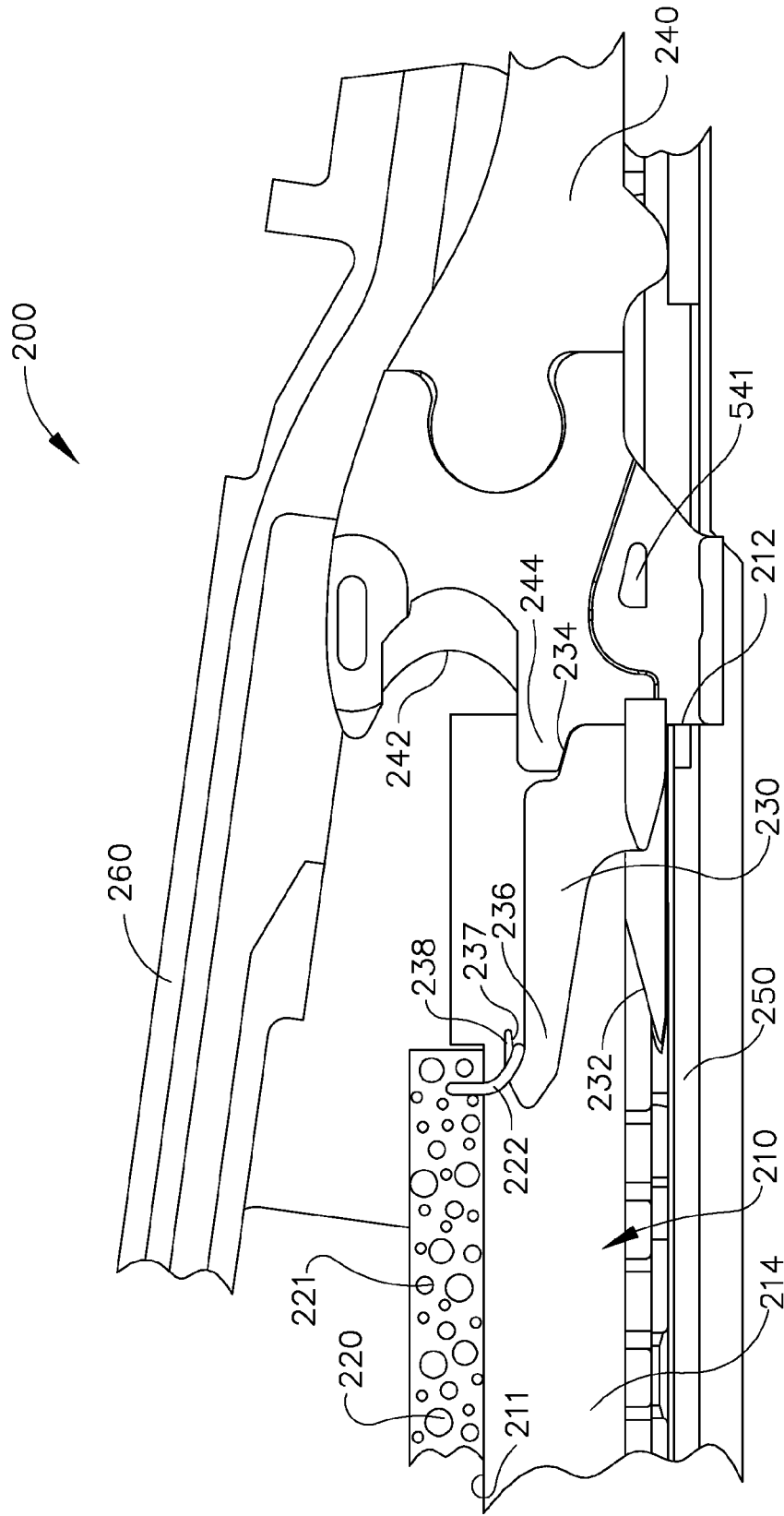
FIG. 48 is a partial cross-sectional elevational view of an end effector of a surgical instrument comprising a fastener cartridge including the tissue thickness compensator of FIG. 47, a sled, and a firing member supported by the sled illustrated with portions removed.
Figure 49:
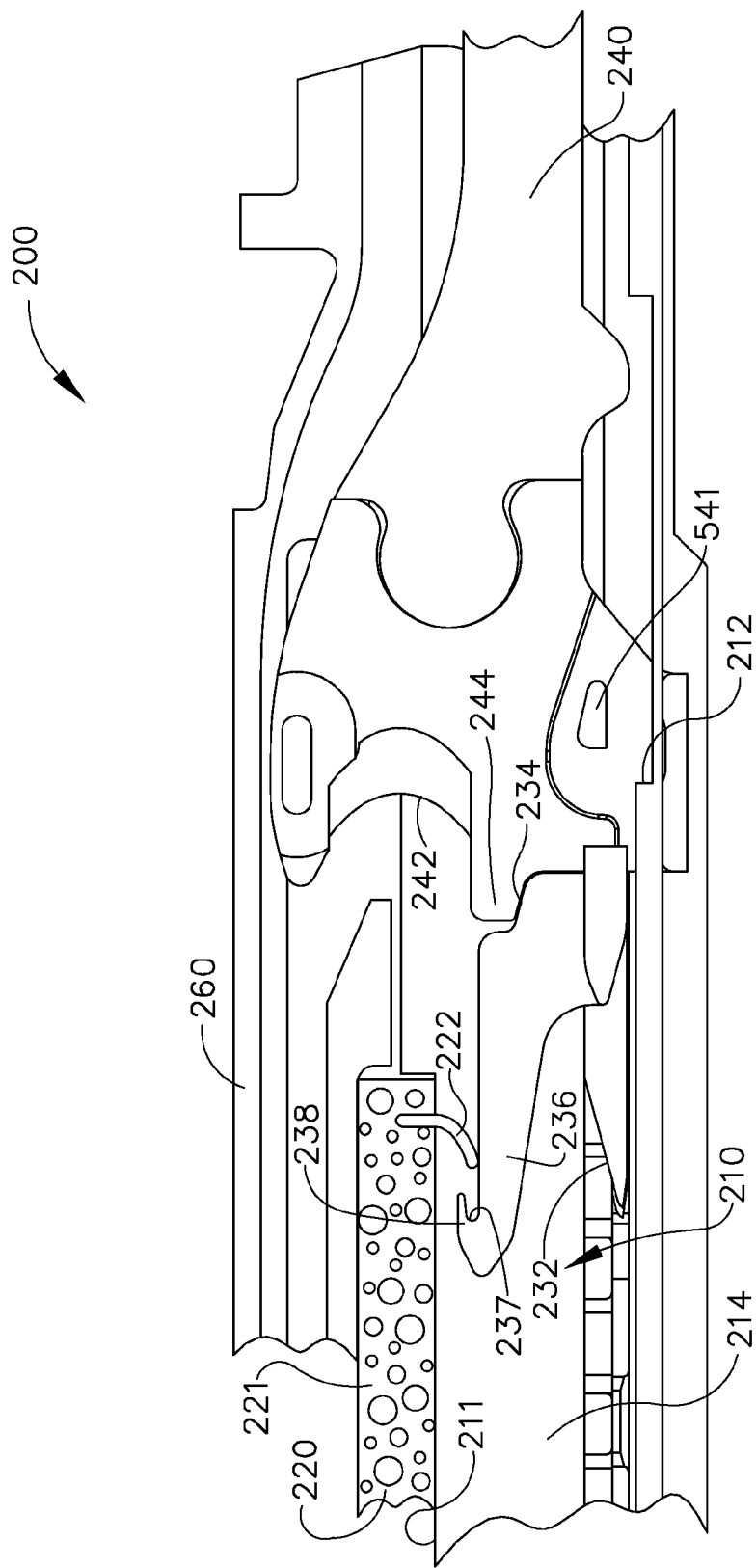
FIG. 49 is a partial cross-sectional elevational view of the end effector of FIG. 48 illustrating the firing member in a partially-fired position.

Referring again to FIGS. 44-46, the tissue thickness compensator 220 can comprise, one, a body 221 configured to be captured by the staples and, two, a loop, or tether, 222 extending from the body 221. In various instances, referring primarily to FIG. 47, the loop 222 can comprise ends which are at least partially embedded in the body 221 and an intermediate portion extending between the ends which can be releasably engaged with the sled 230. In certain instances, the loop 222 can comprise a suture or flexible thread, for example. In some instances, the loop 222 can be comprised of a bioabsorbable material and/or a biocompatible material, for example. Referring primarily to FIG. 48, the sled 230 can include a longitudinal body portion 236, a hook 238 extending from the body portion 236, and a slot 237 defined between the body portion 236 and the hook 238. As illustrated in FIG. 48, the loop 222 is positioned within the slot 237 when the tissue thickness compensator 220 is positioned over the cartridge deck 211 and the sled 230 and the firing member 240 are in an unfired position. As also illustrated in FIG. 48, a distal projection 244 extending from the firing member 240 is positioned against and/or above a support shoulder 234 defined on the sled 230 which holds the firing member 240 in an unlocked position, i.e., in a position in which the distal movement of the firing member 240 will not be impeded, or at least substantially impeded, by a lockout shoulder 212 defined in the end effector 200 when a firing motion is applied to the firing member 240. Thus, when the sled 230 holds the firing member 240 in its unlocked position, referring to FIG. 49, the firing member 240 will slide past the lockout shoulder 212 to advance the sled 230 distally, fire the staples removably stored within the cartridge body 214, and incise the tissue thickness compensator and the tissue positioned within the end effector 200 with a knife edge 242. As illustrated in FIG. 49, the loop 222 can slide out of the slot 237 defined in the sled 230 when the sled 230 is advanced distally.

Figure 50:
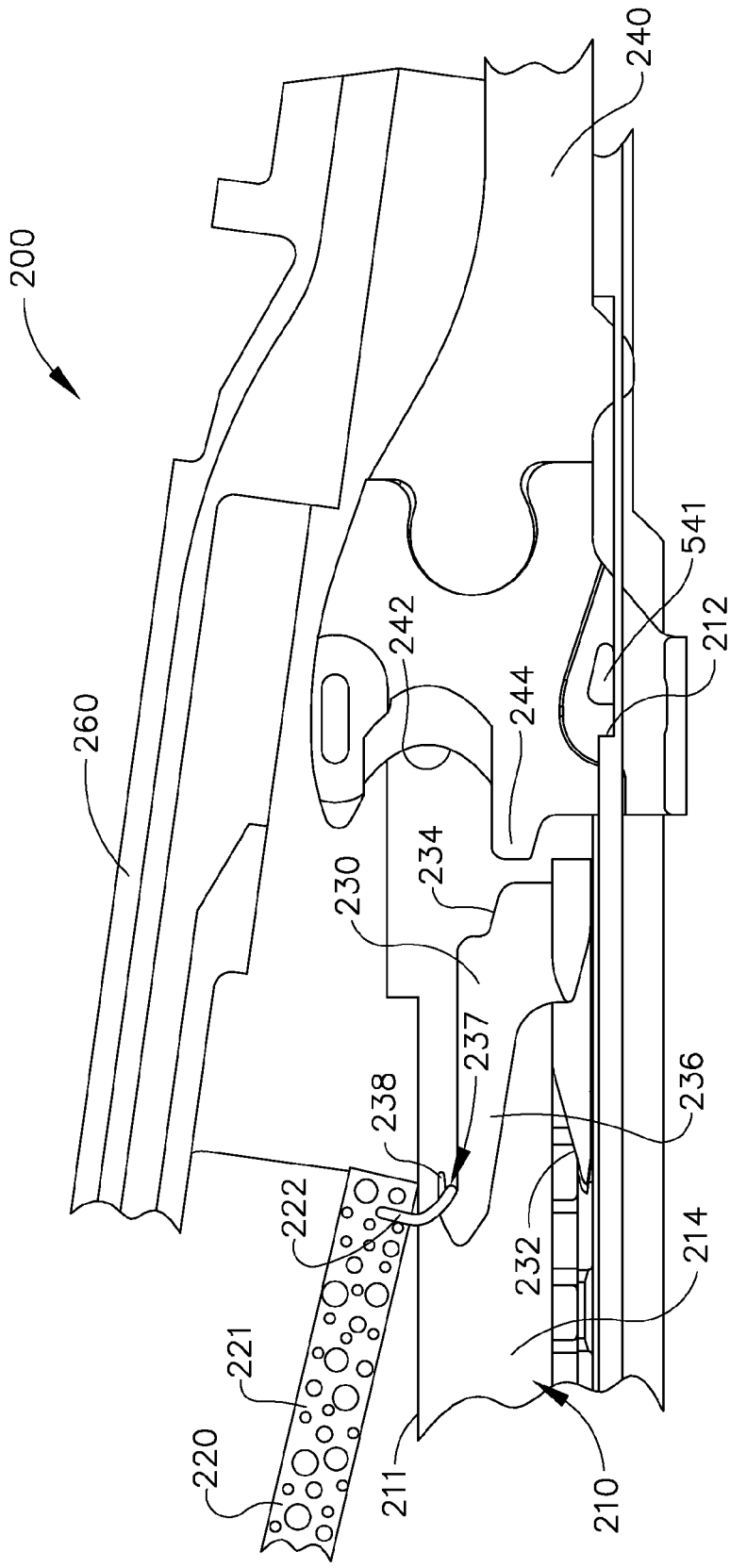
FIG. 50 is a partial cross-sectional elevational view of the end effector of FIG. 48 illustrating the tissue thickness compensator removed from the fastener cartridge and the firing member in a locked-out condition.

In the event that the tissue thickness compensator 220 is removed from the cartridge 210 or substantially moved from a suitable position over the deck 211 of the cartridge 210, referring now to FIG. 50, the tissue thickness compensator 220 can pull the sled 230 distally such that the firing member 240 is no longer supported by the sled 230. More particularly, the loop 222 of the tissue thickness compensator 220 positioned within the slot 237 can pull the sled 230 distally from its unfired position such that the support shoulder 234 is no longer positioned under the distal projection 244 of the firing member 240. In such circumstances, the firing member 240 may shift downwardly into a locked position wherein the distal movement of the firing member 240 can be impeded by the lockout shoulder 212. In certain circumstances, the end effector 200 can further include a biasing member, such as a spring, for example, which can bias the firing member 240 into its locked condition. When the firing member 240 is in its locked condition, the firing member 240 cannot be moved distally to advance the sled 230, fire the staples from the cartridge body 210, and/or incise the tissue captured within the end effector 200. Although the sled 230 may be advanced distally when the tissue thickness compensator 220 is removed from the cartridge 210, the sled 230, in various circumstances, may not be advanced sufficiently to deploy the staples from the cartridge 210. When the user of the surgical instrument recognizes that the firing member 240 is in a locked-out condition, the user can remove the staple cartridge 210 from the end effector 200 and replace it with a staple cartridge 210, for example, in which the tissue thickness compensator 220 is correctly positioned over the deck 211 and the sled 230 has not been advanced distally from its unfired position. Other embodiments are contemplated in which a staple cartridge is not removable from the end effector; in such embodiments, the end effector may be entirely replaced in the event that the tissue thickness compensator is removed from the staple cartridge and/or the firing member enters into a locked-out condition.

Figure 51:
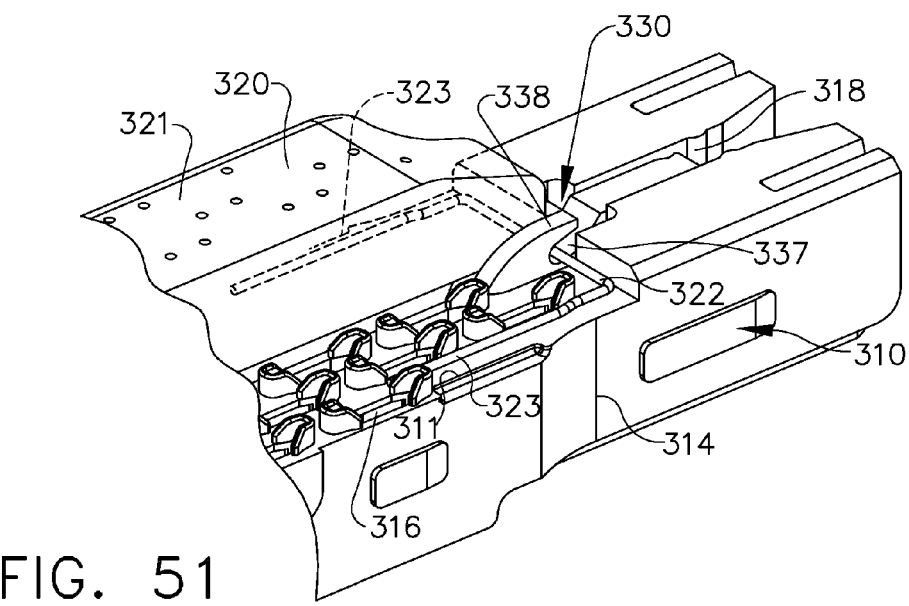
FIG. 51 is a partial perspective view of a fastener cartridge in accordance with at least one embodiment illustrated with portions removed.
Figure 52:
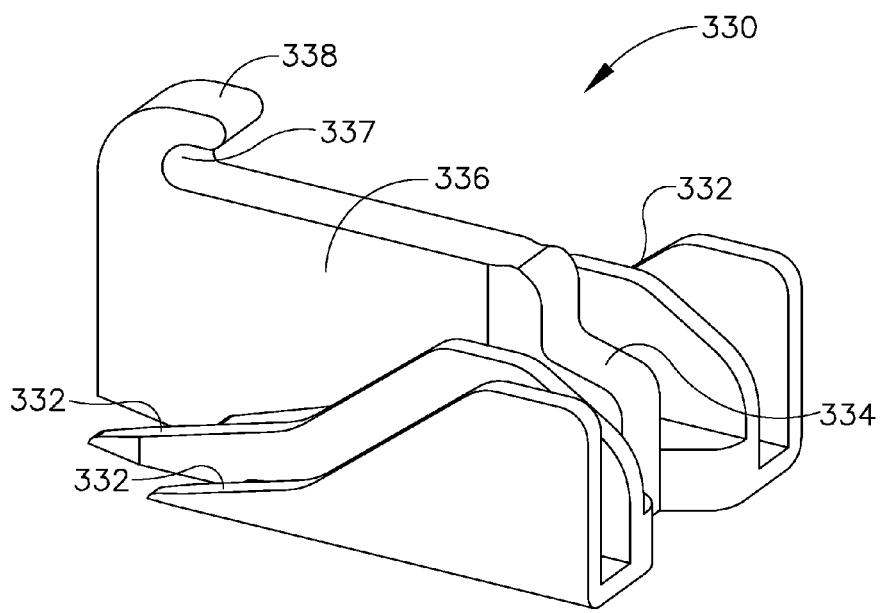
FIG. 52 is a perspective view of a sled of the fastener cartridge of FIG. 51.
Figure 53:
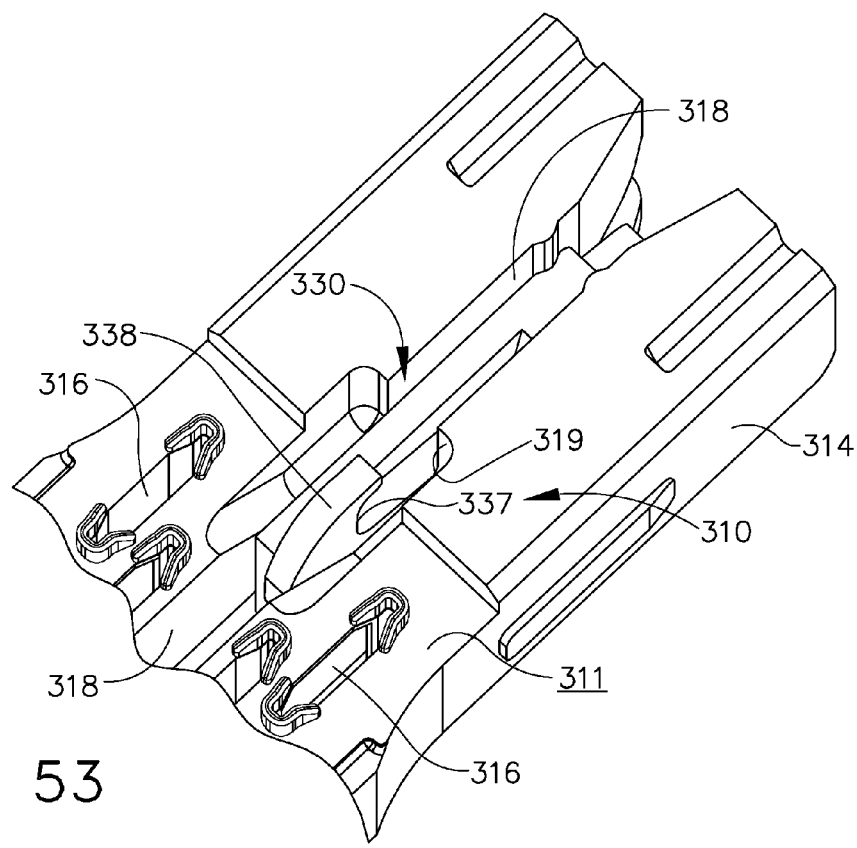
FIG. 53 is a partial perspective view of the fastener cartridge of FIG. 51.
Figure 55:
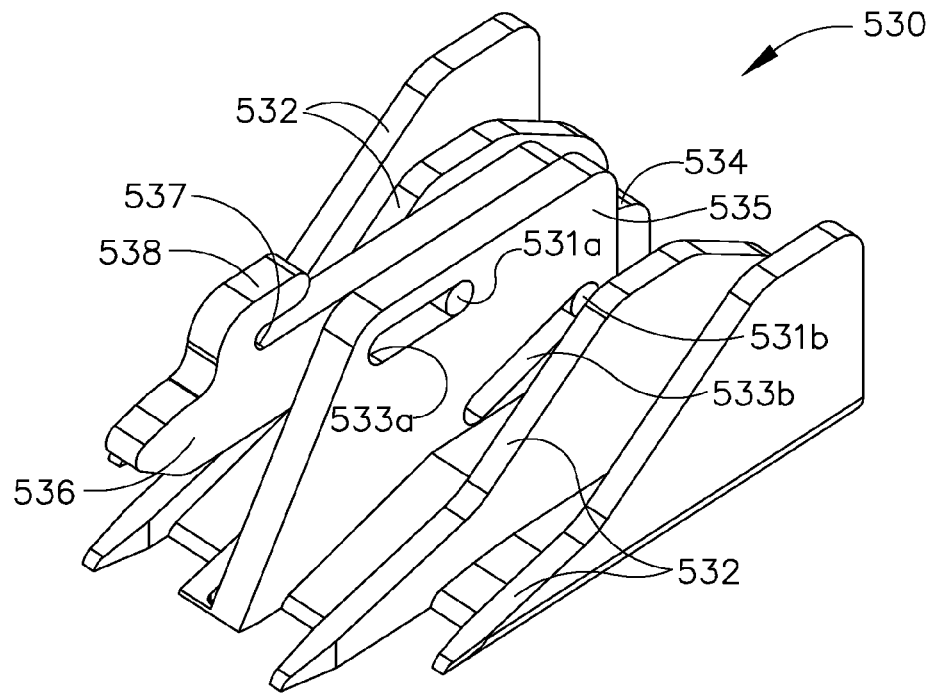
FIG. 55 is a perspective view of a sled in accordance with at least one embodiment illustrated in an unlocked configuration.

Turning now to FIGS. 51-53, a staple cartridge 310 can include a cartridge body 314 and a sled 330 movably positioned within the cartridge body 314. Similar to the above, the cartridge body 314 can include a plurality of fastener cavities, such as fastener cavities 316, for example, and a longitudinal slot, such as knife slot 318, for example, defined therein. The sled 330 can include a central body portion 336 slidably positioned within the knife slot 318 and a hook 338 extending from the central body portion 336. Referring primarily to FIG. 51, a tissue thickness compensator 320 of the cartridge 310 can include a body portion 321 and a catch 322 extending from the body portion 321 wherein the catch 322 can be releasably retained in a slot 337 defined between the hook 338 and the central body portion 336 when the sled 330 is in its unfired, or unadvanced, position. Similar to the above, the catch 322 can include ends 323 mounted within the body 321 and can extend proximally from the body 321 of the tissue thickness compensator 320 wherein, in the event that the tissue thickness compensator 320 is removed from the cartridge body 314, for instance, the catch 322 can pull the sled 330 distally such that a support shoulder 334 defined in the central body portion 336 is no longer able to support a firing member, such as firing member 240, for example, thereon and such that the firing member may enter a locked out state. In various instances, a user of the surgical instrument may attempt to reassemble or reposition the tissue thickness compensator 320 over the deck 311 of the cartridge body 314; however, the firing member 340 will still remain in a locked out condition as the repositioning of the tissue thickness compensator 320 will not reset the sled 330. Thus, such an arrangement can prevent the cartridge 310 from being used if it has been previously tampered with.

In various instances, referring again to FIGS. 51-53, at least a portion of the hook 338 extending from the central portion 336 of the sled 330 and/or the slot 337 defined therebetween can extend above the deck 311. In certain instances, at least a portion of the hook 338 extending from the central portion 336 of the sled 330 and/or the slot 337 defined therebetween can extend above the knife slot 318. In such embodiments, the catch 322 can be easily slid into the slot 337 when the tissue thickness compensator 320 is assembled to the cartridge body 314. In certain instances, the catch 322 can be positioned above or against the deck surface 311 of the cartridge body 314. In various instances, referring primarily to FIG. 53, the cartridge body 314 can include a recess or pocket 319 defined therein within which the hook 338 can be positioned when the sled 330 is in its unfired, or unadvanced, position. In such an embodiment, the top of the hook 338 may be positioned below the deck surface 311. In various instances, the pocket 319 can further include one or more ramped surfaces 313 which are defined in the distal end of the pocket 319 and extend downwardly from the deck surface 311. In some instances, the catch 322 can abut the ramped surfaces 313 when the sled 330 is advanced distally and, in such circumstances, the hook 338 can then separate from the catch 322. In various instances, the recess 319 can be configured to facilitate the assembly of the catch 322 to the sled 330 when the tissue thickness compensator 320 is assembled to the cartridge body 314. In various embodiments, the slot 337 can extend longitudinally and can include a closed distal end an open proximal end wherein the catch 322 can be slid into the slot 337 from the open proximal end. In the event that the tissue thickness compensator 320 is not prematurely removed or dislodged from the cartridge 314, the sled 330 can be advanced distally such that the catch 322 exits the slot 337 through the distal end thereof and such that ramps 332 defined on the sled 330 can eject the staples from the staple cartridge 310.

In various instances, a tissue thickness compensator can be adhered to a sled utilizing at least one adhesive. In such instances, the adhesive attachment between the tissue thickness compensator and the sled can be strong enough to permit the tissue thickness compensator to pull the sled distally in the event that the tissue thickness compensator is removed from the cartridge. When the sled is advanced distally by the firing member as part of the firing stroke, the adhesive attachment between the tissue thickness compensator and the sled may fail thereby permitting the sled to slide distally relative to the tissue thickness compensator. In various instances, a tissue thickness compensator can be bonded to a sled utilizing a heat steak process and/or a thermoform process. In such instances, the bond between the tissue thickness compensator and the sled can be strong enough to permit the tissue thickness compensator to pull the sled distally in the event that the tissue thickness compensator is removed from the cartridge. When the sled is advanced distally by the firing member as part of the firing stroke, the bond between the tissue thickness compensator and the sled may fail thereby permitting the sled to slide distally relative to the tissue thickness compensator.

In some instances, a loop, a catch, and/or tag, for example, can be integrally formed with a tissue thickness compensator. In various instances, the loop, catch, and/or tag, for example, can comprise a unitary piece of material with the tissue thickness compensator. In some instances, an additional layer can be attached to the tissue thickness compensator. This layer, in various instances, can comprise a mounting portion engaged with the sled.

Figure 54:
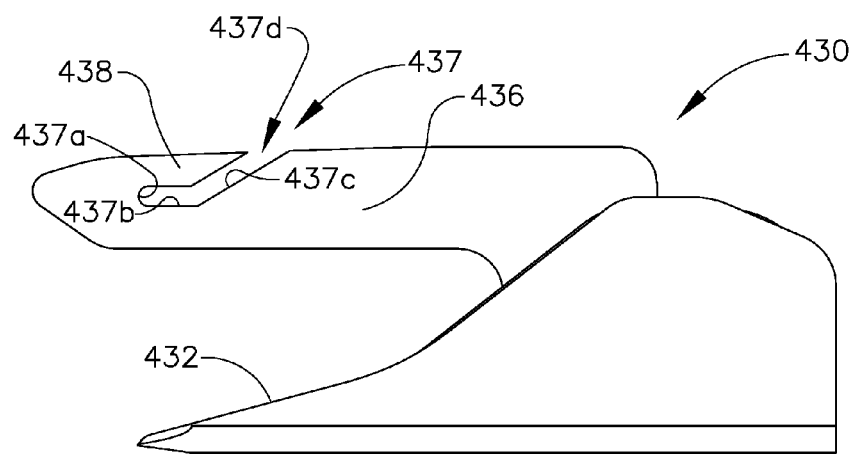
FIG. 54 is an elevational view of a sled in accordance with at least one embodiment.

Turning now to FIG. 54, a sled 430 can include, similar to the above, a central body portion 436 and, in addition, a plurality of ramps 432 which are configured to eject staples removably stored within a cartridge body, for example. Also similar to the above, the body portion 436 can include a hook 438 extending therefrom wherein a slot 437 can be defined between the body portion 436 and the hook 438. In certain instances, the slot 437 can include a closed distal end 437a and an open proximal end 437d. In various instances, the slot 437 can further include a first portion 437b extending in a first direction and a second portion 437c extending in a second direction. In certain instances, the first portion 437b can extend along a longitudinal axis and the second portion 437c can extend along a second axis which is transverse to the longitudinal axis. In at least one such instance, the second portion 437c can extend at an angle relative to the first portion 437b.

Figure 56:
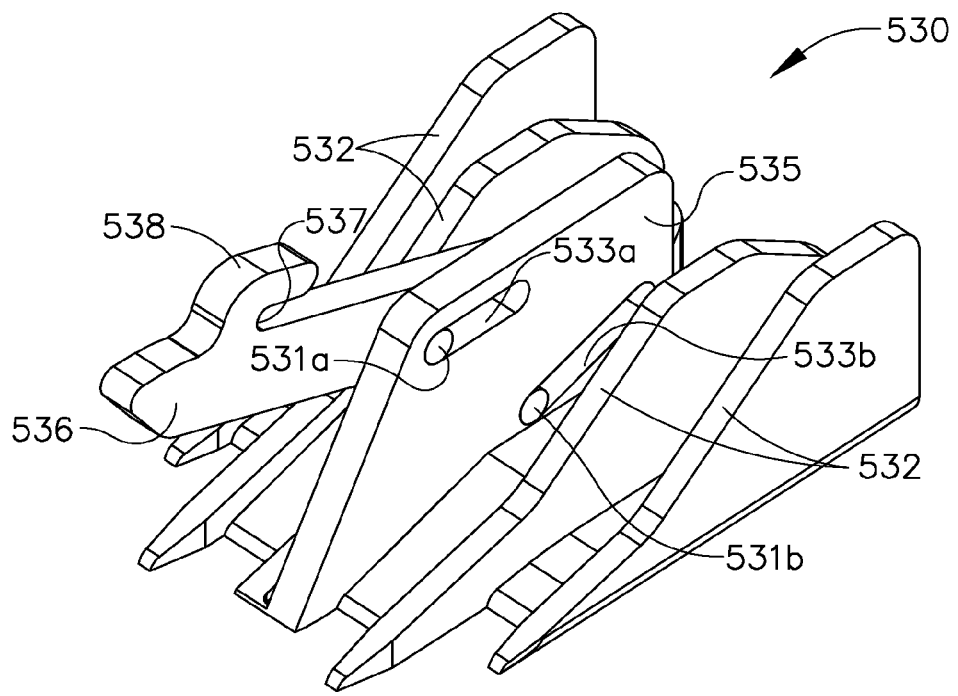
FIG. 56 is a perspective view of the sled of FIG. 55 illustrated in a locked-out configuration.
Figure 57:
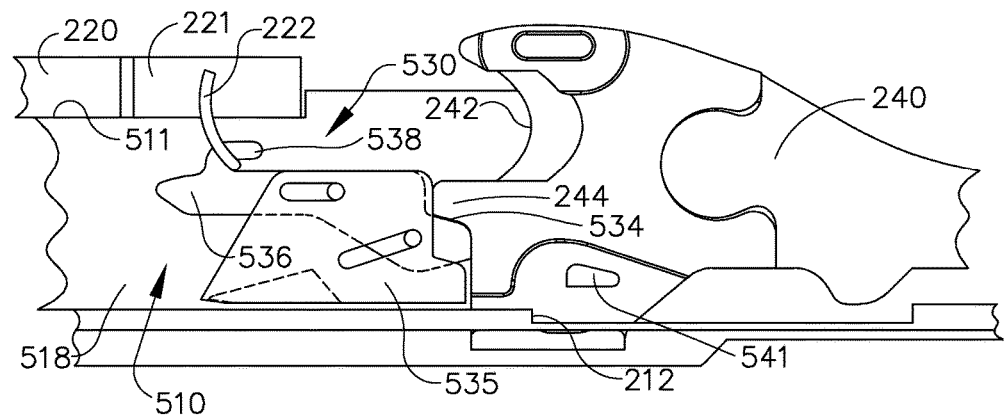
FIG. 57 is a partial cross-sectional elevational view of the sled of FIG. 55 positioned within a fastener cartridge illustrating the sled in its unlocked configuration, a firing member supported by the sled, and a tissue thickness compensator of the fastener cartridge engaged with the sled.
Figure 58:
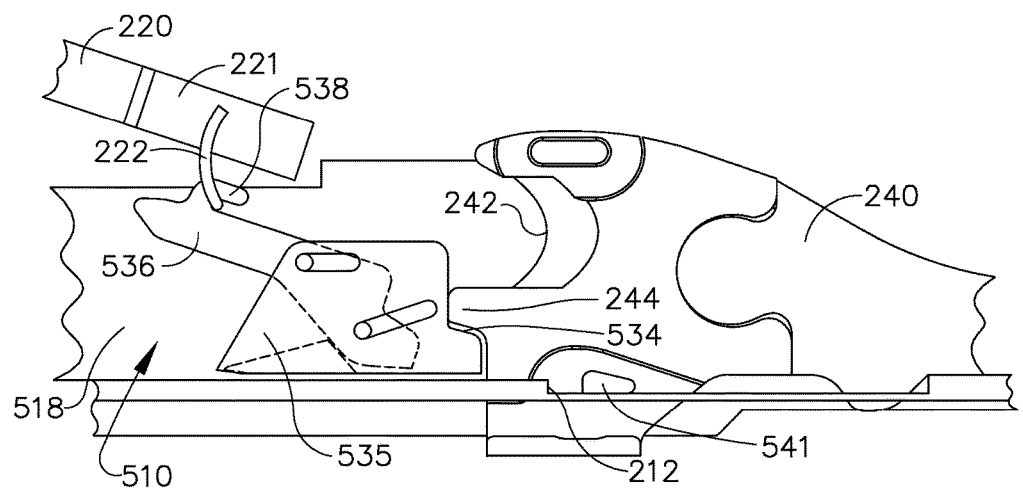
FIG. 58 is a partial cross-sectional elevational view of the tissue thickness compensator of FIG. 57 being removed from the fastener cartridge of FIG. 57 which has placed the sled of FIG. 55 in its locked-out configuration and the firing member of FIG. 57 in a locked-out condition.

Turning now to FIGS. 55-58, a sled assembly 530 can include a first portion 535 and, in addition, a second portion 536 which is movable relative to the first portion 535 between an unlocked position (FIGS. 55 and 57) and a locked position (FIGS. 56 and 58). The first portion 535 can include, one, a central portion configured to slide within a longitudinal slot, such as a knife slot 518 defined in a staple cartridge 510, for instance, and, two, a plurality of ramps 532 configured to eject staples removably stored within the cartridge 510. The central portion of the first portion 535 can include a first slot 533a and a second slot 533b defined therein. The first slot 533a and the second slot 533b can be configured to receive pins 531a and 531b, respectively, extending from the second portion 536. The first pin 531a can be configured to slide within the first slot 533a and the second pin 531b can be configured to slide within the second slot 533b in order to permit the second portion 536 to rotate relative to the first portion 535. In various instances, the first pin 531a can be closely received within the first slot 533a such that the first slot 533a can constrain the motion of the first pin 531a along a first path and, similarly, the second pin 531b can be closely received within the second slot 533b such that the second slot 533b can constrain the motion of the second pin 531b along a second path. Referring primarily to FIG. 57, the second portion 536 of the sled assembly 530 can comprise an arm configured to slide within the knife slot 518 wherein the arm can include a support shoulder 534 defined on the proximal end thereof and a hook 538 defined on the distal end thereof. Similar to the above, the support shoulder 534 can be configured to support a firing member 240, for example, in an unlocked position when the sled assembly 530 is in a proximal, unfired position and the tissue thickness compensator 220, for instance, is positioned over and/or against the deck surface 511 of the cartridge 510. Also similar to the above, the hook 538 can be configured to releasably hold the loop 222 of the tissue thickness compensator 220 such that, in the event that the tissue thickness compensator 220 were to be removed from and/or substantially displaced relative to the cartridge body, the loop 222 could pull on the second portion 536 to pivot the second portion 536 into its locked position as illustrated in FIG. 58. In such a locked position of the second portion 536, the support shoulder 534 may no longer support the distal projection 244 of the firing member 240 and the firing member 240 can drop downwardly into its locked position. As depicted in FIG. 58, the rotation of the second portion 536 into its locked position can move the support shoulder 534 distally and/or downwardly away from the firing member 240. As also depicted in FIG. 58, the firing member 240 can include a lock 541 extending from opposite sides thereof which can be configured to abut the lockout shoulder 212 when the firing member 240 is in its locked position. When the firing member 240 is held in its unlocked position by the sled assembly 530, the locks 541 may not contact the lockout shoulder 212 and the firing member 240 can be advanced through the cartridge 510.

In various instances, as discussed above, a portion of a staple-driving sled may extend above the deck surface of a cartridge body. For instance, referring again to FIGS. 52 and 54, the hook 338 of the sled 330 (FIG. 52) and/or the hook 438 of the sled 430, for example, can extend above the deck surface. In such instances, the hook 338 and/or the hook 438 can translate distally above the deck surface and, in some instances, contact the tissue thickness compensator positioned against or above the deck surface. In certain instances, the hook 338 and/or the hook 438 can lift the tissue thickness compensator upwardly away from the cartridge body and facilitate the progressive release of the tissue thickness compensator from the cartridge. For instance, the hook 338 and/or the hook 438 can begin at the proximal end of the tissue thickness compensator and move toward the distal end of the tissue thickness compensator in order to initially lift the proximal end of the tissue thickness compensator and then progressively lift it away from the cartridge deck until the distal end of the tissue thickness compensator is eventually lifted away from the cartridge body. In other instances, as discussed in greater detail further below. it may be preferable for the portion of the sled contacting the tissue thickness compensator to deflect downwardly and/or otherwise not disturb the tissue thickness compensator as the sled is advanced distally.

Figure 60:
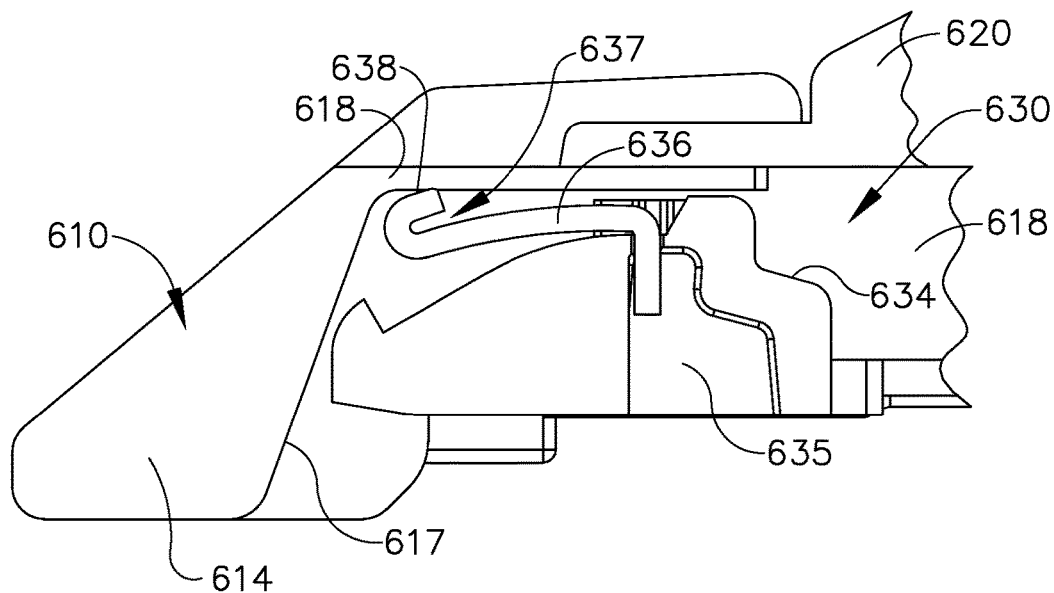
FIG. 60 is a partial cross-sectional elevational view of the sled of FIG. 59 illustrated at the distal end of the fastener cartridge.
Figure 59:
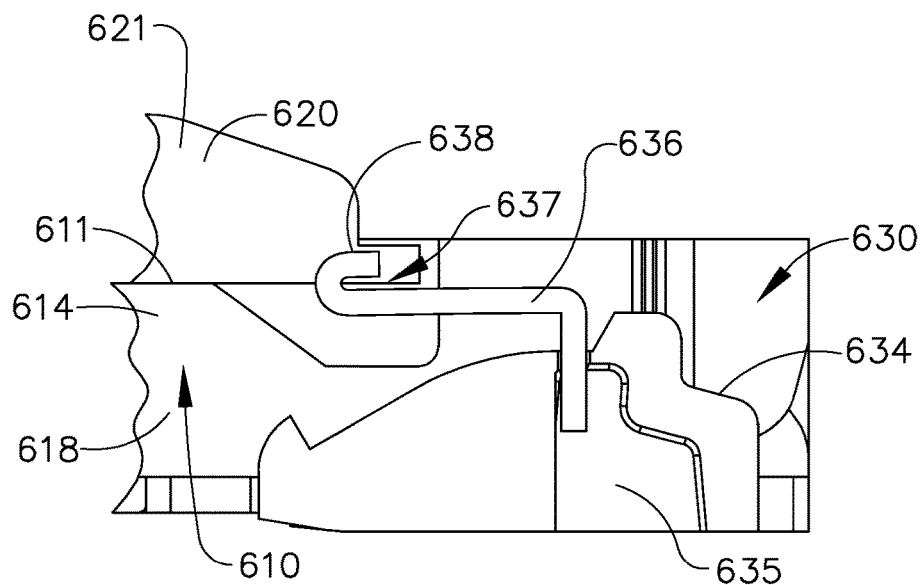
FIG. 59 is a partial cross-sectional elevational view of a sled positioned at the proximal end of a fastener cartridge in accordance with at least one embodiment illustrated with portions removed.

Turning now to FIGS. 59 and 60, a staple cartridge 610 can include a cartridge body 614, a tissue thickness compensator 620 releasably retained to the cartridge body 614, and a sled 630 configured to longitudinally traverse the cartridge body 614 and eject staples removably stored therein. The sled 630 can include a main body portion 635 having a plurality of ramp surfaces defined thereon, a support shoulder 634, and an arm 636 extending from the body portion 635. In various instances, the arm 636 can be assembled to the main body portion 635. For instance, the arm 636 can include a first end embedded in the main body portion 635 and a second end including a hook 638, for example. In various instances, the arm 636 can comprise a cantilever beam extending from the main body portion 635. In certain instances, the arm 636 can be comprised of a resilient and/or flexible material, for example. Similar to the above, a slot 637 can be defined between the hook 638 and the arm 636 which can be configured to releasably hold a portion of the tissue thickness compensator 620 when the sled 630 is in its proximal, unfired position. In the event that the tissue thickness compensator 620 is pulled off of the cartridge body 614, for example, the tissue thickness compensator 620 can pull the sled 630 distally away from a firing member so that the firing member enters into a locked out condition.

In various instances, further to the above, at least a portion of the arm 636, such as the hook 638, for example, can extend above the deck surface 611 of the cartridge body 614. In certain instances, the arm 636 can be engaged with a loop, for example, extending from the tissue thickness compensator 620 when the sled 630 is in its proximal position (FIG. 59) and, as the sled 630 is advanced distally, the arm 636 can disengage from the loop. As the sled 630 is advanced distally, in certain instances, the arm 636 can contact the body portion 621 of the tissue thickness compensator 620 and flex downwardly. In various instances, the deflected arm 636 can slide within a longitudinal knife slot 618 defined in the cartridge body 614 as the sled 630 is advanced distally. In some instances, referring to FIG. 60, the distal end of the longitudinal slot 618 can be defined by a nose wall, or roof, 619 wherein, when the sled 630 reaches a distal end 617 of the cartridge 610, the arm 636 can slide under the nose wall 619 such that the firing stroke of the end effector can be completed. In some instances, the arm 636 may not be deflected, or substantially deflected, downwardly by the tissue thickness compensator 620 wherein, when the arm 636 reaches the end of the longitudinal slot 618, the arm 636 can contact the nose wall 618 and flex downwardly in order to slide thereunder as illustrated in FIG. 60. In various circumstances, as a result, the flexible arm 636 can permit the firing stroke to be completed and for the sled 630 to be parked at the distal end of the cartridge.

Figure 61:
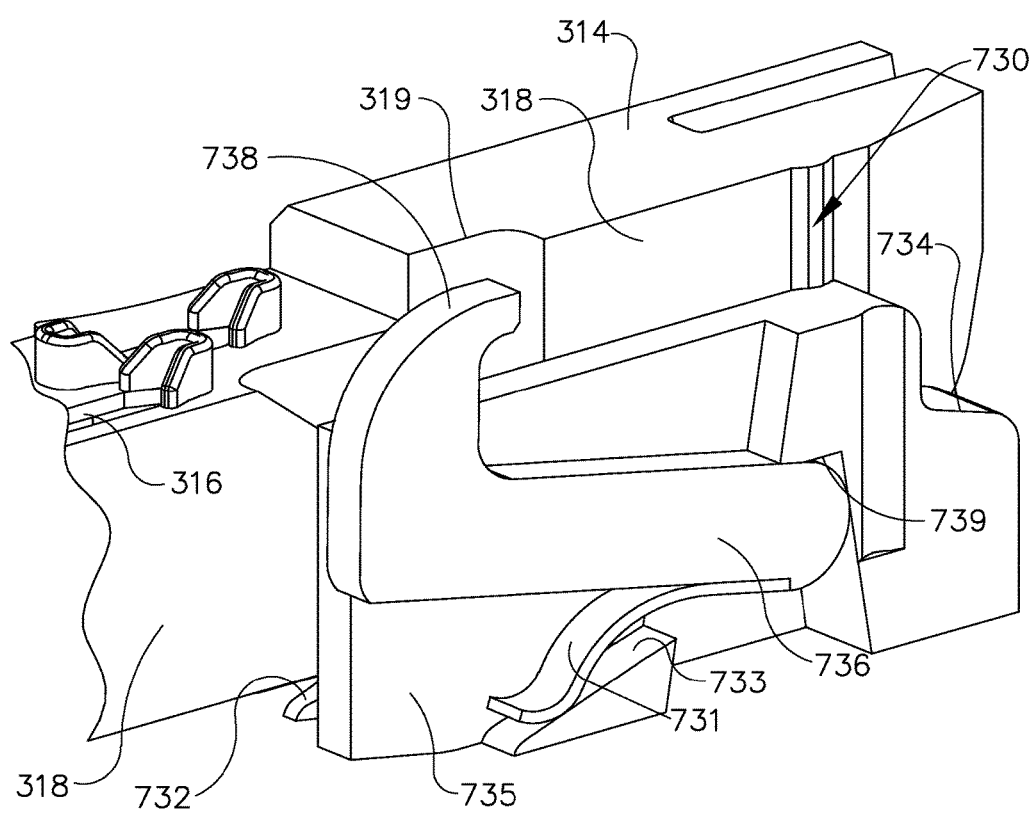
FIG. 61 is a perspective view of a sled in accordance with at least one embodiment.

Turning now to FIG. 61, a sled, such as sled assembly 730, for example, can include a main body portion 735 and a movable arm 736. Similar to the above, the main body portion 735 can include one or more staple-driving ramps 732 and a support shoulder 734 configured to support a firing member in an unlocked position, as described above. The arm 736 can include a first end pivotably and/or rotatably mounted to the main body portion 735 and a second end including a hook 738 configured to be releasably engaged with a tissue thickness compensator, as described above. When the sled assembly 730 is advanced distally, the hook 738 can detach from the tissue thickness compensator; however, the upper surface of the hook 738 can remain in contact with the bottom surface of the tissue thickness compensator. In such circumstances, the arm 736 can pivot downwardly into the knife slot 318, for example, in order to slide under the tissue thickness compensator. More particularly, the arm 736 can pivot from a raised, or uppermost, position (FIG. 61) to a lowered, or depressed, position. In various instances, the sled assembly 730 can further include a resilient biasing member, such as a spring 731, for example, configured to bias the arm 736 into its raised position. When the arm 736 has been rotated downwardly into its lowered position, the spring 731 can apply a biasing force to the arm 736 which is transmitted into the tissue thickness compensator. In certain instances, the spring 731 can be positioned intermediate the arm 736 and a frame portion 733 defined on the main body portion 735. In various instances, the spring 731 can comprise a cantilever spring or leaf spring, for example, extending from the arm 736. When the arm 736 is pushed downwardly, the cantilever spring can be configured to flex and/or slide along the frame portion 731, for instance. In various embodiments, the main body portion 735 can further include a stop shoulder 739, for example, which can limit the upward rotation, or travel, of the arm 736. In any event, similar to the above, the arm 736 can be configured to rotate downwardly when it contacts the roof 619 and permit the firing stroke to be completed.

In various instances, a staple can comprise a base and one or more legs extending from the base. In certain instances, a staple can comprise a base including a first end and a second end, a first leg extending from the first end, and a second leg extending from the second end. In some instances, the staple can be formed from a continuous wire which comprises the first leg, the base, and the second leg. A first end of the continuous wire can comprise a tip of the first staple leg and a second end of the continuous wire can comprise a tip of the second staple leg. One such staple, i.e., staple 800, is depicted in FIG. 62, for example. The staple 800 can include a base 802, a first staple leg 804 extending from a first end of the base 802, and a second staple leg 804 extending from a second end of the base 802. The first staple leg 804 can include a first tip 806 and, similarly, the second staple leg 804 can include a second tip 806. In various instances, the tips 806 can be configured to penetrate tissue, such as tissue T depicted in FIG. 62, for example. In some instances, the tips 806 can be sharp and can be formed by a coining process, for example. In various embodiments, the wire can be comprised of titanium and/or stainless steel, for example.

In various embodiments, the staple 800 can be U-shaped, or at least substantially U-shaped, for example, when it is in its unformed configuration. In such embodiments, the legs 804 of the staple 800 can be parallel, or at least substantially parallel, to one another. Moreover, in such embodiments, the legs 804 can be perpendicular, or at least substantially perpendicular, to the base 802. In certain embodiments, the staple 800 can be V-shaped, or at least substantially V-shaped, for example, when it is in its unformed configuration. In such embodiments, the legs 804 of the staple 800 are not parallel to one another; rather, the legs 804 can extend in non-parallel directions. Moreover, in such embodiments, one or both of the legs 804 are not perpendicular to the base 802 wherein one or both of the legs 804 can extend in directions which are oblique to the base 802. In various instances, the legs 804 may extend, or splay, outwardly with respect to a center or midline of the staple. In any event, the staple 800 can be removably stored within a staple cartridge, ejected from the staple cartridge to penetrate tissue, as illustrated in FIG. 62, and then contact an anvil positioned on the opposite side of the tissue. The anvil can be configured to deform the staple 800 into any suitable shape, such as a B-form configuration, for example, as also illustrated in FIG. 62. Various formed staple configurations, such as the B-form configuration, for example, can define a tissue entrapment area, such as tissue entrapment area 807, for example, configured to entrap tissue within the staple.

Figure 69:
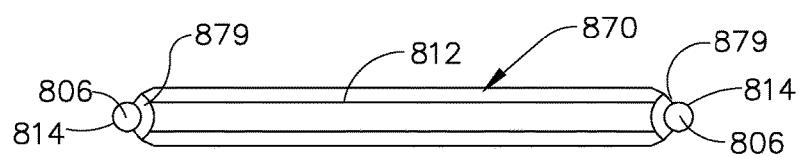
FIG. 69 is a plan view of the staple and the staple cavity of FIG. 68.
Figure 68:
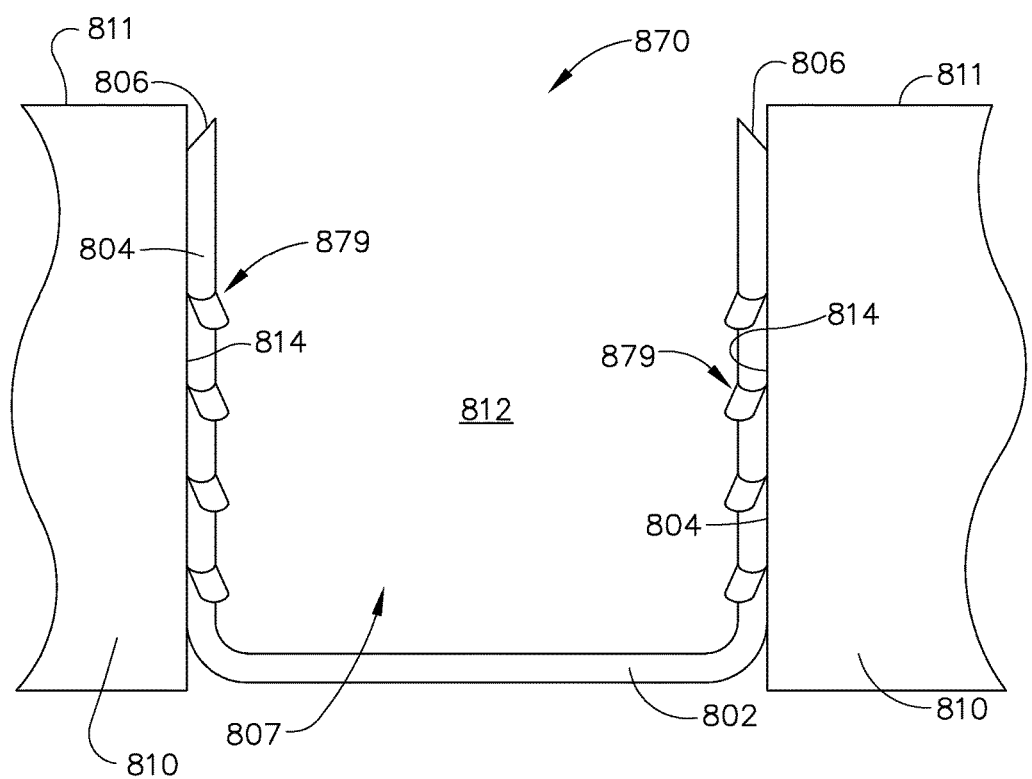
FIG. 68 is an elevational view of the staple including a plurality of barbs in accordance with at least one embodiment, wherein the staple is positioned within a staple cavity in an unfired position.

As discussed above, a staple can be removably stored within a cavity defined in a cartridge body. A cartridge body 810 is depicted in FIG. 63 which can include one or more staple cavities 812 defined therein. Referring to FIGS. 63, 68, and 69, each staple cavity 812 can include a first end 814 and a second end 814. In certain embodiments, such as embodiments including a longitudinal end effector, for example, the first end 814 can comprise a proximal end of the staple cavity 812 and the second end 814 can comprise a distal end of the staple cavity 812. In various instances, a staple can be positioned within a staple cavity 812 such that a first leg 804 of the staple 800 is positioned in the first end 814 of the staple cavity 812 and a second leg 804 is positioned in the second end 814. In various instances, a staple cavity width can be defined between the ends 814 of a staple cavity 812. The base 802 of a staple can be defined by a base width which can be equal to or shorter than the staple cavity width, for example. In certain instances, a staple can comprise a staple width which can be defined between the tips 806 of the staple legs 804. In some embodiments, the staple width can be equal to the staple cavity width. In various embodiments, the staple width can be wider than the staple cavity width. In such embodiments, the legs 804 can be in contact with the ends 814 of a staple cavity 812 and can be resiliently biased inwardly by the ends 814 when the staple is positioned within the staple cavity 812. When the staple is lifted upwardly out of the staple cavity 812, the legs 804 can resiliently splay outwardly as they emerge from the staple cavity 812. For example, the staple can be positioned within the staple cavity 812 such that the tips 806 of the staple legs 804 do not extend above a top surface, or deck, of the cartridge body 810 when the staple is in its unfired, or uplifted, position. In such a position, the tips 806 can be positioned flush with or recessed below the deck 811 of the cartridge body 810. Alternatively, the tips 806 of the legs 804 can at least partially extend above the deck 811 of the cartridge body 810. In any event, as the staple is lifted upwardly, the staple tips 806 can emerge above the deck 811 and splay outwardly as the legs 804 emerge from the cavity 812. At some point during the lifting of the staple, the legs 804 may no longer be in contact with the ends 814 of the staple cavity 812 and the legs 804 may no longer be biased inwardly by the sidewalls of the staple cavity 812.

In various instances, an anvil can include one or more pockets configured to receive the tips 806 of the staple legs 804 as the staple 800 is ejected from the staple cartridge. The anvil pockets can be configured to turn, or bend, the staple legs 804 inwardly toward one another, for example. In other instances, the anvil pockets can be configured to turn, or bend, the staple legs 804 outwardly away from one another, for example. In some instances, however, one or more of the staple legs of a staple may miss a staple pocket and may not be properly deformed. In certain instances, one or more of the staple legs may not contact the anvil and may not be deformed at all. In either event, the staple may not properly capture and/or retain the tissue within its tissue entrapment area. Moreover, the misformed or unformed staple may not be able to apply a desired compressive pressure to the tissue. In some instances, the misformed or unformed staple may not be retained in the tissue and can become dislodged from the tissue.

Referring again to FIG. 62, the staple 800, and/or various other staples disclosed herein, can include one or more barbs extending therefrom. In various instances, the barbs can be configured to engage tissue captured within and/or surrounding the staple. In certain instances, the barbs can assist in retaining the staple within the tissue, especially when the staple has been misformed or unformed. The staple 800 can include barbs extending from one or both of the legs 804. For instance, each leg 804 can include one or more barbs 808 which face outwardly from the center of the staple 800 and/or one or more barbs 809 which face inwardly toward the center of the staple 800, for example. In certain instances, the barbs 808 can extend away from the tissue entrapment area 807 and/or the barbs 809 can extend toward or into the tissue entrapment area 807. As depicted in FIG. 62, both of the staple legs 804 of staple 800 can include barbs 808 and barbs 809. In some instances, the staple legs 804 can include barbs 808, but not barbs 809. A staple 820 is depicted in FIG. 63 which includes barbs 808, but not barbs 809. In some instances, the staple legs 804 can include barbs 809, but not barbs 808. Staples 830, 840, 850, 860, and 870 are depicted in FIGS. 64, 65, 66, 67, and 68, respectively, which include barbs 809, but not barbs 808. In some embodiments, a first leg 804 of a staple can include barbs 808 while a second leg 804 of the staple can include barbs 809, for example.

Figure 67:
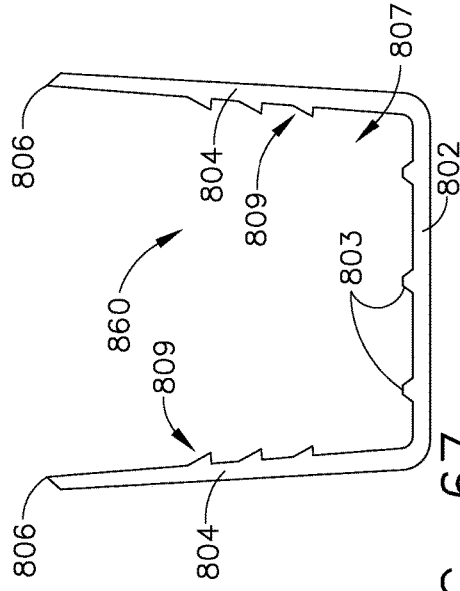
FIG. 67 is an elevational view of a staple including a plurality of barbs in accordance with at least one embodiment.
Figure 64:
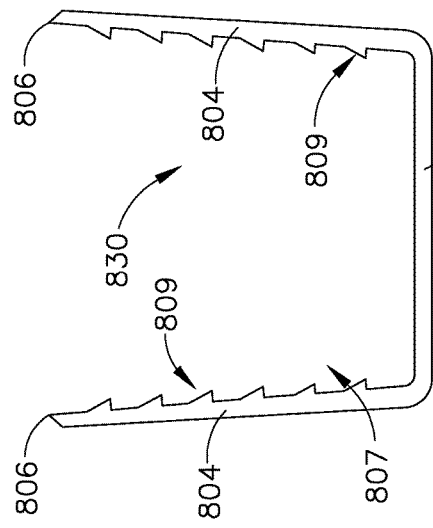
FIG. 64 is an elevational view of a staple including a plurality of barbs in accordance with at least one embodiment.

In various instances, the legs 804 and the base 802 of a staple can define a staple plane when the staple is in an unformed configuration. The barbs 808 can extend outwardly from the legs 804 within such a staple plane. Similarly, the barbs 809 can extend inwardly from the legs 804 within such a plane. In some instances, a staple can include barbs which extend laterally with respect to such a staple plane. Other embodiments are envisioned in which the legs 804 and the base 802 do not lie within, or entirely lie within, a single plane. In such embodiments, the barbs can extend in any suitable direction. In various embodiments, referring now to FIG. 67, a staple, such as staple 860, for example, can include barbs 803 extending from the base 802. In various instances, the barbs 803 can extend inwardly toward the tissue entrapment area 807 of the staple 860. In certain instances, the barbs 803 can extend outwardly away from the tissue entrapment area 807. As illustrated in FIG. 67, the barbs 803 can extend within a staple plane defined by the legs 804 and the base 802. In certain instances, the barbs 803 can extend laterally with respect to such a staple plane. Various exemplary barb configurations are discussed in greater detail further below.

In various instances, a staple leg 804 can comprise an array of barbs 808 which extends along the entire length thereof. In some instances, a staple leg 804 can comprise an array of barbs 808 which extends along less than the entire length thereof. By way of example, referring to FIG. 62, the legs 804 of the staple 800 each comprise an array of barbs 808 which extends along less than the entire length of the legs 804. Similarly, referring to FIG. 63, the legs 804 of the staple 820 each comprise an array of barbs 808 which extends along less than the entire length of the legs 804.

With regard to the staple 800, for example, an array of barbs 808 can extend along each of the legs 804 from the base 802 of the staple 800 toward the tips 806 of the legs 804. As illustrated in FIG. 62, the arrays of barbs 808 may not extend to the tips 806 of the legs 804. In various instances, the arrays of barbs 808 can extend along half, or approximately half, the lengths of the legs 804, for example; however, any suitable length of the barb arrays could be utilized. For instance, the arrays of barbs 808 can extend along less than half or more than half of the lengths of the legs 804. In some embodiments, an array of barbs 808 can extend along each of the legs 804 from the tips 806 of the legs 804 toward the base 802. In such embodiments, the array of barbs 808 may not extend to the base 802. In some embodiments, a leg 804 can comprise an array of barbs 808 which does not extend to the tip 806 of the leg 804 or the base 802. In certain embodiments, a leg 804 can comprise more than one array of barbs 808.

Figure 65:
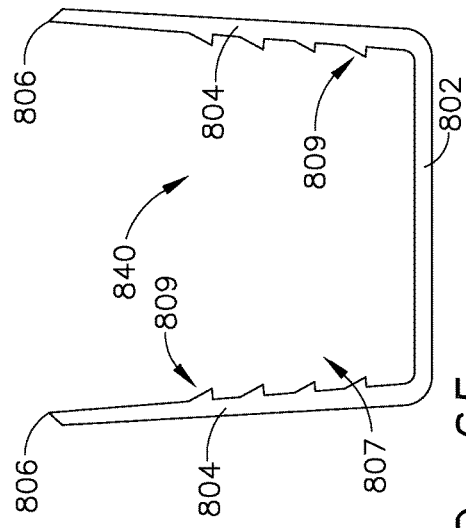
FIG. 65 is an elevational view of a staple including a plurality of barbs in accordance with at least one embodiment.
Figure 66:
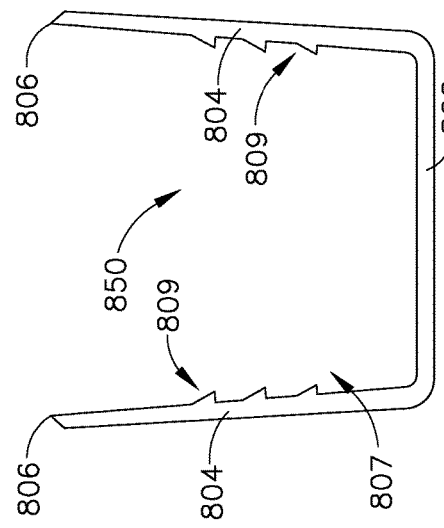
FIG. 66 is an elevational view of a staple including a plurality of barbs in accordance with at least one embodiment.

In various instances, further to the above, a staple leg 804 can comprise an array of barbs 809 which extends along the entire length thereof. By way of example, referring to FIG. 64, the legs 804 of the staple 830 each comprise an array of barbs 809 which extends along the entire length of the legs 804. In some instances, a staple leg 804 can comprise an array of barbs 809 which extends along less than the entire length thereof. By way of example, referring to FIG. 65, the legs 804 of the staple 840 each comprise an array of barbs 809 which extends along less than the entire length of the legs 804. Similarly, referring to FIG. 68, the legs 804 of the staple 870 each comprise an array of barbs 809 which extends along less than the entire length of the legs 804. With regard to the staple 840, for example, an array of barbs 809 can extend along each of the legs 804 from the base 802 of the staple 840 toward the tips 806 of the legs 804. As illustrated in FIG. 65, the arrays of barbs 809 may not extend to the tips 806 of the legs 804. In various instances, the arrays of barbs 809 can extend along half, or approximately half, the lengths of the legs 804, for example; however, any suitable length of the barb arrays could be utilized. For instance, the arrays of barbs 809 can extend along less than half or more than half of the lengths of the legs 804. In some embodiments, an array of barbs 809 can extend along each of the legs 804 from the tips 806 of the legs 804 toward the base 802. In such embodiments, the array of barbs 809 may not extend to the base 802. In some embodiments, as illustrated in FIG. 66, a leg 804 can comprise an array of barbs 809 which does not extend to the tip 806 of the leg 804 or the base 802. In certain embodiments, a leg 804 can comprise more than one array of barbs 809.

Various barb configurations are depicted in FIGS. 70-73, although any suitable barb configuration could be utilized. Referring to FIG. 70, a staple leg 804 can include at least one barb 809, for example. In various instances, the barb 809 can comprise a prong. The prong can include a first surface 809a and a second surface 809b which can extend from the perimeter 805 of the staple leg 804. The first surface 809a can comprise an inclined surface, a convex surface, and/or a concave surface, for example. The second surface 809b can comprise a flat, or an at least substantially flat, surface, for example. In various instances, the first surface 809a and the second surface 809b can converge at an edge 809c, for example. The barb 809 can be formed utilizing any suitable process. For instance, the barb 809 can be formed utilizing a stamping process. In at least one embodiment, a forming die, for example, can be utilized to strike the perimeter 805 of the wire comprising the leg 804 in order to upset, or disturb, enough material to create the barb 809. In various instances, a barb can comprise any suitable nib or spur, for example. In various embodiments, the barb 809 can be tapered. In various instances, the barb 809 can include a base adjacent to the perimeter 805 which is thicker than a tip of the barb 809.

Referring now to FIGS. 68, 69, 71, and 71A, a staple leg 804 can include at least one barb 879, for example. In at least one embodiment, the barb 879 can extend around a portion of the perimeter 805 of the staple leg 804. In various instances, the barb 879 can include a first surface 879a and a second surface 879b which can extend from the perimeter 805 of the staple leg 804. The first surface 879a can comprise an inclined surface, a convex surface, and/or a concave surface, for example. The second surface 879b can comprise a flat, or an at least substantially flat, surface, for example. In various instances, the first surface 879a and the second surface 879b can converge at an edge 879c, for example. In various instances, the edge 879c can be arcuate, for example. The barb 879 can be formed utilizing any suitable process. For instance, the barb 879 can be formed utilizing a stamping process. In at least one embodiment, a forming die, for example, can be utilized to strike the perimeter 805 of the wire comprising the leg 804 in order to upset, or disturb, enough material to create the barb 879. Referring primarily to FIG. 71A, the wire comprising the leg 804 can be defined by a diameter 801 and the barb 879 can be defined by a diameter which is larger than the diameter 801. Correspondingly, the wire comprising the leg 804 can be defined by a radius and the barb 879 can be defined by a radius which is larger than the wire radius. In various embodiments, the barb 879 can be tapered. In various instances, the barb 879 can include a base adjacent to the perimeter 805 which is thicker than a tip of the barb 879.

Figure 72:
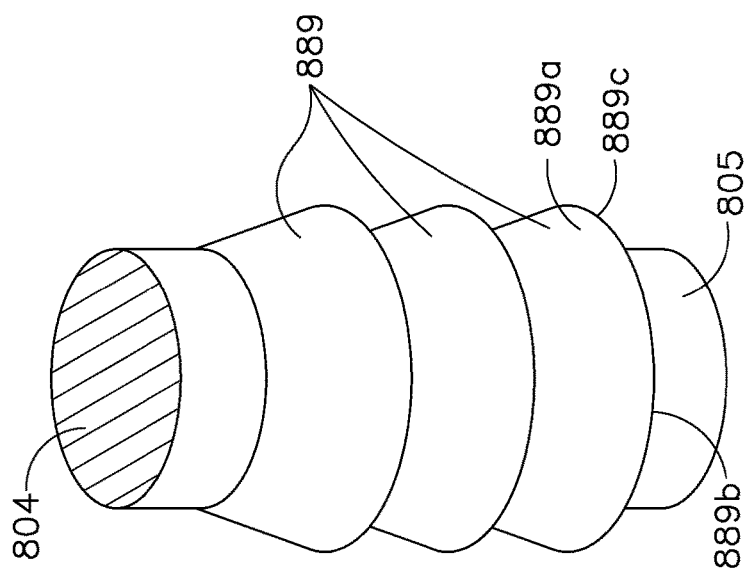
FIG. 72 is a partial perspective view of a barbed staple leg in accordance with at least one embodiment.

Referring now to FIG. 72, a staple leg 804 can include at least one barb 889, for example. In at least one embodiment, the barb 889 can extend around the entirety of the perimeter 805 of the staple leg 804. In various instances, the barb 889 can include a first surface 889a and a second surface 889b which can extend from the perimeter 805 of the staple leg 804. The first surface 889a can comprise an inclined surface, a convex surface, and/or a concave surface, for example. The second surface 889b can comprise a flat, or an at least substantially flat, surface, for example. In various instances, the first surface 889a and the second surface 889b can converge at an edge 889c, for example. In various instances, the edge 889c can be arcuate, for example. The barb 889 can be formed utilizing any suitable process. For instance, the barb 889 can be formed utilizing a stamping process. In at least one embodiment, a forming die, for example, can be utilized to strike the perimeter 805 of the wire comprising the leg 804 in order to upset, or disturb, enough material to create the barb 889. The wire comprising the leg 804 can be defined by a wire diameter and the barb 889 can be defined by a diameter which is larger than the wire diameter. Correspondingly, the wire comprising the leg 804 can be defined by a radius and the barb 889 can be defined by a radius which is larger than the wire radius. In various embodiments, the barb 889 can be tapered. In various instances, the barb 889 can include a base adjacent to the perimeter 805 which is thicker than a tip of the barb 889.

Figure 73:
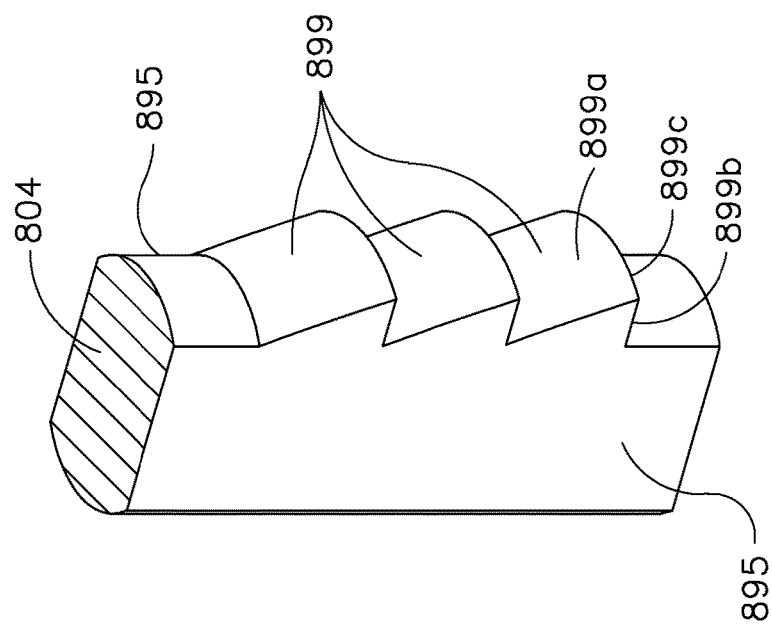
FIG. 73 is a partial perspective view of a barbed staple leg in accordance with at least one embodiment.

Referring now to FIG. 73, a staple leg 804 can include at least one barb 899, for example. In various instances, the barb 899 can comprise a prong. The prong can include a first surface 899a and a second surface 899b which can extend from the perimeter of the staple leg 804. The first surface 899a can comprise an inclined surface, a convex surface, and/or a concave surface, for example. The second surface

899*b* can comprise a flat, or an at least substantially flat, surface, for example. In various instances, the first surface 899*a* and the second surface 899*b* can converge at an edge 899*c*, for example. The barb 899 can be formed utilizing any suitable process. For instance, the barb 899 can be formed utilizing a stamping process. In at least one embodiment, a forming die, for example, can be utilized to strike the perimeter of the wire comprising the leg 804 in order to upset, or disturb, enough material to create the barb 899. In various embodiments, the wire comprising the staple can include one or more flat sides. In at least one embodiment, the wire can include opposing flat sides 895, for example. In at least one such embodiment, the flat sides 895 can be formed into a cylindrical wire. In some instances, the wire can retain one or more cylindrical surfaces in addition to the flat sides 895. In various instances, a barb can comprise any suitable nib or spur, for example. In various embodiments, the barb 899 can be tapered. In various instances, the barb 899 can include a base adjacent to the perimeter of the leg 804 which is thicker than a tip of the barb 899.

In various instances, the legs of a staple can define a staple plane. The base of the staple may or may not be positioned within the staple plane. In either event, one or more barbs extending from the legs and/or the base may extend within and/or extend parallel with respect to the staple plane. In some instances, one or more barbs extending from the legs and/or the base can extend outwardly from the staple plane. One or more barbs extending from the legs and/or the base can extend transversely with respect to the staple plane. In various instances, a barb can extend circumferentially around a staple leg. Such a barb can extend within and outwardly from the staple plane. In some instances, a barb can extend around the entire circumference of a staple leg. In certain instances, the barb can extend less than 360 degrees around a staple leg. A barb extending within a staple plane can readily control tissue within the staple plane. A barb extending outwardly from a staple plane can readily control tissue outside of the staple plane. A staple, and/or a staple leg, can include one or more barbs extending within the staple plane and one or more barbs extending outwardly from the staple plane.

Referring again to FIG. 62, the barbs extending from a staple leg 804 can be configured to retain the staple leg 804 within tissue. As outline above, the staple legs 804 may be malformed and/or unformed by an anvil in certain instances and, owing to the barb, or barbs, extending therefrom, the staple leg 804 may still be retained in the tissue. In various instances, the barbs can be configured to trap tissue within the tissue entrapment area of the staple. In certain instances, the barbs can be configured to hold the tissue against the base 802. In such instances, the barbs can apply a compressive force or pressure to the tissue. As discussed above in connection with the embodiments depicted in FIGS. 70-73, a barb can comprise an inclined, convex, and/or concave top surface, such as surfaces 809*a*, 879*a*, 889*a*, and/or 899*a*, for example. The top surfaces of the barbs can be configured to facilitate the insertion of the barbs and the staple legs 804 into and/or through the tissue. As also discussed above in connection with the embodiments depicted in FIGS. 70-73, a barb can comprise a flat, or at least substantially flat, bottom surface, such as surfaces 809*b*, 879*b*, 889*b*, and/or 899*b*, for example. The bottom surfaces of the barbs can be configured to inhibit the removal of the barbs and the staple legs 804 from the tissue. As a result of the above, in certain circumstances, the top surfaces of the barbs can be configured to pierce the tissue while the bottom surfaces of the barbs can be configured to abut the tissue. In various circumstances, the tips 806 of the staple legs 804 can be configured to puncture a hole in the tissue while the staple legs 804 and the barbs extending therefrom can be configured to resiliently expand the hole such that such that the tissue can flow around the barbs as the staple legs 804 are being pushed through the tissue and flow back underneath the bottom surfaces of the barbs.

In certain embodiments, a first barb can extend from a first leg 804 of the staple and a second barb can extend from a second leg 804 of the staple. In various instances, the first barb and the second barb can be located the same, or at least substantially the same, distance between from the base 802. In certain instances, the first barb and the second barb can be located the same, or at least substantially the same, vertical distance from the base 802. As discussed above, a staple leg 804 can include an array of barbs extending along the length of the staple leg 804. In various embodiments, referring primarily to FIG. 62, a staple can include a first leg 804 including a first array of barbs and a second leg 804 including a second array of barbs wherein the first array of barbs and the second array of barbs can be configured to co-operatively hold the staple within the tissue. In various embodiments, a barb from the first array and a barb from the second array can comprise a pair of barbs configured to engage tissue at the same vertical distance from the base 802, for example. In various instances, a staple can comprise more than one pair of barbs. In certain instances, each of the barb pairs can be configured to engage the tissue at a different vertical distance from the base 802. In such circumstances, a staple can be suitable for use with different tissue thicknesses. For instance, when a staple is used to staple thin tissue, one pair of barbs, or less than all of the barb pairs, may engage the thin tissue. If that staple were used to staple thick tissue, however, additional barb pairs, or all of the barb pairs, may engage the tissue. In certain embodiments, the barbs extending from the legs 804 can be arranged in a manner in accordance with the tissue thickness, or range of tissue thicknesses, that can be stapled by the staple. For instance, referring again to FIG. 62, the barbs 808 and 809 can be selectively positioned along the legs 804 such that they are positioned within and/or adjacent to the tissue captured within the staple. In certain instances, the portions of the staple legs 804 that are deformed by, or come into contact with, an anvil may not include barbs extending therefrom. In at least some instances, an array of barbs extending from the inwardly-facing side of the staple legs 804 may be longer than an array of barbs extending from the outwardly-facing side of the staple legs 804. In other instances, an array of barbs extending from the inwardly-facing side of the staple legs 804 may be shorter than an array of barbs extending from the outwardly-facing side of the staple legs 804. In yet other instances, an array of barbs extending from the inwardly-facing side of the staple legs 804 may be the same length as an array of barbs extending from the outwardly-facing side of the staple legs 804.

As discussed above, the barbs extending from the staple legs 804 can assist in retaining the staple within the tissue if the staple legs 804 are malformed and/or unintentionally unformed. Certain circumstances are contemplated, however, where a staple including one or more of the barbs disclosed herein is inserted into tissue and remains intentionally unformed. In any event, staples including one or more of the barbs disclosed herein can be useful in stapling thick tissue. More particularly, in some instances, the presence of thick and/or dense tissue between a staple cartridge and an anvil and/or the presence of thick and/or dense tissue within a staple may prevent the staple from becoming fully formed or closed. For instance, the staple may not be fully closed into a B-form configuration or the staple may not be closed at all. In such instances, the barbs of the unclosed staples may inhibit or prevent the tissue from being pulled out of the staple, for example. An array of barbs extending along the length of a staple leg may permit the leg to remain retained in the tissue regardless of the thickness of the tissue.

Various embodiments are contemplated in which at least one barbed staple, such as barbed staple 800, for example, are removably stored within a staple cartridge, such as the staple cartridge 22000 illustrated in FIGS. 10-12, for example. Certain embodiments are envisioned in which a staple cartridge includes only barbed staples while other embodiments are envisioned which utilize barbed staples and non-barbed staples. For instance, a first row of staples can comprise barbed staples while a second row of staples can comprise non-barbed staples. In some instances, the staples stored within a staple cartridge can have the same, or essentially the same, unformed height. At least with regard to U-shaped and/or V-shaped staples, for example, the unformed height of a staple can be defined as the vertical distance between the bottom of the base of the staple and the tips of the staple legs. Such a measurement can be taken before the staples are inserted into the staple cartridge, when the staples are removably stored within the staple cartridge, and/or before the staples are deformed against the anvil. In some instances, barbed staples arranged in a first row in a staple cartridge can comprise a first unformed height and barbed staples arranged in a second row in the staple cartridge can comprise a second unformed height. Barbed staples in a third row in the staple cartridge can comprise the first unformed height, the second unformed height, or a third unformed height. The first row, the second row, and/or the third row of barbed staples can be positioned on the same side of a knife slot defined in the staple cartridge or on opposite sides of the knife slot. In use, the barbed staples removably stored in a staple cartridge can be formed to the same formed height or different formed heights. The formed height of a staple can be defined as the overall vertical distance of the staple after it has been deformed against an anvil. At least with regard to a staple that has been deformed into a B-form, for example, the formed height of the staple can be measured between the bottom of the base of the staple and the top-most portion of the staple legs. In some instances, barbed staples arranged in a first row in a staple cartridge can be deformed to a first formed height and barbed staples arranged in a second row in the staple cartridge can be deformed to a second formed height. Barbed staples in a third row in the staple cartridge can comprise the first formed height, the second formed height, or a third formed height. The first row, the second row, and/or the third row of barbed staples can be positioned on the same side of a knife slot defined in the staple cartridge or on opposite sides of the staple cartridge. As the reader will appreciate, the staples depicted in FIGS. 10-12 have been deformed to different formed heights. Barbed staples 800, for example, could be utilized in staple cartridges and/or stapling instruments which create staple rows having different formed heights. A first row of barbed staples 800 could be deformed to a first formed height and a second row of barbed staples 800 could be deformed to a second formed height. In various instances, a third row of barbed staples 800 could be deformed to a third formed height. In some instances, the barbed staples 800 deformed to different heights can begin with the same, or essentially the same, unformed height. In certain instances, the barbed staples 800 deformed to different formed heights can begin with different unformed heights. Various structures can be utilized to form staples to different formed heights. For instance, movable drivers supporting the staples can support the staples at different distances relative to the anvil. In some instances, the anvil can include staple forming pockets having different depths. In various instances, a staple driver can include a cradle configured to support the base of a staple and push the staple upwardly toward a forming pocket defined in the anvil. The formed height of a staple can be determined by the distance between the bottom surface of the cradle and the top surface of the forming pocket. U.S. Pat. No. 8,317,070, entitled SURGICAL STAPLING DEVICES THAT PRODUCE FORMED STAPLES HAVING DIFFERENT LENGTHS, issued on Nov. 27, 2012, is incorporated by reference in its entirety. In certain instances, the deck of a staple cartridge can include stepped surfaces, as illustrated in FIG. 1. A first row of staple cavities can be defined in a first step and a second row of staple cavities can be defined in a second step wherein the first step and the second step can be vertically offset from one another. For instance, the first step can be positioned vertically above, or closer to, the anvil than the second step. In certain instances, a wall can be defined between the first step and the second step. In some instances, the deck of a staple cartridge can comprise a first step, a second step positioned vertically above the first step, and a third step positioned vertically above the second step. Various embodiments are envisioned in which the deck of a staple cartridge includes any suitable number of steps and any suitable number of walls between the steps. A first row of staple cavities can be defined in the first step, a second row of staple cavities can be defined in the second step, and/or a third row of staple cavities can be defined in the third step, for example. The first row of staple cavities can include staples having a first unformed height, the second row of staple cavities can include staples having a second unformed height, and/or the third row of staple cavities can include staples having a third unformed height, for example. Various embodiments are envisioned in which a staple cartridge includes any suitable number of staple rows having different unformed heights. The staples in the first row of staple cavities can be deformed to a first formed height, the staples in the second row of staple cavities can be deformed to a second formed height, and/or the third row of staple cavities can be deformed to a third formed height, for example. Various embodiments are envisioned in which a staple cartridge includes any suitable number of staple rows which are deformed to different formed heights. In addition to or in lieu of having different formed staple heights, an end effector of a stapling instrument can have different tissue gaps. For instance, referring generally to FIGS. 10 and 11, a gap can be defined between the cartridge deck surface 22011 of a staple cartridge and the anvil tissue compression surface 10063 of an anvil. This gap can be configured to receive tissue T. This gap can also be configured to receive a tissue thickness compensator; however, a barbed staple may or may not be used with a tissue thickness compensator and the discussion provided with respect to barbed staples can be applicable in either circumstance. In any event, the reader will appreciate that the anvil tissue compression surface 10063 is stepped. The anvil tissue compression surface 10063 comprises a first portion positioned vertically above a second portion. When the anvil and the staple cartridge of an end effector are in a closed condition, as illustrated in FIG. 11, a first gap distance is defined between an outer portion of the anvil tissue compression surface 10063 and the cartridge deck surface 22011 and a second, different, gap distance is defined between an inner portion of the anvil tissue compression surface 10063 and the cartridge deck surface 22011. The first gap distance is illustrated as being larger than the second gap distance, but it is possible for the first gap distance to be shorter than the second gap distance. Tissue compressed between the anvil and the staple cartridge in the shorter gap distance can be compressed more than tissue in the larger gap distance. The barbs of a barbed staple 800, for example, may engage the tissue differently depending on whether the tissue is positioned within a shorter tissue gap or a larger tissue gap. More particularly, tissue compressed within a shorter tissue gap may seek to re-expand more after it is released from an end effector than tissue compressed within a larger tissue gap and the barbs of a barbed staple may inhibit or resist this re-expansion, depending on their configuration and/or position on the barbs. In other instances, the barbs may be configured and/or positioned so as to not inhibit or resist the re-expansion of the tissue. As the reader will appreciate, anvil tissue compression surface 10063 is stepped and the cartridge deck surface is flat, or at least substantially flat, and, thus, the difference in tissue gaps defined within the end effector is a function of the height of the stepped anvil surfaces. Other embodiments are envisioned. For instance, the anvil tissue compression surface can be flat, or at least substantially flat, and the cartridge deck surface can be stepped. In other instances, the anvil tissue compression surface and the cartridge deck surface can both be stepped. In any event, different gap distances can be defined between the anvil tissue compression surface and the cartridge deck surface. While two gap distances have been illustrated in FIGS. 10 and 11, more than two gap distances may be possible, such as three gap distances, for example. With further reference to FIGS. 10 and 11, a first longitudinal row of forming pockets can be arranged within a first portion of an end effector having first tissue gap distance and a second longitudinal row of forming pockets can be arranged within a second portion of the end effector having a second tissue gap distance which is different than the first tissue gap distance. In some instances, the end effector can include a third longitudinal row of forming pockets arranged within a third portion of the end effector having a third tissue gap distance which is different than the first tissue gap distance and the second tissue gap distance. In certain instances, the end effector can include a third longitudinal row of forming pockets arranged within a third portion of the end effector having a tissue gap distance which is the same as the first tissue gap distance or the second tissue gap distance. The reader will appreciate that an end effector can have different tissue gap distances and/or different formed staple heights. An end effector can have one, the other, or both. In certain instances, shorter formed staple heights can be associated within shorter tissue gap distances while larger formed staple heights can be associated with larger tissue gap distances. In other instances, shorter formed staple heights can be associated with larger tissue gap distances while larger formed staple heights can be associated with shorter tissue gap distances. Further to the above, a staple can include a U-shape configuration in its unformed state. A U-shape staple can comprise a base and two staple legs extending from the base wherein the staple legs extend in parallel directions to each other. Also further to the above, a staple can include a V-shape configuration in its unformed state. A V-shape configuration can comprise a base and two staple legs extending from the base wherein the staple legs extend in directions which are not parallel.

Various embodiments described herein are described in the context of linear end effectors and/or linear fastener cartridges. Such embodiments, and the teachings thereof, can be applied to non-linear end effectors and/or non-linear fastener cartridges, such as, for example, circular and/or contoured end effectors. For example, various end effectors, including non-linear end effectors, are disclosed in U.S. patent application Ser. No. 13/036,647, filed Feb. 28, 2011, entitled SURGICAL STAPLING INSTRUMENT, now U.S. Patent Application Publication No. 2011/0226837, which is hereby incorporated by reference in its entirety. Additionally, U.S. patent application Ser. No. 12/893,461, filed Sep. 29, 2012, entitled STAPLE CARTRIDGE, now U.S. Patent Application Publication No. 2012/0074198, is hereby incorporated by reference in its entirety. U.S. patent application Ser. No. 12/031,873, filed Feb. 15, 2008, entitled END EFFECTORS FOR A SURGICAL CUTTING AND STAPLING INSTRUMENT, now U.S. Pat. No. 7,980,443, is also hereby incorporated by reference in its entirety. The entire disclosure of U.S. Pat. No. 7,845,537, entitled SURGICAL INSTRUMENT HAVING RECORDING CAPABILITIES, which issued on Dec. 7, 2010, is incorporated by reference herein. The entire disclosure of U.S. application Ser. No. 13/118,241, entitled SURGICAL STAPLING INSTRUMENTS WITH ROTATABLE STAPLE DEPLOYMENT ARRANGEMENTS, now U.S. Patent Application Publication No. 2012/0298719, which was filed on May 27, 2011, is incorporated by reference herein.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A method for altering a tissue thickness compensator for use with a surgical instrument, said method comprising the steps of:
    obtaining a tissue thickness compensator comprised at least partially from a material including a glass transition temperature and a melting temperature, wherein said tissue thickness compensator comprises a first shape;
    heating said material to a temperature higher than said glass transition temperature and lower than said melting temperature;
    applying a modifying member to a tissue-facing side of said tissue thickness compensator;
    manipulating said tissue thickness compensator with said modifying member to a second shape different than said first shape by inducing a localized change in a portion of said tissue thickness compensator in contact with said modifying member;
    allowing said material to cool below said glass transition temperature; and
    releasing said modifying member from said portion of said tissue thickness compensator.

2. The method of claim 1, wherein said step of obtaining said tissue thickness compensator comprises the steps of:
    obtaining a biocompatible polymer comprising a glass transition temperature and a melting temperature;
    dissolving said biocompatible polymer in a solvent to produce a solution; and
    lyophilizing said solution.

3. The method of claim 1, wherein said step of manipulating said tissue thickness compensator comprises applying at least one compressive force to said tissue thickness compensator.

4. The method of claim 1, wherein said step of manipulating said tissue thickness compensator comprises applying at least one tensile force to said tissue thickness compensator.

5. The method of claim 1, further comprising the step of actively cooling said manipulated tissue thickness compensator below said glass transition temperature.

6. A customized tissue thickness compensator for use with a surgical stapler, wherein said customized tissue thickness compensator is prepared by a process comprising the steps of:
    obtaining a tissue thickness compensator comprising a first shape;
    transitioning at least a portion of said tissue thickness compensator from an original state to a glassy state;
    applying a modifying member to a tissue-facing side of said tissue thickness compensator;
    manipulating said at least a portion of said tissue thickness compensator with said modifying member to a second shape by inducing a localized change in a portion of said tissue thickness compensator in contact with said modifying member;
    allowing said at least a portion of said tissue thickness compensator to return from said glassy state to a non-glassy state; and
    releasing said modifying member from said at least a portion of said tissue thickness compensator.

7. The customized tissue thickness compensator of claim 6, wherein said step of obtaining said tissue thickness compensator comprises the steps of:
    obtaining a biocompatible polymer comprising a glass transition temperature and a melting temperature;
    dissolving said biocompatible polymer in a solvent to produce a solution; and
    lyophilizing said solution.

8. The customized tissue thickness compensator of claim 6, wherein said step of manipulating said at least a portion of said tissue thickness compensator comprises applying at least one compressive force to said at least a portion of said tissue thickness compensator.

9. The customized tissue thickness compensator of claim 6, wherein said step of manipulating said at least a portion of said tissue thickness compensator comprises applying at least one tensile force to said at least a portion of said tissue thickness compensator.

10. The customized tissue thickness compensator of claim 6, wherein said process comprises the step of actively cooling said at least a portion of said tissue thickness compensator to remove said at least a portion of said tissue thickness compensator from said glassy state to said non-glassy state.

11. The customized tissue thickness compensator of claim 6, wherein said process comprises the step of maintaining said manipulation of said at least a portion of said tissue thickness compensator for a period of time sufficient to permit said at least a portion of said tissue thickness compensator to maintain said manipulation.

12. The method of claim 1, wherein said second shape has a greater density than said first shape.

13. The customized tissue thickness compensator of claim 6, wherein the density of said second shape of said tissue thickness compensator is greater than the density of the first shape of said tissue thickness compensator.

* * * * *